US011535659B2

(12) United States Patent
Erickson et al.

(10) Patent No.: US 11,535,659 B2
(45) Date of Patent: Dec. 27, 2022

(54) ENGINEERED POLYPEPTIDES HAVING ENHANCED DURATION OF ACTION

(71) Applicant: Amryt Pharmaceuticals Inc., Cambridge, MA (US)

(72) Inventors: Mary Erickson, San Diego, CA (US); David C. Litzinger, San Diego, CA (US); Soumitra S. Ghosh, San Diego, CA (US); Zijian Guo, San Diego, CA (US); Jonathan David Roth, San Diego, CA (US)

(73) Assignee: Amryt Pharmaceuticals Inc., Cambridge, MA (US)

( * ) Notice: Subject to any disclaimer, the term of this patent is extended or adjusted under 35 U.S.C. 154(b) by 0 days.

(21) Appl. No.: 16/751,538

(22) Filed: Jan. 24, 2020

(65) Prior Publication Data

US 2020/0362006 A1 Nov. 19, 2020

Related U.S. Application Data

(63) Continuation of application No. 14/800,537, filed on Jul. 15, 2015, now abandoned, which is a continuation of application No. 13/852,671, filed on Mar. 28, 2013, now abandoned, which is a continuation of application No. PCT/US2011/053786, filed on Sep. 28, 2011.

(60) Provisional application No. 61/422,091, filed on Dec. 10, 2010, provisional application No. 61/387,402, filed on Sep. 28, 2010.

(51) Int. Cl.
| | | |
|---|---|---|
| *A61K 38/22* | (2006.01) | |
| *C07K 14/575* | (2006.01) | |
| *C07K 14/00* | (2006.01) | |
| *A61K 38/00* | (2006.01) | |

(52) U.S. Cl.
CPC .......... *C07K 14/5759* (2013.01); *C07K 14/00* (2013.01); *C07K 14/575* (2013.01); *A61K 38/00* (2013.01); *A61K 38/2264* (2013.01); *C07K 2319/33* (2013.01)

(58) Field of Classification Search
CPC ............................ C07K 14/5759; A61K 38/00
See application file for complete search history.

(56) References Cited

U.S. PATENT DOCUMENTS

| | | |
|---|---|---|
| 4,002,531 A | 1/1977 | Royer |
| 4,179,337 A | 12/1979 | Davis et al. |
| 4,695,463 A | 9/1987 | Yang et al. |
| 4,695,623 A | 9/1987 | Stabinsky |
| 4,703,008 A | 10/1987 | Lin |
| 4,766,106 A | 8/1988 | Katre et al. |
| 4,810,643 A | 3/1989 | Souza |
| 4,897,471 A | 1/1990 | Stabinsky |
| 4,904,584 A | 2/1990 | Shaw |
| 4,999,291 A | 3/1991 | Souza |
| 5,075,222 A | 12/1991 | Hannum et al. |
| 5,166,322 A | 11/1992 | Shaw et al. |
| 5,372,808 A | 12/1994 | Blatt et al. |
| 5,441,868 A | 8/1995 | Lin |
| 5,521,283 A | 5/1996 | DiMarchi et al. |
| 5,525,705 A | 6/1996 | DiMarchi et al. |
| 5,532,336 A | 7/1996 | DiMarchi et al. |
| 5,541,293 A | 7/1996 | Stabinsky |
| 5,547,933 A | 8/1996 | Lin |
| 5,552,522 A | 9/1996 | DiMarchi et al. |
| 5,552,523 A | 9/1996 | Basinski et al. |
| 5,552,524 A | 9/1996 | Basinski et al. |
| 5,554,727 A | 9/1996 | Basinski et al. |
| 5,559,208 A | 9/1996 | Basinski et al. |
| 5,563,243 A | 10/1996 | DiMarchi et al. |
| 5,563,244 A | 10/1996 | DiMarchi et al. |
| 5,563,245 A | 10/1996 | DiMarchi et al. |
| 5,567,678 A | 10/1996 | DiMarchi et al. |

(Continued)

FOREIGN PATENT DOCUMENTS

| | | |
|---|---|---|
| EP | 0401384 A1 | 12/1990 |
| EP | 0539167 A2 | 4/1993 |

(Continued)

OTHER PUBLICATIONS

Malik et al., "Polythylene Glycol (PEG)-modified Granulocyte-Macrophage Colony-stimulating Factor (GM-CSF) with Conserved Biological Activity", Exp. Hematol. 1992, vol. 20, pp. 1028-1035.
[Author Unknown] "Intensive Blood-Glucose Control With Sulphonylureas or Insulin Compared With Conventional Treatment and Risk of Complications in Patients with Type 2 Diabetes (UKPDS33)." UK Prospective Diabetes Study (UKPDS) Group, Lancet, 1998; vol. 352(9131), pp. 837-853.
Abate, N., et al., "Estimation of Adipose Tissue Mass by Magnetic Resonance Imaging: Validation Against Dissection in Human Cadavers," J. Lipid Res, 1994; vol. 35, 1490-1496.
Ahima, R.S., et al., "Role of Leptin in the Neuroendocrine Response to Fasting," Nature (1996); 382: 250-252.

(Continued)

*Primary Examiner* — Gyan Chandra
(74) *Attorney, Agent, or Firm* — Cooley LLP

(57) ABSTRACT

Compounds are provided having inter alia good duration of action, high potency and/or convenient dosing regimens including once weekly administration. The compounds are engineered polypeptides which incorporate an albumin binding domain in combination with one or more biologically active polypeptides. Also provided are pharmaceutical compositions and methods of treatment for diseases and disorders including lipodystrophy, dyslipidemia, hyperlipidemia, overweight, obesity, hypothalamic amenorrhea, Alzheimer's disease, leptin deficiency, fatty liver disease or diabetes (including type I and type II). Additional diseases and disorders which can be treated by the compounds and methods described herein include nonalcoholic steatohepatitis (NASH) and nonalcoholic fatty liver disease (NAFLD), metabolic syndrome X and Huntington's Disease.

8 Claims, 29 Drawing Sheets

Specification includes a Sequence Listing.

(56) References Cited

U.S. PATENT DOCUMENTS

| | | |
|---|---|---|
| 5,567,803 A | 10/1996 | Basinski et al. |
| 5,569,743 A | 10/1996 | DiMarchi et al. |
| 5,569,744 A | 10/1996 | Basinski et al. |
| 5,574,133 A | 11/1996 | DiMarchi et al. |
| 5,580,954 A | 12/1996 | DiMarchi et al. |
| 5,581,476 A | 12/1996 | Osslund |
| 5,582,823 A | 12/1996 | Souza |
| 5,594,101 A | 1/1997 | Becker |
| 5,594,104 A | 1/1997 | Basinski et al. |
| 5,605,886 A | 2/1997 | Basinski et al. |
| 5,614,379 A | 3/1997 | MacKellar |
| 5,618,698 A | 4/1997 | Lin |
| 5,621,080 A | 4/1997 | Lin |
| 5,686,411 A | 11/1997 | Gaeta et al. |
| 5,691,309 A | 11/1997 | Basinski et al. |
| 5,719,266 A | 2/1998 | DiMarchi et al. |
| 5,756,461 A | 5/1998 | Stephens |
| 5,824,778 A | 10/1998 | Ishikawa et al. |
| 5,824,784 A | 10/1998 | Kinsller et al. |
| 5,831,017 A | 11/1998 | Hoftman |
| 5,851,995 A | 12/1998 | Basinski et al. |
| 5,922,678 A | 7/1999 | Stephans |
| 5,935,810 A | 8/1999 | Friedman et al. |
| 6,001,968 A | 12/1999 | Friedman et al. |
| 6,025,324 A | 2/2000 | Bailon et al. |
| 6,025,325 A | 2/2000 | Campfield et al. |
| 6,048,837 A | 4/2000 | Friedman et al. |
| 6,258,932 B1 | 7/2001 | Vahlne |
| 6,309,853 B1 | 10/2001 | Friedman et al. |
| 6,319,685 B1 | 11/2001 | Gilligan et al. |
| 6,326,468 B1 | 12/2001 | Canne et al. |
| 6,420,339 B1 | 7/2002 | Gegg et al. |
| 6,475,984 B2 | 11/2002 | Kirwin |
| 6,872,700 B1 | 3/2005 | Young et al. |
| 6,899,892 B2 | 5/2005 | Gallahar et al. |
| 7,045,318 B2 | 5/2006 | Balance |
| 7,057,015 B1 | 6/2006 | Gage et al. |
| 7,183,254 B2 | 2/2007 | DePaoli et al. |
| 8,318,666 B2 | 11/2012 | Depaoli et al. |
| 8,937,153 B2 | 1/2015 | Abrahmsen et al. |
| 9,211,344 B2 | 12/2015 | Ekblad et al. |
| 9,382,304 B2 | 7/2016 | Erickson et al. |
| 9,593,154 B2 | 3/2017 | Erickson et al. |
| 9,879,063 B2 | 1/2018 | Erickson et al. |
| 10,087,228 B2 | 10/2018 | Erickson |
| 10,696,960 B2 * | 6/2020 | Song .............. C12Y 304/21021 |
| 2003/0219875 A1 | 11/2003 | Rosen et al. |
| 2005/0020496 A1 | 1/2005 | Depaoli et al. |
| 2005/0239854 A1 | 10/2005 | Sugiyama et al. |
| 2006/0030530 A1 | 2/2006 | Yen et al. |
| 2007/0020284 A1 | 1/2007 | Mann et al. |
| 2007/0099836 A1 | 5/2007 | Depaoli et al. |
| 2007/0238669 A1 | 10/2007 | Haque et al. |
| 2007/0244047 A1 | 10/2007 | Rosen et al. |
| 2008/0176804 A1 | 7/2008 | Mack et al. |
| 2008/0207512 A1 | 8/2008 | Roth et al. |
| 2008/0274952 A1 | 11/2008 | Soares et al. |
| 2009/0016957 A1 | 1/2009 | Nillson et al. |
| 2009/0214534 A1 | 8/2009 | Holmes et al. |
| 2010/0104588 A1 | 4/2010 | Dennis |
| 2010/0184641 A1 | 7/2010 | Dorwald et al. |
| 2010/0239554 A1 | 9/2010 | Schellenberger et al. |
| 2010/0273979 A1 | 10/2010 | Abrahmsén et al. |
| 2010/0330108 A1 | 12/2010 | Song et al. |
| 2011/0092417 A1 | 4/2011 | Artymiuk et al. |
| 2011/0306540 A1 | 12/2011 | Schellenberger et al. |
| 2012/0149636 A1 | 6/2012 | Kraynov et al. |
| 2013/0190225 A1 | 7/2013 | Depaoli et al. |
| 2013/0203661 A1 | 8/2013 | Erickson |
| 2013/0274182 A1 | 10/2013 | Erickson et al. |
| 2014/0256621 A1 | 9/2014 | Erickson et al. |
| 2016/0083446 A1 | 3/2016 | Erickson |
| 2016/0137709 A1 | 5/2016 | Erickson et al. |
| 2016/0207974 A1 | 7/2016 | Erickson et al. |
| 2017/0095535 A1 | 4/2017 | Depaoli et al. |
| 2018/0305430 A1 | 10/2018 | Erickson et al. |
| 2019/0321447 A1 | 10/2019 | Depaoli et al. |
| 2020/0268853 A1 | 8/2020 | DePaoli et al. |

FOREIGN PATENT DOCUMENTS

| | | |
|---|---|---|
| EP | 0725078 A1 | 8/1996 |
| EP | 0725079 A1 | 8/1996 |
| EP | 0736599 A2 | 10/1996 |
| EP | 0741187 A2 | 11/1996 |
| EP | 0744408 A2 | 11/1996 |
| EP | 0745610 A2 | 12/1996 |
| EP | 0822199 A2 | 2/1998 |
| EP | 0835879 A2 | 4/1998 |
| JP | 2001-199887 A | 7/2001 |
| JP | 2016-190855 A | 11/2016 |
| WO | WO 1983/004053 A1 | 11/1983 |
| WO | WO 1991/005795 A1 | 5/1991 |
| WO | WO 1992/017505 A1 | 10/1992 |
| WO | WO 1994/017185 A1 | 8/1994 |
| WO | WO 1995/017206 A1 | 6/1995 |
| WO | WO 1996/005309 A2 | 2/1996 |
| WO | WO 1996/022308 A2 | 7/1996 |
| WO | WO 1996/023513 A1 | 8/1996 |
| WO | WO 1996/023514 A1 | 8/1996 |
| WO | WO 1996/023515 A1 | 8/1996 |
| WO | WO 1996/023516 A1 | 8/1996 |
| WO | WO 1996/023517 A1 | 8/1996 |
| WO | WO 1996/023518 A1 | 8/1996 |
| WO | WO 1996/023519 A1 | 8/1996 |
| WO | WO 1996/023520 A1 | 8/1996 |
| WO | WO 1996/023815 A1 | 8/1996 |
| WO | WO 1996/027385 A1 | 9/1996 |
| WO | WO 1996/031526 A1 | 10/1996 |
| WO | WO 1996/034111 A1 | 10/1996 |
| WO | WO 1996/034885 A2 | 11/1996 |
| WO | WO 1996/035787 A1 | 11/1996 |
| WO | WO 1996/037517 A1 | 11/1996 |
| WO | WO 1996/040912 A1 | 12/1996 |
| WO | WO 1997/000128 A2 | 1/1997 |
| WO | WO 1997/000886 A1 | 1/1997 |
| WO | WO 1997/001010 A1 | 1/1997 |
| WO | WO 1997/001331 A2 | 1/1997 |
| WO | WO 1997/002004 A2 | 1/1997 |
| WO | WO 1997/006816 A1 | 2/1997 |
| WO | WO 1997/016550 A1 | 5/1997 |
| WO | WO 1997/018833 A1 | 5/1997 |
| WO | WO 1997/020933 A2 | 6/1997 |
| WO | WO 1997/023614 A1 | 7/1997 |
| WO | WO 1997/038014 A1 | 10/1997 |
| WO | WO 1997/046585 A1 | 12/1997 |
| WO | WO 1998/008512 A1 | 3/1998 |
| WO | WO 1998/012224 A1 | 3/1998 |
| WO | WO 1998/024896 A2 | 6/1998 |
| WO | WO 1998/028427 A1 | 7/1998 |
| WO | WO 1998/041222 A1 | 9/1998 |
| WO | WO 1998/042861 A1 | 10/1998 |
| WO | WO 1998/055139 A1 | 12/1998 |
| WO | WO 2000/009165 A1 | 2/2000 |
| WO | WO 2000/020872 A1 | 4/2000 |
| WO | WO 2000/021574 A2 | 4/2000 |
| WO | WO 2000/047741 A1 | 8/2000 |
| WO | WO 2902/004488 A2 | 1/2002 |
| WO | WO 2003/034996 A2 | 5/2003 |
| WO | WO 2004/039832 A2 | 5/2004 |
| WO | WO 2004/039853 A1 | 5/2004 |
| WO | WO 2005/027978 A2 | 3/2005 |
| WO | WO 2006/083254 A1 | 8/2006 |
| WO | WO 2007/114838 A1 | 10/2007 |
| WO | WO 2007/139941 A2 | 12/2007 |
| WO | WO 2007/140284 A2 | 12/2007 |
| WO | WO 2008/082274 A1 | 7/2008 |
| WO | WO 2009/011544 A2 | 1/2009 |
| WO | WO 2009/016043 A2 | 2/2009 |
| WO | WO 2009/042922 A2 | 4/2009 |
| WO | WO 2009/064298 A1 | 6/2009 |
| WO | WO 2009/100255 A2 | 8/2009 |
| WO | WO 2009/149379 A2 | 12/2009 |
| WO | WO 2010/054699 A1 | 5/2010 |

(56) References Cited

FOREIGN PATENT DOCUMENTS

| WO | WO 2012/050925 A1 | 4/2012 |
|---|---|---|
| WO | WO 2012/050930 A2 | 4/2012 |
| WO | WO 2013/009539 A1 | 1/2013 |
| WO | WO 2013/009545 A1 | 1/2013 |

OTHER PUBLICATIONS

Arioglu, E., et al., "Efficacy and Safety of Troglitazone in the Treatment of Lipodystrophy Syndromes," An Intern Med., 2000, 263-274, vol. 133.
Arslanian, et al., "Plasma leptin in children: Relationship to puberty, gender, body composition, insulin sensitivity, and energy expenditure". Metabolism, 1998; 47: 309-312.
Barinaga, M., ""Obese" Protein Slims Mice", Science, 1995, vol. 269, pp. 475-476.
Bays et al., "Current and Investigational Antiobesity Agents and Obesity Therapeutic Treatment Targets", Obesity Research, 2004, vol. 12, No. 8, pp. 1197-1211.
Bendele, et al., "Short Communication: Renal Tubular Vacuolation in Animals Treated with Polyethylene-Glycol-Conjugated Proteins", Toxicological Sciences, 1998, vol. 42, pp. 152-157.
Berasain, C, et al., "Pathological and Virological Findings in Patients With Persistent Hypertransaminassaemia of Unknown Etiology," Gut, 2000, 429-435, vol. 47.
Berg, A.H., et al., "The Adipocyte-Secreted Protein Acrp30 Enhances Hepatic Insulin Action," Nat. Med., 2001, 947-953, vol. 7.
Berg, J.P., "Leptin is a Potent Anti-Diabetic in Mice with Lipodystrophy and Insulin Resistance," European Journal of Endocrinology, 2000, 114-116, vol. 142.
Bolan, C, et al., "Intensive, Long-Term Plasma Exchange Therapy for Severe Hypertriglyceridemia in Acquired Generalized Lipoatrophy," J. Clin. Endocrin and Metab. 2002, 87: 380-384.
Burant, C.F., et al., "Troglitazone Action is Independent of Adipose Tissue," J. Clin. Invest, 1997, 2900-2908; vol. 100.
Vatier, C., "Therapeutic use of recombinant methionyl human leptin", Biochimie, Elsevier, 2012, 94 (10), pp. 2116-2125.
Campfield, L.A., et al., "Recombinant Mouse OB Protein: Evidence for a Peripheral Signal Linking Adiposity and Central Neural Networks," Science, 1995, 546-549, vol. 269.
Cao, H., et al., "Nuclear Lamin A/C R482q Mutation in Canadian Kindreds With Cunningan-Type Familial Partial Lipodystrophy," Hum. Mol. Genet., 2000, 109-112, vol. 9.
Chao, et al., "Adipose Tissue is Required for the Antidiabetic, but not for the Hypolipidemic, Effect of Thiazolidinediones", The Journal of Clinical Investigation, vol. 106, No. 10, Nov. 2000, pp. 1221-1228.
Chen et al., Disappearance of body fat in normal rats induced by adenovirus-mediated leptin gene therapy, PNAS, vol. 93, pp. 14795-14999, Dec. 1996.
Chicurel, "Whatever happened to leptin", Nature, 2000, vol. 404, pp. 538-540.
Clinical Trials, Leptin to treat Lipodystrophy, posted online Jun. 12, 2000, ClinicalTrials.gov identifier NCT00005905.
Conover, et al., "Physiological Effect of Polyethylene Glycol Conjugation on Stroma-Free Bovine Hemoglobin in the Conscious Dog After Partial Exchange Transfusion", Artificial Organs, 1997, vol. 21(5), pp. 369-378.
Considine, R.V., et al., "Serum Immunoreactive-Leptin Concentrations in Normal-Weight and Obese Humans," N. Engl. J. Med., 1996, 292-295, vol. 334.
Dennis et al., "Albumin Binding as a General Strategy for Improving the Pharmacokinetics of Proteins", JBC, 2002, vol. 277, No. 38, pp. 35035-35043.
Ebihara, K., et al., "Transgenic Overexpression of Leptin Rescues Insulin Resistance and Diabetes in a Mouse Model of Lipoatrophic Diabetes," Diabetes, 2001 1440-1448, vol. 50.
Supplementary European Search Report in European Application No. 02793811.7 dated Mar. 29, 2006, 3 pages.

Extended European Search Report For European Application No. EP 11833080.2 dated Jun. 5, 2014, 7 pages.
Extended European Search Report in European Application No. 10165256.8, dated Jul. 8, 2010, 6 pages.
Extended European Search Report in European Application No. EP 11833075.2, dated Jun. 13, 2014,12 pages.
Extended European Search Report in European Application No. EP 17163203.7, dated Apr. 17, 2018,13 pages.
Extended European Search Report in European Application No. EP 17174544.1, dated Mar. 5, 2018,10 pages.
Extended European Search Report in European Application No. EP 12811361.0, dated Dec. 19, 2014, 6 pages.
Farooqi, I.S., et al., "Effects of Recombinant Leptin Therapy in a Child With Congenital Leptin Deficiency," N. Engl. J. Med., 1999, vol. 341, pp. 879-884.
Feskanich, D., et al., "Reproducibility and Validity of Food Intake Measurements From a Semiquantitative Food Frequency Questionnaire," J. Am. Diet Assoc, 1993, vol. 93, 790-796.
Ford, et al., "Fusion Tails for the Recovery and Purification of Recombinant Proteins", Protein Expression and Purification, 1991, vol. 2, pp. 95-107.
Friedman, J., "The Alphabet of Weight Control", Nature, 1997, vol. 385, pp. 119-120.
Fruebis, J., et al., "Proteolytic Cleavage Product of 30-Kda Adipocyte Complement-Related Protein Increases Fatty Acid Oxidation in Muscle and Causes Weight Loss in Mice," Proc. Natl. Acad. Sci. USA, 2001, vol. 98, 2005-2010.
Garg, A., et al., "Adipose Tissue Distribution Pattern in Patients with Familiar Partial Lipodystrophy (Dunnigan Variety)," J. Clin. Endocrinol. Metab., 1999, vol. 84, pp. 170-174.
Garg, A., et al., "Lipodystrophies," Am. J. Med., 2000, vol. 108, pp. 143-152.
Garg, A., et al., "Peculiar Distribution of Adipose Tissue in Patients With Congenital Generalized Lipodystrophy," J. Clin. Endocrinol. Metab., 1992, vol. 75, 358-361.
Gavrilova et al., "Leptin and diabetes in lipoatrophic mice", Nature, Feb. 24, 2000, vol. 403, pp. 850-851.
Gavrilova, O., et al., "Surgical Implantation of Adipose Tissue Reverses Diabetes in Lipoatrophic Mice," J. Clin. Invest., 2000, vol. 105, 271-278.
Gotto, A.M., Jr., "Triglyceride as a Risk Factor for Coronary Artery Disease," Am. J. Cariol., 1998, vol. 82, 22Q-25Q.
Grasso, et al., "In VivoEffects of Leptin-Related Synthetic Peptides on BodyWeight and Food Intake in Female ob/obMice: Localization of Leptin Activity to Domains Between Amino Acid Residues 106-140". Endocrinol., 1997, 138: 1413-1418.
Hadigan, Colleen, et al., "Metformin in the Treatment of HIV Lipodystrophy Syndrome," Journal of the American Medical Association, Jul. 26, 2000; 284: 4: 472-477.
Halaas, et al., "Weight-Reducing Effects of the Plasma Protein Encoded by the obese Gene", Science, 1995, vol. 269, pp. 543-546.
Hammond, et al., "Molecular cloning and expression of leptin in gray and harbor seal blubber, bone marrow, and lung and its potential role in marine mammal respiratory physiology". Am J Physiol Regul Integr Comp Physiol (2005); 289: R545-R553. Epub Apr. 14, 2005.
Hanaki, et al., "Leptin Before and After Insulin Therapy in Children with New-Onset Type 1 Diabetes", J. Clin. Endocr. Metab. 84: 1524-1526, 1999.
Harrision, L.C., et al., "Correlation Between Insulin Receptor Binding in Isolated Fat Cells and Insulin Sensitivity in Obese Human Subjects," J. Clin. Invest., 1976, 1435-1441, vol. 58.
He et al., "Atomic structure and chemistry of human serum albumin", Nature, 1992, vol. 358, pp. 358:209.
Healthline, Nutrition and Metabolism Disorders, http://www.healthline.com/health/nutrition-metabolism-disorders, accessed on Feb. 19, 2017.
Heymsfield, S.B., et al., "Recombinant Leptin for Weight Loss in Obese and Lean Adults: A Randomized, Controlled, Dose-Escalation Trial [See Comments]," JAMA, 1999, vol. 282, pp. 1568-1575.
International Preliminary Examination Report for International Application No. PCT/US1999/024401, dated Dec. 29, 2000, 8 pages.

(56) References Cited

OTHER PUBLICATIONS

International Preliminary Examination Report dated Sep. 7, 2004 in International Application No. PCT/US2002/033875, 6 pages.
International Preliminary Report on Patentability for International Application No. PCT/US11/53774, dated Feb. 23, 2012, 8 pages.
International Preliminary Reporton Patentability in International Application No. PCT/US2011/053786, dated Feb. 1, 2013, 185 pages.
International Preliminary Reporton Patentability in International Application No. PCT/US2012/045398, dated Jan. 14, 2014, 6 pages.
International Search Report and Written Opinion for International Application No. PCT/US11/53774, dated Feb. 23, 2012, 8 pages.
International Search Report and Written Opinion in International Application No. PCT/US2011/053786, dated Apr. 25, 2012, 8 pages.
International Search Report and Written Opinion in International Application No. PCT/US2012/045398, dated Sep. 28, 2012, 9 pages.
International Search Report for International Application No. PCT/US1999/024401, dated May 2, 2000, 6 pages.
International Search Report mailed Oct. 21, 2003 in related International Application No. PCT/US2002/033875, filed Oct. 22, 2002, 3 pages.
Jaquet, D., et al., "Extremely Low Values of Serum Leptin in Children With Congenital Generalized Lipoatrophy," European Journal of Endocrinology, 1999, vol. 140, No. 1, pp. 107-109.
Johansson et al., "Structure, Specificity, and Mode of Interaction for Bacterial Albumin-binding Modules", Journal of Biological Chemistry, 2002, 277: 8114-8120.
Jonsson et al., "Engineering of a femtomolar affinity binding protein to human serum albumin", Protein Eng. Design & Selection, 2008, vol. 221, pp. 515-527.
Reue and Péterfy, "Mouse Models of Lipodystrophy". Current Atherosclerosis Reports, 2000, 2: 390-396.
Kreisberg, R.A., "Diabetic Dyslipidemia," Am. J. Cardiol., 1998, vol. 82, pp. 67U-73U.
Lambrinoudaki, I., et al., "Body Composition Assessment by Dual-Energy X-Ray Absorptionmetry: Comparison of Prone and Supine Measurements," Metabolism, 1998, vol. 47, 1379-1382.
Larcher et al., "A cutaneous gene therapy approach to human leptin deficiencies: correction of the murine ob/ob phenotype using leptin-targeted keratinocyte grafts," FASEB J., Jul. 2001, vol. 9, pp. 1529-1538.
Lawrence, R.D., "Lipodystrophy and Hepatomegaly With Diabetes, Lipaemia, and Other Metabolic Disturbances: A Case Throwing New Light on the Action of Insulin," Lancet, 1946, vol. 1., pp. 724-731 and 773-775.
Luyckx, F.H., et al., "Non-Alcoholic Steatohepatitis: Association with Obesity and Insulin Resistance, and Influence of Weight Loss," Diabetes Metab., 2000, vol. 26, 98-106.
Magre, J., et al., "Identification of the Gene Altered in Berardinelli-Seip Congenital Lipodystrophy on Chromosome 11q13," Nat. Genet, 2001, vol. 28, pp. 365-370.
Malik et al., "Polyethylene Glycol (PEG)-modified Granulocyte-Macrophage Colony-stimulating Factor (GM-CSF) with Conserved Biological Activity", Exp. Hematol, 1992, vol. 20, pp. 1028-1035 (abstract).
Manton, N.D., et al., "Non-Alcoholic Steatohepatitis in Children and Adolescents," Med. J. Aust, 2000, vol. 173, pp. 476-476.
Mantzoros, C.S., et al., "Editorial: Leptin as a Therapeutic Agent-Trials and Tribulations," J. Clin. Endocrinol. Metab., 2000, vol. 85, pp. 4000-4002.
Moitra, et al., "Life Without Fat: A Transgenic Mouse," Genes. Dev., 1998, vol. 12, pp. 3168-3181.
Montague, C.T., et al., "Congenital Leptin Deficiency is Associated with Severe Early Onset Obesity in Humans," Nature, 1997, vol. 387, pp. 903-908.
Stephens, et al., "The role of neuropeptide Y in the antiobesity action of the obese gene product", Nature, 1995, vol. 377, pp. 530-532.
Murakami, et al., "Cloning of Rat Obese cDNA and its Expression in Obese Rats", Biochemical and Biophysical Research Communications, 1995, vol. 209(3), pp. 944-952.
Ogawa, Y., et al., "Increased Glucose Metabolism and Insulin Sensitivity in Transgenic Skinny Mice Overexpressing Leptin," Diabetes, 1999, 1822-1829, vol. 48, No. 9.
Pardini, et al., "Leptin Levels, β-Cell Function, and Insulin Sensitivity in Families with Congenital and Acquired Generalized Lipoatropic Diabetes". J. Clin. Endocrinol Metab, 1998, 83: 503-508.
Partial European Search Report in European Application No. EP 17163203.7, dated Aug. 2, 2017, 12 pages.
Pelleymounter, et al., "Effects of the obese Gene Product on Body Weight Regulation in ob/ob Mice", Science, 1995, vol. 269, pp. 540-543.
Peters, A.L., "The New Diagnostic Criteria for Diabetes: The Impact of Management of Diabetes and Macrovascular Risk Factors". Am. J. Med., 1998, vol. 105, pp. 15s-19s.
Reitman et al., "A-ZIP/F1 mice lacking white fat: a model for understanding lipoatrophic diabetes, International Journal of Obesity and Related Metabolic Disorders". Journal of the International Association for the Study of Obesity, Nov. 2000, vol. 24, Suppl 4, pp. S114.
Reitman, M.L., et al., "Lipoatrophy Revisited," Trends Endoctrinol. Metab., 2000, vol. 11, pp. 410-416.
Ricci, et al., "Mutational Approach to Improve Physical Stability of Protein Therapeutics Susceptible to Aggregation", Misbehaving Proteins: Protein (Mis)Folding, Aggression, and Stability, 2006, Murphy et al. Eds, New York. Springer, pp. 331-350.
Rohner-Jeanrenaud, et al., "Obesity, Leptin, and the Brain". The New Eng. J. Med., 1996, vol. 334, pp. 324-325.
Scarpace et al., "Leptin resistance exacerbate diet-induced obesity and is associated with diminished maximal leptin signaling capacity in rats", Diabetalogia, 2005, vol. 48, pp. 1075-1083.
Seip, "Generalized lipodystrophy, congenital and acquired (lipoatrophy)", Acta Paediatrica, 1996, vol. 85, s413, pp. 2 and 19.
Sheffield, "Modification of Clearance of Therapeutic and Potentially Therapeutic Proteins", Curr. Drug Targets—Cardiovascular & Hematological Disorders, 2001, vol. 1, pp. 1-22.
Shimomura, I., et al., "Decreased IRS-2 and Increased SREBP-1c Lead to Mixed Insulin Resistance and Sensitivity in Livers of Lipodystrophic and ob/ob Mice," Mol. Cell, 2000, vol. 6, pp. 77-86.
Shimomura, I., et al., "Insulin Resistance and Diabetes Mellitus in Transgenic Mice Expressing Nuclear SREBP-1c in Adipose Tissue: Model for Congenital Generalized Lipodystrophy," Genes Dev., 1998, vol. 12, 3182-3194.
Shimomura, I., et al., "Leptin Reverses Insulin Resistance and Diabetes Mellitus in Mice with Congenital Lipodystrophy," Nature, 1999, vol. 401, pp. 73-76.
Shimomura, I., et al., "Increased Levels of Nuclear SREBP-1c Associated with Fatty Livers in Two Mouse Models of Diabetes Mellitus". The Journal of Biological Chemistry, 1999, vol. 27 4, No. 42, pp. 30028-30032.
Slifka et al., "Rapid on/off cycling of cytokine production by virus-specific CD8+ T cells," Nature, 1999, 401(6748), pp. 76-79.
Tenenbaum, "Leptin's Legacy", HHMI Bulletin, 2003, pp. 25-27.
Trygstad, O., et al., "Lipodystrophic Diabetes Treated with Fenfluramine," Int. J. Obesity, 1977, vol. 1, pp. 287-292.
Unger, R.H., et al., "Lipotoxicity in the Pathogenesis of Obesity-Dependent NIDDM, Genetic and Clinical Implications," Diabetes, 1995, vol. 44, pp. 863-870.
Unger, R.H., et al., "Regulation of Fatty Acid Homeostasis in Cells: Novel Role of Leptin," Proc. Natl. Acad. Sci. USA, 1999, vol. 96, pp. 2327-2332.
Uniprot Protein Database, Protein Accession P41159 (LEP HUMAN), accessed on Jul. 10, 2014.
UniProtKB Direct Submission Q706DO.LEP_HALGR (Jul. 10, 2007) Retrieved from the Internet Oct. 7, 2013, www.uniprot.org/uniprot/Q706DQ.txt?version=22>.
Van Der Merwe, M. T., "Free Fatty Acids and Insulin Levels: Relationship to Leptin Levels and Body Composition in Various Patient Groups from South Africa," International Journal of Obesity, 1999, 909-917, vol. 23, No. 9.

(56) References Cited

OTHER PUBLICATIONS

Written Opinion for International Application No. PCT/US1999/024401, dated Jul. 10, 2000, 7 pages.

Yamamuchi, T., et al., "The Fat-Derived Hormone Adiponectin Reverses Insulin Resistance Associated with Both Lipoatrophy and Obesity," Nat. Med., 2001, vol. 7, pp. 941-946.

Young, et al., "Characterization of the Receptor Binding Determinants of Granulocyte Colony Stimulating Factor", Protein Science, 1997, vol. 6, pp. 1228-1236.

Zhang, Y., et al., "Positional Cloning of the Mouse Obese Gene and Its Human Homologue," Nature, 1994, vol. 372, pp. 425-432.

Zhang, Y., et al., "Positional Cloning of the Mouse Obese Gene and Its Human Homologue," Correction at Nature, 1995, vol. 374, pp. 479.

\* cited by examiner

Detection of SEQ ID NO:33 (Continuous subcutaneous infusion)
and SEQ ID NO: 54 (once-weekly injection)
in DIO Rats

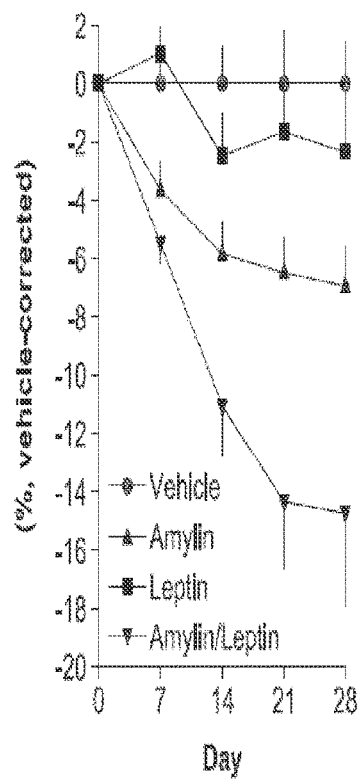
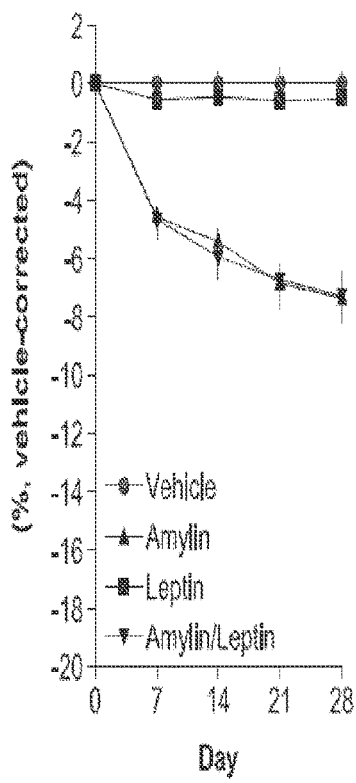
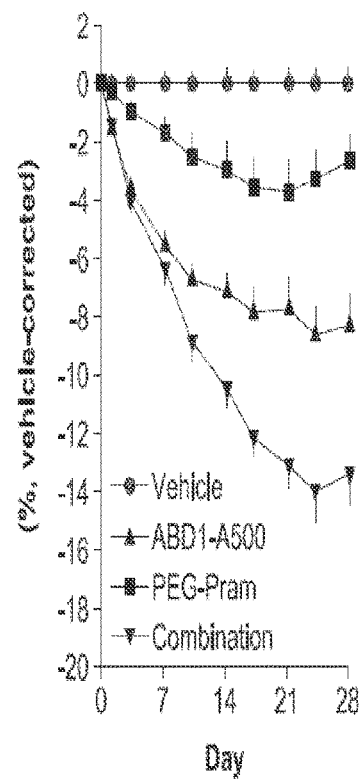
*FIG. 21A*   *FIG. 21B*   *FIG. 21C*

ENGINEERED POLYPEPTIDES HAVING ENHANCED DURATION OF ACTION

CROSS-REFERENCES TO RELATED APPLICATIONS

This application is a continuation of U.S. application Ser. No. 14/800,537, filed Jul. 15, 2015, which is a continuation of U.S. application Ser. No. 13/852,671, filed Mar. 28, 2013, which is a continuation of International Patent Application No. PCT/US2011/053786, filed Sep. 28, 2011, which claims priority to U.S. Application No. 61/387,402 filed Sep. 28, 2010, and U.S. Application No. 61/422,091 filed Dec. 10, 2010, the contents of each of which are herein incorporated by reference in their entirety.

SEQUENCE LISTING

The instant application contains a Sequence Listing which has been submitted in ASCII format via EFS-Web and is hereby incorporated by reference in its entirety. Said ASCII copy, created on Mar. 25, 2013, is named 92494-867824_ST25.TXT and is 275,743 bytes in size.

BACKGROUND OF THE INVENTION

The present application relates to compounds having good duration of action, high potency and/or convenient dosing regimens including oral administration, and method of use thereof. There are provided herein engineered polypeptides which incorporate an albumin binding domain in combination with a biologically active peptide. Without wishing to be bound by any theory, it is believed that because the engineered polypeptides described herein can bind albumin, the compounds can be sequestered (e.g., bound to albumin) while in the circulation leading to increased duration of action, due for example to decreased renal clearance and/or degradation. Diseases amendable to such treatment include lipodystrophy, dyslipidemia, hyperlipidemia, overweight, obesity, hypothalamic amenorrhea, Alzheimer's disease, leptin deficiency, fatty liver disease, diabetes (including type I and type II), nonalcoholic steatohepatitis (NASH), nonalcoholic fatty liver disease (NAFLD), metabolic syndrome X and Huntington's Disease, or combinations thereof.

There remains a need to develop polypeptides useful in the above described metabolic diseases, conditions and disorders. Accordingly, it is an object of the present invention to provide engineered polypeptides with extended half-lives useful to treat the above conditions and methods for producing and using them.

Each patent, patent application, and publication cited herein is hereby incorporated herein by reference in its entirety and for all purposes.

BRIEF SUMMARY OF THE INVENTION

There are provided engineered polypeptide compounds having binding affinity for albumin and an additional therapeutic utility. The compounds are engineered polypeptides which include an albumin binding domain (ABD) polypeptide capable of binding albumin and a hormone domain (HD) polypeptide, which HD polypeptides can be biologically active and can elicit a beneficial biological response, in covalent linkage with the ABD. Any of the ABD or HD polypeptides described herein can be optionally covalently bonded in the engineered polypeptide through a linker L, for example L1 as described herein. Without wishing to be bound by any theory, it is believed that because the engineered polypeptides described herein can bind albumin, the compounds can be sequestered in a subject leading to increased duration of action in the subject.

In a first aspect, there is provided an engineered polypeptide as described herein. The engineered polypeptide includes an albumin binding domain polypeptide (ABD) and a hormone domain (HD1). The hormone domain includes a polypeptide which is a leptin, an analog of a leptin or an active fragment thereof.

In another aspect, there is provided a method for treating a disease or disorder in a subject in need of treatment. The method includes administering an engineered polypeptide as described herein to the subject.

In yet another aspect, there is provided a pharmaceutical composition which includes an engineered polypeptide compound described herein in combination with a pharmaceutically acceptable excipient.

In yet another aspect are polynucleotides encoding the engineered polypeptide and their intermediates, expression vectors bearing such polynucleotides, host cells expressing such polynucleotides, and means for their expression, synthesis, post-translational modification and isolation.

BRIEF DESCRIPTION OF THE DRAWINGS

FIG. 1A: food intake. FIG. 1B: change in body weight (% vehicle-corrected). Legend: Vehicle (box); Cmpd 1 at 2.6 mg/kg (triangle tip up); Cmpd 2 at 2.7 mg/kg (triangle tip down); Cmpd 4 at 2.7 mg/kg (diamond); Cmpd C2 at 10 mg/kg (circle).

FIG. 2A: food intake. FIG. 2B: change in body weight (% vehicle-corrected). Legend: Vehicle (box); Cmpd 2 at 0.3 mg/kg (triangle tip up); Cmpd 2 at 1.0 mg/kg (triangle tip down); Cmpd 2 at 3.0 mg/kg (diamond).

FIG. 3A: food intake. FIG. 3B: change in body weight (% vehicle-corrected). Legend: Vehicle (box); Cmpd C2 at 1.1 mg/kg (circle); Cmpd C2 at 3.3 mg/kg (box); Cmpd C2 at 11.1 mg/kg (triangle tip up).

FIG. 4A: food intake. FIG. 4B: change in body weight (% vehicle-corrected). Legend: Vehicle (box); Cmpd C6 at 2.2 mg/kg (triangle tip down).

FIG. 9A: food intake. FIG. 4B: change in body weight (% vehicle-corrected).

FIG. 14A: plasma drug concentration (y-axis) as a function of time in hours (x-axis); FIG. 14B: plasma drug concentration (y-axis) as a function of time in days (x-axis).

FIG. 21A depicts an effect on body weight of administration of leptin and amylin, either alone or in combination over four weeks, in moderately obese rats. FIG. 21B depicts the lack of an effect on body weight of administration of leptin and amylin, either alone or in combination over four weeks, in severely obese rats. FIG. 21C depicts an effect on body weight of administration of Compound 2 (120 nmol/kg) and PEG-rat amylin (Des-Lys1-[Lys26(mPEG40K)]-Rat Amylin (SEQ ID NO: 148) (125 nmol/kg), either alone or in combination over four weeks, in severely obese rats.

FIGS. 22A-22B depict an effect on body weight of administration of: (FIG. 22A) Compound 15 (120 nmol/kg) or (FIG. 22B) Compound 2 (120 nmol/kg) and amylin (50 µg/kg/day), either alone or in combination over four weeks, in severely obese rats.

FIG. 23A: blood glucose (y-axis) as a function of time (x-axis); FIG. 23B: histogram of change in blood glucose from baseline at week 2 for vehicle, Cmpd 15, Cmpd2, and insulin.

FIG. 24A: HbA1c (y-axis) as a function of time (x-axis); FIG. 24B: histogram of change in HbA1c from baseline at week 2 for vehicle, Cmpd 15, Cmpd 2, and insulin.

FIG. 25A: body weight (y-axis) as a function of time (x-axis) for vehicle, Cmpd 15, Cmpd 2, insulin, and normal; FIG. 25B: cumulative food intake (y-axis) as a function of time (x-axis) for vehicle, Cmpd 15, Cmpd 2, insulin, and normal.

FIG. 26A: blood glucose (y-axis) as a function of time (x-axis); FIG. 26B: histogram of blood glucose change from baseline at week 2 for vehicle/placebo, vehicle/insulin, Cmpd 15/placebo, and Cmpd15/insulin.

FIG. 27A: HbA1c (y-axis) as a function of time (x-axis); FIG. 27B: HbA1c percent change from baseline at week 2 for vehicle/placebo, vehicle/insulin, Cmpd 15/placebo, and Cmpd 15/insulin.

FIG. 28A: cumulative food intake (y-axis) as a function of time (x-axis); FIG. 28B: percent body weight change from baseline (y-axis) as a function of time (x-axis).

DETAILED DESCRIPTION OF THE INVENTION

I. Definitions

Figure 1A:
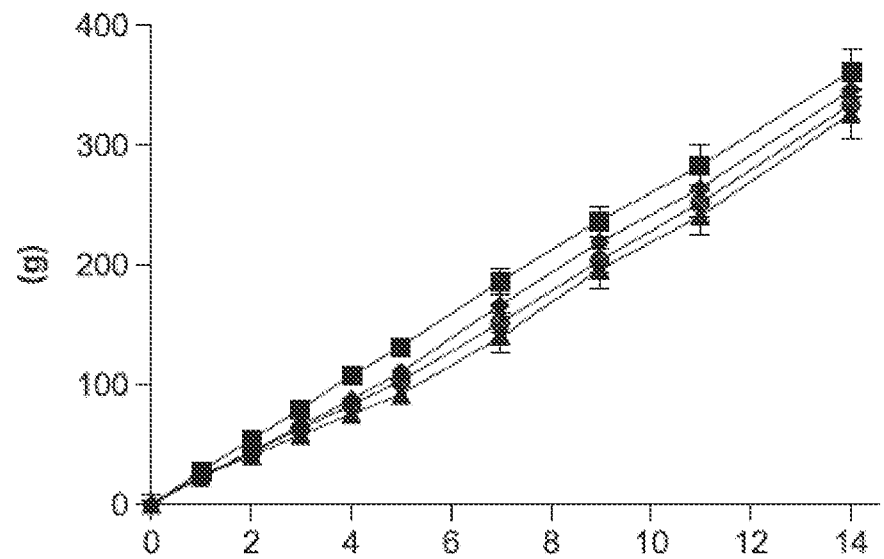
FIGS. 1A-1B depict the effects of a single administration of engineered polypeptides as described herein on food intake and body weight upon administration to lean rats as described in Example 3.

"Obesity" and "overweight" refer to mammals having a weight greater than normally expected, and may be determined by, e.g., physical appearance, body mass index (BMI)

as known in the art, waist-to-hip circumference ratios, skinfold thickness, waist circumference, and the like. The Centers for Disease Control and Prevention (CDC) define overweight as an adult human having a BMI of 25 to 29.9; and define obese as an adult human having a BMI of 30 or higher. Additional metrics for the determination of obesity exist. For example, the CDC states that a person with a waist-to-hip ratio greater than 1.0 is overweight.

"Lean body mass" refers to the fat-free mass of the body, i.e., total body weight minus body fat weight is lean body mass. Lean body mass can be measured by methods such as hydrostatic weighing, computerized chambers, dual-energy X-ray absorptiometry, skin calipers, magnetic resonance imaging (MRI) and bioelectric impedance analysis (BIA) as known in the art.

"Mammal" refers to warm-blooded animals that generally have fur or hair, that give live birth to their progeny, and that feed their progeny with milk. Mammals include humans; companion animals (e.g., dogs, cats); farm animals (e.g., cows, horses, sheep, pigs, goats); wild animals; and the like. In one embodiment, the mammal is a female. In one embodiment, the mammal is a female human. In one embodiment, the mammal is a cat or dog. In one embodiment, the mammal is a diabetic mammal, e.g., a human having type 2 diabetes. In one embodiment, the mammal is an obese diabetic mammal, e.g., an obese mammal having type 2 diabetes. The term "subject" in the context of methods described herein refers to a mammal.

"Fragment" in the context of polypeptides refers herein in the customary chemical sense to a portion of a polypeptide. For example, a fragment can result from N-terminal deletion or C-terminal deletion of one or more residues of a parent polypeptide, and/or a fragment can result from internal deletion of one or more residues of a parent polypeptide. "Fragment" in the context of an antibody refers to a portion of an antibody which can be linked to a biologically active molecule to modulate solubility, distribution within a subject, and the like. For example, leptin A200 described herein is a conjugate of an Fc antibody fragment with a leptin, as known in the art. See e.g. WO 98/28427 and US2007/002084. The term "parent" in the context of polypeptides refers, in the customary sense, to a polypeptide which serves as a reference structure prior to modification, e.g., insertion, deletion and/or substitution. The term "conjugate" in the context of engineered polypeptides described herein refers to covalent linkage between component polypeptides, e.g., ABD, HD1 and the like. The term "fusion" in the context of engineered polypeptides described herein refers to covalent linkage between component polypeptides, e.g., ABD, HD1 and the like, via either or both terminal amino or carboxy functional group of the peptide backbone. Engineered polypeptides can be synthetically or recombinantly made. Typically, fusions are made using recombinant biotechnology, however, can also be made by chemical synthesis and conjugation methods known in the art.

"Analog" as used herein in the context of polypeptides refers to a compound that has insertions, deletions and/or substitutions of amino acids relative to a parent compound. An analog may have superior stability, solubility, efficacy, half-life, and the like. In some embodiments, an analog is a compound having at least 50%, for example 50%, 55%, 60%, 65%, 70%, 75%, 80%, 85%, 90%, 95%, 98%, or even higher, sequence identity to the parent compound.

"Identity," "sequence identity" and the like in the context of comparing two or more nucleic acids or polypeptide sequences, refer to two or more sequences or subsequences that are the same or have a specified percentage of amino acid residues or nucleotides that are the same (i.e., about 50% identity, preferably 50%, 55%, 60%, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a sequence comparison algorithms as known in the art, for example BLAST or BLAST 2.0. This definition includes sequences that have deletions and/or additions, as well as those that have substitutions, as well as naturally occurring, e.g., polymorphic or allelic variants, and man-made variants. In preferred algorithms, account is made for gaps and the like, as known in the art. For sequence comparison, typically one sequence acts as a reference sequence, to which test sequences are compared. When using a sequence comparison algorithm, test and reference sequences are entered into a computer, subsequence coordinates are designated if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters. Optimal alignment of sequences for comparison can be conducted, e.g., by the local homology algorithm of Smith & Waterman, 1981, *Adv. Appl. Math.* 2:482, by the homology alignment algorithm of Needleman & Wunsch, 1970, *J. Mol. Biol.* 48:443, by the search for similarity method of Pearson & Lipman, 1988, *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. See e.g., *Current Protocols in Molecular Biology* (Ausubel et al., eds. 1995 supplement)). Preferred examples of algorithms that are suitable for determining percent sequence identity and sequence similarity include the BLAST and BLAST 2.0 algorithms, which are described in Altschul et al., 1977, *Nuci. Acids Res.* 25:3389-3402 and Altschul et al., 1990, *J. Mol. Biol.* 215:403-410. BLAST and BLAST 2.0 are used, as known in the art, to determine percent sequence identity for the nucleic acids and proteins of the invention. Software for performing BLAST analyses is publicly available through the web site of the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., Id.). These initial neighborhood word hits act as seeds for initiating searches to find longer HSPs containing them. The word hits are extended in both directions along each sequence for as far as the cumulative alignment score can be increased. Cumulative scores are calculated using, e.g., for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, 1989, Proc. Natl. Acad. Sci. USA 89:10915) alignments (B) of 50, expectation (E) of 10, M=5, N=−4, and a comparison of both strands.

The term "about" in the context of a numeric value refers to +/−10% of the numeric value, unless expressly indicated otherwise.

The terms "peptide" and "polypeptide" in the context of components of the engineered polypeptides described herein are synonymous.

II. Compounds

In a first aspect, engineered polypeptide compounds are provided which include an albumin binding domain (ABD) polypeptide and at least one polypeptide hormone domain (HD1). The terms "albumin binding domain," "ABD" and the like refer to polypeptides capable of binding albumin as described herein. The terms "hormone domain," "hormone domain polypeptide" and the like refer to a polypeptide capable of eliciting a biological response in a subject. Exemplary hormone domains include, but are not limited to, a leptin, an analog of a leptin or an active fragment thereof, but could be a leptin derivative such as a PEGylated derivative.

It was surprisingly found that a leptin, a leptin analog, a active leptin fragment, or a leptin derivative thereof can be fused to an very-high-affinity albumin binding domain (ABD) derived from the albumin-binding domains of bacterial proteins as described herein, while retaining sufficient leptin biological activity and having an extended duration of action, for example of at least 3 days and even 5 days in a rodent, which translates to at least a one week duration or longer in a human subject. This was surprising in part because such ABD peptides have not been extensively demonstrated to be a robust platform as a therapeutic protein carrier, they are relatively hydrophobic which could interact adversely with an attached therapeutic peptide, and were not able to act as a carrier for at least one family of peptide hormones. For instance, rat amylin compounds (e.g., SEQ ID NO:108), when conjugated or fused to the ABDs described herein, did not display any significant or long-acting in vivo activity in the same rodent models in which various leptin engineered polypeptide constructs of the invention were found to be active and with long duration of action.

Biologically Active Components.

Biologically active compound components contemplated for use in the compounds and methods described herein include leptins. The terms "biologically active compound" and the like refer in the customary sense to compounds, e.g., polypeptides and the like, which can elicit a biological response.

Leptins.

"Leptins" and "a leptin" means: leptins, leptin active fragments, leptin analogs, and leptin derivatives; and a leptin, a leptin active fragment, a leptin analog, and a leptin derivative; respectfully. Accordingly, unless otherwise noted, reference to "leptins" is meant to leptins, leptin active fragments, leptin analogs, and leptin derivatives, as disclosed herein. Similarly, unless otherwise noted, reference to "a leptin" is meant to encompass a leptin, a leptin active fragment, a leptin analog, and a leptin derivative, as disclosed herein. Exemplary such leptins which may be employed in the design, preparation, and use of the engineered polypeptides disclosed herein include those which elicit one or more biological responses known in the art to be elicited when leptins are administered to subjects (see, e.g., published U.S. Patent application Nos. US 2007/0020284 and US 2008/0207512, U.S. Pat. Nos. 6,309,853, and 7,183,254, and PCT Published Application Nos. WO 96/005309, WO 98/28427, and WO 2009/064298), such as: reduction of food intake, reduction of body weight, reduction of body weight gain, induction of satiety, reduction of caloric availability, reduction of caloric efficiency, reduction of metabolic plateau, increase in insulin sensitivity, reduction of hyperlipidemia, correction of dyslipidemia, reduction of hypertriglyceridemia, amelioration of obesity, amelioration of overweight, amelioration of diabetes mellitus (including type I diabetes, type II diabetes, and gestational diabetes), amelioration of insulin resistance, amelioration of lipodystrophy conditions associated therewith, as well as other biological responses known in the art to be elicited upon administration of a leptin (see, e.g., published U.S. Patent Application Nos. US 2007/0020284 and US 2008/0207512, U.S. Pat. Nos. 6,309,853, and 7,183,254, and PCT Published Application Nos. WO 96/005309, WO 98/28427, and WO 2009/064298.

Exemplary leptins suitable for the design, preparation, and use of the engineered polypeptides described herein include, but are not limited to, the compounds described in U.S. Pat. Nos. 5,594,101, 5,851,995, 5,691,309, 5,580,954, 5,554,727, 5,552,523, 5,559,208, 5,756,461, 6,309,853, published U.S. Patent application No. US 2007/0020284, and PCT Published Application Nos. WO 96/23517, WO 96/005309, WO 98/28427, WO 2004/039832, WO 98/55139, WO 98/12224, and WO 97/02004, each of which is incorporated herein in its entirety and for all purposes. Methods to assay for leptin activities and biological responses in vitro and in vivo, including satiety, food intake inhibition activity and weight loss activity, are known in the art and are described herein and also in the above references and other references recited herein.

Any leptin, leptin analog, leptin active fragment, or leptin derivative known in the art may be employed in order to prepare and use engineered polypeptides as disclosed herein throughout. Representative leptins, leptin analogs, leptin active fragments, and leptin derivatives contemplated for use in the engineered polypeptides and methods described herein also include the following:

Mature Murine Leptins:

```
                                               (SEQ ID NO: 1)
VPIQKVQDDTKTLIKTIVTRINDISHT-Xaa-SVSSKQKVTGLDFIPGLH

PILTLSKMDQTLAVYQQILTSMPSRNVIQISNDLENLRDLLHVLAFSKSC

HLPQASGLETLESLGGVLEASGYSTEVVALSRLQGSLQDMLQQLDLSPG

C,
wherein Xaa at position 28 is Q or absent.
```

Mature Murine Leptin Form 1:

```
                                              (SEQ ID NO: 143)
VPIQKVQDDTKTLIKTIVTRINDISHTQSVSAKQRVTGLDFIPGLHPILS

LSKMDQTLAVYQQVLTSLPSQNVLQIANDLENLRDLLHLLAFSKSCSLPQ

TSGLQKPESLDGVLEASLYSTEVVALSRLQGSLQDILQQLDVSPEC.
```

Mature Murine Leptin Form 2:

(SEQ ID NO: 144)
VPIQKVQDDTKTLIKTIVTRINDISHTSVSAKQRVTGLDFIPGLHPILSL

SKMDQTLAVYQQVLTSLPSQNVLQIANDLENLRDLLHLLAFSKSCSLPQT

SGLQKPESLDGVLEASLYSTEVVALSRLQGSLQDILQQLDVSPEC.

Mature Murine Leptins with N-Terminal Methionine:

(SEQ ID NO: 2)
MVPIQKVQDDTKTLIKTIVTRINDISHT-Xaa-SVSSKQKVTGLDFIPGL

HPILTLSKMDQTLAVYQQILTSMPSRNVIQISNDLENLRDLLHVLAFSKS

CHLPQASGLETLESLGGVLEASGYSTEVVALSRLQGSLQDMLQQLDLSPG

C,
wherein Xaa at position 29 is Q or absent.

Mature Murine Leptin Form 1 with N-Terminal Methionine:

(SEQ ID NO: 145)
MVPIQKVQDDTKTLIKTIVTRINDISHTQSVSAKQRVTGLDFIPGLHPIL

SLSKMDQTLAVYQQVLTSLPSQNVLQIANDLENLRDLLHLLAFSKSCSLP

QTSGLQKPESLDGVLEASLYSTEVVALSRLQGSLQDILQQLDVSPEC.

Mature Murine Leptin Form 2 with N-Terminal Methionine:

(SEQ ID NO: 146)
MVPIQKVQDDTKTLIKTIVTRINDISHTSVSAKQRVTGLDFIPGLHPILS

LSKMDQTLAVYQQVLTSLPSQNVLQIANDLENLRDLLHLLAFSKSCSLPQ

TSGLQKPESLDGVLEASLYSTEVVALSRLQGSLQDILQQLDVSPEC.

Mature Porcine Leptin:

(SEQ ID NO: 3)
VPIWRVQDDTKTLIKTIVTRISDISHMQSVSSKQRVTGLDFIPGLHPVLS

LSKMDQTLAIYQQILTSLPSRNVIQISNDLENLRDLLHLLASSKSCPLPQ

ARALETLESLGGVLEASLYSTEVVALSRLQGALQDMLRQLDLSPGC.

Mature Porcine Leptin with N-Terminal Methionine:

(SEQ ID NO: 4)
MVPIWRVQDDTKTLIKTIVTRISDISHMQSVSSKQRVTGLDFIPGLHPVL

SLSKMDQTLAIYQQILTSLPSRNVIQISNDLENLRDLLHLLASSKSCPLP

QARALETLESLGGVLEASLYSTEVVALSRLQGALQDMLRQLDLSPGC.

Mature Bovine Leptins:

(SEQ ID NO: 5)
VPICKVQDDTKTLIKTIVTRINDISHT-Xaa-SVSSKQRVTGLDFIPGLH

PLLSLSKMDQTLAIYQQILTSLPSRNVVQISNDLENLRDLLHLLAASKSC

PLPQVRALESLESLGVVLEASLYSTEVVALSRLQGSLQDMLRQLDLSPG

C,
wherein Xaa at position 28 is Q or absent.

Mature Bovine Leptins with N-Terminal Methionine:

(SEQ ID NO: 6)
MVPICKVQDDTKTLIKTIVTRINDISHT-Xaa-SVSSKQRVTGLDFIPGL

HPLLSLSKMDQTLAIYQQILTSLPSRNVVQISNDLENLRDLLHLLAASKS

CPLPQVRALESLESLGVVLEASLYSTEVVALSRLQGSLQDMLRQLDLSPG

C,
wherein Xaa at position 29 is Q or absent.

Unprocessed Full-Length Human Leptin (i.e., Includes 21-Residue N-Terminal Signal Sequence):

(SEQ ID NO: 7)
MHWGTLCGFLWLWPYLFYVQAVPIQKVQDDTKTLIKTIVTRINDISHTQS

VSSKQKVTGLDFIPGLHPILTLSKMDQTLAVYQQILTSMPSRNVIQISND

LENLRDLLHVLAFSKSCHLPWASGLETLDSLGGVLEASGY STEVVALSR

LQGSLQDMLWQLDLSPGC

Mature Human Leptins (with N-Terminal 21 Amino Acid Signal Sequence Removed):

(SEQ ID NO: 8)
VPIQKVQDDTKTLIKTIVTRINDISH-Xaa-Xaa-SVSSKQKVTGLDFIP

GLHPILTLSKMDQTLAVYQQILTSMPSRNVIQISNDLENLRDLLHVLAFS

KSCHLPWASGLETLDSLGGVLEASGYSTEVVALSRLQGSLQDMLWQLDLS

PGC,
wherein: Xaa at position 27 is T or A;
and

Xaa at position 28 is Q or absent.

Mature Human Leptins with N-Terminal Methionine:

(SEQ ID NO: 9)
MVPIQKVQDDTKTLIKTIVTRINDISH-Xaa-Xaa-SVSSKQKVTGLDFI

PGLHPILTLSKMDQTLAVYQQILTSMPSRNVIQISNDLENLRDLLHVLAF

SKSCHLPWASGLETLDSLGGVLEASGYSTEVVALSRLQGSLQDMLWQLDL

SPGC,
wherein: Xaa at position 28 is T or A;
and

Xaa at position 29 is Q or absent.

Mature Rhesus Leptin:

(SEQ ID NO: 10)
VPIQKVQSDTKTLIKTIVTRINDISHTQSVSSKQRVTGLDFIPGLHPVLT

LSQMDQTLAIYQQILINLPSRNVIQISNDLENLRDLLHLLAFSKSCHLPL

ASGLETLESLGDVLEASLYSTEVVALSRLQGSLQDMLWQLDLSPGC.

Mature Rhesus Leptin with N-Terminal Methionine:

(SEQ ID NO: 11)
MVPIQKVQSDTKTLIKTIVTRINDISHTQSVSSKQRVTGLDFIPGLHPVL

TLSQMDQTLAIYQQILINLPSRNVIQISNDLENLRDLLHLLAFSKSCHLP

LASGLETLESLGDVLEASLYSTEVVALSRLQGSLQDMLWQLDLSPGC.

Mature Rat Leptin:

(SEQ ID NO: 12)
VPIHKVQDDTKTLIKTIVTRINDISHTQSVSARQRVTGLDFIPGLHPILS

LSKMDQTLAVYQQILTSLPSQNVLQIAHDLENLRDLLHLLAFSKSCSLPQ

TRGLQKPESLDGVLEASLYSTEVVALSRLQGSLQDILQQLDLSPEC.

Mature Rat Leptin with N-Terminal Methionine:

(SEQ ID NO: 13)
MVPIHKVQDDTKTLIKTIVTRINDISHTQSVSARQRVTGLDFIPGLHPIL

SLSKMDQTLAVYQQILTSLPSQNVLQIAHDLENLRDLLHLLAFSKSCSLP

QTRGLQKPESLDGVLEASLYSTEVVALSRLQGSLQDILQQLDLSPEC.

Mature Platypus Leptin: The Mature Platypus Leptin Sequence Follows:

(SEQ ID NO: 14)
ISIEKIQADTKTLTKTIITRIIQLSTQNGVSTDQRVSGLDFIPGNQQFQN

LADMDQTLAVYQQILSSLPMPDRTQISNDLENLRSLFALLATLKNCPFTR

SDGLDTMEIWGGIVEESLYSTEVVTLDRLRKSLKNIEKQLDHIQG.

Unprocessed Full-Length Platypus Leptin (i.e., Includes 21-Residue N-Terminal Signal Sequence):

A full length sequence of platypus leptin, including a 21-residue N-terminal signal sequence follows:

(SEQ ID NO: 15)
MRCILLYGFLCVWQHLYYSHPISIEKIQADTKTLTKTIITRIIQLSTQNG

VSTDQRVSGLDFIPGNQQFQNLADMDQTLAVYQQILSSLPMPDRTQISND

LENLRSLFALLATLKNCPFTRSDGLDTMEIWGGIVEESLYSTEVVTLDRL

RKSLKNIEKQLDHIQG.

Mature Human Leptin form 1:

(SEQ ID NO: 16)
VPIQKVQDDTKTLIKTIVTRINDISHTQSVSSKQKVTGLDFIPGLHPILT

LSKMDQTLAVYQQILTSMPSRNVIQISNDLENLRDLLHVLAFSKSCHLPW

ASGLETLDSLGGVLEASGYSTEVVALSRLQGSLQDMLWQLDLSPGC.

Mature Human Leptin form 2:

(SEQ ID NO: 17)
VPIQKVQDDTKTLIKTIVTRINDISHAQSVSSKQKVTGLDFIPGLHPILT

LSKMDQTLAVYQQILTSMPSRNVIQISNDLENLRDLLHVLAFSKSCHLPW

ASGLETLDSLGGVLEASGYSTEVVALSRLQGSLQDMLWQLDLSPGC.

Mature Human Leptin form 3:

(SEQ ID NO: 18)
VPIQKVQDDTKTLIKTIVTRINDISHTSVSSKQKVTGLDFIPGLHPILTL

SKMDQTLAVYQQILTSMPSRNVIQISNDLENLRDLLHVLAFSKSCHLPWA

SGLETLDSLGGVLEASGYSTEVVALSRLQGSLQDMLWQLDLSPGC.

Mature Human Leptin form 4:

(SEQ ID NO: 19)
VPIQKVQDDTKTLIKTIVTRINDISHASVSSKQKVTGLDFIPGLHPILTL

SKMDQTLAVYQQILTSMPSRNVIQISNDLENLRDLLHVLAFSKSCHLPWA

SGLETLDSLGGVLEASGYSTEVVALSRLQGSLQDMLWQLDLSPGC.

Mature Human Leptin Form 1 with N-Terminal Methionine (Also Known as Metreleptin, or A100):

(SEQ ID NO: 20)
MVPIQKVQDDTKTLIKTIVTRINDISHTQSVSSKQKVTGLDFIPGLHPIL

TLSKMDQTLAVYQQILTSMPSRNVIQISNDLENLRDLLHVLAFSKSCHLP

WASGLETLDSLGGVLEASGYSTEVVALSRLQGSLQDMLWQLDLSPGC.

Mature Human Leptin Form 2 with N-Terminal Methionine:

(SEQ ID NO: 21)
MVPIQKVQDDTKTLIKTIVTRINDISHAQSVSSKQKVTGLDFIPGLHPIL

TLSKMDQTLAVYQQILTSMPSRNVIQISNDLENLRDLLHVLAFSKSCHLP

WASGLETLDSLGGVLEASGYSTEVVALSRLQGSLQDMLWQLDLSPGC.

Mature Human Leptin Form 3 with N-Terminal Methionine:

(SEQ ID NO: 22)
MVPIQKVQDDTKTLIKTIVTRINDISHTSVSSKQKVTGLDFIPGLHPILT

LSKMDQTLAVYQQILTSMPSRNVIQISNDLENLRDLLHVLAFSKSCHLPW

ASGLETLDSLGGVLEASGYSTEVVALSRLQGSLQDMLWQLDLSPGC.

Mature Human Leptin Form 4 with N-Terminal Methionine:

(SEQ ID NO: 23)
MVPIQKVQDDTKTLIKTIVTRINDISHASVSSKQKVTGLDFIPGLHPILT

LSKMDQTLAVYQQILTSMPSRNVIQISNDLENLRDLLHVLAFSKSCHLPW

ASGLETLDSLGGVLEASGYSTEVVALSRLQGSLQDMLWQLDLSPGC.

Seal Leptin:

(SEQ ID NO: 24)
PIQRVQDDTKTLIKTIITRINDISPPQGVCSRPRVAGLDFIPRVQSVRTL

SGMDQILATYQQILTSLQSRSVVQIANDLANLRALLRLLASAKSCPVPRA

RGSDTIKGLGNVLRASVHSTEVVALSRLKAALQDMLRQLDRNPGC.

Seal Leptin with Amino Acids 71-92 Replaced with Amino Acids 73-94 (Helix 3) of Metreleptin, Respectively:

(SEQ ID NO: 25)
PIQRVQDDTKTLIKTIITRINDISPPQGVCSRPRVAGLDFIPRVQSVRTL

SGMDQILATYQQILTSLQSRNVIQISNDLENLRDLLHVLAFSKSCPVPRA

RGSDTIKGLGNVLRASVHSTEVVALSRLKAALQDMLRQLDRNPGC.

Seal Leptin with Amino Acids 30 and 71-92 Replaced with Amino Acids 32 and 73-94 (Helix 3) of Metreleptin, Respectively:

```
                                            (SEQ ID NO: 26)
PIQRVQDDTKTLIKTIITRINDISPPQGVSSRPRVAGLDFIPRVQSVRTL

SGMDQILATYQQILTSLQSRNVIQISNDLENLRDLLHVLAFSKSCPVPRA

RGSDTIKGLGNVLRASVHSTEVVALSRLKAALQDMLRQLDRNPGC.
```

Seal Leptin with N-Terminal Methionine:

```
                                            (SEQ ID NO: 27)
MPIQRVQDDTKTLIKTIITRINDISPPQGVCSRPRVAGLDFIPRVQSVRT

LSGMDQILATYQQILTSLQSRSVVQIANDLANLRALLRLLASAKSCPVPR

ARGSDTIKGLGNVLRASVHSTEVVALSRLKAALQDMLRQLDRNPGC.
```

Seal Leptin with N-Terminal Methionine, and with Amino Acids 71-92 Replaced with Amino Acids 73-94 (Helix 3) of Metreleptin, Respectively:

```
                                            (SEQ ID NO: 28)
MPIQRVQDDTKTLIKTIITRINDISPPQGVCSRPRVAGLDFIPRVQSVRT

LSGMDQILATYQQILTSLQSRNVIQISNDLENLRDLLHVLAFSKSCPVPR

ARGSDTIKGLGNVLRASVHSTEVVALSRLKAALQDMLRQLDRNPGC.
```

Seal Leptin with N-Terminal Methionine, and with Amino Acids 30 and 71-92 Replaced with Amino Acids 32 and 73-94 (Helix 3) of Metreleptin, Respectively:

```
                                            (SEQ ID NO: 29)
MPIQRVQDDTKTLIKTIITRINDISPPQGVSSRPRVAGLDFIPRVQSVRT

LSGMDQILATYQQILTSLQSRNVIQISNDLENLRDLLHVLAFSKSCPVPR

ARGSDTIKGLGNVLRASVHSTEVVALSRLKAALQDMLRQLDRNPGC.
```

Leptin A200:

Leptin A200 is an Fc antibody fragment condensation product with leptin, as known in the art. See e.g., Lo et al., 2005, *Protein Eng. Design & Selection,* 18:1-10. The amino acid sequence of A200 is as follows:

```
                                            (SEQ ID NO: 30)
MDKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKEY

KCKVSNKALPAPIEKTISKAKGQPREPQVYTLPPSRDELTKNQVSLTCLV

KGFYPSDIAVEWESNGQPENNYKTTPPVLDSDGSFFLYSKLTVDKSRWQQ

GNVFSCSVMHEALHNHYTQKSLSLSPGKVPIQKVQDDTKTLIKTIVTRIN

DISHTQSVSSKQKVTGLDFIPGLHPILTLSKMDQTLAVYQQILTSMPSRN

VIQISNDLENLRDLLHVLAFSKSCHLPWASGLETLDSLGGVLEASGYSTE

VVALSRLQGSLQDMLWQLDLSPGC
```

Leptin A300:

Leptin A300 is metreleptin with substitutions W101Q and W139Q (N-terminal ¹Met counted as residue 1):

```
                                            (SEQ ID NO: 31)
MVPIQKVQDDTKTLIKTIVTRINDISHTQSVSSKQKVTGLDFIPGLHPIL

TLSKMDQTLAVYQQILTSMPSRNVIQISNDLENLRDLLHVLAFSKSCHLP

QASGLETLDSLGGVLEASGYSTEVVALSRLQGSLQDMLQQLDLSPGC.
```

Leptin A400:

Leptin A400 is metreleptin with the serine residue at position 78 replaced with a cysteine residue, as set forth following: MVPIQKVQDDTKTLIKTIVTRINDISHTQSV-SSKQKVTGLDFIPGLHPILTLSKMDQTLAVYQQILTS-MPSRNVIQICNDLENLRDLLHVLAFSKSCHLPWAS-GLETLDSLGGVLEASGYSTEVVALSRLQGSLQDML-WQLDLSPGC (SEQ ID NO: 32); to which a 20 kilodalton (kDa) PEG moiety has been attached via the cysteine residue at position 78.

Leptin A500:

Research by a number of investigators including the inventors has focused on the effects on aggregation of residue substitution in leptin. See e.g., Ricci et al., 2006. "Mutational approach to improve physical stability of protein therapeutics susceptible to aggregation: Role of altered conformation in irreversible precipitation," Book Chapter. In: MISBEHAVING PROTEINS: PROTEIN (MIS)FOLDING, AGGREGATION, AND STABILITY, Murphy R M, Tsai A M, Eds., New York. Springer. pp. 331-350, which is incorporated herein by reference and for all purposes. Accordingly, leptin A500 with sequence following has been used in certain compounds and methods described herein:

```
                                            (SEQ ID NO: 33)
MVPIQKVQDDTKTLIKTIVTRINDISHTQSVSSKQKVTGLEFIPGLHPIL

TLSKMDQTLAVYQQILTSMPSRNVIQISNDLENLRDLLHVLAFSKSCHLP

QASGLETLESLGGVLEASGYSTEVVALSRLQGSLQDMLQQLDLSPGC.
```

Leptin A100 Variants:

Variants of Leptin A100 with the following residue substitutions follow:

D41E, H98S, W101Q, D109E, G113E, M137I, W139Q and G146E:

```
                                            (SEQ ID NO: 664)
MVPIQKVQDDTKTLIKTIVTRINDISHTQSVSSKQKVTGLEFIPGLHPIL

TLSKMDQTLAVYQQILTSMPSRNVIQISNDLENLRDLLHVLAFSKSCSLP

QASGLETLESLGEVLEASGYSTEVVALSRLQGSLQDILQQLDLSPEC.
```

H98S, W101Q, A102T, G113E, M137I, W139Q, and G146E:

```
                                            (SEQ ID NO: 665)
MVPIQKVQDDTKTLIKTIVTRINDISHTQSVSSKQKVTGLDFIPGLHPIL

TLSKMDQTLAVYQQILTSMPSRNVIQISNDLENLRDLLHVLAFSKSCSLP

QASGLETLDSLGGVLEASGYSTEVVALSRLQGSLQDILQQLDLSPEC.
```

H98S, W101Q, G113E, M137I, W139Q, and G146E:

```
                                            (SEQ ID NO: 666)
MVPIQKVQDDTKTLIKTIVTRINDISHTQSVSSKQKVTGLDFIPGLHPIL

TLSKMDQTLAVYQQILTSMPSRNVIQISNDLENLRDLLHVLAFSKSCSLP

QASGLETLDSLGEVLEASGYSTEVVALSRLQGSLQDILQQLDLSPEC.
```

W101Q, G113E, M137I, W139Q, and G146E:

(SEQ ID NO: 667)
MVPIQKVQDDTKTLIKTIVTRINDISHTQSVSSKQKVTGLDFIPGLHPIL
TLSKMDQTLAVYQQILTSMPSRNVIQISNDLENLRDLLHVLAFSKSCHLP
QASGLETLDSLGEVLEASGYSTEVVALSRLQGSLQDILQQLDLSPEC.

H98S, W101Q, M137I, W139Q, and G146E:

(SEQ ID NO: 668)
MVPIQKVQDDTKTLIKTIVTRINDISHTQSVSSKQKVTGLDFIPGLHPIL
TLSKMDQTLAVYQQILTSMPSRNVIQISNDLENLRDLLHVLAFSKSCSLP
QASGLETLDSLGGVLEASGYSTEVVALSRLQGSLQDILQQLDLSPEC.

W101Q, G113E, M137I, W139Q, L143V, and G146E:

(SEQ ID NO: 669)
MVPIQKVQDDTKTLIKTIVTRINDISHTQSVSSKQKVTGLDFIPGLHPIL
TLSKMDQTLAVYQQILTSMPSRNVIQISNDLENLRDLLHVLAFSKSCHLP
QASGLETLDSLGEVLEASGYSTEVVALSRLQGSLQDILQQLDVSPEC.

H98S, W101Q, A102T, M137I, W139Q, and G146E:

(SEQ ID NO: 670)
MVPIQKVQDDTKTLIKTIVTRINDISHTQSVSSKQKVTGLDFIPGLHPIL
TLSKMDQTLAVYQQILTSMPSRNVIQISNDLENLRDLLHVLAFSKSCSLP
QTSGLETLDSLGGVLEASGYSTEVVALSRLQGSLQDILQQLDLSPEC.

H98S, W101Q, D109E, G113E, and G146E:

(SEQ ID NO: 671)
MVPIQKVQDDTKTLIKTIVTRINDISHTQSVSSKQKVTGLDFIPGLHPIL
TLSKMDQTLAVYQQILTSMPSRNVIQISNDLENLRDLLHVLAFSKSCSLP
QASGLETLESLGEVLEASGYSTEVVALSRLQGSLQDMLWQLDLSPEC.

W101Q, M137I, W139Q, and G146E:

(SEQ ID NO: 672)
MVPIQKVQDDTKTLIKTIVTRINDISHTQSVSSKQKVTGLDFIPGLHPIL
TLSKMDQTLAVYQQILTSMPSRNVIQISNDLENLRDLLHVLAFSKSCHLP
QASGLETLDSLGGVLEASGYSTEVVALSRLQGSLQDILQQLDLSPEC.

W101Q, M137I, W139Q, L143V, and G146E:

(SEQ ID NO: 673)
MVPIQKVQDDTKTLIKTIVTRINDISHTQSVSSKQKVTGLDFIPGLHPIL
TLSKMDQTLAVYQQILTSMPSRNVIQISNDLENLRDLLHVLAFSKSCHLP
QASGLETLDSLGGVLEASGYSTEVVALSRLQGSLQDILQQLDVSPEC.

H98S, W101Q, A102T, M137I, W139Q, L143V, and G146E:

(SEQ ID NO: 674)
MVPIQKVQDDTKTLIKTIVTRINDISHTQSVSSKQKVTGLDFIPGLHPIL
TLSKMDQTLAVYQQILTSMPSRNVIQISNDLENLRDLLHVLAFSKSCSLP
QTSGLETLDSLGGVLEASGYSTEVVALSRLQGSLQDILQQLDVSPEC.

H98S, W101Q, A102T, G113E, and G146E:

(SEQ ID NO: 675)
MVPIQKVQDDTKTLIKTIVTRINDISHTQSVSSKQKVTGLDFIPGLHPIL
TLSKMDQTLAVYQQILTSMPSRNVIQISNDLENLRDLLHVLAFSKSCSLP
QTSGLETLDSLGEVLEASGYSTEVVALSRLQGSLQDMLWQLDLSPEC.

W101Q, G113E, and W139Q:

(SEQ ID NO: 676)
MVPIQKVQDDTKTLIKTIVTRINDISHTQSVSSKQKVTGLDFIPGLHPIL
TLSKMDQTLAVYQQILTSMPSRNVIQISNDLENLRDLLHVLAFSKSCHLP
QASGLETLDSLGEVLEASGYSTEVVALSRLQGSLQDMLQQLDLSPGC.

W101Q, G113E, W139Q, and G146E:

(SEQ ID NO: 677)
MVPIQKVQDDTKTLIKTIVTRINDISHTQSVSSKQKVTGLDFIPGLHPIL
TLSKMDQTLAVYQQILTSMPSRNVIQISNDLENLRDLLHVLAFSKSCHLP
QASGLETLDSLGEVLEASGYSTEVVALSRLQGSLQDMLQQLDLSPEC.

Any of the above leptins, leptin analogs or their active fragments, as well as leptins as described below, are suitable for use in the present engineered polypeptides, with or without a linker to the ABD.

Albumin Binding Domain (ABD) Peptides.

Albumin binding domain (ABD) peptides for use in the invention are those with comparably high affinity for albumin and derive from albumin-binding domains of bacterial protein G of *Streptococcus* strain G148. As such, ABD peptides contemplated for the engineered polypeptides described herein include those having the albumin binding motifs as described by Jonsson et al. (*Protein Eng. Design & Selection*, 2008, 21:515-527) as well as the ABD peptides described therein, and those motifs and ABD peptides further described in PCT Published Appl. No. WO2009/016043, as well as analogs thereof, particularly those having at least 85% amino acid identity. In one embodiment the ABD peptide can comprise an albumin binding motif ("ABM") that consists of the amino acid sequence:

(SEQ ID NO: 34)
GVSD $X_5$ YK $X_8$ $X_9$ I $X_{11}$ $X_{12}$ A $X_{14}$ TVEGV $X_{20}$ AL $X_{23}$ $X_{24}$ $X_{25}$ I wherein, independently of each other,
$X_5$ is selected from Y and F;
$X_8$ is selected from N, R and S;
$X_9$ is selected from V, I, L, M, F and Y;
$X_{11}$ is selected from N, S, E and D;
$X_{12}$ is selected from R, K and N;
$X_{14}$ is selected from K and R;
$X_{20}$ is selected from D, N, Q, E, H, S, R and K;
$X_{23}$ is selected from K, I and T;
$X_{24}$ is selected from A, S, T, G, H, L and D; and
$X_{25}$ is selected from H, E and D.

In certain embodiments, $X_5$ is Y. In certain embodiments, $X_8$ is N. In certain embodiments, $X_{23}$ is T. In certain embodiments, $X_{23}$ is I. In certain embodiments, $X_{24}$ is S. In certain embodiments, $X_{24}$ is L. In certain embodiments, $X_{25}$ is E. In certain embodiments, $X_{25}$ is H. In certain embodiments, independently from each other, $X_5$ is Y, and/or Xg is N, and/or $X_{23}$ is T or I, and/or $X_{24}$ is S or L, and/or $X_{25}$ is E. In certain embodiments, the albumin binding motif ("ABM") is GVSDYYKNLINKAKTVEGVEALTLHI (SEQ ID NO:114). In certain embodiments, the albumin binding motif ("ABM") is GVSDYYKNLINKAKTVEG-VEALISEI (SEQ ID NO:115).

Preferably the ABD peptide binds to albumin with a K value of the interaction that is at most $1\times10^{-6}$ M, and even more preferably at most $1\times10^{-9}$ M (even tighter affinity). More preferably the K value of the interaction that is at most $1\times10^{-10}$ M, even more preferably is at most $1\times10^{-11}$ M, yet even more preferably is at most $1\times10^{-12}$ M, and even further is at most $1\times10^{-13}$ M. For example, a $K_D$ value of $1\times10^{-14}$ M is a K value of the interaction that is at most $1\times10^{-13}$ M. The K values can be determined as described in PCT Published Appl. No. WO 2009/016043, preferably to human serum albumin. In one embodiment is contemplated the above genus with the proviso that the amino acid sequence is not GVSDYYKNLINNAKTVEGVKALIDEI (SEQ ID NO:35).

As demonstrated herein and in the cited references, the albumin binding capacity of the ABD peptide can be retained despite amino acid changes so long as such changes retain sufficient tertiary structure of the ABD peptide. Such changes include, for example, a substitution where an amino acid residue belonging to a certain functional grouping of amino acid residues (e.g. hydrophobic, hydrophilic, polar etc.) is exchanged for another amino acid residue from the same functional group. Accordingly, in one such embodiment of the ABD peptide, the motif $X_5$ is Y. In one embodiment of the ABD $X_8$ is selected from N and R, and may in particular be R. In one embodiment $X_9$ is L. In one embodiment $X_{11}$ is selected from N and S, and may in particular be N. In one embodiment $X_{12}$ is selected from R and K, such as $X_{12}$ being R or $X_{12}$ being K. In one embodiment $X_{14}$ is K. In one embodiment $X_{20}$ is selected from D, N, Q, E, H, S and R, and may in particular be E. In one embodiment $X_{23}$ is selected from K and I, and may in particular be K. In one embodiment $X_{24}$ is selected from A, S, T, G, H and L. In a more specific embodiment $X_{24}$ is L. In an even more specific embodiment "$X_{23} X_{24}$" is KL. In another even more specific embodiment "$X_{23} X_{24}$" is TL. In one embodiment $X_{24}$ is selected from A, S, T, G and H. In a more specific embodiment $X_{24}$ is selected from A, S, T, G and H and $X_{23}$ is I. In one embodiment $X_{25}$ is H.

The sequences of individual albumin binding motifs within the above formula include those presented as SEQ ID NOs: 1-257 in PCT Published Appl. No. WO 2009/016043, incorporated herein by reference. In certain embodiments of the albumin binding polypeptide the albumin binding motif consists of an amino acid sequence selected from SEQ ID NO:1-257. In a more specific embodiment of this aspect of the invention, the motif sequence is selected from SEQ ID NO:2, SEQ ID NO:3, SEQ ID NO:9, SEQ ID NO:15, SEQ ID NO:25, SEQ ID NO:27, SEQ ID NO:46, SEQ ID NO:49, SEQ ID NO:53, SEQ ID NO:54, SEQ ID NO:55, SEQ ID NO:1 55, SEQ ID NO:239, SEQ ID NO:240, SEQ ID NO:241, SEQ ID NO:242, SEQ ID NO:243, SEQ ID NO:244 and SEQ ID NO:245 of PCT Published Appl. No. WO 2009/016043. In yet more specific embodiments of this aspect of the invention, the motif sequence is selected from SEQ ID NO:3, SEQ ID NO:53 and SEQ ID NO:239 of PCT Published Appl. No. WO 2009/016043. Albumin binding polypeptides containing albumin binding motifs, and thus suitable for conjugation or fusion to a hormone domain as described herein, are further described herein and below and exemplified in Table 1 and the Examples. Not to be bound by theory but it is believed that the albumin binding motif can form part of a three-helix bundle protein domain. For example, the motif may essentially constitute or form part of two alpha helices with an interconnecting loop, within said three-helix bundle protein domain. Accordingly, in particular embodiments of the invention, such a three-helix bundle protein domain is selected from the group consisting of three-helix domains of bacterial receptor protein G from *Streptococcus* strain G148. In different variants of this embodiment, the three-helix bundle protein domain of which the motif forms a part is selected from the group consisting of domain GA1, domain GA2 and domain GA3 of protein G from *Streptococcus* strain G148, in particular domain GA3.

In embodiments of the present invention wherein the motif "forms part of a three-helix bundle protein domain," this is understood to mean that the sequence of the albumin binding motif is "inserted" into or "grafted" onto or "fused" to the sequence of the naturally occurring (or otherwise original) three-helix bundle domain, such that the motif replaces a similar structural motif in the original domain. For example and without wishing to be bound by theory, the motif is thought to constitute two of the three helices of a three-helix bundle, and can replace such a two-helix motif within any three-helix bundle. The replacement of two helices of the three-helix bundle domain by the two motif helices disclosed herein is performed so as not to affect the basic structure of the polypeptide. That is, the overall folding of the backbone of the polypeptide according to this embodiment of the invention will be substantially the same as that of the three-helix bundle protein domain of which it forms a part, e.g. having the same elements of secondary structure in the same order etc. Thus, a motif useful to the engineered polypeptides herein can form part of a three-helix bundle domain if the polypeptide according to this embodiment has the same fold as the original domain, implying that the basic structural properties are shared, those properties e.g. resulting in similar CD spectra.

Accordingly, in one embodiment the albumin binding domain polypeptide is a three-helix bundle protein domain, which comprises the albumin binding motif as defined above and additional sequences making up the remainder of the three-helix configuration. To such an albumin binding domain polypeptide can be fused to a leptin, a leptin analog, a leptin active fragment, or a leptin derivative thereof to create the engineered polypeptides as described herein. An albumin binding domain polypeptide suitable for conjugation or fusion to a leptin, a leptin analog, a leptin active fragment, or a leptin derivative thereof can comprise the amino acid sequence:

(SEQ ID NO: 36)
LAEAK $X_a$ $X_b$ A $X_c$ $X_d$ EL $X_e$ KY -[ABM]- LAALP wherein
[ABM] is an albumin binding motif as defined above, and, independently of each other,
$X_a$ is selected from V and E;
$X_b$ is selected from L, E and D;
$X_c$ is selected from N, L and I;
$X_d$ is selected from R and K; and
$X_e$ is selected from D and K.

In certain embodiments, $X_a$ is E. In certain embodiments $X_b$ is D. In certain embodiments, $X_c$ is I. In certain embodiments, $X_d$ is K. In certain embodiments, $X_a$ independently is E, and/or independently $X_b$ is D, and/or independently $X_c$ is I, and/or independently $X_d$ is K. In certain embodiments, the leucine at position 45 is present or absent. In certain embodiments, the proline at position 46 is absent. In certain embodiments, the albumin binding domain polypeptide is LAEAKEDAIKELDKYGVSDYYKNLINKAKTVEG-VEALTLHILAALP (SEQ ID NO: 50). In certain embodiments, the albumin binding domain polypeptide is LAEAKEDAIKELDKYGVSDYYKNLINKAKTVEG-VEALISEILAALP (SEQ ID NO:51).

In a further embodiment, the ABD comprises one or more N-terminal helix-capping amino acids, and in a further embodiment the helix-capping amino acid may be serine, or may be glycine-serine. Accordingly for each albumin binding domain sequence disclosed herein, including those in the figures and sequenced listing, also specifically contemplated for all aspects as disclosed herein in the engineered polypeptide, are albumin binding domains, their Ser-ABD, Gly-Ser-ABD, Gly-ABD, Ala-ABD and their des-C-terminal-proline sequences.

Because of the presence of an albumin binding motif, the ABD peptide binds to albumin with a K value of the interaction that is at most $1\times10^{-6}$ M and even more preferably at most $1\times10^{-9}$ M (even tighter affinity). More preferably the K value of the interaction that is at most $1\times10^{-10}$ M, even more preferably is at most $1\times10^{-11}$ M, yet even more preferably is at most $1\times10^{-12}$ M, and even further is at most $1\times10^{-13}$ M.

In one embodiment of this albumin binding polypeptide $X_a$ is V. In one embodiment of this polypeptide $X_b$ is L. In one embodiment of this polypeptide $X_c$ is N. In one embodiment of this polypeptide $X_d$ is R. In one embodiment of this polypeptide $X_e$ is D.

Sequences of individual albumin binding domain polypeptides suitable for fusion with the active hormone domain peptides as described herein are presented in Jonsson et al. (Id.) and as SEQ ID NOs:258-514 in PCT Published Appl. No. WO 2009/016043, incorporated herein by reference. Selected compounds are disclosed in Table 1 below. Also encompassed by the present invention is an albumin binding polypeptide having an amino acid sequence with 85% or greater identity to a sequence selected from SEQ ID NOs: 258-514. In particular embodiments, the sequence of the albumin binding polypeptide is selected from SEQ ID NO:259, SEQ ID NO:260, SEQ ID NO:266, SEQ ID NO:272, SEQ ID NO:282, SEQ ID NO:284, SEQ ID NO:303, SEQ ID NO:306, SEQ ID NO:310, SEQ ID NO:311, SEQ ID NO:312, SEQ ID NO:412, SEQ ID NO:496, SEQ ID NO:497, SEQ ID NO:498, SEQ ID NO:499, SEQ ID NO:500, SEQ ID NO:501 and SEQ ID NO:502 in PCT Published Appl. No. WO 2009/016043, and sequences having 85% or greater identity thereto. In yet further embodiments, the sequence of the albumin binding polypeptide is selected from SEQ ID NO:260, SEQ ID NO:270, SEQ ID NO:272, SEQ ID NO:291, SEQ ID NO:294, SEQ ID NO:298, SEQ ID NO:299, SEQ ID NO:300, SEQ ID NO:400, SEQ ID NO:484, SEQ ID NO:485, SEQ ID NO:486, SEQ ID NO:487, SEQ ID NO:488, SEQ ID NO:489 and SEQ ID NO:490 in PCT Published Appl. No. WO 2009/016043, and sequences having 85% or greater identity thereto. In still further embodiments, the sequence of the albumin binding polypeptide is selected from SEQ ID NO:260, SEQ ID NO:310, SEQ ID NO:496, and SEQ ID NO: 511 in PCT Published Appl. No. WO 2009/016043 and sequences having 85% or greater identity thereto.

In one embodiment, the albumin binding polypeptide further comprises one or more additional amino acid residues positioned at the N- and/or the C-terminal of the sequence defined in SEQ ID NO:36. These additional amino acid residues may play a role in enhancing the binding of albumin by the polypeptide, and improving the conformational stability of the folded albumin binding domain, but may equally well serve other purposes, related for example to one or more of production, purification, stabilization in vivo or in vitro, coupling, labeling or detection of the polypeptide, as well as any combination thereof. Such additional amino acid residues may comprise one or more amino acid residue(s) added for purposes of chemical coupling, e.g. to an HD1.

The amino acids directly preceding or following the alpha helix at the N- or C-terminus of the amino acid sequence in SEQ ID NO:36 may thus in one embodiment affect the conformational stability. One example of an amino acid residue which may contribute to improved conformational stability is a serine residue positioned at the N-terminal of SEQ ID NO:36 as defined above. The N-terminal serine residue may in some cases form a canonical S-X-X-E capping box, by involving hydrogen bonding between the gamma oxygen of the serine side chain and the polypeptide backbone NH of the glutamic acid residue. This N-terminal capping may contribute to stabilization of the first alpha helix of the three helix domain constituting the albumin binding polypeptide according to the first aspect of the disclosure.

Thus, in one embodiment, the additional amino acids comprise at least one serine residue at the N-terminal of the polypeptide. The amino acid sequence is in other words preceded by one or more serine residue(s). In another embodiment of the albumin binding polypeptide, the additional amino acids comprise a glycine residue at the N-terminal of the polypeptide. It is understood that the amino acid sequence of SEQ ID NO:36 may be preceded by one, two, three, four or any suitable number of amino acid residues. Thus, the amino acid sequence may be preceded by a single serine residue, a single glycine residue or a combination of the two, such as a glycine-serine (GS) combination or a glycine-serine-serine (GSS) combination. In yet another embodiment, the additional amino acid residues comprise a glutamic acid at the N-terminal of the polypeptide as defined by the sequence of SEQ ID NO:36.

Exemplary ABD species include, but are not limited to, the compounds set forth in Table 1 following and the Examples. See also PCT Published Appl. No. WO 2009/016043, incorporated herein by reference in its entirety and for all purposes. An ABD peptide useful in compounds, methods and pharmaceuticals compositions described herein can be a fragment or analog of an ABD peptide disclosed herein or known in the art so long as it contains an albumin binding motif and binds albumin with the affinity described herein.

TABLE 1

Selected ABD peptides

| ABD peptide sequence | SEQ ID NO: |
|---|---|
| LAEAKVLANRELDKYGVSDYYKNLINNAKTVEGVKALIDEILAALP | 37 |
| LAEAKVLANRELDKYGVSDFYKSYINRAKTVEGVHTLIGHILAALP | 38 |
| LAEAKVLANRELDKYGVSDFYKRLINKAKTVEGVNALTHHILAALP | 39 |
| LAEAKVLANRELDKYGVSDYYKNLINRARTVEGVHALIDHILAALP | 40 |
| LAEAKVLANRELDKYGVSDYYKNIINRAKTVEGVRALKLHILAALP | 41 |
| LAEAKVLANRELDKYGVSDFYKNLINRAKTVEGVSSLKGHILAALP | 42 |
| LAEAKVLANRELDKYGVSDYYKNLINKAKTVEGVEALTLHILAALP | 43 |
| LAEAKVLANRELDKYGVSDFYKNLINRAKTVEGVDALIAHILAALP | 44 |
| LAEAKVLANRELDKYGVSDFYKSLINRAKTVEGVDALTSHILAALP | 45 |
| LAEAKVLANRELDKYGVSDFYKNLINRAKTVEGVNSLTSHILAALP | 46 |
| LAEAKVLANRELDKYGVSDFYKNVINKAKTVEGVEALIADILAALP | 47 |
| LAEAKVLANRELDKYGVSDYYKNLINKAKTVEGVQALIAHILAALP | 48 |
| LAEAKVLANRELDKYGVSDFYKRLINKAKTVEGVEALKLHILAALP | 49 |
| LAEAKEDAIKELDKYGVSDYYKNLINKAKTVEGVEALTLHILAALP | 50 |
| LAEAKEDAIKELDKYGVSDYYKNLINKAKTVEGVEALISEILAALP | 51 |
| LAEAKEDAIKELDKYGVSDYYKRLISKAKTVEGVKALISEILAALP | 52 |

Binding to Albumin.

Serum albumin is the most abundant protein in mammalian sera (40 g/L; approximately 0.7 mM in humans) where it binds a variety of molecules including but not limited to lipids and bilirubin (Peters T, 1985, Advances in Protein Chemistry 37:161). It has been observed that the half-life of serum albumin is directly proportional to the size of the animal, where for example human serum albumin (HSA) has a half-life of 19 days and rabbit serum albumin has a half-life of about 5 days (McCurdy T R et al., *J. Lab. Clin. Med.* 143:115, 2004). Human serum albumin is widely distributed throughout the body, in particular in the intestinal and blood compartments, where it is mainly involved in the maintenance of osmolarity. Structurally, albumins are single-chain proteins comprising three homologous domains and totaling 584 or 585 amino acids (Dugaiczyk L et al., 1982, *Proc. Natl. Acad. Sci. USA* 79:71). Albumins contain 17 disulfide bridges and a single reactive thiol, C34, but lack N-linked and O-linked carbohydrate moieties (Peters, 1985, Id.; Nicholson J P et al., 2000, *Br J Anaesth* 85:599). The lack of glycosylation simplifies recombinant expression of albumin. This property of albumin, together with the fact that its three-dimensional structure is known (see e.g., He X M & Carter D C, 1992, *Nature* 358:209), has made it an attractive candidate for use in recombinant fusion proteins. Such fusion proteins generally combine a therapeutic protein (which would be rapidly cleared from the body upon administration of the protein per se) and a plasma protein (which exhibits a natural slow clearance) in a single polypeptide chain. See e.g., Sheffield W P, 2001, *Curr. Drug Targets Cardiovacs. Haematol. Disord.* 1:1). Such proteins may provide clinical benefits in requiring less frequent injection and higher levels of therapeutic protein in vivo. However, the engineered polypeptides herein are not conjugated to albumin, but instead contain motifs that allow non-covalent binding to albumin.

Further Embodiments

It is understood that each of the polypeptides disclosed herein are also contemplated to include (optionally) a methionine at the N-terminus in frame with the naturally-occurring first amino acid thereof. For example, metreleptin (leptin A100) consists of mature human leptin to which has been added an N-terminal methionine, as disclosed in SEQ ID NO:20. Similarly, a methionine residue may be included at the N-terminus of any of the amino acid sequences and Formulae disclosed herein throughout. It is further understood that where a C-terminal Gly appears in an engineered polypeptide sequence set forth herein, the residue may be lost during subsequent amidation.

In some embodiments, a leptin, a leptin analog, a leptin active fragment, or a leptin derivative can have at least 50%, for example 50%, 55%, 60%, 65%, 70%, 75%, 80%, 85%, 90%, 95%, 98% or even higher, sequence identity relative to a parent leptin. In some embodiments, the parent leptin is a leptin set out in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, ID NO:143, SEQ ID NO:144, SEQ ID NO:145, or SEQ ID NO:146. Accordingly, in some embodiments, a leptin, a leptin analog, a leptin active fragment, or a leptin derivative may have at least 50%, for example 50%, 55%, 60%, 65%, 70%, 75%, 80%, 85%, 90%, 95%, 98% or even higher, sequence identity relative to any leptin selected from the group consisting of SEQ ID NO:7, SEQ ID NO:8, SEQ ID NO:9, SEQ ID NO:16, SEQ ID NO:17, SEQ ID NO:18, SEQ ID NO:19, SEQ ID NO:20, SEQ ID NO:21, SEQ ID NO:22, and SEQ ID NO:23. In some embodiments, a leptin, a leptin analog, a leptin active fragment, or a leptin derivative may have at least 50%, for example 50%, 55%, 60%, 65%, 70%, 75%, 80%, 85%, 90%, 95%, 98% or even higher, sequence identity relative to the leptin set forth in SEQ ID NO:20. In some embodiments, a leptin, a leptin analog, a leptin active fragment, or a leptin derivative may have at least 50%, for example 50%, 55%, 60%, 65%, 70%, 75%, 80%, 85%, 90%, 95%, 98% or even higher, sequence identity relative to any leptin selected from the group consisting SEQ ID NO:24, SEQ ID NO: 25, SEQ ID NO:26, SEQ ID NO:27, SEQ ID NO: 28, or SEQ ID NO:29. In some embodiments, a leptin analog may have at least 90% sequence identity relative to the leptin set forth in SEQ ID NO:20. In some embodiments, a leptin analog may have at least 50% sequence identity relative to the leptin set forth in SEQ ID NO:1, SEQ ID NO:2, ID NO:143, SEQ ID NO:144, SEQ ID NO:145, or SEQ ID NO:146. In some embodiments, a leptin analog may have at least 90% sequence identity relative to the leptin set forth in SEQ ID NO:1, SEQ ID NO: 2, ID NO:143, SEQ ID NO:144, SEQ ID NO:145, or SEQ ID NO:146. In some embodiments, a leptin analog may have at least 50% sequence identity relative to the leptin set forth in SEQ ID NO:14 or SEQ ID NO:15. In some embodiments, a leptin analog may have at least 90% sequence identity relative to the leptin set forth in SEQ ID NO:14 or SEQ ID NO:15. In some embodiments, a leptin analog may have at least 50% sequence identity relative to the leptin set forth in SEQ ID NO: 32. In some embodiments, a leptin analog may have at least 90% sequence identity relative to the leptin set forth in SEQ ID NO:32. In some embodiments, a leptin analog may have at least 50% sequence identity relative to the leptin set forth in SEQ ID NO: 33. In some embodiments, a leptin analog may have at least 90% sequence identity relative to the leptin set forth in SEQ ID NO:33. In some embodiments, a leptin analog may have at least 50% sequence identity relative to the leptin set forth in SEQ ID NO:10 or SEQ ID NO:11. In some embodiments, a leptin analog may have at least 90% sequence identity relative to the leptin set forth in SEQ ID NO:10 or SEQ ID NO:11. In some embodiments, a leptin analog may have at least 50% sequence identity relative to the leptin set forth in SEQ ID NO:12 or SEQ ID NO:13. In some embodiments, a leptin analog may have at least 90% sequence identity relative to the leptin set forth in SEQ ID NO:12 or SEQ ID NO:13. Additionally, leptins may be designed, prepared, and used in accordance with the invention in which 1, 2, 3, 4, 5, 6, 7, 8, 9, 10, 11, 12, 13, 14, 15, 16, 17, 18, 19, 20 or even 21 amino acids of a leptin selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:143, SEQ ID NO:144, SEQ ID NO:145, and SEQ ID NO:146; is/are substituted with another amino acid, such as a conservative amino acid or a non-conservative amino acid, or is/are otherwise altered. As customary in the art, the term "conservative" in the context of amino acid substitutions refers to substitution which maintains properties of charge type (e.g., anionic, cationic, neutral, polar and the like), hydrophobicity or hydrophilicity, bulk (e.g., van der Waals contacts and the like), and/or functionality (e.g., hydroxy, amine, sulhydryl and the like). The term "non-conservative" refers to an amino acid substitution which is not conservative.

Additionally, as is understood in the art, for example, murine leptins, rat leptins, bovine leptins, porcine leptins, and rhesus monkey leptins, such as those disclosed herein, are each substantially homologous to human leptins; in particular, the mature forms of these leptins are substantially homologous to mature leptins, and further, particularly near the N-terminal portion of the protein. One may prepare analogs of such leptins, such as mature human leptin form 1 (SEQ ID NO:16) and metreleptin (SEQ ID NO:20), such as by substituting or otherwise altering amino acid residues at one or more positions in such sequences where divergence is observed in a corresponding mature mouse, rat, bovine, porcine, or rhesus monkey leptin. For example, mature human leptins (e.g., SEQ ID NO:20) elicits biological responses in, for example, mice, rat, and monkey). See, e.g., WO 98/28427, WO 2009/064298, US2007/0020284, US2008/0207512, and Murakami et al., 1995, *Biochem. Biophys. Res. Comm.* 209: 944-952. Because human mature leptins have biological activity in, e.g., such species, leptins may be designed and prepared in which one or more amino acids at positions which are divergent at the corresponding position(s) in a leptin from one or more of such species are substituted with the amino acid(s) at such corresponding divergent positions.

For example, using a human mature leptin protein according to SEQ ID NO:16 wherein the first amino acid is valine and the amino acid at position 146 is cysteine, one may substitute with another amino acid one or more of the amino acids at positions 32, 35, 50, 64, 68, 71, 74, 77, 89, 97, 100, 101, 105, 106, 107, 108, 111, 118, 136, 138, 142, and 145 with the corresponding amino acid(s) found at the corresponding position(s) in SEQ ID NO:143) in order to design, prepare, and use engineered polypeptides in accordance with the invention. Additionally, one may also substitute another amino acid, such as a conservative amino acid or a non-conservative amino acid, into one or more of positions 32, 35, 50, 64, 68, 71, 74, 77, 89, 97, 100, 101, 105, 106, 107, 108, 111, 118, 136, 138, 142, and 145 of, for example, SEQ ID NO:16 in order to design, prepare, and use engineered polypeptides in accordance with the invention.

One may further prepare additional leptins based on the mature rat leptin protein sequence (SEQ ID NO:12). See, e.g., WO 98/28427, US2007/0020284, and Murakami et al., 1995, Id., herein incorporated by reference in their entireties and for all purposes. Mature rat leptin differs from mature human leptin form 1 (SEQ ID NO:16) at the following positions: 4, 32, 33, 35, 50, 68, 71, 74, 77, 78, 89, 97, 100, 101, 102, 105, 106, 107, 108, 111, 118, 136, 138 and 145. Accordingly, at one or more of such positions in SEQ ID NO:16, one may substitute the amino acid found at the corresponding position(s) found in mature rat leptin (SEQ ID NO:12) in order to design, prepare, and use engineered polypeptides in accordance with the invention. Additionally, one may also substitute another amino acid, such as a conservative amino acid or a non-conservative amino acid, into one or more of positions 4, 32, 33, 35, 50, 68, 71, 74, 77, 78, 89, 97, 100, 101, 102, 105, 106, 107, 108, 111, 118, 136, 138 and 145 of, for example, SEQ ID NO:16, in order to design, prepare, and use engineered polypeptides in accordance with the invention.

The positions from both mature rat leptin (SEQ ID NO:12) and mature murine leptin form 1 (SEQ ID NO:143) which diverge from the mature human leptin form 1 (SEQ ID NO:16) are: 4, 32, 33, 35, 50, 64, 68, 71, 74, 77, 78, 89, 97, 100, 102, 105, 106, 107, 108, 111, 118, 136, 138, 142, and 145. Accordingly, at one or more of such positions in SEQ ID NO:16, one may substitute the amino acid found at the corresponding position(s) found in mature rat leptin sequence (SEQ ID NO:12) or mature murine form 1 sequence (SEQ ID NO:143) in order to design, prepare, and use engineered polypeptides in accordance with the invention. Additionally, one may also substitute another amino acid, such as a conservative amino acid or a non-conservative amino acid, into one or more of positions 4, 32, 33, 35, 50, 64, 68, 71, 74, 77, 78, 89, 97, 100, 102, 105, 106, 107, 108, 111, 118, 136, 138, 142, and 145 in order to design, prepare, and use engineered polypeptides in accordance with the invention.

In addition, the amino acids found in rhesus monkey mature leptin (SEQ ID NO:10) which diverge from mature human leptin form 1 (SEQ ID NO:16) are (with amino acid residues noted in parentheses in one letter amino acid abbreviation): 8 (S), 35 (R), 48(V), 53(Q), 60(I), 66(I), 67(N), 68((L), 89(L), 100(L), 108(E), 112 (D), and 118 (L). Since human mature leptins elicit biological response monkeys, a leptin, such as mature human leptin form 1 (SEQ ID NO:16) having one or more of the rhesus monkey divergent amino acids replaced with another amino acid, such as the amino acids in parentheses, may be employed in designing, preparing, and using engineered polypeptides in accordance with the invention. It should be noted that certain rhesus divergent amino acids are also those found in, for example, the above mature murine leptin form 1 (positions 35, 68, 89, 100 and 112). Thus, one may prepare leptins in which one or more amino acids at positions 4, 8, 32, 33, 35, 48, 50, 53, 60, 64, 66, 67, 68, 71, 74, 77, 78, 89, 97, 100, 102, 105, 106, 107, 108, 111, 112, 118, 136, 138, 142, and 145 of, e.g., mature human leptin form 1 (SEQ ID NO:16) are replaced by the corresponding amino acid(s) at such position(s) in murine or rhesus monkey leptins (e.g., SEQ ID NO:143 and/or SEQ ID NO:10).

Other leptins may be prepared by deleting a part of a leptin amino acid sequence, provided that such a leptin amino acid sequence may elicit a biological response. Such leptin amino acid sequences are leptin active fragments. For example, mature murine leptins, mature rhesus monkey leptins, mature human leptins, and mature rat leptins, and other leptins all lack the N-terminal 21 amino acid signal sequence that is present in the unprocessed, full-length forms of such leptin.

One may prepare the following active leptin fragments of such mature leptins:
(a) amino acids 98-146
(b) amino acids 1-32
(c) amino acids 40-116
(d) amino acids 1-99 and (connected to) 112-146
(e) amino acids 1-99 and (connected to) 112-146 having one or more of amino acids 100-111 placed between amino acids 99 and 112.

In addition, such active leptin fragments may also be prepared in which one or more of the amino acids at positions in, e.g., mature human leptin form 1 that are substituted with the amino acids found at the corresponding position(s) found in, e.g., rat, murine, monkey, porcine, and/or bovine mature leptins as disclosed above. Furthermore, any substitutions or alterations may be in the form of altered amino acids, such as peptidomimetics or D-amino acids.

Additionally, the present invention encompasses engineered polypeptides which comprise a leptin, a leptin analog, a leptin active fragment, or a leptin derivative as described above, wherein the a leptin, a leptin analog, a leptin active fragment, or a leptin derivative is selected from:
(a) the amino acid sequence 1-146 of a leptin selected from the group consisting of: SEQ ID NO:1, SEQ ID NO:2, SEQ ID NO:3, SEQ ID NO:5, SEQ ID NO:8, SEQ ID NO:10, SEQ ID NO:12.SEQ ID NO:13, SEQ ID NO:16, SEQ ID NO:17, SEQ ID NO:18, SEQ ID NO:19, SEQ ID NO:143, and SEQ ID NO:144; in which a different amino acid is substituted in one or more of the following positions and retaining the same numbering (even in the absence of a glutaminyl residue at position 28): 4, 32, 33, 35, 50, 64, 68, 71, 74, 77, 78, 89, 97, 100, 102, 105, 106, 107, 108, 111, 118, 136, 138, 142, and 145;
(b) the amino acid sequence of subpart (a) in which the glutaminyl residue at position 28 is absent;
(c) the amino acid sequence of subparts (a) or (b) in which a methionyl residue is added at the N-terminus;
(d) a leptin consisting of a fragment of the amino acid sequence of (a), (b), or (c) selected from the group consisting of:
(i) amino acids 98-146
(ii) amino acids 1-32
(iii) amino acids 40-116
(iv) amino acids 1-99 and 112-146
(v) amino acids 1-99 and 112-146 in which one or more of amino acids 100-111 is placed between amino acids 99 and 112; and,
(vi) the amino acid sequence of subpart (i) wherein one or more of amino acids 100, 102, 105, 106, 107, 108, 111, 118, 136, 138, 142, and 145 is substituted with another amino acid;
(vii) the amino acid sequence of subpart (ii) wherein one or more of amino acids 4, 8 and 32 is substituted with another amino acid;
(viii) the amino acid sequence of subpart (iii) wherein one or more of amino acids 50, 53, 60, 64, 66, 67, 68, 71, 74, 77, 78, 89, 97, 100, 102, 105, 106, 107, 108, 111 and 112 is replaced with another amino acid;
(ix) the amino acid sequence of subpart (iv) wherein one or more of amino acids 4, 8, 32, 33, 35, 48, 50, 53, 60, 64, 66, 67, 68, 71, 74, 77, 78, 89, 97, 112, 118, 136, 138, 142, and 145 is replaced with another amino acid; and
(x) the amino acid sequence of subpart (v) wherein one or more of amino acids 4, 32, 33, 35, 50, 64, 68, 71, 74, 77, 78, 89, 97, 100, 102, 105, 106, 107, 108, 111, 118, 136, 138, 142, and 145 is replaced with another amino acid;
(xi) the leptin of any of subparts (i)-(x) wherein a methionine has been added at the N-terminus; and
(e) the leptin of any of subparts (a) through (e) to which a chemical moiety is attached;
(f) the leptin of subpart (g) wherein said chemical moiety is a water soluble polymer moiety;
(g) a leptin of subpart (f) wherein said water soluble polymer moiety is polyethylene glycol;
(h) a leptin of subpart (f) wherein said water soluble polymer moiety is a polyaminoacid moiety; and
(i) a leptin of any one of subparts (e) through (h) wherein said moiety is attached at solely the N-terminus of said protein moiety.

With regard to the above, leptins to which a chemical moiety is attached are leptin derivatives. Derivatization of leptins by attachment of one or more chemical moieties has been found to provide some advantage under certain circumstances, such as increasing the stability and circulation time of the therapeutic protein and decreasing immunogenicity and propensity for, for example, generation of neutralizing antibodies and/or incidence of injection site reactions. See, e.g., WO 98/28427, US2007/0020284, U.S. Pat. No. 4,179,337, Davis et al., issued Dec. 18, 1979. For a review, see Abuchowski et al., in ENZYMES AS DRUGS. (J. S. Holcerberg and J. Roberts, eds. pp. 367-383 (1981)); Francis et al., Id. Accordingly, when employing a derivatized leptin and an ABM or an ABD, one may advantageously generate engineered polypeptides of the invention possessing advantages provided by both entities.

Leptin derivatives may constitute leptins to which a chemical modification has been made of one or more of its amino acid side groups, α-carbon atoms, terminal amino group, or terminal carboxylic acid group. A chemical modification includes, but is not limited to, attaching one or more chemical moieties, creating new bonds, and removing one or more chemical moieties. Modifications at amino acid side groups include, without limitation, alkylation, acylation, ester formation, amide formation, maleimide coupling, acylation of lysine ε-amino groups, N-alkylation of arginine, histidine, or lysine, alkylation of glutamic or aspartic carboxylic acid groups, and deamidation of glutamine or asparagine. Modifications of the terminal amino include, without limitation, the desamino, N-lower alkyl, N-di-lower alkyl, and N-acyl modifications. Modifications of the terminal amino include, without limitation, the desamino, N-lower alkyl, N-di-lower alkyl, and N-acyl modifications, such as alkylacyls, branched alkylacyls, alkylaryl-acyls. Modifications of the terminal carboxy group include, without limitation, the amide, lower alkyl amide, dialkyl amide, arylamide, alkylarylamide and lower alkyl ester modifications. Lower alkyl is $C_1$-$C_4$ alkyl. Furthermore, one or more side groups, or terminal groups, may be protected by protective groups known to the ordinarily-skilled synthetic chemist. The α-carbon of an amino acid may be mono- or dimethylated.

Such derivatives include leptins conjugated to one or more water soluble polymer molecules, such as polyethylene glycol ("PEG") or fatty acid chains of various lengths (e.g., stearyl, palmitoyl, octanoyl), by the addition of polyamino acids, such as poly-his, poly-arg, poly-lys, and poly-ala, or by addition of small molecule substituents include short alkyls and constrained alkyls (e.g., branched, cyclic, fused, adamantyl), and aromatic groups. In some embodiments, the water soluble polymer molecules will have a molecular weight ranging from about 500 Daltons to about 60,000 Daltons.

Such polymer-conjugations may occur singularly at the N- or C-terminus or at the side chains of amino acid residues within the sequence of a leptin as disclosed herein. Alternatively, there may be multiple sites of derivatization along the amino acid sequence of such a leptin. Substitution of one or more amino acids with lysine, aspartic acid, glutamic acid, or cysteine may provide additional sites for derivatization. See, e.g., U.S. Pat. Nos. 5,824,784 and 5,824,778. In some embodiments, a leptin may be conjugated to one, two, or three polymer molecules.

In some embodiments, the water soluble polymer molecules are linked to an amino, carboxyl, or thiol group, and may be linked by N or C termini, or at the side chains of lysine, aspartic acid, glutamic acid, or cysteine. Alternatively, the water soluble polymer molecules may be linked with diamine and dicarboxylic groups. In some embodiments, a leptin is conjugated to one, two, or three PEG molecules through an epsilon amino group on a lysine amino acid.

Leptin derivatives also include leptins with chemical alterations to one or more amino acid residues. Such chemical alterations include amidation, glycosylation, acylation, sulfation, phosphorylation, acetylation, and cyclization. The chemical alterations may occur singularly at the N- or C-terminus or at the side chains of amino acid residues within the sequence of a leptin. In one embodiment, the C-terminus of these peptides may have a free —OH or —NH$_2$ group. In another embodiment, the N-terminal end may be capped with an isobutyloxycarbonyl group, an isopropyloxycarbonyl group, an n-butyloxycarbonyl group, an ethoxycarbonyl group, an isocaproyl group ("isocap"), an octanyl group, an octyl glycine group (denoted as "G(Oct)" or "octylGly"), an 8-aminooctanic acid group, a dansyl, and/or a Fmoc group. In some embodiments, cyclization can be through the formation of disulfide bridges. Alternatively, there may be multiple sites of chemical alteration along the leptin amino acid sequence.

In certain embodiments, leptins are chemically altered to include a Bolton-Hunter group. Bolton-Hunter reagents are known in the art ("Radioimmunoassay and related methods," A. E. Bolton and W. M. Hunter, Chapter 26 of HANDBOOK OF EXPERIMENTAL IMMUNOLOGY, VOLUME I, IMMUNOCHEMISTRY, edited by D. M. Weir, Blackwell Scientific Publications, 1986), and may be used to introduce tyrosine-like moieties with a neutral linkage, through amino-terminal α-amino groups or ε-amino groups of lysine. In some embodiments, the N-terminal end of a leptin is modified with a Bolton-Hunter group. In some embodiments, an internal lysine residue is modified with a Bolton-Hunter group. In some embodiments, there may be multiple sites of Bolton-Hunter modification along the leptin amino acid sequence. Bolton-Hunter reagents used for polypeptide modification are commercially available, and may include, but are not limited to, water-soluble Bolton-Hunter reagent, Sulfosuccinimidyl-3-[4-hydrophenyl]propionate (Pierce Biotechnology, Inc., Rockford, Ill.) and Bolton-Hunter reagent-2, N-Succinimidyl 3-(4-hydroxy-3-iodophenyl) Priopionate (Wako Pure Chemical Industries, Ltd., Japan, catalog #199-09341). An exemplary Bolton-Hunter group conjugated through an amide linkage to a leptin is illustrated below, wherein the dashed line passes through the amide bond:

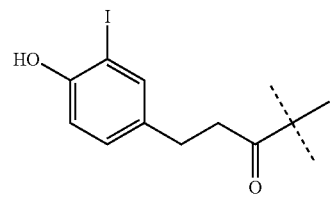

Leptins may be iodinated (such as radiolabeled with $^{125}$I) before or after Bolton-Hunter modification.

In order to prepare engineered polypeptides in accordance with the invention, a leptin derivative for use in the preparation of such may include one or more modifications of a "non-essential" amino acid residue. In the context of the invention, a "non-essential" amino acid residue is a residue that can be altered, e.g., derivatized, without abolishing or substantially reducing the activity (e.g., the agonist activity) of the leptin. The engineered polypeptides of the invention may include derivatizations of 1, 2, 3, 4, 5, 6, 7, 8, 9, 10 or more amino acid residues of the leptin moiety; of these, one or more amino acid residues may be non-essential amino acid residues. Additionally, the polypeptides of the invention may be derivatized such that they include additions of at least 1, 2, 3, 4, 5, 6, 7, 8, 9, 10 or more amino acids of the leptin moiety without abolishing or substantially reducing the activity of the polypeptide. Additionally, such non-essential amino acid residues may be substituted with an amino acid residue that is amenable to derivatization as described throughout.

As used throughout, "amino acid," "amino acid residue" and the like refer to natural amino acids, unnatural amino acids, and modified amino acids. Unless stated to the contrary, any reference to an amino acid, generally or specifically by name, includes reference to both the D and the L stereoisomers if their structure allow such stereoisomeric forms. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), Lysine (Lys), methionine (Met), phenylalanine (Phe), proline (Pro), serine (Ser), threonine (Thr), tryptophan (Trp), tyrosine (Tyr) and valine (Val). Unnatural amino acids include, but are not limited to homolysine, homoarginine, homoserine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, pentylglycine, pipecolic acid and thioproline. Additional unnatural amino acids include modified amino acid residues which are chemically blocked, reversibly or irreversibly, or chemically modified on their N-terminal amino group or their side chain groups, as for example, N-methylated D and L amino acids or residues wherein the side chain functional groups are chemically modified to another functional group. For example, modified amino acids include methionine sulfoxide; methionine sulfone; aspartic acid- (beta-methyl ester), a modified amino acid of aspartic acid; N-ethylglycine, a modified amino acid of glycine; or alanine carboxamide, a modified amino acid of alanine. Additional residues that can be incorporated are described in Sandberg et al., *J. Med. Chem.* 41: 2481-91, 1998.

As mentioned above, chemical moieties suitable for such derivatization of leptins and other polypeptides include, for example, various water soluble polymers. Preferably, for therapeutic use of the end-product preparation, the polymer will be pharmaceutically acceptable. One skilled in the art will be able to select the desired polymer based on such considerations as whether the polymer/protein conjugate will be used therapeutically, and if so, the desired dosage, circulation time, resistance to proteolysis, and other considerations. For the engineered polypeptides and leptins, the effectiveness of the derivatization may be ascertained by administering the derivatized leptin or the derivatized engineered polypeptide, in the desired form (i.e., by osmotic pump, or, more preferably, by injection or infusion, or, further formulated for oral, pulmonary or nasal delivery, for example), and observing biological effects and biological responses as described herein.

Such a water soluble polymer may be selected from the group consisting of, for example, polyethylene glycol, copolymers of ethylene glycol/propylene glycol, carboxymethylcellulose, dextran, polyvinyl alcohol, polyvinyl pyrolidone, poly-1,3-dioxolane, poly-1,3,6-trioxane, ethylene/maleic anhydride copolymer, polyaminoacids (either homopolymers or random copolymers), and dextran or poly(n-vinyl pyrolidone)polyethylene glycol, propylene glycol homopolymers, polypropylene oxide/ethylene oxide copolymers, polyoxyethylated polyols and polyvinyl alcohol. Polyethylene glycol propionaldehyde may have advantages in manufacturing due to its stability in water. Also, succinate and styrene may also be used.

Leptin derivatives used in the design and preparation of engineered polypeptides in accordance with the invention may be prepared by attaching polyaminoacids or branch point amino acids to the leptin moiety. For example, the polyaminoacid may be an additional carrier protein, such as an Fc moiety, which can serve to also increase the circulation half life of the leptin or the engineered polypeptide, in addition to the advantages achieved via attachment of an ABM or an ABD. Additionally, such polyaminoacids may be selected from the group consisting of serum album (such as human serum albumin), an additional antibody or portion thereof (e.g. the Fc region), or other polyaminoacids, e.g. polylysines. As indicated below, the location of attachment of the polyaminoacid may be at the N-terminus of the leptin moiety, or C-terminus, or other places in between, and also may be connected by a chemical "linker" moiety to the leptin, such as a peptidic linker or a non-peptidic linker.

The polymer may be of any molecular weight, and may be branched or unbranched. For polyethylene glycol, the preferred molecular weight is between about 2 kilodaltons (kDa) and about 100 kDa (the term "about" indicating that in preparations of polyethylene glycol, some molecules will weigh more, some less, than the stated molecular weight) for ease in handling and manufacturing. In certain embodiments, the polyethylene glycol is between about 2 kDa and about 60 kDa. In certain embodiments, the polyethylene glycol is between about 2 kDa and about 40 kDa. In certain embodiments, the polyethylene glycol is between about 5 kDa and about 40 kDa. In certain embodiments, the polyethylene glycol is between about 10 kDa and about 40 kDa. In certain embodiments, the polyethylene glycol is between about 5 kDa and about 30 kDa. In certain embodiments, the polyethylene glycol is between about 5 kDa and about 20 kDa. In certain embodiments, the polyethylene glycol is between about 10 kDa and about 20 kDa. Other sizes may be used, depending on the desired therapeutic profile (e.g., the duration of sustained release desired, solubility characteristics, the effects, if any, on biological activity, the ease in handling, the degree or lack of antigenicity and other known effects of the polyethylene glycol attached to a leptin and/or to an engineered polypeptide of the invention). Additional considerations that may influence the selection of a PEG of a particular molecular weight which may be attached to a leptin to generate a leptin derivative in accordance with the invention include the extent to which such a molecular weight PEG may: mitigate aggregation and/or increase the solubility of the leptin and/or the engineered polypeptide, when present in a pharmaceutically acceptable composition or formulation, or when exposed to physiological fluids or tissues upon administration to a subject (such as by injection); mitigate the incidence of injection site reactions caused by administration of the leptin or the engineered polypeptide upon administration to a subject by injection; mitigate the generation of neutralizing antibodies that may be raised against the leptin or the engineered polypeptide as a result of administration of such a leptin or an engineered polypeptide to a subject; and the like.

The number of polymer molecules so attached may vary, and one skilled in the art will be able to ascertain the resultant effect on function. One may mono-derivatize, or may provide for a di-, tri-, tetra- or some combination of derivatization, with the same or different chemical moieties (e.g., polymers, such as different weights of polyethylene glycols). The proportion of polymer molecules to leptin molecules or engineered polypeptide molecules to be derivatized will vary, as will their concentrations in the reaction mixture. In general, the optimum ratio, in terms of efficiency of reaction in that there is no excess unreacted leptin (or engineered polypeptide, as the case may be) or polymer, will be determined by factors such as the desired degree of derivatization (e.g., mono, di-, tri-, etc.), the molecular weight of the polymer selected, whether the polymer is branched or unbranched, and the reaction conditions.

The chemical moieties should be attached to the leptin and/or the engineered polypeptide with consideration of the effects on functional or antigenic domains of the leptin and/or to the engineered polypeptide. There are a number of attachment methods available to those skilled in the art. E.g., EP 0 401 384 herein incorporated by reference (coupling PEG to G-CSF), see also Malik et al., 1992, *Exp. Hematol.*

20:1028-1035 (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residue. Those having a free carboxyl group may include aspartic acid residues, glutamic acid residues, and the C-terminal amino acid residue. Sulfhydryl groups may also be used as a reactive group for attaching the polyethylene glycol molecule(s). Preferred for therapeutic purposes is attachment at an amino group, such as attachment at the N-terminus or lysine group. Attachment at residues important for receptor binding should be avoided if receptor binding is desired.

One may specifically desire to design and prepare an N-terminally chemically modified leptin for use in the preparation of engineered polypeptides of the invention. Using polyethylene glycol as an illustration of the present compositions, one may select from a variety of polyethylene glycol molecules (by molecular weight, branching, etc.), the proportion of polyethylene glycol molecules to leptin or engineered polypeptide molecules, as the case may be, in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective N-terminal chemical modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved. For example, one may selectively N-terminally pegylate the protein by performing the reaction at a pH which allows one to take advantage of the $pK_a$ differences between the ε-amino group of the lysine residues and that of the α-amino group of the N-terminal residue of the protein. By such selective derivatization, attachment of a water soluble polymer to a protein is controlled: the conjugation with the polymer takes place predominantly at the N-terminus of the protein and no significant modification of other reactive groups, such as the lysine side chain amino groups, occurs. Using reductive alkylation, the water soluble polymer may be of the type described above, and should have a single reactive aldehyde for coupling to the protein. Polyethylene glycol propionaldehyde, containing a single reactive aldehyde, may be used.

In some embodiments, compounds are provided having a linker, for example L1, as described herein, covalently linking a polypeptide hormone domain with an ABD peptide. In some embodiments, a first linker (L1) covalently links HD1 within the engineered polypeptide. In some embodiments, the polypeptide hormone domain (e.g., HD1) as described herein can be covalently linked to the ABD peptide via a peptide linker. Any linker is optional; i.e., any linker may simply be a bond. When present the chemical structure of a linker is not critical because it serves mainly a spacer function. In one embodiment the linker comprises from 1 to 30 or less amino acids linked by peptide bonds. The amino acids can be selected from the 20 naturally occurring amino acids. Alternatively, non-natural amino acids can be incorporated either by chemical synthesis, post-translational chemical modification or by in vivo incorporation by recombinant expression in a host cell. Some of these amino acids may be glycosylated.

In certain embodiments the 1 to 30 or less amino acids are selected from glycine, alanine, proline, asparagine, glutamine, lysine, aspartate, and glutamate. In a further embodiment the linker is made up of a majority of amino acids that are sterically unhindered, such as glycine, alanine and/or serine. Polyglycines are particularly useful, e.g. (Gly)$_3$, (Gly)$_4$ (SEQ ID NO:116), (Gly)$_5$ (SEQ ID NO:117), as are polyalanines, poly(Gly-Ala), poly(Glyn-Ser), poly (Gly$_n$-Glu), poly(Gly$_n$-Lys), poly(Gly$_n$-Asp), and poly(Gly$_n$-Arg) motifs. Other specific examples of linkers are (Gly)$_3$Lys (Gly)$_4$ (SEQ ID NO:118); (Gly)$_3$AsnGlySer(Gly)$_2$ (SEQ ID NO:119); (Gly)$_3$Cys(Gly)$_4$ (SEQ ID NO:120); and Gly-ProAsnGlyGly (SEQ ID NO:121). Combinations of Gly and Ala are particularly useful as are combination of Gly and Ser. Thus, in a further embodiment the peptide linker is selected from the group consisting of a glycine rich peptide, e.g. Gly-Gly-Gly; the sequences [Gly-Ser]$_n$ (SEQ ID NO:122), [Gly-Gly-Ser]$_n$ (SEQ ID NO:123), [Gly-Gly-Gly-Ser]$_n$ (SEQ ID NO:124) and [Gly-Gly-Gly-Gly-Ser]$_n$ (SEQ ID NO:125), where n is 1, 2, 3, 4, 5, 6, 7, 8, 9, or 10, for example, [Gly-Gly-Gly Ser]$_1$ (SEQ ID NO: 149), [Gly-Gly-Gly-Gly Ser]$_1$ (SEQ ID NO: 150), [Gly-Gly-Gly Ser]$_4$ (SEQ ID NO: 151), or [Gly-Gly-Gly-Gly Ser]$_3$ (SEQ ID NO: 152).

In certain embodiments, charged linkers may be used. Such charges linkers may contain a significant number of acidic residues (e.g., Asp, Glu, and the like), or may contain a significant number of basis residues (e.g., Lys, Arg, and the like), such that the linker has a pI lower than 7 or greater than 7, respectively. As understood by the artisan, and all other things being equal, the greater the relative amount of acidic or basic residues in a given linker, the lower or higher, respectively, the pI of the linker will be. Such linkers may impart advantages to the engineered polypeptides disclosed herein, such as improving solubility and/or stability characteristics of such polypeptides at a particular pH, such as a physiological pH (e.g., between pH 7.2 and pH 7.6, inclusive), or a pH of a pharmaceutical composition comprising such polypeptides.

For example, an "acidic linker" is a linker that has a pI of less than 7; between 6 and 7, inclusive; between 5 and 6, inclusive; between 4 and 5, inclusive; between 3 and 4, inclusive; between 2 and 3, inclusive; or between 1 and 2, inclusive. Similarly, a "basic linker" is a linker that has a pI of greater than 7; between 7 and 8, inclusive; between 8 and 9, inclusive; between 9 and 10, inclusive; between 10 and 11, inclusive; between 11 and 12 inclusive, or between 12 and 13, inclusive. In certain embodiments, an acidic linker will contain a sequence that is selected from the group consisting of [Gly-Glu]$_n$ (SEQ ID NO:126); [Gly-Gly-Glu]$_n$ (SEQ ID NO:127); [Gly-Gly-Gly-Glu]$_n$ (SEQ ID NO:128); [Gly-Gly-Gly-Gly-Glu]$_n$ (SEQ ID NO:129), [Gly-Asp]$_n$ (SEQ ID NO:130); [Gly-Gly-Asp]$_n$ (SEQ ID NO:131); [Gly-Gly-Gly-Asp]$_n$ (SEQ ID NO:132); [Gly-Gly-Gly-Gly-Asp]$_n$ (SEQ ID NO:133) where n is 1, 2, 3, 4, 5, 6, 7, 8, 9, 10, or more; for example, [Gly-Gly-Glu]$_6$ (SEQ ID NO: 153). In certain embodiments, a basic linker will contain a sequence that is selected from the group consisting of [Gly-Lys]$_n$ (SEQ ID NO:134); [Gly-Gly-Lys]$_n$ (SEQ ID NO:135); [Gly-Gly-Gly-Lys]$_n$ (SEQ ID NO:136); [Gly-Gly-Gly-Gly-Lys]$_n$ (SEQ ID NO:137), [Gly-Arg]$_n$ (SEQ ID NO:138); [Gly-Gly-Arg]$_n$ (SEQ ID NO:139); [Gly-Gly-Gly-Arg]$_n$ (SEQ ID NO:140); [Gly-Gly-Gly-Gly-Arg]$_n$ (SEQ ID NO:141) where n is 1, 2, 3, 4, 5, 6, 7, 8, 9, 10, or more; for example, [Gly-Gly-Lys]$_6$ (SEQ ID NO: 154).

Additionally, linkers may be prepared which possess certain structural motifs or characteristics, such as an a helix. For example, such a linker may contain an sequence that is selected from the group consisting of [Glu-Ala-Ala-Ala-Lys]$_n$ (SEQ ID NO:142), where n is 1, 2, 3, 4, 5, 6, 7, 8, 9, 10, or more; for example, [Glu-Ala-Ala-Ala-Lys]$_3$ (SEQ ID NO: 155), [Glu-Ala-Ala-Ala-Lys]$_4$ (SEQ ID NO: 156), or [Glu-Ala-Ala-Ala-Lys]$_5$ (SEQ ID NO: 157).

Additionally, a non-peptidic linker may be employed to serve as the L1 moiety of an engineered polypeptide described herein. For example, as understood in the art, an exemplary non-peptide linker such as a PEG linker may be so-employed. See, e.g., WO2000024782. In certain embodiments, such a PEG linker has a molecular weight of 100 Da to 1000 kDa. In certain embodiments, such a PEG linker has a molecular weight of 100 Da to 500 kDa. In certain embodiments, such a PEG linker has a molecular weight of 100 Da to 100 kDa. In certain embodiments, such a PEG linker has a molecular weight of 100 Da to 50 kDa. In certain embodiments, such a PEG linker has a molecular weight of 100 Da to 10 kDa. In certain embodiments, such a PEG linker has a molecular weight of 100 Da to 5 kDa. In certain embodiments, such a PEG linker has a molecular weight of 100 Da to 1 kDa. In certain embodiments, such a PEG linker has a molecular weight of 100 Da to 500 Da.

It is also to be understood that linkers suitable for use in accordance with the invention may possess one or more of the characteristics and motifs described above. For example, a linker may comprise an acidic linker as well as a structural motif, such as an alpha helix. Similarly, a linker may comprise a basic linker and a structural motif, such as an alpha helix. A linker may comprise an acidic linker, a basic linker, and a structural motif, such as an a helix. Additionally, it is also to be understood that engineered polypeptides in accordance with the invention may possess more than one linker, and each such linker may possess one or more of the characteristics described above.

The linkers described herein are exemplary, and linkers within the scope of this invention may be much longer and may include other residues. In one embodiment, expressly excluded are engineered polypeptides in which the leptin compound is linked directly to the ABD without a linker.

In some embodiments, the engineered polypeptide includes an ABD at the N-terminal, and a HD1 at the C-terminal. Conversely, in some embodiments, the engineered polypeptide includes an ABD at the C-terminal, and a HD1 at the N-terminal. In some embodiments, either the N-terminal or the C-terminal is a leptin, a leptin fragment, or a leptin analog. Preferably, the ABD is at the N-terminus of a leptin compound. Further to embodiments which include an ABD and a HD1, the engineered polypeptide can have the structure ABD-HD1 or HD1-ABD (both read in the N-terminal to C-terminal orientation).

It is understood that absent an express indication of the N-terminus and/or C-terminus of a engineered polypeptide set forth herein, the engineered polypeptide is to be read in the N-terminus to C-terminus orientation. For example, where HD1 is a leptin or analog thereof, the terms HD1-ABD, HD1-L1-ABD, HD1-ABD, and the like mean, in the absence of an express indication of the N-terminus and/or the C-terminus, that the leptin compound resides at the N-terminus of the engineered polypeptide, and the ABD resides at the C-terminus. Conversely, if the N-terminus and/or C-terminus is expressly indicated, then the engineered polypeptide is to be read according to the express indication of the terminii. For example, the terms HD1$_{C\text{-}term}$-ABD, HD1-L1-ABD$_{N\text{-}term}$ and the like mean that the ABD resides at the N-terminus of the engineered polypeptide, and HD1 resides at the C-terminus.

In some embodiments of the above described engineered polypeptides, HD1 is human leptin or metreleptin. In some further embodiments, HD1 is a leptin analog as described herein. In some embodiments, the leptin analog is leptin A100, A300 or A500.

In some embodiments, the engineered polypeptide described herein has an affinity for serum albumin which is different than the affinity of the ABD polypeptide alone, i.e., in the absence of a conjugated hormone domain. In order to obtain effective association, the engineered polypeptide can have a binding affinity for serum albumin such that the dissociation constant $K_D$ is, for example, less than about $10^{-6}$ M, $10^{-7}$ M, $10^{-8}$ M, $10^{-9}$ M, $10^{-10}$ M, $10^{-11}$ M, $10^{-12}$ M, $10^{-13}$ M, $10^{-14}$ M or even $10^{-15}$ M. In some embodiments, the affinity is not excessively tight such that the engineered polypeptide can dissociate from the albumin and elicit a biological response, for example binding to a receptor, for example, a leptin receptor. The affinity can be measured as described in PCT Published Appl. No. WO 2009/016043, preferably to human serum albumin.

In some embodiments, an engineered polypeptide described herein is superior to a corresponding compound having a different moiety that can extend plasma half-life (e.g., PEG or of Fc or albumin) conjugated with a hormone domain(s). In this context, the term "superior" refers to a variety of functional properties which could be weighed in the evaluation of a treatment for a disease or disorder. For example, the engineered polypeptide described herein could require less biologically active (hormone domain) component, for example 1×, 2×, 3×, 4×, 5×, or even less, than the corresponding compound having a different moiety conjugated with the hormone domain(s). For further example, the engineered polypeptide described herein could have higher potency, for example, 1.5×, 2×, 3×, 4×, 5×, 10×, 20×, 50×, or even higher potency.

Engineered polypeptide compounds contemplated herein include the compounds as set forth in Table 2 following.

TABLE 2

Selected engineered polypeptides

| Cmpd | Sequence | MW |
|---|---|---|
| 1 | MLAEAKVLANRELDKYGVSDFYKRLINKAKTVEGVE ALKLHILAALPTGGGGASVPIQKVQDDTKTLIKTIV TRINDISHTQSVSSKQKVTGLEFIPGLHPILTLSKM DQTLAVYQQILTSMPSRNVIQISNDLENLRDLLHVL AFSKSCHLPQASGLETLESLGGVLEASGYSTEVVAL SRLQGSLQDMLQQLDLSPGC (SEQ ID NO: 53) | 21647.2 |
| 2 | MLAEAKVLANRELDKYGVSDFYKRLINKAKTVEGVE ALKLHILAALPTGGGSGGGSGGGSGGGSASVPIQK VQDDTKTLIKTIVTRINDISHTQSVSSKQKVTGLEF IPGLHPILTLSKMDQTLAVYQQILTSMPSRNVIQIS NDLENLRDLLHVLAFSKSCHLPQASGLETLESLGGV LEASGYSTEVVALSRLQGSLQDMLQQLDLSPGC (SEQ ID NO: 54) | 22509.0 |
| 3 | MVPIQKVQDDTKTLIKTIVTRINDISHTQSVSSKQK VTGLEFIPGLHPILTLSKMDQTLAVYQQILTSMPSR NVIQISNDLENLRDLLHVLAFSKSCHLPQASGLETL ESLGGVLEASGYSTEVVALSRLQGSLQDMLQQLDLS PGCTGGGGSASLAEAKVLANRELDKYGVSDFYKRLI NKAKTVEGVEALKLHILAALP (SEQ ID NO: 55) | 21734.3 |

TABLE 2-continued

Selected engineered polypeptides

| Cmpd | Sequence | MW |
|---|---|---|
| 4 | MVPIQKVQDDTKTLIKTIVTRINDISHTQSVSSKQK VTGLEFIPGLHPILTLSKMDQTLAVYQQILTSMPSR NVIQISNDLENLRDLLHVLAFSKSCHLPQASGLETL ESLGGVLEASGYSTEVVALSRLQGSLQDMLQQLDLS PGCTGGGGSGGGSGGGSGGGSASLAEAKVLANRELD KYGVSDFYKRLINKAKTVEGVEALKLHILAALP (SEQ ID NO: 56) | 22509.0 |
| 9 | MLAEAKVLANRELDKYGVSDFYKRLINKAKTVEGVE ALKLHILAALPTGGGGSGGGSGGGSGGGSASISIEK IQADTKTLTKTIITRIIQLSTQNGVSTDQRVSGLDF IPGNQQFQNLADMDQTLAVYQQILSSLPMPDRTQIS NDLENLRSLFALLATLKNCPFTRSDGLDTMEIWGGI VEESLYSTEVVTLDRLRKSLKNIEKQLDHIQGC (SEQ ID NO: 57) | 22984.4 |
| 12 | MLAEAKVLANRELDKYGVSDFYKRLINKAKTVEGVE ALKLHILAALPTGGGGSGGGSGGGSGGGSASVPIQK VQDDTKTLIKTIVTRINDISHTQSVSSKQKVTGLDF IPGLHPILTLSKMDQTLAVYQQILTSMPSRNVIQIS NDLENLRDLLHVLAFSKSCHLPWASGLETLDSLGGV LEASGYSTEVVALSRLQGSLQDMLWQLDLSPGC (SEQ ID NO: 58) | 22597.1 |
| 13 | MVPIQKVQDDTKTLIKTIVTRINDISHTQSVSSKQK VTGLDFIPGLHPILTLSKMDQTLAVYQQILTSMPSR NVIQISNDLENLRDLLHVLAFSKSCHLPWASGLETL DSLGGVLEASGYSTEVVALSRLQGSLQDMLWQLDLS PGCTGGGGSGGGSGGGSGGGSASLAEAKVLANRELD KYGVSDFYKRLINKAKTVEGVEALKLHILAALP (SEQ ID NO: 59) | 22597.1 |
| 14 | MLAEAKVLANRELDKYGVSDFYKRLINKAKTVEGVE ALKLHILAALPTGGGGSGGGSGGGSGGGSASPIQRV QDDTKTLIKTIITRINDISPPQGVCSRPRVAGLDFI PRVQSVRTLSGMDQILATYQQILTSLQSRNVIQISN DLENLRDLLHVLAFSKSCPVPRARGSDTIKGLGNVL RASVHSTEVVALSRLKAALQDMLRQLDRNPGC (SEQ ID NO: 60) | 22592.9 |
| 15 | MLAEAKVLANRELDKYGVSDFYKRLINKAKTVEGVE ALKLHILAALPTGGGGSGGGSGGGSGGGSASPIQRV QDDTKTLIKTIITRINDISPPQGVSSRPRVAGLDFI PRVQSVRTLSGMDQILATYQQILTSLQSRNVIQISN DLENLRDLLHVLAFSKSCPVPRARGSDTIKGLGNVL RASVHSTEVVALSRLKAALQDMLRQLDRNPGC (SEQ ID NO: 61) | 22576.7 |
| 16 | MLAEAKVLANRELDKYGVSDFYKRLINKAKTVEGVE ALKLHILAALPTGPIQRVQDDTKTLIKTIITRINDI SPPQGVCSPRVAGLDFIPRVQSVRTLSGMDQILATY QQILTSLQSRNVIQISNDLENLRDLLHVLAFSKSCP VPRARGSDTIKGLGNVLRASVHSTEVVALSRLKAAL QDMLRQLDRNPGC (SEQ ID NO: 62) | 21332.7 |
| 17 | MLAEAKVLANRELDKYGVSDYYKNIINRAKTVEGVR ALKLHILAALPTGGGGSGGGSGGGSGGGSASVPIQK VQDDTKTLIKTIVTRINDISHTQSVSSKQKVTGLDF IPGLHPILTLSKMDQTLAVYQQILTSMPSRNVIQIS NDLENLRDLLHVLAFSKSCHLPWASGLETLDSLGGV LEASGYSTEVVALSRLQGSLQDMLWQLDLSPGC (SEQ ID NO: 63) | 22624.7 |
| 18 | MLAEAKVLANRELDKYGVSDYYKNIINRAKTVEGVR ALKLHILAALPTGGGGSGGGSGGGSGGGSASVPIQK VQDDTKTLIKTIVTRINDISHTQSVSSKQKVTGLEF IPGLHPILTLSKMDQTLAVYQQILTSMPSRNVIQIS NDLENLRDLLHVLAFSKSCHLPQASGLETLESLGGV LEASGYSTEVVALSRLQGSLQDMLQQLDLSPGC (SEQ ID NO: 64) | 22536.6 |
| 19 | MLAEAKVLANRELDKYGVSDFYKRLINKAKTVEGVE ALKLHILAALPTGGGGSGGGSGGGSGGGSASVPIQK VQDDTKTLIKTIVTRINDISHTQSVSSKQKVTGLDF IPGLHPILTLSKMDQTLAVYQQILTSMPSRNVIQIS NDLENLRDLLHVLAFSKSCHLPQASGLETLDSLGGV LEASGYSTEVVALSRLQGSLQDMLQQLDLSPGC (SEQ ID NO: 65) | 22480.95 |
| 20 | MLAEAKVLANRELDKYGVSDFYKRLINKAKTVEGVE ALKLHILAALPTGLAEAAAKEAAAKEAAAKEAAAKE AAAKAAAASVPIQKVQDDTKTLIKTIVTRINDISHT QSVSSKQKVTGLEFIPGLHPILTLSKMDQTLAVYQQ ILTSMPSRNVIQISNDLENLRDLLHVLAFSKSCHLP QASGLETLESLGGVLEASGYSTEVVALSRLQGSLQD MLQQLDLSPGC (SEQ ID NO: 66) | 24224.6 |
| 21 | MLAEAKVLANRELDKYGVSDFYKRLINKAKTVEGVE ALKLHILAALPTGGEGGEGGEGGEGGEGGEASVPIQ KVQDDTKTLIKTIVTRINDISHTQSVSSKQKVTGLE FIPGLHPILTLSKMDQTLAVYQQILTSMPSRNVIQI SNDLENLRDLLHVLAFSKSCHLPQASGLETLESLGG VLEASGYSTEVVALSRLQGSLQDMLQQLDLSPGC (SEQ ID NO: 67) | 22876.9 |
| 22 | MLAEAKVLANRELDKYGVSDFYKRLINKAKTVEGVE ALKLHILAALPTGGKGGKGGKGGKGGKGGKASVPIQ KVQDDTKTLIKTIVTRINDISHTQSVSSKQKVTGLE FIPGLHPILTLSKMDQTLAVYQQILTSMPSRNVIQI SNDLENLRDLLHVLAFSKSCHLPQASGLETLESLGG VLEASGYSTEVVALSRLQGSLQDMLQQLDLSPGC (SEQ ID NO: 68) | 22871.2 |
| 23 | MLAEAKVLANRELDKYGVSDFYKRLINKAKTVEGVE ALKLHILAALPTGGGGSGGGSGGGSGGGSASVPIQK VQDDTKTLIKTIVTRINDISHTQSVSSKQKVTGLEF IPGLHPILTLSKMDQTLAVYQQILTSMPSRNVIQIS NDLENLRDLLHVLAFSKSCSLPQASGLETLESLGEV LEASGYSTEVVALSRLQGSLQDILQQLDSPEC (SEQ ID NO: 69) | 22583.6 |
| 24 | MLAEAKEDAIKELDKYGVSDYYKNLINKAKTVEGVE ALTLHILAALPTGGGGASVPIQKVQDDTKTLIKTIV TRINDISHTQSVSSKQKVTGLEFIPGLHPILTLSKM DQTLAVYQQILTSMPSRNVIQISNDLENLRDLLHVL AFSKSCHLPQASGLETLESLGGVLEASGYSTEVVAL SRLQGSLQDMLQQLDLSPGC (SEQ ID NO: 70) | 21597.02 |
| 25 | MLAEAKEDAIKELDKYGVSDYYKNLINKAKTVEGVE ALTLHILAALPTGGGGSGGGSGGGSGGGSASVPIQK VQDDTKTLIKTIVTRINDISHTQSVSSKQKVTGLEF IPGLHPILTLSKMDQTLAVYQQILTSMPSRNVIQIS NDLENLRDLLHVLAFSKSCHLPQASGLETLESLGGV LEASGYSTEVVALSRLQGSLQDMLQQLDLSPGC (SEQ ID NO: 71) | 22458.80 |
| 26 | MVPIQKVQDDTKTLIKTIVTRINDISHTQSVSSKQK VTGLEFIPGLHPILTLSKMDQTLAVYQQILTSMPSR NVIQISNDLENLRDLLHVLAFSKSCHLPQASGLETL ESLGGVLEASGYSTEVVALSRLQGSLQDMLQQLDLS PGCTGGGGSASLAEAKEDAIKELDKYGVSDYYKNLI NKAKTVEGVEALTLHILAALP (SEQ ID NO: 72) | 21684.10 |
| 27 | MVPIQKVQDDTKTLIKTIVTRINDISHTQSVSSKQK VTGLEFIPGLHPILTLSKMDQTLAVYQQILTSMPSR NVIQISNDLENLRDLLHVLAFSKSCHLPQASGLETL ESLGGVLEASGYSTEVVALSRLQGSLQDMLQQLDLS PGCTGGGGSGGGSGGGSGGGSASLAEAKEDAIKELD KYGVSDYYKNLINKAKTVEGVEALTLHILAALP (SEQ ID NO: 73) | 22458.80 |
| 28 | MLAEAKEDAIKELDKYGVSDYYKNLINKAKTVEGVE ALTLHILAALPTGGGGSGGGSGGGSGGGSASISIEK IQADTKTLTKTIITRIIQLSTQNGVSTDQRVSGLDF IPGNQQFQNLADMDQTLAVYQQILSSLPMPDRTQIS | 22934.18 |

TABLE 2-continued

Selected engineered polypeptides

| Cmpd | Sequence | MW |
|---|---|---|
|  | NDLENLRSLFALLATLKNCPFTRSDGLDTMEIWGGI VEESLYSTEVVTLDRLRKSLKNIEKQLDHIQGC (SEQ ID NO: 74) |  |
| 29 | MLAEAKEDAIKELDKYGVSDYYKNLINKAKTVEGVE ALTLHILAALPTGGGGSGGGSGGGSGGGSASVPIQK VQDDTKTLIKTIVTRINDISHTQSVSSKQKVTGLDF IPGLHPILTLSKMDQTLAVYQQILTSMPSRNVIQIS NDLENLRDLLHVLAFSKSCHLPWASGLETLDSLGGV LEASGYSTEVVALSRLQGSLQDMLWQLDLSPGC (SEQ ID NO: 75) | 22546.92 |
| 30 | MVPIQKVQDDTKTLIKTIVTRINDISHTQSVSSKQK VTGLDFIPGLHPILTLSKMDQTLAVYQQILTSMPSR NVIQISNDLENLRDLLHVLAFSKSCHLPWASGLETL DSLGGVLEASGYSTEVVALSRLQGSLQDMLWQLDLS PGCTGGGGSGGGSGGGSGGGSASLAEAKEDAIKELD KYGVSDYYKNLINKAKTVEGVEALTLHILAALP (SEQ ID NO: 76) | 22546.92 |
| 31 | MLAEAKEDAIKELDKYGVSDYYKNLINKAKTVEGVE ALTLHILAALPTGGGGSGGGSGGGSGGGSASPIQRV QDDTKTLIKTIITRINDISPPQGVCSRPRVAGLDFI PRVQSVRTLSGMDQILATYQQILTSLQSRNVIQISN DLENLRDLLHVLAFSKSCPVPRARGSDTIKGLGNVL RASVHSTEVVALSRLKAALQDMLRQLDRNPGC (SEQ ID NO: 77) | 22544.03 |
| 32 | MLAEAKEDAIKELDKYGVSDYYKNLINKAKTVEGVE ALTLHILAALPTGGGGSGGGSGGGSGGGSASPIQRV QDDTKTLIKTIITRINDISPPQGVSSRPRVAGLDFI PRVQSVRTLSGMDQILATYQQILTSLQSRNVIQISN DLENLRDLLHVLAFSKSCPVPRARGSDTIKGLGNVL RASVHSTEVVALSRLKAALQDMLRQLDRNPGC (SEQ ID NO: 78) | 22527.96 |
| 33 | MLAEAKEDAIKELDKYGVSDYYKNLINKAKTVEGVE ALTLHILAALPTGPIQRVQDDTKTLIKTIITRINDI SPPQGVCSPRVAGLDFIPRVQSVRTLSGMDQILATY QQILTSLQSRNVIQISNDLENLRDLLHVLAFSKSCP VPRARGSDTIKGLGNVLRASVHSTEVVALSRLKAAL QDMLRQLDRNPGC (SEQ ID NO: 79) | 21196.74 |
| 34 | MLAEAKEDAIKELDKYGVSDYYKNLINKAKTVEGVE ALTLHILAALPTGGGGSGGGSGGGSGGGSASVPIQK VQDDTKTLIKTIVTRINDISHTQSVSSKQKVTGLDF IPGLHPILTLSKMDQTLAVYQQILTSMPSRNVIQIS NDLENLRDLLHVLAFSKSCHLPWASGLETLDSLGGV LEASGYSTEVVALSRLQGSLQDMLWQLDLSPGC (SEQ ID NO: 80) | 22546.92 |
| 35 | MLAEAKEDAIKELDKYGVSDYYKNLINKAKTVEGVE ALTLHILAALPTGGGGSGGGSGGGSGGGSASVPIQK VQDDTKTLIKTIVTRINDISHTQSVSSKQKVTGLEF IPGLHPILTLSKMDQTLAVYQQILTSMPSRNVIQIS NDLENLRDLLHVLAFSKSCHLPQASGLETLESLGGV LEASGYSTEVVALSRLQGSLQDMLQQLDLSPGC (SEQ ID NO: 81) | 22458.80 |
| 36 | MLAEAKEDAIKELDKYGVSDYYKNLINKAKTVEGVE ALTLHILAALPTGGGSGGGSGGGSGGGSASVPIQK VQDDTKTLIKTIVTRINDISHTQSVSSKQKVTGLEF IPGLHPILTLSKMDQTLAVYQQILTSMPSRNVIQIS NDLENLRDLLHVLAFSKSCHLPQASGLETLDSLGGV LEASGYSTEVVALSRLQGSLQDMLQQLDLSPGC (SEQ ID NO: 82) | 22430.75 |
| 37 | MLAEAKEDAIKELDKYGVSDYYKNLINKAKTVEGVE ALTLHILAALPTGLAEAAAKEAAAKEAAAKEAAAKE AAAKAAAASVPIQKVQDDTKTLIKTIVTRINDISHT QSVSSKQKVTGLEFIPGLHPILTLSKMDQTLAVYQQ ILTSMPSRNVIQISNDLENLRDLLHVLAFSKSCHLP QASGLETLESLGGVLEASGYSTEVVALSRLQGSLQD MLQQLDLSPGC (SEQ ID NO: 83) | 24175.99 |
| 38 | MLAEAKEDAIKELDKYGVSDYYKNLINKAKTVEGVE ALTLHILAALPTGEGGEGGEGGEGGEGGEASVPIQ KVQDDTKTLIKTIVTRINDISHTQSVSSKQKVTGLE FIPGLHPILTLSKMDQTLAVYQQILTSMPSRNVIQI SNDLENLRDLLHVLAFSKSCHLPQASGLETLESLGG VLEASGYSTEVVALSRLQGSLQDMLQQLDLSPGC (SEQ ID NO: 84) | 22828.13 |
| 39 | MLAEAKEDAIKELDKYGVSDYYKNLINKAKTVEGVE ALTLHILAALPTGGKGGKGGKGGKGGKGGKASVPIQ KVQDDTKTLIKTIVTRINDISHTQSVSSKQKVTGLE FIPGLHPILTLSKMDQTLAVYQQILTSMPSRNVIQI SNDLENLRDLLHVLAFSKSCHLPQASGLETLESLGG VLEASGYSTEVVALSRLQGSLQDMLQQLDLSPGC (SEQ ID NO: 85) | 22836.51 |
| 40 | MLAEAKEDAIKELDKYGVSDYYKNLINKAKTVEGVE ALTLHILAALPTGGGGSGGGSGGGSGGGSASVPIQK VQDDTKTLIKTIVTRINDISHTQSVSSKQKVTGLEF IPGLHPILTLSKMDQTLAVYQQILTSMPSRNVIQIS NDLENLRDLLHVLAFSKSCSLPQASGLETLESLGEV LEASGYSTEVVALSRLQGSLQDILQQLDLSPEC (SEQ ID NO: 86) | 22534.83 |
| 41 | MLAEAKEDAIKELDKYGVSDYYKNLINKAKTVEGVE ALISEILAALPTGGGGASVPIQKVQDDTKTLIKTIV TRINDISHTQSVSSKQKVTGLEFIPGLHPILTLSKM DQTLAVYQQILTSMPSRNVIQISNDLENLRDLLHVL AFSKSCHLPQASGLETLESLGGVLEASGYSTEVVAL SRLQGSLQDMLQQLDLSPGC (SEQ ID NO: 87) | 21574.96 |
| 42 | MLAEAKEDAIKELDKYGVSDYYKNLINKAKTVEGVE ALISEILAALPTGGGSGGGSGGGSGGGSASVPIQK VQDDTKTLIKTIVTRINDISHTQSVSSKQKVTGLEF IPGLHPILTLSKMDQTLAVYQQILTSMPSRNVIQIS NDLENLRDLLHVLAFSKSCHLPQASGLETLESLGGV LEASGYSTEVVALSRLQGSLQDMLQQLDLSPGC (SEQ ID NO: 88) | 22436.75 |
| 43 | MVPIQKVQDDTKTLIKTIVTRINDISHTQSVSSKQK VTGLEFIPGLHPILTLSKMDQTLAVYQQILTSMPSR NVIQISNDLENLRDLLHVLAFSKSCHLPQASGLETL ESLGGVLEASGYSTEVVALSRLQGSLQDMLQQLDLS PGCTGGGGSASLAEAKEDAIKELDKYGVSDYYKNLI NKAKTVEGVEALISEILAALP (SEQ ID NO: 89) | 21662.04 |
| 44 | MVPIQKVQDDTKTLIKTIVTRINDISHTQSVSSKQK VTGLEFIPGLHPILTLSKMDQTLAVYQQILTSMPSR NVIQISNDLENLRDLLHVLAFSKSCHLPQASGLETL ESLGGVLEASGYSTEVVALSRLQGSLQDMLQQLDLS PGCTGGGGSGGGSGGGSGGGSASLAEAKEDAIKELD KYGVSDYYKNLINKAKTVEGVEALISEILAALP (SEQ ID NO: 90) | 22436.75 |
| 45 | MLAEAKEDAIKELDKYGVSDYYKNLINKAKTVEGVE ALISEILAALPTGGGGSGGGSGGGSGGGSASISIEK IQADTKTLTKTIITRIIQLSTQNGVSTDQRVSGLDF IPGNQQFQNLADMDQTLAVYQQILSSLPMPDRTQIS NDLENLRSLFALLATLKNCPFTRSDGLDTMEIWGGI VEESLYSTEVVTLDRLRKSLKNIEKQLDHIQGC (SEQ ID NO: 91) | 22912.13 |
| 46 | MLAEAKEDAIKELDKYGVSDYYKNLINKAKTVEGVE ALISEILAALPTGGGGSGGGSGGGSGGGSASVPIQK VQDDTKTLIKTIVTRINDISHTQSVSSKQKVTGLDF IPGLHPILTLSKMDQTLAVYQQILTSMPSRNVIQIS NDLENLRDLLHVLAFSKSCHLPWASGLETLDSLGGV LEASGYSTEVVALSRLQGSLQDMLWQLDLSPGC (SEQ ID NO: 92) | 22524.86 |
| 47 | MVPIQKVQDDTKTLIKTIVTRINDISHTQSVSSKQK VTGLDFIPGLHPILTLSKMDQTLAVYQQILTSMPSR NVIQISNDLENLRDLLHVLAFSKSCHLPWASGLETL | 22524.86 |

TABLE 2-continued

Selected engineered polypeptides

| Cmpd | Sequence | MW |
|---|---|---|
| | DSLGGVLEASGYSTEVVALSRLQGSLQDMLWQLDLS<br>PGCTGGGGSGGGSGGGSGGGSASLAEAKEDAIKELD<br>KYGVSDYYKNLINKAKTVEGVEALISEILAALP<br>(SEQ ID NO: 93) | |
| 48 | MLAEAKEDAIKELDKYGVSDYYKNLINKAKTVEGVE<br>ALISEILAALPTGGGGSGGGSGGGSGGGSASPIQRV<br>QDDTKTLIKTIITRINDISPPQGVCSRPRVAGLDFI<br>PRVQSVRTLSGMDQILATYQQILTSLQSRNVIQISN<br>DLENLRDLLHVLAFSKSCPVPRARGSDTIKGLGNVL<br>RASVHSTEVVALSRLKAALQDMLRQLDRNPGC<br>(SEQ ID NO: 94) | 22521.97 |
| 49 | MLAEAKEDAIKELDKYGVSDYYKNLINKAKTVEGVE<br>ALISEILAALPTGGGGSGGGSGGGSGGGSASPIQRV<br>QDDTKTLIKTIITRINDISPPQGVSSRPRVAGLDFI<br>PRVQSVRTLSGMDQILATYQQILTSLGSRNVIQISN<br>DLENLRDLLHVLAFSKSCPVPRARGSDTIKGLGNVL<br>RASVHSTEVVALSRLKAALQDMLRQLDRNPGC<br>(SEQ ID NO: 95) | 22505.91 |
| 50 | MLAEAKEDAIKELDKYGVSDYYKNLINKAKTVEGVE<br>ALISEILAALPTGPIQRVQDDTKTLIKTIITRINDI<br>SPPQGVCSPRVAGLDFIPRVQSVRTLSGMDQILATY<br>QQILTSLQSRNVIQISNDLENLRDLLHVLAFSKSCP<br>VPRARGSDTIKGLGNVLRASVHSTEVVALSRLKAAL<br>QDMLRQLDRNPGC<br>(SEQ ID NO: 96) | 21174.68 |
| 51 | MLAEAKEDAIKELDKYGVSDYYKNLINKAKTVEGVE<br>ALISEILAALPTGGGGSGGGSGGGSGGGSASVPIQK<br>VQDDTKTLIKTIVTRINDISHTQSVSSKQKVTGLDF<br>IPGLHPILTLSKMDQTLAVYQQILTSMPSRNVIQIS<br>NDLENLRDLLHVLAFSKSCHLPWASGLETLDSLGGV<br>LEASGYSTEVVALSRLQGSLQDMLWQLDLSPGC<br>(SEQ ID NO: 97) | 22524.86 |
| 52 | MLAEAKEDAIKELDKYGVSDYYKNLINKAKTVEGVE<br>ALISEILAALPTGGGGSGGGSGGGSGGGSASVPIQK<br>VQDDTKTLIKTIVTRINDISHTQSVSSKQKVTGLEF<br>IPGLHPILTLSKMDQTLAVYQQILTSMPSRNVIQIS<br>NDLENLRDLLHVLAFSKSCHLPQASGLETLESLGGV<br>LEASGYSTEVVALSRLQGSLQDMLQQLDLSPGC<br>(SEQ ID NO: 98) | 22436.75 |
| 53 | MLAEAKEDAIKELDKYGVSDYYKNLINKAKTVEGVE<br>ALISEILAALPTGGGGSGGGSGGGSGGGSASVPIQK<br>VQDDTKTLIKTIVTRINDISHTQSVSSKQKVTGLEF<br>IPGLHPILTLSKMDQTLAVYQQILTSMPSRNVIQIS<br>NDLENLRDLLHVLAFSKSCHLPQASGLETLDSLGGV<br>LEASGYSTEVVALSRLQGSLQDMLQQLDLSPGC<br>(SEQ ID NO: 99) | 22408.70 |
| 54 | MLAEAKEDAIKELDKYGVSDYYKNLINKAKTVEGVE<br>ALISEILAALPTGLAEAAAKEAAAKEAAAKEAAAKE<br>AAAKAAAASVPIQKVQDDTKTLIKTIVTRINDISHT<br>QSVSSKQKVTGLEFIPGLHPILTLSKMDQTLAVYQQ<br>ILTSMPSRNVIQISNDLENLRDLLHVLAFSKSCHLP<br>QASGLETLESLGGVLEASGYSTEVVALSRLQGSLQD<br>MLQQLDLSPGC<br>(SEQ ID NO: 100) | 24153.93 |
| 55 | MLAEAKEDAIKELDKYGVSDYYKNLINKAKTVEGVE<br>ALISEILAALPTGGEGGEGGEGGEGGEASVPIQ<br>KVQDDTKTLIKTIVTRINDISHTQSVSSKQKVTGLE<br>FIPGLHPILTLSKMDQTLAVYQQILTSMPSRNVIQI<br>SNDLENLRDLLHVLAFSKSCHLPQASGLETLESLGG<br>VLEASGYSTEVVALSRLQGSLQDMLQQLDLSPGC<br>(SEQ ID NO: 101) | 22806.08 |
| 56 | MLAEAKEDAIKELDKYGVSDYYKNLINKAKTVEGVE<br>ALISEILAALPTGGKGGKGGKGGKGGKASVPIQ<br>KVQDDTKTLIKTIVTRINDISHTQSVSSKQKVTGLE<br>FIPGLHPILTLSKMDQTLAVYQQILTSMPSRNVIQI<br>SNDLENLRDLLHVLAFSKSCHLPQASGLETLESLGG<br>VLEASGYSTEVVALSRLQGSLQDMLQQLDLSPGC<br>(SEQ ID NO: 102) | 22800.43 |
| 58 | MLAEAKEDAIKELDKYGVSDYYKNLINKAKTVEGVE<br>ALISEILAALPTGGGGSGGGSGGGSGGGSASVPIQK<br>VQDDTKTLIKTIVTRINDISHTQSVSSKQKVTGLEF<br>IPGLHPILTLSKMDQTLAVYQQILTSMPSRNVIQIS<br>NDLENLRDLLHVLAFSKSCSLPQASGLETLESLGEV<br>LEASGYSTEVVALSRLQGSLQDILQQLDLSPEC<br>(SEQ ID NO: 103) | 22512.78 |
| 59 | MLAEAKVLANRELDKYGVSDYYKNLINKAKTVEGVE<br>ALTLHILAALPTGGGGSGGGSGGGSGGGSASVPIQK<br>VQDDTKTLIKTIVTRINDISHTQSVSSKQKVTGLEF<br>IPGLHPILTLSKMDQTLAVYQQILTSMPSRNVIQIS<br>NDLENLRDLLHVLAFSKSCHLPQASGLETLESLGGV<br>LEASGYSTEVVALSRLQGSLQDMLQQLDLSPGC<br>(SEQ ID NO: 104) | 22455.85 |
| 60 | MLAEAKEDAIKELDKYGVSDYYKRLISKAKTVEGVK<br>ALISEILAALPTGGGGSGGGSGGGSGGGSASVPIQK<br>VQDDTKTLIKTIVTRINDISHTQSVSSKQKVTGLEF<br>IPGLHPILTLSKMDQTLAVYQQILTSMPSRNVIQIS<br>NDLENLRDLLHVLAFSKSCHLPQASGLETLESLGGV<br>LEASGYSTEVVALSRLQGSLQDMLQQLDLSPGC<br>(SEQ ID NO: 105) | 22450.87 |
| 61 | MLAEAKEDAIKELDKYGVSDYYKNLINKAKTVEGVE<br>ALTLHILAALPTGGGGSGGGSGGGSGGGSASVPIQK<br>VQDDTKTLIKTIVTRINDISHTQSVSSKQKVTGLEF<br>IPGLHPILTLSKMDQTLAVYQQILTSMPSRNVIQIS<br>NDLENLRDLLHVLAFSKSCHLPQASGLETLESLGGV<br>LEASGYSTEVVALSRLQGSLQDMLQQLDLSPGC<br>(SEQ ID NO: 106) | 22458.80 |
| 62 | MLAEAKEDAIKELDKYGVSDYYKNLINKAKTVEGVE<br>ALISEILAALPTGGGGSGGGSGGGSGGGSASVPIQK<br>VQDDTKTLIKTIVTRINDISHTQSVSSKQKVTGLEF<br>IPGLHPILTLSKMDQTLAVYQQILTSMPSRNVIQIS<br>NDLENLRDLLHVLAFSKSCHLPQASGLETLESLGGV<br>LEASGYSTEVVALSRLQGSLQDMLQQLDLSPGC<br>(SEQ ID NO: 107) | 22436.75 |

Specifically contemplated are compounds of the above sequences in which the N-terminal methionine is absent, e.g. where the N-terminal commences with VPIQKV (SEQ ID NO: 158) or LAEAK (SEQ ID NO: 159) for example, for leptin compounds The N-terminal methionine is present primarily as a convenience for bacterial expression. However, conjugate peptides of the present invention can be expressed in a eukaryotic host cell (e.g. yeast (e.g. *Pichia*), mammalian, baculovirus) or other host cell having post-translational N-terminal proteolytic processing to yield an N-terminal amino acid as found in a naturally occurring mature peptide counterpart of the desired hormone or ABD sequence. Alternatively, an N-terminal sequence used for expression and/or secretion can be one that can be removed post-translationally, e.g. as by use of a protease such as TEV.

III. Methods of Design and Production

Design of Constructs.

The engineered polypeptides described herein can be designed at the amino acid level. These sequences can then be back translated using a variety of software products known in the art such that the nucleotide sequence is optimized for the desired expression host, e.g. based protein expression, codon optimization, restriction site content. For example, the nucleotide sequence can be optimized for *E.*

*coli* based protein expression and for restriction site content. Based on the nucleotide sequence of interest, overlapping oligonucleotides can be provided for multistep PCR, as known in the art. These oligonucleotides can be used in multiple PCR reactions under conditions well known in the art to build the cDNA encoding the protein of interest. For one example is 1× Amplitaq Buffer, 1.3 mM $MgCl_2$, 200 uM dNTPs, 4 U Amplitaq Gold, 0.2 uM of each primer (AmpliTaq Gold, ABI), with cycling parameters: (94C:30s, 58C:1 min, 72C:1 min), 35 cycles.

Restriction sites can be added to the ends of the PCR products for use in vector ligation as known in the art. Specific sites can include NdeI and XhoI, such that the cDNA can then be in the proper reading frame in a pET45b expression vector (Novagen). By using these sites, any N-terminal His Tag that are in this vector can be removed as the translation start site would then be downstream of the tag. Once expression constructs are completed, verification can be conduct by sequencing using e.g., T7 promoter primer, T7 terminator primer and standard ABI BigDye Term v3.1 protocols as known in the art. Sequence information can be obtained from e.g., an ABI 3730 DNA Analyzer and can be analyzed using Vector NTI v.10 software (Invitrogen). Expression constructs can be designed in a modular manner such that linker sequences can be easily cut out and changed, as known in the art.

Protease recognition sites, known in the art or described herein, can be incorporated into constructs useful for the design, construction, manipulation and production of recombinant engineering polypeptides described herein.

General Methods of Production.

The engineered polypeptides described herein may be prepared using biological, chemical, and/or recombinant DNA techniques that are known in the art. Exemplary methods are described herein and in U.S. Pat. No. 6,872,700; WO 2007/139941; WO 2007/140284; WO 2008/082274; WO 2009/011544; and US Publication No. 2007/0238669, the disclosures of which are incorporated herein by reference in their entireties and for all purposes. Other methods for preparing the compounds are set forth herein.

The engineered polypeptides described herein may be prepared using standard solid-phase peptide synthesis techniques, such as an automated or semiautomated peptide synthesizer. Typically, using such techniques, an alpha-N-carbamoyl protected amino acid and an amino acid attached to the growing peptide chain on a resin are coupled at RT in an inert solvent (e.g., dimethylformamide, N-methylpyrrolidinone, methylene chloride, and the like) in the presence of coupling agents (e.g., dicyclohexylcarbodiimide, 1-hydroxybenzo-triazole, and the like) in the presence of a base (e.g., diisopropylethylamine, and the like). The alpha-N-carbamoyl protecting group is removed from the resulting peptide-resin using a reagent (e.g., trifluoroacetic acid, piperidine, and the like) and the coupling reaction repeated with the next desired N-protected amino acid to be added to the peptide chain. Suitable N-protecting groups are well known in the art, such as t-butyloxycarbonyl (tBoc) fluorenylmethoxycarbonyl (Fmoc), and the like. The solvents, amino acid derivatives and 4-methylbenzhydryl-amine resin used in the peptide synthesizer may be purchased from Applied Biosystems Inc. (Foster City, Calif.).

For chemical synthesis solid phase peptide synthesis can be used for the engineered polypeptides, since in general solid phase synthesis is a straightforward approach with excellent scalability to commercial scale, and is generally compatible with relatively long engineered polypeptides. Solid phase peptide synthesis may be carried out with an automatic peptide synthesizer (Model 430A, Applied Biosystems Inc., Foster City, Calif.) using the NMP/HOBt (Option 1) system and tBoc or Fmoc chemistry (See Applied Biosystems User's Manual for the ABI 430A Peptide Synthesizer, Version 1.3B Jul. 1, 1988, section 6, pp. 49-70, Applied Biosystems, Inc., Foster City, Calif.) with capping. Boc-peptide-resins may be cleaved with HF (−5° C. to 0° C., 1 hour). The peptide may be extracted from the resin with alternating water and acetic acid, and the filtrates lyophilized. The Fmoc-peptide resins may be cleaved according to standard methods (e.g., Introduction to Cleavage Techniques, Applied Biosystems, Inc., 1990, pp. 6-12). Peptides may also be assembled using an Advanced Chem Tech Synthesizer (Model MPS 350, Louisville, Ky.).

The compounds described herein may also be prepared using recombinant DNA techniques using methods known in the art, such as Sambrook et al., 1989, MOLECULAR CLONING: A LABORATORY MANUAL, 2d Ed., Cold Spring Harbor. Non-peptide compounds may be prepared by art-known methods. For example, phosphate-containing amino acids and peptides containing such amino acids, may be prepared using methods known in the art, such as described in Bartlett et al, 1986, *Biorg. Chem.* 14:356-377.

The engineered polypeptides may alternatively be produced by recombinant techniques well known in the art. See, e.g., Sambrook et al., 1989 (Id.). These engineered polypeptides produced by recombinant technologies may be expressed from a polynucleotide. One skilled in the art will appreciate that the polynucleotides, including DNA and RNA, that encode such engineered polypeptides may be obtained from the wild-type cDNA, e.g. human leptin, taking into consideration the degeneracy of codon usage, and may further engineered as desired to incorporate the indicated substitutions. These polynucleotide sequences may incorporate codons facilitating transcription and translation of mRNA in microbial hosts. Such manufacturing sequences may readily be constructed according to the methods well known in the art. See, e.g., WO 83/04053, incorporated herein by reference in its entirety and for all purposes. The polynucleotides above may also optionally encode an N-terminal methionyl residue. Non-peptide compounds useful in the present invention may be prepared by art-known methods. For example, phosphate-containing amino acids and peptides containing such amino acids may be prepared using methods known in the art. See, e.g., Bartlett and Landen, 1986, *Bioorg. Chem.* 14: 356-77.

A variety of expression vector/host systems may be utilized to contain and express a engineered polypeptide coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems. Mammalian cells that are useful in recombinant protein productions include but are not limited to VERO cells, HeLa cells, Chinese hamster ovary (CHO) cell lines, COS cells (such as COS-7), WI 38, BHK, HepG2, 3T3, RIN, MDCK, A549, PC12, K562 and 293 cells. Exemplary protocols for the recombinant expression of the protein are described herein and/or are known in the art.

As such, polynucleotide sequences are useful in generating new and useful viral and plasmid DNA vectors, new and useful transformed and transfected prokaryotic and eukaryotic host cells (including bacterial, yeast, and mammalian cells grown in culture), and new and useful methods for cultured growth of such host cells capable of expression of the present engineered polypeptides. The polynucleotide sequences encoding engineered polypeptides herein may be useful for gene therapy in instances where underproduction of engineered polypeptides would be alleviated, or the need for increased levels of such would be met.

The present invention also provides for processes for recombinant DNA production of the present engineered polypeptides. Provided is a process for producing the engineered polypeptides from a host cell containing nucleic acids encoding the engineered polypeptide comprising: (a) culturing the host cell containing polynucleotides encoding the engineered polypeptide under conditions facilitating the expression of the DNA molecule; and (b) obtaining the engineered polypeptide.

Host cells may be prokaryotic or eukaryotic and include bacteria, mammalian cells (such as Chinese Hamster Ovary (CHO) cells, monkey cells, baby hamster kidney cells, cancer cells or other cells), yeast cells, and insect cells.

Mammalian host systems for the expression of the recombinant protein also are well known to those of skill in the art. Host cell strains may be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Post-translational processing, which cleaves a "prepro" form of the protein, may also be important for correct insertion, folding and/or function. Different host cells, such as CHO, HeLa, MDCK, 293, W138, and the like, have specific cellular machinery and characteristic mechanisms for such post-translational activities, and may be chosen to ensure the correct modification and processing of the introduced foreign protein.

Alternatively, a yeast system may be employed to generate the engineered polypeptides of the present invention. The coding region of the engineered polypeptides DNA is amplified by PCR. A DNA encoding the yeast pre-pro-alpha leader sequence is amplified from yeast genomic DNA in a PCR reaction using one primer containing nucleotides 1-20 of the alpha mating factor gene and another primer complementary to nucleotides 255-235 of this gene (Kurjan and Herskowitz, 1982, Cell, 30:933-43). The pre-pro-alpha leader coding sequence and engineered polypeptide coding sequence fragments are ligated into a plasmid containing the yeast alcohol dehydrogenase (ADH2) promoter, such that the promoter directs expression of a fusion protein consisting of the pre-pro-alpha factor fused to the mature engineered polypeptide. As taught by Rose and Broach, Meth. Enz. 185: 234-79, Goeddel ed., Academic Press, Inc., San Diego, Calif. (1990), the vector further includes an ADH2 transcription terminator downstream of the cloning site, the yeast "2-micron" replication origin, the yeast leu-2d gene, the yeast REP1 and REP2 genes, the E. coli beta-lactamase gene, and an E. coli origin of replication. The beta-lactamase and leu-2d genes provide for selection in bacteria and yeast, respectively. The leu-2d gene also facilitates increased copy number of the plasmid in yeast to induce higher levels of expression. The REP1 and REP2 genes encode proteins involved in regulation of the plasmid copy number.

The DNA construct described in the preceding paragraph is transformed into yeast cells using a known method, e.g., lithium acetate treatment (Stearns et al., 1990. Meth. Enz. 185: 280-297). The ADH2 promoter is induced upon exhaustion of glucose in the growth media (Price et al., 1987, Gene 55:287). The pre-pro-alpha sequence effects secretion of the fusion protein from the cells. Concomitantly, the yeast KEX2 protein cleaves the pre-pro sequence from the mature engineered polypeptides (Bitter et al., 1984, Proc. Natl. Acad. Sci. USA 81:5330-5334).

Engineered polypeptides of the invention may also be recombinantly expressed in yeast, e.g., Pichia, using a commercially available expression system, e.g., the Pichia Expression System (Invitrogen, San Diego, Calif.), following the manufacturer's instructions. This system also relies on the pre-pro-alpha sequence to direct secretion, but transcription of the insert is driven by the alcohol oxidase (AOX1) promoter upon induction by methanol. The secreted engineered polypeptide is purified from the yeast growth medium by, e.g., the methods used to purify said engineered polypeptide from bacterial and mammalian cell supernatants.

Alternatively, the DNA encoding a engineered polypeptide may be cloned into a baculovirus expression vector, e.g. pVL1393 (PharMingen, San Diego, Calif.). This engineered-polypeptide-encoding vector is then used according to the manufacturer's directions (PharMingen) or known techniques to infect Spodoptera frugiperda cells, grown for example in sF9 protein-free media, and to produce recombinant protein. The protein is purified and concentrated from the media using methods known in the art, e.g. a heparin-Sepharose column (Pharmacia, Piscataway, N.J.) and sequential molecular sizing columns (Amicon, Beverly, Mass.), and resuspended in appropriate solution, e.g. PBS. SDS-PAGE analysis can be used to characterize the protein, for example by showing a single band that confirms the size of the desired engineered polypeptide, as can full amino acid amino acid sequence analysis, e.g. Edman sequencing on a Proton 2090 Peptide Sequencer, or confirmation of its N-terminal sequence.

For example, the DNA sequence encoding the predicted mature engineered polypeptide may be cloned into a plasmid containing a desired promoter and, optionally, a leader sequence (see, e.g., Better et al., 1988, Science 240:1041-1043). The sequence of this construct may be confirmed by automated sequencing. The plasmid is then transformed into E. coli, strain MC1061, using standard procedures employing CaCl2 incubation and heat shock treatment of the bacteria (Sambrook et al., Id.). The transformed bacteria are grown in LB medium supplemented with carbenicillin, and production of the expressed protein is induced by growth in a suitable medium. If present, the leader sequence will affect secretion of the mature engineered polypeptide and be cleaved during secretion. The secreted recombinant engineered polypeptide is purified from the bacterial culture media by the method described herein.

Alternatively, the engineered polypeptides may be expressed in an insect system. Insect systems for protein expression are well known to those of skill in the art. In one such system, Autographa californica nuclear polyhedrosis virus (AcNPV) is used as a vector to express foreign genes in Spodoptera frugiperda cells or in Trichoplusia larvae. The engineered polypeptide coding sequence is cloned into a nonessential region of the virus, such as the polyhedrin gene, and placed under control of the polyhedrin promoter. Successful insertion of a engineered polypeptide will render the polyhedrin gene inactive and produce recombinant virus lacking coat protein coat. The recombinant viruses are then used to infect S. frugiperda cells or Trichoplusia larvae in which engineered polypeptide of the present invention is expressed (Smith et al., 1983, J. Virol. 46:584; Engelhard et al., 1994, Proc. Natl. Acad. Sci. USA 91:3224-3227).

In another example, the DNA sequence encoding the engineered polypeptides may be amplified by PCR and cloned into an appropriate vector, for example, pGEX-3X (Pharmacia, Piscataway, N.J.). The pGEX vector is designed to produce a fusion protein comprising glutathione-S-transferase (GST), encoded by the vector, and a protein encoded by a DNA fragment inserted into the vector's cloning site. The primers for the PCR may be generated to include, for example, an appropriate cleavage site. The recombinant fusion protein may then be cleaved from the GST portion of the fusion protein. The pGEX-3x/engineered polypeptide construct is transformed into E. coli XL-1 Blue cells (Stratagene, La Jolla, Calif.), and individual transformants are isolated and grown at 37° C. in LB medium (supplemented with carbenicillin) to an optical density at wavelength 600 nm of 0.4, followed by further incubation for 4 hours in the presence of 0.5 mM Isopropyl beta-D-thiogalactopyranoside (Sigma Chemical Co., St. Louis, Mo.). Plasmid DNA from individual transformants is purified and partially sequenced using an automated sequencer to confirm the presence of the desired engineered polypeptide-encoding gene insert in the proper orientation.

The fusion protein, when expected to be produced as an insoluble inclusion body in the bacteria, may be purified as described above or as follows. Cells are harvested by centrifugation; washed in 0.15 M NaCl, 10 mM Tris, pH 8, 1 mM EDTA; and treated with 0.1 mg/mL lysozyme (Sigma Chemical Co.) for 15 min. at RT. The lysate is cleared by sonication, and cell debris is pelleted by centrifugation for 10 min. at 12,000×g. The fusion protein-containing pellet is resuspended in 50 mM Tris, pH 8, and 10 mM EDTA, layered over 50% glycerol, and centrifuged for 30 min. at 6000×g. The pellet is resuspended in standard phosphate buffered saline solution (PBS) free of Mg++ and Ca++. The fusion protein is further purified by fractionating the resuspended pellet in a denaturing SDS polyacrylamide gel (Sambrook et al., supra). The gel is soaked in 0.4 M KCl to visualize the protein, which is excised and electroeluted in gel-running buffer lacking SDS. If the GST/engineered polypeptide fusion protein is produced in bacteria as a soluble protein, it may be purified using the GST Purification Module (Pharmacia Biotech).

The fusion protein may be subjected to digestion to cleave the GST from the mature engineered polypeptide. The digestion reaction (20-40 μg fusion protein, 20-30 units human thrombin (4000 U/mg (Sigma) in 0.5 mL PBS) is incubated 16-48 hrs. at RT and loaded on a denaturing SDS-PAGE gel to fractionate the reaction products. The gel is soaked in 0.4 M KCl to visualize the protein bands. The identity of the protein band corresponding to the expected molecular weight of the engineered polypeptide may be confirmed by partial amino acid sequence analysis using an automated sequencer (Applied Biosystems Model 473A, Foster City, Calif.).

In a particularly exemplary method of recombinant expression of the engineered polypeptides of the present invention, 293 cells may be co-transfected with plasmids containing the engineered polypeptides cDNA in the pCMV vector (5' CMV promoter, 3' HGH poly A sequence) and pSV2neo (containing the neo resistance gene) by the calcium phosphate method. In one embodiment, the vectors should be linearized with ScaI prior to transfection. Similarly, an alternative construct using a similar pCMV vector with the neo gene incorporated can be used. Stable cell lines are selected from single cell clones by limiting dilution in growth media containing 0.5 mg/mL G418 (neomycin-like antibiotic) for 10-14 days. Cell lines are screened for engineered polypeptides expression by ELISA or Western blot, and high-expressing cell lines are expanded for large scale growth.

It is preferable that the transformed cells are used for long-term, high-yield protein production and as such stable expression is desirable. Once such cells are transformed with vectors that contain selectable markers along with the desired expression cassette, the cells may be allowed to grow for 1-2 days in an enriched media before they are switched to selective media. The selectable marker is designed to confer resistance to selection, and its presence allows growth and recovery of cells that successfully express the introduced sequences. Resistant clumps of stably transformed cells can be proliferated using tissue culture techniques appropriate to the cell.

A number of selection systems may be used to recover the cells that have been transformed for recombinant protein production. Such selection systems include, but are not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for dhfr, that confers resistance to methotrexate; gpt, that confers resistance to mycophenolic acid; neo, that confers resistance to the aminoglycoside, G418; also, that confers resistance to chlorsulfuron; and hygro, that confers resistance to hygromycin. Additional selectable genes that may be useful include trpB, which allows cells to utilize indole in place of tryptophan, or hisD, which allows cells to utilize histinol in place of histidine. Markers that give a visual indication for identification of transformants include anthocyanins, beta-glucuronidase and its substrate, GUS, and luciferase and its substrate, luciferin.

The engineered polypeptides of the present invention may be produced using a combination of both automated peptide synthesis and recombinant techniques. For example, either or both of: the leptin; a leptin analog, a active leptin fragment, or leptin derivative; and an ABD; and optionally a linker; employed in the preparation of the engineered polypeptides as disclosed herein can be made synthetically or recombinantly and then ligated together using methods known in the art, such as "native chemical ligation" and known variations thereof in which an amide bond is formed joining the parent compounds. See for example U.S. Pat. No. 6,326,468, which is incorporated herein by reference for al purposes. Alternatively, for example, an engineered polypeptide of the present invention may contain a combination of modifications including deletion, substitution, insertion and derivatization by PEGylation (or other moiety, e.g. polymer, fatty acyl chain, C-terminal amidation). Such a engineered polypeptide may be produced in stages. In the first stage, an intermediate engineered polypeptide containing the modifications of deletion, substitution, insertion, and any combination thereof, may be produced by recombinant techniques as described. Then after an optional purification step as described herein, the intermediate engineered polypeptide is PEGylated (or subjected to other chemical derivatization, e.g., acylation, C-terminal amidation) through chemical modification with an appropriate PEGylating reagent (e.g., from NeKtar Transforming Therapeutics, San Carlos, Calif.) to yield the desired engineered polypeptide derivative. One skilled in the art will appreciate that the above-described procedure may be generalized to apply to a engineered polypeptide containing a combination of modifications selected from deletion, substitution, insertion, derivation, and other means of modification well known in the art and contemplated by the present invention.

C-terminal amidation can be achieved by use of a glycine amino acid-C-terminally extended precursor, synthesized for example in yeast (e.g. *Pichia*) as alpha-factor fusion protein that will be secreted into culture medium. After purification, the C-terminal glycine of the engineered polypeptide precursor can be converted to amide by enzymatic amidation, e.g. peptidylglycine alpha-amidating monooxygenase (PAM). See e.g., Cooper et al., 1989, *Biochem. Biophys. Acta,* 1014:247-258. See also U.S. Pat. No. 6,319,685, which is incorporated herein by reference in its entirety and for all purposes, which teaches methods for enzymatic amidation, including an alpha-amidating enzyme from rat being sufficiently pure in alpha-amidating enzyme to exhibit a specific activity of at least about 25 mU per mg of protein, and being sufficiently free of proteolytic impurities to be suitable for use with substrates purified from natural sources or produced by recombinant DNA techniques.

Peptides may be purified by any number of methods known in the art, including as described herein In one method peptides are purified by RP-HPLC (preparative and analytical) using a Waters Delta Prep 3000 system. A C4, C8 or C18 preparative column (10μ, 2.2×25 cm; Vydac, Hesperia, Calif.) may be used to isolate peptides, and purity may be determined using a C4, C8 or C18 analytical column (5μ, 0.46×25 cm; Vydac). Solvents (A=0.1% TFA/water and B=0.1% TFA/CH$_3$CN) may be delivered to the analytical column at a flow rate of 1.0 ml/min and to the preparative column at 15 ml/min. Amino acid analyses may be performed on the Waters Pico Tag system and processed using the Maxima program. Peptides may be hydrolyzed by vapor-phase acid hydrolysis (115° C., 20-24 h). Hydrolysates may be derivatized and analyzed by standard methods (Cohen et al, THE PICO TAG METHOD: A MANUAL OF ADVANCED TECHNIQUES FOR AMINO ACID ANALYSIS, pp. 11-52, Millipore Corporation, Milford, Mass. (1989)). Fast atom bombardment analysis may be carried out by M-Scan, Incorporated (West Chester, Pa.). Mass calibration may be performed using cesium iodide or cesium iodide/glycerol. Plasma desorption ionization analysis using time of flight detection may be carried out on an Applied Biosystems Bio-Ion 20 mass spectrometer.

Engineered Polypeptide Expression Assay.

Methods are available for assaying the level of protein expression by a host cell. Procedures useful for assaying the level of protein expression by a host cell are exemplified in the following typical protocol. About 25 μl BL21 *E. coli* cells are transformed with 2 ul plasmid DNA (expression vector for the engineered polynucleotide). Cells can be plated and incubated overnight at 37 degrees C. or at room temperature (RT) over a 48-hr period. A single colony can be selected and used to grow starter culture in 4 ml LB media with appropriate antibiotic for ~6 hrs. Glycerol stocks can be prepared by adding 100 ul 80% sterile glycerol to 900 ul stock, which can then be mixed gently and stored at −80C. A 250 μl sample can be removed for TCP uninduced sample. An aliquot, for example, 2 ml of Magic media containing appropriate antibiotic can be inoculated with 5 μl starter culture, which can then be incubated overnight (up to 24 hrs) at 37C, 300 rpm. As known in the art, Magic Media is autoinducing. Alternatively, 60 ml Magic Media containing appropriate antibiotic can be inoculated with 60 μl starter culture in a 250 ml or 125 ml Thompson flask, which can then be incubated overnight (up to 24 hrs) at 30C, 300 rpm. After incubation, 250 μl culture can be removed from each tube and the cells pelleted. The cell can be resuspended in 1 ml 50 mM Tris pH 8, 150 mM NaCl, to which can be added 0.1 volumes (100 ul) POP culture reagent and 1 μl r-lysozyme (1:750 dilution in r-lysozyme buffer). The mixture can be mixed well and incubated at least 10 min at RT. The preparation can then be centrifuge 10 min at 14000×G. The supernatant (soluble fraction) can be removed and retained, and samples can be prepared for gel analysis (15 μl+5 μl LDS). The remaining inclusion body pellet can be resuspended in 1 ml 1% SDS with sonication. The sample can be prepared for gel analysis (15 ul+5 μl LDS). For uninduced samples, 1.0 volumes POP culture reagent and 1 μl r-lysozyme (1:750 dilution in r-lysozyme buffer) can be added. The mixture can be mixed well and incubated at least 10 min at RT. These samples may not need to be centrifuged. The sample can then be prepared for gel analysis (15 μl+5 μl LDS). NU-PAGE gels (4-12%) non-reduced in 1XMES buffer can be run and stained with SimplyBlue microwave protocol. Destaining can be conducted overnight, as known in the art. A gel image can be retained, and analyzed to determine protein expression levels.

Inclusion Body Preparation.

For engineered polypeptides that are found in the inclusion body fraction, the following procedure can be beneficial. The cell pellet can be resuspended in a minimum of 100 ml Lysis buffer for each 50 ml culture. Upon the addition of 30 ml, a 10 ml pipette can be used to resuspend, then the tube can be washed out with an additional 70 ml. The resuspended cell solution can be multiply run, e.g., 4 passes, through a microfluidizer at 100 PSI (min) taking care to keep chamber in ice water through the entire process. The fluidized slurry can be centrifuged at 14000×g, 20 min (e.g., JLA 10.5, 10,000 rpm, using 250 ml Nalgene® bottles). The inclusion body pellet can be resuspended on ice in chilled lysis buffer with stir bar and stir plate for 1 hour at 4C after disruption with pipette tip. The pellet can be resuspended a second time in distilled H$_2$O with stir bar and stir plate for 1 hour at 4C after disruption with pipette tip, followed by centrifugation at 14000×g, 15 min. The supernatant can be removed and discarded. The resultant can be stored at −80C.

Protein Purification.

As described herein, numerous methods are known for isolation of expressed polypeptides. The following is one example. Inclusion body pellets can be solubilized in appropriate volume of solubilization buffer (8M urea or 8M guanidine, 50 mM Tris, 10 mM DTT, pH 7.75) for 1 hour at RT. The solubilized pellets can be centrifuged for 20 min at 27 000 g. Filtered (e.g., 0.4 um) supernatant can be transferred drop by drop into appropriate volume of refolding buffer (50 mM Tris-HCl, 1 M urea, 0.8 M arginine, 4 mM cysteine, 1 mM cystamine; pH 8) at RT. The result can then be placed at 4° C. overnight or longer with gentle mixing. Samples can be concentrated and run on a gel filtration column (Superdex™ 75 26/60) at 1-2 ml/min in 4C environment using a GE Healthsciences AKTAFPLC™. Appropriate protein containing fractions can be identified via SDS-PAGE, pooled and run through a second gel filtration column. Pooled protein can then be concentrated in Amicon filter to appropriate concentration and assayed for endotoxin levels using, e.g., Endosafe® PTS Reader (Charles River), as known in the art. Once a protein sample has passed the endotoxin criteria, it can be sterile filtered, dispensed into aliquots and run through quality control assays. Quality control assays can include analytical HPLC-SEC, non reducing SDS PAGE and RP HPLC-MS to obtain approximate mass. Proteins can be obtained in 1×PBS (137 mM sodium chloride, 2.7 mM potassium chloride, 4.3 mM disodium phosphate, 1.4 mM monopotassium phosphate, pH7.2), distributed into aliquots and flash frozen for storage at −70 to −80° C.

IV. Methods of Use and Treating Disease

Indications.

A variety of diseases and disorders are contemplated to be beneficially treated by the polypeptide compounds and methods described herein.

Obesity and Overweight.

Obesity and its associated disorders including overweight are common and serious public health problems in the United States and throughout the world. Upper body obesity is the strongest risk factor known for type 2 diabetes mellitus and is a strong risk factor for cardiovascular disease. Obesity is a recognized risk factor for hypertension, atherosclerosis, congestive heart failure, stroke, gallbladder disease, osteoarthritis, sleep apnea, reproductive disorders such as polycystic ovarian syndrome, cancers of the breast, prostate, and colon, and increased incidence of complications of general anesthesia. See, e.g., Kopelman, 2000, *Nature* 404:635-43.

Obesity reduces life-span and carries a serious risk of the co-morbidities listed above, as well disorders such as infections, varicose veins, acanthosis nigricans, eczema, exercise intolerance, insulin resistance, hypertension hypercholesterolemia, cholelithiasis, orthopedic injury, and thromboembolic disease. See e.g., Rissanen et al, 1990, *Br. Med. J.,* 301:835-7. Obesity is also a risk factor for the group of conditions called insulin resistance syndrome, or "Syndrome X" and metabolic syndrome. The worldwide medical cost of obesity and associated disorders is enormous.

The pathogenesis of obesity is believed to be multifactoral. A problem is that, in obese subjects, nutrient availability and energy expenditure do not come into balance until there is excess adipose tissue. The central nervous system (CNS) controls energy balance and coordinates a variety of behavioral, autonomic and endocrine activities appropriate to the metabolic status of the animal. The mechanisms or systems that control these activities are broadly distributed across the forebrain (e.g., hypothalamus), hindbrain (e.g., brainstem), and spinal cord. Ultimately, metabolic (i.e., fuel availability) and cognitive (i.e., learned preferences) information from these systems is integrated and the decision to engage in appetitive (food seeking) and consummatory (ingestion) behaviors is either turned on (meal procurement and initiation) or turned off (meal termination). The hypothalamus is thought to be principally responsible for integrating these signals and then issuing commands to the brainstem. Brainstem nuclei that control the elements of the consummatory motor control system (e.g., muscles responsible for chewing and swallowing). As such, these CNS nuclei have literally been referred to as constituting the "final common pathway" for ingestive behavior.

Neuroanatomical and pharmacological evidence support that signals of energy and nutritional homeostasis integrate in forebrain nuclei and that the consummatory motor control system resides in brainstem nuclei, probably in regions surrounding the trigeminal motor nucleus. There are extensive reciprocal connection between the hypothalamus and brainstem. A variety of CNS-directed anti-obesity therapeutics (e.g., small molecules and peptides) focus predominantly upon forebrain substrates residing in the hypothalamus and/or upon hindbrain substrates residing in the brainstem.

Obesity remains a poorly treatable, chronic, essentially intractable metabolic disorder. Accordingly, a need exists for new therapies useful in weight reduction and/or weight maintenance in a subject. Such therapies would lead to a profound beneficial effect on the subject's health. Methods and therapies employing the engineered peptides disclosed herein, either alone or in combination with other anti-obesity agents (see, e.g., WO 2009064298 and US 20080207512 may provide such beneficial effects.

Leptin Deficiency.

Leptin deficiency has been shown to result in obesity. One form of leptin deficiency is congenital leptin deficiency, a rare genetic disorder. See Montague et al., 1997, *Nature* 387: 903-908. Severe leptin deficiency can be a result of uncontrolled insulin-deficient diabetes mellitus that results from destruction of insulin-secreting β-cells. It is theorized that the lack of insulin leads to synthesis and storage of triglycerides in adipose tissue, which prevents weight gain and in turn dramatically reduces plasma leptin levels since leptin is synthesized in adipose tissue. These and other Leptin deficiencies, and disease and disorders that result from such deficiencies, can be treated with leptin replacement therapy, such as via daily leptin or leptin agonist injections. The engineered polypeptides described herein can provide a more convenient and advantageous therapeutic treatment of such diseases and disorders.

Diabetes and Cardiovascular Disease.

Diabetes mellitus is recognized as a complex, chronic disease in which 60% to 70% of all case fatalities among diabetic patients are a result of cardiovascular complications. Diabetes is not only considered a coronary heart disease risk equivalent but is also identified as an independent predictor of adverse events, including recurrent myocardial infarction, congestive heart failure, and death following a cardiovascular incident. The adoption of tighter glucose control and aggressive treatment for cardiovascular risk factors would be expected to reduce the risk of coronary heart disease complications and improve overall survival among diabetic patients. Yet, diabetic patients are two to three times more likely to experience an acute myocardial infarction than non-diabetic patients, and diabetic patients live eight to thirteen years less than non-diabetic patients.

Understanding the high risk nature of diabetic/acute myocardial infarction patients, the American College of Cardiology/American Heart Association ("ACC/AHA") clinical practice guidelines for the management of hospitalized patients with unstable angina or non-ST-elevation myocardial infarction (collectively referred to as "ACS") recently recognized that hospitalized diabetic patients are a special population requiring aggressive management of hyperglycemia. Specifically, the guidelines state that glucose-lowering therapy for hospitalized diabetic/ACS patients should be targeted to achieve preprandial glucose less than 10 mg/dL, a maximum daily target than 180 mg/dL, and a post-discharge hemoglobin A1c less than 7%.

In a nationwide sample of elderly ACS patients, it was demonstrated that an increase in 30-day mortality in diabetic patients corresponded with the patients having higher glucose values upon admission to the hospital. See "Diabetic Coronary Artery Disease & Intervention," *Coronary Therapeutics* 2002, Oak Brook, Ill., Sep. 20, 2002. There is increasing evidence that sustained hyperglycemia rather than transient elevated glucose upon hospital admission is related to serious adverse events. Although the ideal metric for hyperglycemia and vascular risk in patients is not readily known, it appears that the mean glucose value during hospitalization is most predictive of mortality. In a separate study of ACS patients form over forty hospitals in the United States, it was found that persistent hyperglycemia, as opposed to random glucose values upon admission to the hospital, was more predictive of in-hospital mortality. See *Acute Coronary Syndrome Summit: A State of the Art*

Approach, Kansas City, Mo., Sep. 21, 2002. Compared with glucose values upon admission, a logistic regression model of glucose control over the entire hospitalization was most predictive of mortality. There was nearly a two-fold increased risk of mortality during hospitalization for each 10 mg/dL increase in glucose over 120 mg/dL. In a smaller cohort of consecutive diabetic/ACS patients, there was a graded increase in mortality at one year with increasing glucose levels upon hospital admission. In the hospital setting, the ACC/AHA guidelines suggest initiation of aggressive insulin therapy to achieve lower blood glucose during hospitalization.

It has been reported that leptin can have direct benefit to treating diabetes, particularly in type I diabetes and type II diabetes, with or without the presence of obesity, and more particularly in conditions of low serum leptin. It has been reported that leptin replenishment reduced or prevented hyperinsulinemia, insulin resistance and hyperglycemia in various animal models of diabetes type 1 and 2 with or without attendant obesity. For example, high leptin plasma levels generated either by pharmacological administration of leptin or with adenoviral gene therapy reduced hyperglycemia and associated increases of plasma glucagon levels in STZ-induced diabetes, despite persistently low insulin levels.

Lipid Regulation Diseases.

As known in the art, lipodystrophy is characterized by abnormal or degenerative conditions of the body's adipose tissue. Dyslipidemia is a disruption in the normal lipid component in the blood. It is believed that prolonged elevation of insulin levels can lead to dyslipidemia. Hyperlipidemia is the presence of raised or abnormal levels of lipids and/or lipoproteins in the blood. Hypothalamic amenorrhea is a condition in which menstruation stops for several months due to a problem involving the hypothalamus. It has been found that leptin replacement therapy in women with hypothalamic amenorrhea improves reproductive, thyroid, and growth hormone axes and markers of bone formation without causing adverse effects. See e.g., Oral et al., *N Engl J Med.* 2004, 351: 959-962, 987-997. Fatty liver disease, e.g., nonalcoholic fatty liver disease (NAFLD) refers to a wide spectrum of liver disease ranging from simple fatty liver (steatosis), to nonalcoholic steatohepatitis (NASH), to cirrhosis (irreversible, advanced scarring of the liver). All of the stages of NAFLD have in common the accumulation of fat (fatty infiltration) in the liver cells (hepatocytes). It is believed that leptin is one of the key regulators for inflammation and progression of fibrosis in various chronic liver diseases including NASH. See e.g., Ikejima et al., *Hepatology Res.* 33:151-154.

Additionally, without wishing to be bound by any theory, it is believed that relative insulin deficiency in type 2 diabetes, glucose toxicity, and increased hepatic free fatty acid burden through elevated delivery from intra-abdominal adipose tissue via the portal vein, are implicated as possible causes in fatty liver disorders. Indeed, it has been hypothesized that eating behavior is the key factor driving the metabolic syndrome of obesity with its many corollaries, including NASH. Accordingly, treatments aimed at decreasing food intake and increasing the number of small meals, as has already been demonstrated in type 2 diabetes, may effectively treat and prevent NASH. Drugs that promote insulin secretion and weight loss, and delay gastric emptying are also effective at improving glucose tolerance and thus may improve fatty liver with its attendant hyperinsulinemia. Thus, use of a leptin, leptin analog, e.g., metreleptin, or an active fragment thereof, can be well suited as a treatment modality for this condition. Accordingly, engineered polypeptides described herein which include a leptin, leptin analog or an active fragment thereof, can be useful in the treatment of fatty liver disorders.

Alzheimer's Disease.

Alzheimer's disease (AD), as known in the art, is associated with plaques and tangles in the brain which include dysregulation of the A-beta protein. It is believed that brain lipids are intricately involved in A-beta-related pathogenic pathways, and that an important modulator of lipid homeostasis is leptin. Accordingly, leptin can modulate bidirectional A-beta kinesis, reducing its levels extracellularly. Indeed, it has been demonstrated that chronic administration of leptin to AD-transgenic animals reduced the brain A-beta load, underlying its therapeutic potential. See Fewlass et al., 2004, *FASEB J.*, 18:1870-1878. Additionally, type 2 diabetes mellitus and AD share epidemiological and biochemical features in that both are characterized by insoluble protein aggregates with a fibrillar conformation—amylin in type 2 DM pancreatic islets, and Aβ in AD brain. Without wishing to be bound by any theory, it is believed that similar toxic mechanisms may characterize type-2 DM and AD. See Lim et al., *FEBS Lett.*, 582:2188-2194.

Metabolic Syndrome X.

Metabolic Syndrome X is characterized by insulin resistance, dyslipidemia, hypertension, and visceral distribution of adipose tissue, and plays a pivotal role in the pathophysiology of type 2 diabetes. It has also been found to be strongly correlated with NASH, fibrosis, and cirrhosis of the liver. Accordingly, engineered polypeptides described herein can be useful in the treatment of metabolic syndrome X.

Huntington's Disease.

Huntington's Disease is an autosomal dominant, neurogenerative disease. Features of the disease include motor disturbances, dementia, psychiatric problems, and unintended weight loss. Chimeric polypeptides described herein can be useful in the treatment of Huntington's Disease.

Accordingly, in one aspect, there is provided a method for treating a disease or disorder in a subject. The subject is in need of treatment for the disease or disorder. The disease or disorder can be lipodystrophy, dyslipidemia, hyperlipidemia, overweight, obesity, hypothalamic amenorrhea, Alzheimer's disease, leptin deficiency, fatty liver disease or diabetes (including type I and type II). Additional diseases and disorders which can be treated by the compounds and methods described herein include nonalcoholic steatohepatitis (NASH) and nonalcoholic fatty liver disease (NAFLD), metabolic syndrome X and Huntington's Disease. The method of treatment includes administration to the subject of a engineered polypeptide as described herein in an amount effective to treatment the disease or disorder. The engineered polypeptide will include as HD1a leptin, a leptin fragment or a leptin analog. Accordingly, the engineered polypeptide can have one of the following structures: ABD-HD1, HD1-ABD, ABD-L1-HD1 or HD1-L1-ABD.

In all of the treatment embodiments described herein, the leptin can be human leptin or metreleptin. In some embodiments, the leptin analog has at least 50%, for example, 50%, 55%, 60%, 65%, 70%, 75%, 80%, 85%, 90%, 95%, 98% or even higher, identity with human leptin. In some embodiments, the leptin analog has at least 50%, for example, 50%, 55%, 60%, 65%, 70%, 75%, 80%, 85%, 90%, 95%, 98% or even higher, identity with mouse leptin. In some embodiments, the leptin analog has at least 50%, for example, 50%, 55%, 60%, 65%, 70%, 75%, 80%, 85%, 90%, 95%, 98% or even higher, identity with rat leptin. In some embodiments, the leptin analog has at least 50%, for example, 50%, 55%, 60%, 65%, 70%, 75%, 80%, 85%, 90%, 95%, 98% or even higher, identity with platypus leptin. In some embodiments, the leptin analog has at least 50%, for example, 50%, 55%, 60%, 65%, 70%, 75%, 80%, 85%, 90%, 95%, 98% or even higher, identity with seal leptin. In some embodiments, the leptin analog is leptin A100, A300 or A500.

V. Assays

Methods for production and assay of engineered polypeptides described herein are generally available to the skilled artisan. Further, specific methods are described herein as well as in the patent publications and other references cited herein, which are incorporated by reference for this additional purpose.

Food Intake.

Without wishing to be bound by any theory, it is believed that food intake is useful in the assessment of the utility of a compound as described herein. For example, it is known that a number of metabolic pathologies are related to food intake (e.g., diabetes, obesity). Accordingly, an initial screening can be conducted to determine the extent to which food intake is modulated by administration of compounds described herein, and a positive initial screening can be useful in subsequent development of a compound.

A variety of food intake assays are available to one of skill in the art. For example, in the so-called "home cage model" of food intake, subjects (e.g., rats) are maintained in their home cage, and food intake along with total weight of the subject is measured following injection of test compound. In the so-called "feeding patterns model" of food intake assay, subjects (e.g., rats) are habituated to a feeding chamber and to injections prior to testing. After test compound administration, the subjects are immediately placed into the feeding chamber, and food intake is automatically determined as a function of time (e.g., 1-min intervals). For both tests, the food is standard chow or any of a variety of chows (e.g., high fat) known in the art. In the so-called "mouse food intake" assay, a test compound may be tested for appetite suppression, or for an effect on body weight gain in diet-induced obesity (DIO) mice. In a typical mouse food intake assay, female NIH/Swiss mice (8-24 weeks old) are group housed with a 12:12 hour light:dark cycle with lights on at 0600. Water and a standard pelleted mouse chow diet are available ad libitum, except as noted. Animals are fasted starting at approximately 1500 hrs, 1 day prior to experiment. The morning of the experiment, animals are divided into experimental groups. In a typical study, n=4 cages with 3 mice/cage. At time=0 min, all animals are given an intraperitoneal injection of vehicle or compound, typically in an amount ranging from about 10 nmol/kg to 75 nmol/kg, and immediately given a pre-weighed amount (10-15 g) of the standard chow. Food is removed and weighed at various times, typically 30, 60, and 120 minutes, to determine the amount of food consumed. See e.g., Morley et al., 1994, *Am. J. Physiol.* 267:R178-R184). Food intake is calculated by subtracting the weight of the food remaining at the e.g. 30, 60, 120, 180 and/or 240 minute time point, from the weight of the food provided initially at time=0. Significant treatment effects are identified by ANOVA ($p<0.05$). Where a significant difference exists, test means are compared to the control mean using Dunnett's test (Prism v. 2.01, GraphPad Software Inc., San Diego, Calif.). For any test described herein, administration of test compound can be by any means, including injection (e.g., subcutaneous, intraperitoneal, and the like), oral, or other methods of administration known in the art.

In Vitro Assays.

Without wishing to be bound by any theory or mechanism of action, it is believed that correlations exist between the results of in vitro (e.g., receptor) assays, and the utility of agents for the treatment of metabolic diseases and disorders. Accordingly, in vitro assays (e.g., cell based assays) are useful as a screening strategy for potential metabolic agents, such as described herein. A variety of in vitro assays are known in the art, including those described as follows.

Leptin binding assay. Leptin binding can be measured by the potency of a test compound in displacing $^{125}$I-recombinant-Leptin (murine) from the surface membrane expressing chimeric Leptin (Hu)-EPO (Mu) receptor presented by the 32D OBECA cell line (*J Biol Chem* 1998; 273(29): 18365-18373). Purified cell membranes can be prepared by homogenization from harvested confluent cell cultures of 32D OBECA cells. Membranes can be incubated with $^{125}$I-rec-Murine-Leptin and increasing concentrations of test compound for 3 hours at ambient temperature in 96-well polystyrene plates. Bound and unbound ligand fractions can then be separated by rapid filtration onto 96-well GF/B plates pre-blocked for at least 60' in 0.5% PEI (polyethyleneimine). Glass fiber plates can then be dried, scintillant added, and CPM determined by reading on a multiwell scintillation counter capable of reading radiolabeled iodine.

Leptin Functional Assay.

Increased levels of phosphorylated STAT5 (Signal Transducer and Activator of Transcription 5) can be measured following treatment of 32D-Keptin cells ectopically expressing chimeric Hu-Leptin/Mu-EPO receptor with a test compound. The 32D-Keptin cells (identical to 32D-OBECA cells but maintained in culture with leptin) can be leptin weaned overnight and then treated with test compounds in 96-well plates for 30 minutes at 37° C. followed by cell extraction. The pSTAT5 levels in the cell lysates can be determined using the Perkin Elmer AlphaScreen® SureFire® pSTAT5 assay kit in a 384-well format (Proxiplate™ 384 Plus). The efficacy of test compounds can be determined relative to the maximal signal in cell lysates from cells treated with Human leptin.

VI. Pharmaceutical Compositions

In one aspect, there are provided pharmaceutical compositions comprising compounds described herein in combination with a pharmaceutically acceptable excipient (e.g., carrier). The term "pharmaceutically acceptable carrier," as used herein refers to pharmaceutical excipients, for example, pharmaceutically, physiologically, acceptable organic or inorganic carrier substances suitable for enteral or parenteral application that do not deleteriously react with the active agent. Suitable pharmaceutically acceptable carriers include water, salt solutions (e.g., Ringer's solution and the like), alcohols, oils, gelatins, and carbohydrates such as lactose, amylose or starch, fatty acid esters, hydroxymethycellulose, and polyvinyl pyrrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention.

In a further aspect, there is provided a pharmaceutical composition which includes a engineered polypeptide as described herein in combination with a pharmaceutically acceptable excipient. In one embodiment, the pharmaceutical composition is an oral pharmaceutical composition, as described herein. In some embodiments, the pharmaceutical composition is a long lasting pharmaceutical composition. The term "long lasting" in the context of administration of a pharmaceutical composition refers to duration of action. Accordingly, a long lasting pharmaceutical composition may be administered at intervals of, for example, 1 hr, 2 hr, 4 hr, 8 hr, 12 hr, 1 day, 2 days, 3 days, 4 days, 5 days, 6 days, 1 week, 2 weeks, 3 weeks, 1 month or even longer. In a preferred embodiment, administration is once a day (i.e., "once daily"). In a more preferred embodiments, administration is once a week (i.e., "once weekly").

A. Methods

The engineered polypeptides described herein can be administered alone or can be co-administered to a subject. Co-administration is meant to include simultaneous or sequential administration of the compounds individually or in combination (more than one compound). For example, it has been found that obesity can be beneficially treated with a combination therapy including a leptin (e.g., metreleptin) and certain other anti-obesity compounds. See e.g., U.S. Published Appl. No. 2008/0207512. Accordingly, an engineered polypeptide described herein comprising an ABD and a leptin could be useful for treatment of obesity. Alternatively, the individual engineered polypeptides having can be co-administered with other anti-obesity agents, such as exenatide or liraglutide.

The preparations can also be co-administered, when desired, with other active substances (e.g. to reduce metabolic degradation) as known in the art or other therapeutically active agents.

Amylins.

Amylin is a peptide hormone synthesized by pancreatic β-cells that is co-secreted with insulin in response to nutrient intake. The sequence of amylin is highly preserved across mammalian species, with structural similarities to calcitonin gene-related peptide (CGRP), the calcitonins, the intermedins, and adrenomedullin, as known in the art. The glucoregulatory actions of amylin complement those of insulin by regulating the rate of glucose appearance in the circulation via suppression of nutrient-stimulated glucagon secretion and slowing gastric emptying. In insulin-treated patients with diabetes, pramlintide, a synthetic and equipotent analogue of human amylin, reduces postprandial glucose excursions by suppressing inappropriately elevated postprandial glucagon secretion and slowing gastric emptying. The sequences of rat amylin, human amylin and pramlintide follow:

```
rat amylin:
                              (SEQ ID NO: 108)
KCNTATCATQRLANFLVRSSNNLGPVLPPTNVGSNTY;

human amylin:
                              (SEQ ID NO: 109)
KCNTATCATQRLANFLVHSSNNFGAILSSTNVGSNTY;

Pramlintide:
                              (SEQ ID NO: 110)
KCNTATCATQRLANFLVHSSNNFGPILPPTNVGSNTY.
```

Davalintide.

Davalintide, also known as "AC-2307" is a potent amylin agonist useful in the treatment of a variety of disease indications. See WO 2006/083254 and WO 2007/114838, each of which is incorporated by reference herein in its entirety and for all purposes. Davalintide is a chimeric peptide, having an N-terminal loop region of amylin or calcitonin and analogs thereof, an alpha-helical region of at least a portion of an alpha-helical region of calcitonin or analogs thereof or an alpha-helical region having a portion of an amylin alpha-helical region and a calcitonin alpha-helical region or analog thereof, and a C-terminal tail region of amylin or calcitonin. The sequences of human calcitonin, salmon calcitonin and davalintide follow:

```
human calcitonin:
                              (SEQ ID NO: 111)
CGNLSTCMLGTYTQDFNKFHTFPQTAIGVGAP;

salmon calcitonin:
                              (SEQ ID NO: 112)
CSNLSTCVLGKLSQELHKLQTYPRTNTGSGTP;

davalintide:
                              (SEQ ID NO: 113)
KCNTATCVLGRLSQELHRLQTYPRTNTGSNTY.
```

Without wishing to be bound by any theory, it is believed that amylins and davalintide, and fragments and analogs thereof, can require C-terminal amidation to elicit a full biological response. It is understood that amylin compounds such as those described herein which include amylins and/or davalintide, and fragment and analogs thereof, can be amidated at the C-terminal.

"Amylin agonist compounds" include native amylin peptides, amylin analog peptides, and other compounds (e.g., small molecules) that have amylin agonist activity. The "amylin agonist compounds" can be derived from natural sources, can be synthetic, or can be derived from recombinant DNA techniques. Amylin agonist compounds have amylin agonist receptor binding activity and may comprise amino acids (e.g., natural, unnatural, or a combination thereof), peptide mimetics, chemical moieties, and the like. The skilled artisan will recognize amylin agonist compounds using amylin receptor binding assays or by measuring amylin agonist activity in soleus muscle assays. In one embodiment, amylin agonist compounds will have an $IC_{50}$ of about 200 nM or less, about 100 nM or less, or about 50 nM or less, in an amylin receptor binding assay, such as that described herein, in U.S. Pat. No. 5,686,411, and US Publication No. 2008/0176804, the disclosures of which are incorporated by reference herein in their entireties and for all purposes. In one embodiment, amylin agonist compounds will have an $EC_{50}$ of about 20 nM or less, about nM 15 or less, about nM 10 or less, or about nM 5 or less in a soleus muscle assay, such as that described herein and in U.S. Pat. No. 5,686,411. In one embodiment, the amylin agonist compound has at least 90% or 100% sequence identity to $^{25,28,29}$Pro-human-amylin. In one embodiment, the amylin agonist compound is a peptide chimera of amylin (e.g., human amylin, rat amylin, and the like) and calcitonin (e.g., human calcitonin, salmon calcitonin, and the like). Suitable and exemplary amylin agonist compounds are also described in US Publication No. 2008/0274952, the disclosure of which is incorporated by reference herein in its entirety and for all purposes.

By "amylin analog" as used herein is meant an amylin agonist that has at least 50% sequence identity, preferably at least 70% sequence identity, to a naturally-occurring form of amylin, either rat or human or from any other species, and is derived from them by modifications including insertions, substitutions, extensions, and/or deletions of the reference amino acid sequence.

The amylin analog sequence can have at least 50%, 55%, 60%, 65%, 70%, 75%, 80%, 90%, or 95% amino acid sequence identity with the reference amylin. In one aspect the analog has 0, 1, 2, 3, 4, 5, 6, 7, 8, 9, 10, 11, 12, 13, 14, 15 or even 16 amino acid substitutions, insertions, extensions, and/or deletions relative to the reference compound. In one embodiment, the amylin analog may comprise conservative or non-conservative amino acid substitutions (including non-natural amino acids and L and D forms). These analogs are preferably peptides, peptide derivatives or peptide mimics. Typical amylin analogs will be peptides, especially of 32-37 amino acids, e.g. 27 to 45, especially 28 to 38, and even 31-36.

Amylin analogs with identity to rat and human amylin include $^{25,28,29}$Pro-h-amylin (pramlintide) (SEQ ID NO: 110); des-$^1$Lys-h-amylin (SEQ ID NO: 161); $^{25}$Pro, $^{26}$Val, $^{28,29}$Pro-h-amylin (SEQ ID NO: 162); $^{18}$Arg, $^{25,28}$Pro-h-amylin (SEQ ID NO: 163); des-$^1$L-h amylin (SEQ ID NO: 164); $^{18}$Arg, $^{25,28,29}$Pro-h-amylin (SEQ ID NO: 165); des-$^1$Lys, $^{18}$Arg, $^{25,28,29}$Pro-h-amylin (SEQ ID NO: 166); des-$^1$, Lys$^{25,28,29}$Pro-h-amylin (SEQ ID NO: 167); $^{25}$Pro, $^{26}$Val, $^{28,29}$Pro-h-amylin (SEQ ID NO: 168); $^{28}$Pro-h-amylin, 2,7-Cyclo-[$^2$Asp,$^7$Lys]-h-amylin (SEQ ID NO: 169); $^{2-37}$h-amylin (SEQ ID NO: 170); $^1$Ala-h-amylin (SEQ ID NO: 171); $^2$Ala-h-amylin (SEQ ID NO: 172); $^{2,7}$Ala-h-amylin (SEQ ID NO: 173); $^1$Ser-h-amylin (SEQ ID NO: 174); $^{29}$Pro-h-amylin (SEQ ID NO: 175); $^{25,28}$Pro-h-amylin (SEQ ID NO: 176); des-$^1$Lys, $^{25,28}$Pro-h-amylin (SEQ ID NO: 177); $^{23}$Leu, $^{25}$Pro, $^{26}$Val, $^{28,29}$Pro-h-amylin (SEQ ID NO: 178); $^{23}$Leu$^{25}$Pro$^{26}$Val$^{28}$Pro-h-amylin (SEQ ID NO: 179); des-$^1$Lys, $^{23}$Leu, $^{25}$Pro, $^{26}$Val, $^{28}$Pro-h-amylin (SEQ ID NO: 180); $^{18}$Arg, $^{23}$Leu, $^{25}$Pro, $^{26}$Val, $^{28}$Pro-h-amylin (SEQ ID NO: 181); $^{18}$Arg, $^{23}$Leu, $^{25,28,29}$Pro-h-amylin (SEQ ID NO: 182); $^{18}$Arg$^{23}$Leu, $^{25,28}$Pro-h-amylin (SEQ ID NO: 183); $^{17}$Ile, $^{23}$Leu, $^{25,28,29}$Pro-h-amylin (SEQ ID NO: 184); $^{17}$Ile, $^{25,28,29}$Pro-h-amylin (SEQ ID NO: 185); des-$^1$Lys, $^{17}$Ile, $^{23}$Leu, $^{25,28,29}$Pro-h-amylin (SEQ ID NO: 186); $^{17}$Ile, $^{18}$Arg, $^{23}$Leu-h-amylin (SEQ ID NO: 187); $^{17}$Ile, $^{18}$Arg, $^{23}$Leu, $^{26}$Val, $^{29}$Pro-h-amylin (SEQ ID NO: 188); $^{17}$Ile, $^{18}$Arg, $^{23}$Leu, $^{25}$Pro, $^{26}$Val, $^{28,29}$Pro-h-amylin (SEQ ID NO: 189); $^{13}$Thr, $^{21}$His, $^{23}$Leu, $^{26}$Ala, $^{28}$Leu, $^{29}$Pro, $^{31}$Asp-h-amylin (SEQ ID NO: 190); $^{13}$Thr, $^{21}$His, $^{23}$Leu, $^{26}$Ala, $^{29}$Pro, $^{31}$Asp-h-amylin (SEQ ID NO: 191); des-$^1$Lys, $^{13}$Thr, $^{21}$His, $^{23}$Leu, $^{26}$Ala, $^{28}$Pro, $^{31}$Asp-h-amylin (SEQ ID NO: 192); $^{13}$Thr, $^{18}$Arg, $^{21}$His, $^{23}$Leu, $^{26}$Ala, $^{29}$Pro, $^{31}$Asp-h-amylin (SEQ ID NO: 193); $^{13}$Thr, $^{18}$Arg, $^{21}$His, $^{23}$Leu, $^{28,29}$Pro, $^{31}$Asp-h-amylin (SEQ ID NO: 194); and $^{13}$Thr, $^{18}$Arg, $^{21}$His, $^{23}$Leu, $^{25}$Pro, $^{26}$Ala, $^{28,29}$Pro, $^{31}$Asp-h-amylin (SEQ ID NO: 195).

Suitable and exemplary amylin agonist compounds are also described in PCT Patent Publication WO2010/085700.

Amylin analogs include amino acid sequences of residues 1-37 of Formula (I) following, wherein up to 25% of the amino acids set forth in Formula (I) may be deleted or substituted with a different amino acid:

```
                                              (SEQ ID NO: 800)
X'-Xaa¹-Cys²-Asn³-Thr⁴-Ala⁵-Thr⁶-Cys⁷-Ala⁸-Thr⁹-

Gln¹⁰-Arg¹¹-Leu¹²-Ala¹³-Asn¹⁴-Phe¹⁵-Leu¹⁶-Val¹⁷-

His¹⁸-Ser¹⁹-Ser²⁰-Xaa²¹-Asn²²-Phe²³-Xaa²⁴-Xaa²⁵-

Xaa²⁶-Xaa²⁷-Xaa²⁸-Xaa²⁹-Thr³⁰-Xaa³¹-Val³²-Gly³³-

Ser³⁴-Asn³⁵-Thr³⁶-Tyr³⁷-X
(I).
```

In Formula (I), X' is hydrogen, an N-terminal capping group, or a linker to a duration enhancing moiety. Xaa¹ is Lys or a bond, Xaa²¹ is Lys, Cys, or Asn, Xaa²⁴ is Lys, Cys, or Gly, Xaa²⁵ is Lys, Cys, or Pro, Xaa²⁶ is Lys, Cys, or Ile, Xaa²⁷ is Lys, Cys, or Leu, Xaa²⁸ is Lys, Cys, or Pro, Xaa²⁹ is Lys, Cys, or Pro and Xaa³¹ is Lys, Cys, or Asn. Further regarding Formula (I), the variable X represents a C-terminal functionality (e.g., a C-terminal cap). X is substituted or unsubstituted amino, substituted or unsubstituted alkylamino, substituted or unsubstituted dialkylamino, substituted or unsubstituted cycloalkylamino, substituted or unsubstituted arylamino, substituted or unsubstituted aralkylamino, substituted or unsubstituted alkyloxy, substituted or unsubstituted aryloxy, substituted or unsubstituted aralkyloxy, or hydroxyl. If the C-terminal of the polypeptide component with the sequence of residues 1-37 of Formula (I) is capped with a functionality X, then X is preferably amine thereby forming a C-terminal amide. In some embodiments, up to 5%, 10%, 15%, 20%, 25%, 30%, 35%, 40%, 45% or even 50% of the amino acids of residues 1-37 of Formula (I) are deleted or substituted in a polypeptide component according to Formula (I). In some embodiments, the amylin analog component has 0, 1, 2, 3, 4, 5, 6, 7, 8, 9, 10, 11, 12, 13, 14, 15 or even 16 amino acid substitutions relative to the amino acid sequence set forth in Formula (I). In some embodiments, the amylin analog has a sequence which has a defined sequence identity with respect to the residues 1-37 of the amino acid sequence according to Formula (I). In some embodiments, the sequence identity between an amylin analgo described herein and residues 1-37 of Formula (I) is 50%, 55%, 60%, 65%, 70%, 75%, 80%, 85%, 90%, 95% or even higher. In some embodiments, up to 50%, 45%, 40%, 35%, 30%, 25%, 20%, 15%, 10%, 5% or even less of the amino acids set forth in residues 1-37 of Formula (I) may be deleted or substituted with a different amino acid. In some embodiments, the sequence identity is within the range 75%-100%. In some embodiments, the sequence identity is within the range 75%-90%. In some embodiments, the sequence identity is within the range 80%-90%. In some embodiments, the sequence identity is at least 75%. In some embodiments, the amylin analog has the sequence of residues 1-37 of Formula (I).

In some embodiments, amylin analogs including those of Formula (I), form the basis of a polypeptide component to which one or more duration enhancing moieties are linked, optionally through a linker, to form an amylin polypeptide conjugate. Thus, the polypeptide component serves as a template ("polypeptide template") to which is attached, preferably by covalent attachment, one or more duration enhancing moieties. Linkage of the duration enhancing moiety to the polypeptide component can be through a linker as described herein. Alternatively, linkage of the duration enhancing moiety to the polypeptide component can be via a direct covalent bond. The duration enhancing moiety can be a water soluble polymer as described herein. In some embodiments, a plurality of duration enhancing moieties are attached to the polypeptide component, in which case each linker to each duration enhancing moiety is independently selected from the linkers described herein.

Amylin analogs useful as polypeptide components described herein include, but are not limited to, the compounds set forth in residues 1-37 of Formula (I) provided in Table 3 below. Unless indicated to the contrary, all peptides described herein, including peptides having an expressly provided sequence, are contemplated in both free carboxylate and amidated forms.

TABLE 3

Component polypeptides useful in the compounds described herein.

| Cmpd | Description (sequence) |
|---|---|
| 101 | KCNTATCATQRLANFLVRSSNNLGPVLPPTNVGSNTY-NH$_2$ (SEQ ID NO: 160) |
| 102 | CNTATCATQRLANFLVRSSNNLGPVLPPTNVGSNTY-NH$_2$ (SEQ ID NO: 801) ([desLys$^1$]-Cmpd 101) |
| 103 | KCNTATCATQRLANFLVRSSKNLGPVLPPTNVGSNTY-NH$_2$ (SEQ ID NO: 802) |
| 104 | CNTATCATQRLANFLVRSSKNLGPVLPPTNVGSNTY-NH$_2$ (SEQ ID NO: 803) ([desLys$^1$]-Cmpd 103) |
| 105 | KCNTATCATQRLANFLVRSSNNEGPKEPPTNVGSNTY-NH$_2$ (SEQ ID NO: 804) |
| 106 | CNTATCATQRLANFLVRSSNNLGPKLPPTNVGSNTY-NH$_2$ (SEQ ID NO: 805) ([desLys$^1$]-Cmpd 105) |
| 107 | KCNTATCATQRLANFLVRSSNNLGPVLPPTKVGSNTY-NH$_2$ (SEQ ID NO: 806) |
| 108 | CNTATCATQRLANFLVRSSNNLGPVLPPTKVGSNTY-NH$_2$ (SEQ ID NO: 807) ([desLys$^1$]-Cmpd 107) |
| 109 | KCNTATCATQRLANFLVHSSNNFGPILPPTNVGSNTY-NH$_2$ (SEQ ID NO: 808) |
| 110 | CNTATCATQRLANFLVHSSNNFGPILPPTNVGSNTY-NH$_2$ (SEQ ID NO: 809) ([desLys$^1$]-Cmpd 109) |
| 111 | CNTATCATQRLANFLVHSSKNFGPILPPTNVGSNTY-NH$_2$ (SEQ ID NO: 810) |
| 112 | CNTATCATQRLANFLVHSSNNFGPKLPPTNVGSNTY-NH$_2$ (SEQ ID NO: 811) |
| 113 | CNTATCATQRLANFLVHSSNNFGPILPPTKVGSNTY-NH$_2$ (SEQ ID NO: 812) |
| 114 | CNTATCATQRLANFLVHSSNNFKPILPPTNVGSNTY-NH$_2$ (SEQ ID NO: 813) |
| 115 | CNTATCATQRLANFLVHSSNNFGKILPPTNVGSNTY-NH$_2$ (SEQ ID NO: 814) |
| 116 | CNTATCATQRLANFLVHSSNNFGPIKPPTNVGSNTY-NH$_2$ (SEQ ID NO: 815) |
| 117 | CNTATCATQRLANFLVHSSNNFGPILKPTNVGSNTY-NH$_2$ (SEQ ID NO: 816) |
| 118 | CNTATCATQRLANFLVHSSNNFGPILPKTNVGSNTY-NH$_2$ (SEQ ID NO: 817) |

The terms "linker" and the like, in the context of attachment of duration enhancing moieties to a polypeptide component in an amylin polypeptide conjugate described herein, means a divalent species (-L-) covalently bonded in turn to a polypeptide component having a valency available for bonding and to a duration enhancing moiety having a valency available for bonding. The available bonding site on the polypeptide component is conveniently a side chain residue (e.g., lysine, cysteine, aspartic acid, and homologs thereof). In some embodiments, the available bonding site on the polypeptide component is the side chain of a lysine or a cysteine residue. In some embodiments, the available bonding site on the polypeptide component is the N-terminal amine. In some embodiments, the available bonding site on the polypeptide component is the C-terminal carboxyl. In some embodiments, the available bonding site on the polypeptide component is a backbone atom thereof. As used herein, the term "linking amino acid residue" means an amino acid within residues 1-37 of Formula (I) to which a duration enhancing moiety is attached, optionally through a linker.

In some embodiments, compounds are provided having a linker covalently linking a polypeptide component with a duration enhancing moiety. The linker is optional; i.e., any linker may simply be a bond. In some embodiments, the linker is attached at a side chain of the polypeptide component. In some embodiments, the linker is attached to a backbone atom of the polypeptide component.

In another aspect, there is provided an amylin polypeptide conjugate, which is a derivative of pramlintide with SEQ ID NO:110 or an analog thereof, wherein the amino acid residue in position 1 is absent (i.e., des-Lys) and an amino acid residue in position 2 to 37 has been substituted with a lysine residue or cysteine residue and wherein said lysine residue or cysteine residue is linked to a polyethylene glycol polymer, optionally via a linker, wherein the amino acid numbering conforms with the amino acid number in SEQ ID NO:110.

In another aspect, the invention relates to an amylin polypeptide conjugate, which is a derivative of pramlintide with SEQ ID NO:110 or an analog thereof, wherein the amino acid residue in position 1 is absent (i.e., des-Lys) and wherein an amino acid residue in any one of position 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 31, 32, 33, 34, 35, 36, or 37 is substituted with a lysine residue and wherein said lysine residue is linked to a polyethylene glycol polymer, optionally via a linker.

In another aspect, the invention relates to an amylin polypeptide conjugate, which is a derivative of pramlintide with SEQ ID NO:110 or an analog thereof, wherein the amino acid residue in position 1 is absent (i.e., des-Lys) and wherein an amino acid residue in any one of position 21, 24-29, or 31 is substituted with a lysine residue and wherein said lysine residue is linked to a polyethylene glycol polymer, optionally via a linker.

In another aspect, the invention relates to an amylin polypeptide conjugate, which is a derivative of pramlintide with SEQ ID NO:110 or an analog thereof, wherein the amino acid residue in position 1 is absent (i.e., des-Lys) and wherein an amino acid residue in position 21 is substituted with a lysine residue and wherein said lysine residue is linked to a polyethylene glycol polymer, optionally via a linker.

In another aspect, the invention relates to an amylin polypeptide conjugate, which is a derivative of pramlintide with SEQ ID NO:110 or an analog thereof, wherein the amino acid residue in position 1 is absent (i.e., des-Lys) and wherein an amino acid residue in position 24 is substituted with a lysine residue and wherein said lysine residue is linked to a polyethylene glycol polymer, optionally via a linker.

In another aspect, the invention relates to an amylin polypeptide conjugate, which is a derivative of pramlintide with SEQ ID NO:110 or an analog thereof, wherein the amino acid residue in position 1 is absent (i.e., des-Lys) and wherein an amino acid residue in position 25 is substituted with a lysine residue and wherein said lysine residue is linked to a polyethylene glycol polymer, optionally via a linker.

In another aspect, the invention relates to an amylin polypeptide conjugate, which is a derivative of pramlintide with SEQ ID NO:110 or an analog thereof, wherein the amino acid residue in position 1 is absent (i.e., des-Lys) and wherein an amino acid residue in position 26 is substituted with a lysine residue and wherein said lysine residue is linked to a polyethylene glycol polymer, optionally via a linker.

In another aspect, the invention relates to an amylin polypeptide conjugate, which is a derivative of pramlintide with SEQ ID NO:110 or an analog thereof, wherein the amino acid residue in position 1 is absent (i.e., des-Lys) and wherein an amino acid residue in position 27 is substituted with a lysine residue and wherein said lysine residue is linked to a polyethylene glycol polymer, optionally via a linker.

In another aspect, the invention relates to an amylin polypeptide conjugate, which is a derivative of pramlintide with SEQ ID NO:110 or an analog thereof, wherein the amino acid residue in position 1 is absent (i.e., des-Lys) and wherein an amino acid residue in position 28 is substituted with a lysine residue and wherein said lysine residue is linked to a polyethylene glycol polymer, optionally via a linker.

In another aspect, the invention relates to an amylin polypeptide conjugate, which is a derivative of pramlintide with SEQ ID NO:110 or an analog thereof, wherein the amino acid residue in position 1 is absent (i.e., des-Lys) and wherein an amino acid residue in position 29 is substituted with a lysine residue and wherein said lysine residue is linked to a polyethylene glycol polymer, optionally via a linker.

In another aspect, the invention relates to an amylin polypeptide conjugate, which is a derivative of pramlintide with SEQ ID NO:110 or an analog thereof, wherein the amino acid residue in position 1 is absent (i.e., des-Lys) and wherein an amino acid residue in position 31 is substituted with a lysine residue and wherein said lysine residue is linked to a polyethylene glycol polymer, optionally via a linker.

In some embodiments, the duration enhancing moiety is a water-soluble polymer. A "water soluble polymer" means a polymer which is sufficiently soluble in water under physiologic conditions of e.g., temperature, ionic concentration and the like, as known in the art, to be useful for the methods described herein. A water soluble polymer can increase the solubility of a peptide or other biomolecule to which such water soluble polymer is attached. Indeed, such attachment has been proposed as a means for improving the circulating life, water solubility and/or antigenicity of administered proteins, in vivo. See e.g., U.S. Pat. No. 4,179,337; U.S. Published Appl. No. 2008/0032408. Many different water-soluble polymers and attachment chemistries have been used towards this goal, such as polyethylene glycol, copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and the like.

In some embodiments, the linked duration enhancing moiety includes a polyethylene glycol. Polyethylene glycol ("PEG") has been used in efforts to obtain therapeutically usable polypeptides. See e.g., Zalipsky, S., 1995, *Bioconjugate Chemistry*, 6:150-165; Mehvar, R., 2000, *J. Pharm. Pharmaceut. Sci.*, 3:125-136. As appreciated by one of skill in the art, the PEG backbone [(CH$_2$CH$_2$—O—)$_n$, n: number of repeating monomers] is flexible and amphiphilic. Without wishing to be bound by any theory or mechanism of action, the long, chain-like PEG molecule or moiety is believed to be heavily hydrated and in rapid motion when in an aqueous medium. This rapid motion is believed to cause the PEG to sweep out a large volume and prevents the approach and interference of other molecules. As a result, when attached to another chemical entity (such as a peptide), PEG polymer chains can protect such chemical entity from immune response and other clearance mechanisms. As a result, pegylation can lead to improved drug efficacy and safety by optimizing pharmacokinetics, increasing bioavailability, and decreasing immunogenicity and dosing frequency. "Pegylation" refers in the customary sense to conjugation of a PEG moiety with another compound. For example, attachment of PEG has been shown to protect proteins against proteolysis. See e.g., Blomhoff, H. K. et al., 1983, *Biochim Biophys Acta*, 757:202-208. Unless expressly indicated to the contrary, the terms "PEG," "polyethylene glycol polymer" and the like refer to polyethylene glycol polymer and derivatives thereof, including methoxy-PEG (mPEG).

A variety of means have been used to attach polymer moieties such as PEG and related polymers to reactive groups found on the protein. See e.g., U.S. Pat. Nos. 4,179,337; 4,002,531; Abuchowski et al., 1981, in "Enzymes as Drugs," J. S. Holcerberg and J. Roberts, (Eds.), pp. 367-383; Zalipsky, S., 1995, *Bioconjugate Chemistry*, 6:150-165. The use of PEG and other polymers to modify proteins has been discussed. See e.g., Cheng, T.-L. et al., 1999m, *Bioconjugate Chem.*, 10:520-528; Belcheva, N. et al., 1999, *Bioconjugate Chem.*, 10:932-937; Bettinger, T. et al., 1998, *Bioconjugate Chem.*, 9:842-846; Huang, S.-Y. et al., 1998, *Bioconjugate Chem.*, 9:612-617; Xu, B. et al. 1998, *Langmuir*, 13:2447-2456; Schwarz, J. B. et al., 1999, *J. Amer. Chem. Soc.*, 121:2662-2673; Reuter, J. D. et al., 1999, *Bioconjugate Chem.*, 10:271-278; Chan, T.-H. et al., 1997, *J. Org. Chem.*, 62:3500-3504. Typical attachment sites in proteins include primary amino groups, such as those on lysine residues or at the N-terminus, thiol groups, such as those on cysteine side-chains, and carboxyl groups, such as those on glutamate or aspartate residues or at the C-terminus. Common sites of attachment are to the sugar residues of glycoproteins, cysteines or to the N-terminus and lysines of the target polypeptide. The terms "pegylated" and the like refer to covalent attachment of polyethylene glycol to a polypeptide or other biomolecule, optionally through a linker as described herein and/or as known in the art.

In some embodiments, a PEG moiety in an amylin polypeptide conjugate described herein has a nominal molecular weight within a specified range. As customary in the art, the size of a PEG moiety is indicated by reference to the nominal molecular weight, typically provided in kilodaltons (kD). The molecular weight is calculated in a variety of ways known in the art, including number, weight, viscosity and "Z" average molecular weight. It is understood that polymers, such as PEG and the like, exist as a distribution of molecule weights about a nominal average value.

Exemplary of the terminology for molecular weight for PEGs, the term "mPEG40KD" refers to a methoxy polyethylene glycol polymer having a nominal molecular weight of 40 kilodaltons. Reference to PEGs of other molecular weights follows this convention. In some embodiments, the PEG moiety has a nominal molecular weight in the range 10-100 KD, 20-80 KD, 20-60 KD, or 20-40 KD. In some embodiments, the PEG moiety has a nominal molecular weight of 10, 15, 20, 25, 30, 35, 40, 45, 50, 55, 60, 65, 70, 75, 80, 85, 90, 95 or even 100 KD. Preferably, the PEG moiety has a molecular weight of 20, 25, 30, 40, 60 or 80 KD.

PEG molecules useful for derivatization of polypeptides are typically classified into linear, branched and Warwick (i.e., PolyPEG®) classes of PEGs, as known in the art. Unless expressly indicated to the contrary, the PEG moieties described herein are linear PEGs. Furthermore, the terms "two arm branched," "Y-shaped" and the like refer to branched PEG moieties, as known in the art. The term "Warwick" in the context of PEGs, also known as "comb" or "comb-type" PEGs, refers to a variety of multi-arm PEGs attached to a backbone, typically poly(methacrylate), as known in the art. Regarding nomenclature including conventions employed in the table provided herein, absent indication to the contrary a PEG moiety is attached to the backbone of the peptide. For example, Cmpd 119 is the result of the conjugation of mPEG40KD to the N-terminal nitrogen of Cmpd 101. Similarly, Cmpd 120 is the result of conjugation of mPEG40KD to the N-terminal nitrogen of Cmpd 102. Standard single letter abbreviations for amino acids can be used, as can standard three-letter abbreviations. For example, Cmpd 124 is an analog of Cmpd 110 wherein the residue at position 26 of Cmpd 109 is substituted for lysine, and the pendant amine functionality of lysine 26 (i.e., $K^{26}$) is conjugated with a PEG40KD moiety. Exemplary compounds are provided in Table 4 below.

TABLE 4

Pegylated compounds

| Cmpd | SEQ ID NO: | Description |
|---|---|---|
| 119 | 196 | mPEG40KD-Cmpd 101 |
| 120 | 197 | mPEG40KD-Cmpd 102 |
| 121 | 198 | [$K^{21}$(mPEG40KD)]-Cmpd 103 |
| 122 | 199 | [$K^{21}$(mPEG40KD)]-Cmpd 104 |
| 123 | 200 | [$K^{26}$(mPEG40KD)]-Cmpd 105 |
| 124 | 201 | [$K^{26}$(mPEG40KD)]-Cmpd 106 |
| 125 | 202 | [$K^{31}$(mPEG40KD)]-Cmpd 107 |
| 126 | 203 | [$K^{31}$(mPEG40KD)]-Cmpd 108 |
| 127 | 204 | [$K^{26}$(Y-shaped-mPEG40KD)]-Cmpd 105 |
| 128 | 205 | [$K^{21}$(mPEG40KD)]-Cmpd 111 |
| 129 | 206 | [$K^{26}$(mPEG40KD)]-Cmpd 112 |
| 130 | 207 | [$K^{31}$(mPEG40KD)]-Cmpd 113 |
| 131 | 208 | [$K^{26}$(Y-shaped-mPEG40KD)]-Cmpd 112 |
| 132 | 209 | [$K^{24}$(mPEG40KD)]-Cmpd 114 |
| 133 | 210 | [$K^{25}$(mPEG40KD)]-Cmpd 115 |
| 134 | 211 | [$K^{27}$(mPEG40KD)]-Cmpd 116 |
| 135 | 212 | [$K^{28}$(mPEG40KD)]-Cmpd 117 |
| 136 | 213 | [$K^{29}$(mPEG40KD)]-Cmpd 118 |

Amylins and amylin analogs to which a chemical moiety is attached are amylin derivatives. Amylin derivatives may constitute amylins to which a chemical modification has been made of one or more of its amino acid side groups, α-carbon atoms, terminal amino group, or terminal carboxylic acid group. A chemical modification includes, but is not limited to, attaching one or more chemical moieties, creating new bonds, and removing one or more chemical moieties. Modifications at amino acid side groups include, without limitation, alkylation, acylation, ester formation, amide formation, maleimide coupling, acylation of lysine ε-amino groups, N-alkylation of arginine, histidine, or lysine, alkylation of glutamic or aspartic carboxylic acid groups, and deamidation of glutamine or asparagine. Modifications of the terminal amino include, without limitation, the desamino, N-lower alkyl, N-di-lower alkyl, and N-acyl modifications. Modifications of the terminal amino include, without limitation, the desamino, N-lower alkyl, N-di-lower alkyl, and N-acyl modifications, such as alkylacyls, branched alkylacyls, alkylaryl-acyls. Modifications of the terminal carboxy group include, without limitation, the amide, lower alkyl amide, dialkyl amide, arylamide, alkylarylamide and lower alkyl ester modifications. Lower alkyl is $C_1$-$C_4$ alkyl. Furthermore, one or more side groups, or terminal groups, may be protected by protective groups known to the ordinarily-skilled synthetic chemist. The α-carbon of an amino acid may be mono- or dimethylated.

Amylin derivatives include amylins and amylin analogs conjugated to one or more water soluble polymer molecules, such as polyethylene glycol ("PEG"), as described above, or fatty acid chains of various lengths (e.g., stearyl, palmitoyl, octanoyl), by the addition of polyamino acids, such as poly-his, poly-arg, poly-lys, and poly-ala, or by addition of small molecule substituents include short alkyls and constrained alkyls (e.g., branched, cyclic, fused, adamantyl), and aromatic groups. In some embodiments, the water soluble polymer molecules will have a molecular weight ranging from about 500 Daltons to about 60,000 Daltons. See, e.g., PCT Patent Publications WO 2007/104789, WO 2009/034119, and WO 2010/046357 for amylin derivatives suitable for use as anti-obesity agents in combination with the engineered polypeptides of the invention.

Such polymer-conjugations may occur singularly at the N- or C-terminus or at the side chains of amino acid residues within the sequence of an amylin or amylin analog as disclosed herein. Alternatively, there may be multiple sites of derivatization along the amino acid sequence of such an amylin or amylin analog. Substitution of one or more amino acids with lysine, aspartic acid, glutamic acid, or cysteine may provide additional sites for derivatization. In some embodiments, an amylin or amylin analog may be conjugated to one, two, or three polymer molecules.

In some embodiments, the water soluble polymer molecules are linked to an amino, carboxyl, or thiol group, and may be linked by N or C termini, or at the side chains of lysine, aspartic acid, glutamic acid, or cysteine. Alternatively, the water soluble polymer molecules may be linked with diamine and dicarboxylic groups. In some embodiments, an amylin or amylin analog is conjugated to one, two, or three PEG molecules through an epsilon amino group on a lysine amino acid.

It has been surprisingly discovered that the engineered polypeptides of the invention provide beneficial synergistic anti-obesity effects to both moderately obese (BMI equal to or greater than 30) and severely obese (BMI equal to or greater than 35) subjects when administered in combination with certain other anti-obesity compounds. As described previously in, e.g., U.S. Published Appl. No. 2008/0207512, it has been found that a state of leptin resistance exists in obese subjects. See also, e.g., Tenenbaum, D., *HHMI Bulletin*, pp. 25-27 (March 2003); Chicurel, M., *Nature*, Vol. 404, pp. 538-540 (2000); Scarpace et al., *Diabetalogia*, Vol. 48, pp. 1075-1083 (2005); and Bays et al., *Obesity Research*, Vol. 12, (8), pp. 1197-1211 (2004). This leptin resistance, characterized at least in part by the presence of abnormally high serum leptin levels in obese subjects, makes these subjects unable to respond effectively to leptin, whether endogenous or exogenously administered. It had been previously found that this leptin resistance could be overcome in moderately obese subjects, with a combination therapy including a leptin (e.g., metreleptin) and certain other anti-obesity compounds. See e.g., U.S. Published Appl. No. 2008/0207512. It has further been found that the synergistic anti-obesity effects of the leptin combination therapy are absent in severely obese, high BMI subjects, presumably due to a severe leptin resistance. The inventors have surprisingly discovered that the engineered compounds of the invention are able to overcome even severe leptin resistance when administered in combination with certain other anti-obesity compounds. Accordingly, also provided by the invention are methods of treating obesity and obesity related conditions, disorders, and diseases in subjects, including high BMI subjects, by the administration of at least two different anti-obesity agents, wherein one anti-obesity agent is an engineered polypeptide of the invention and another anti-obesity agent is an amylin, an amylin analog, an amylin agonist, or an amylin derivative (i.e. an amylin agent).

In certain embodiments, the invention provides methods of treating obesity in subjects in need thereof comprising administration of a first anti-obesity agent selected from an engineered polypeptide of the invention in combination with a second anti-obesity agent selected from an amylin, an amylin analog, an amylin agonist, or an amylin derivative wherein the administration of the agents result in a synergistic effect as compared to administration of either agent alone.

In one aspect, methods of the invention provide a synergistic anti-obesity effect among the administered agents. Accordingly, in certain embodiments, administration of a combination of anti-obesity agents results in an effect, e.g., a reduction in nutrient availability, reduction in body weight, reduction in food intake, increase in metabolism, which is greater than the combination of the results of administration of the anti-obesity agent alone (monotherapy).

"Reduced nutrient availability" is meant to include any means by which the body reduces the nutrients available to the body to store as fat. In other words, reducing nutrient availability may be by means that include, but are not limited to, reducing appetite, increasing satiety, affecting food choice/taste aversion, increasing metabolism, and/or decreasing or inhibiting food absorption. Exemplary mechanisms that may be affected include delayed gastric emptying or decreased absorption of food in the intestines.

As used herein, a "subject in need thereof" includes subjects who are overweight, obese, or desirous of losing weight. Obese subjects include both the moderately obese, low BMI population and the severely obese, high BMI population. In addition, subjects who are insulin resistant, glucose intolerant, or have any form of diabetes mellitus (e.g., type 1, 2 or gestational diabetes) can benefit from the methods of the invention.

By "metabolic rate" is meant the amount of energy liberated/expended per unit of time. Metabolism per unit time can be estimated by food consumption, energy released as heat, or oxygen used in metabolic processes. It is generally desirable to have a higher metabolic rate when one wants to lose weight. For example, a person with a high metabolic rate may be able to expend more energy (e.g., the body burns more calories) to perform an activity than a person with a low metabolic rate for that activity.

As used herein, "lean mass" or "lean body mass" refers to muscle and bone. Lean body mass does not necessarily indicate fat free mass. Lean body mass contains a small percentage of fat (roughly 3%) within the central nervous system (brain and spinal cord), marrow of bones, and internal organs. Lean body mass is measured in terms of density. Methods of measuring fat mass and lean mass include, but are not limited to, underwater weighing, air displacement plethysmograph, x-ray, DEXA scans, MRIs and CT scans. In certain embodiments, fat mass and lean mass is measured using underwater weighing as known in the art.

By "fat distribution" is meant the location of fat deposits in the body. Such locations of fat deposition include, for example, subcutaneous, visceral and ectopic fat depots.

By "subcutaneous fat" is meant the deposit of lipids just below the skin's surface. The amount of subcutaneous fat in a subject can be measured using any method available for the measurement of subcutaneous fat. Methods of measuring subcutaneous fat are known in the art, for example, those described in U.S. Pat. No. 6,530,886, the entirety of which is incorporated herein by reference.

By "visceral fat" is meant the deposit of fat as intra-abdominal adipose tissue. Visceral fat surrounds vital organs and can be metabolized by the liver to produce blood cholesterol. Visceral fat has been associated with increased risks of conditions such as polycystic ovary syndrome, metabolic syndrome and cardiovascular diseases.

By "ectopic fat storage" is meant lipid deposits within and around tissues and organs that constitute the lean body mass (e.g., skeletal muscle, heart, liver, pancreas, kidneys, blood vessels). Generally, ectopic fat storage is an accumulation of lipids outside classical adipose tissue depots in the body.

As used herein, and as well-understood in the art, "treatment" is an approach for obtaining beneficial or desired results, including clinical results. "Treating" or "palliating" a disease, disorder, or condition means that the extent and/or undesirable clinical manifestations of a condition, disorder, or a disease state are lessened and/or time course of the progression is slowed or lengthened, as compared to not treating the disorder. For example, in treating obesity, a decrease in body weight, e.g., at least a 5% decrease in body weight, is an example of a desirable treatment result. For purposes of this invention, beneficial or desired clinical results include, but are not limited to, alleviation or amelioration of one or more symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Further, treating does not necessarily occur by administration of one dose, but often occurs upon administration of a series of doses. Thus, a therapeutically effective amount, an amount sufficient to palliate, or an amount sufficient to treat a disease, disorder, or condition may be administered in one or more administrations.

As used herein, the term "therapeutically effective amount" means the amount of the active compounds in the composition that will elicit the biological or medical response in a tissue, system, subject, or human that is being sought by the researcher, veterinarian, medical doctor or other clinician, which includes alleviation of the symptoms of the disorder being treated. The novel methods of treatment of this invention are for disorders known to those skilled in the art.

As used herein, the term "prophylactically effective amount" means the amount of the active compounds in the composition that will elicit the biological or medical response in a tissue, system, subject, or human that is being sought by the researcher, veterinarian, medical doctor or other clinician, to prevent the onset of obesity or an obesity-related disorder, condition or disease in subjects as risk for obesity or the obesity-related disorder, condition or disease.

In another aspect of the present invention, methods for reducing the risk of developing metabolic disorders are provided, where the method comprises administering to the subject a combination of anti-obesity agents in effective amounts to reduce the weight of a subject.

In some embodiments of the invention, methods of the invention are used to increase the metabolic rate in a subject, decrease a reduction in the metabolic rate in a subject, or preserve the metabolic rate in a subject. In certain embodiments, the metabolic rate may involve the preferential use of the body's fat as an energy source over lean body tissue. In one aspect, lean body mass is not decreased following administration of the combination of anti-obesity agents. In another aspect, a reduction in the lean body mass is lessened or prevented following administration of the combination of anti-obesity agents. In still another aspect, lean body mass is increased following administration of the combination of anti-obesity agents. Such preference for fat as the energy source may be determined by comparing the amount of fatty tissue to lean body tissue, ascertained by measuring total body weight and fat content at the beginning and end of the treatment period. An increase in metabolic rate is a higher level of the use of calories or another energy source by a subject over a period of time compared with the level of use of calories or other energy source by the subject over another period of time under substantially similar or identical conditions without administration of the combination of anti-obesity agents. In certain embodiments, the metabolic rate is increased at least about 5% in a subject, in other embodiments, the metabolic rate is increased at least about 10%, 15%, 20% 25%, 30%, or 35% in a subject compared with the level of use of calories or other energy source by the subject over another period of time under substantially similar or identical conditions without administration of the combination of anti-obesity agents. The increase in metabolic rate can be measured using a respiratory calorimeter, for example. An effective amount of the anti-obesity agents as used in these embodiments is an amount of each agent effective to increase the metabolic rate in a subject when administered in combination compared to a subject not receiving the agents or only one of the agents.

In another embodiment, a method is provided to reduce a decrease in metabolic rate in a subject. Such a decrease in metabolic rate can be the result of any condition or nutritional or physical regimen that leads to a reduction in metabolic rate, for example, due to a reduced calorie diet, a restricted diet, or weight loss. A restricted diet includes allowances or prohibitions, or both on the types of food or the amounts of food or both permitted in a diet, not necessarily based on calories. For example, as in individual diets, the body compensates with a reduced metabolic rate based on the lower caloric intake. In essence, the body downregulates the requirement for food, thereby subsisting on less food. As dieting continues, the threshold for caloric intake is reduced. When dieting has ended, the individual typically gains weight while eating a normal diet because of the lowered caloric intake threshold and lower-basal metabolic rate (NIH Technology Assessment Conference Panel (1992) *Ann. Intern. Med.* 116:942-949; Wadden (1993) *Ann. Intern. Med.* 119:688-693). In one aspect, a method is provided to reduce the loss of metabolic rate in a subject, where the loss of metabolic rate is the result of a reduced calorie diet or weight loss. By using such a method, the subject's reduction in metabolic rate is decreased by at least about 10%, 15%, 20% 25%, 30%, 35%, 40%, 50%, 60%, 70%, 80%, 90%, or 95% in a subject. For such methods, it may be desirable to administer the combination of anti-obesity agents at the time the condition or nutritional or physical regimen is initiated which leads to a loss or reduction in metabolic rate. However, it is also contemplated that administration of the agents is commenced before the condition or nutritional or physical regimen is initiated. In one instance, metabolic rate is measured using a respiratory calorimeter. An effective amount of the anti-obesity agents of as used in this embodiment is an amount of each agent effective to decrease the reduction of the metabolic rate in a subject when administered in combination.

In another aspect, methods for reducing metabolic plateaus are provided, where a method comprises administering effective amounts of anti-obesity agents in combination to a subject. In certain embodiments, the subject is losing weight, or has lost weight, for example, due to a reduced calorie diet, increased exercise or a combination thereof. By "metabolic plateau" is meant time intervals of steady metabolic rate while the body adjusts to changes in caloric or energy input. Changes in caloric input or expenditure can be the result of, for example, reduced calorie diets or increased physical activity. Such plateaus can be observed, for example, during a weight loss regimen when weight loss slows or stops. In certain embodiments, a method of the present invention reduces the duration of a metabolic plateau in a subject compared with the duration of metabolic plateaus in an otherwise identical subject over the same period of time under substantially similar or identical conditions without administration of the combination of anti-obesity agents. In other embodiments, a method of the present invention reduces the frequency of metabolic plateaus compared with the frequency of metabolic plateaus in an otherwise identical subject over the same period of time under substantially similar or identical conditions without administration of the combination of anti-obesity agents. In still other embodiments, a method of the present invention delays the onset of a metabolic plateau compared with the onset of a metabolic plateau in an otherwise identical subject over the same period of time under substantially similar or identical conditions without administration of the combination of anti-obesity agents. In certain embodiments, metabolic plateaus are identified by charting periods of reduced or no weight loss. In certain embodiments, at least one metabolic plateau is reduced. In other embodiments, at least two, three, four, five, six, seven, eight, nine, or ten metabolic plateaus are reduced. In another aspect, metabolic plateaus are delayed one day as compared to a subject not administered the combination of anti-obesity agents under identical or similar conditions. In other aspects, metabolic plateaus are delayed 2 days, 3 days, 4 days, 5 days, 6 days, 1 week, 10 days, 2 weeks or 3 weeks in a subject.

In yet other embodiments, a method is provided to preserve the metabolic rate in a subject. In certain embodiments, the subject may be at risk of losing metabolic rate, for example, due to the initiation of a reduced calorie diet, restricted diet, or anticipated weight loss. A preservation of metabolic rate is a maintenance of the level of the use of calories or another energy source by a subject over a period of time compared with the level of use of calories or other energy source by an otherwise identical subject over the same period of time under substantially similar or identical conditions without administration of the combination of anti-obesity agents. In one aspect, the metabolic rate is maintained within 15% of the subject's metabolic rate prior to the initiation of the event that results in the decrease in metabolic rate. In other aspects, the metabolic rate is maintained within 10%, within 7%, within 5%, within 3% or less of the subject's metabolic rate. In one aspect, the combination of anti-obesity agents is administered at the initiation of a reduced calorie diet, restricted diet, or exercise regimen.

Metabolic rates can be assessed using any method available for determining such rates, for example by using a respiratory calorimeter. Such methods and devices for assaying metabolic rates are known in the art and are described, for example, in U.S. Pat. Nos. 4,572,208, 4,856,531, 6,468,222, 6,616,615, 6,013,009, and 6,475,158. Alternatively, the metabolic rate of an animal can be assessed by measuring the amount of lean tissue versus fatty tissue catabolized by the animal following the diet period. Thus, total body weight and fat content can be measured at the end of the dietary period. In rats, a frequently used method to determine total body fat is to surgically remove and weigh the retroperitoneal fat pad, a body of fat located in the retroperitoneum, the area between the posterior abdominal wall and the posterior parietal peritoneum. The pad weight is considered to be directly related to percent body fat of the animal. Since the relationship between body weight and body fat in rats is linear, obese animals have a correspondingly higher percent of body fat and retroperitoneal fat pad weight.

In another aspect of the present invention, methods for reducing fat mass by increasing the metabolic rate in a subject are provided, where the methods comprise administering a combination of anti-obesity agents in amounts effective to reduce fat mass by increasing the subject's metabolic rate. Fat mass can be expressed as a percentage of the total body mass. In some aspects, the fat mass is reduced by at least 1%, at least 5%, at least 10%, at least 15%, at least 20%, or at least 25% over the course of treatment. In one aspect, the subject's lean mass is not decreased over the course of the treatment. In another aspect, the subject's lean mass is maintained or increased over the course of the treatment. In another aspect, the subject is on a reduced calorie diet or restricted diet. By "reduced calorie diet" is meant that the subject is ingesting fewer calories per day than compared to the same subject's normal diet. In one instance, the subject is consuming at least 50 fewer calories per day. In other instances, the subject is consuming at least 100, 150, 200, 250, 300, 400, 500, 600, 700, 800, 900, or 1000 fewer calories per day.

In certain embodiments of the present invention, a method for altering the fat distribution in a subject is provided where the method comprises administering a combination of anti-obesity agents in amounts effective to alter fat distribution in the subject. In one aspect, the alteration results from an increased metabolism of visceral or ectopic fat, or both in the subject. In some embodiments, the method involves the metabolism of visceral or ectopic fat or both at a rate of at least about 5%, 10%, 15%, 20%, 25%, 30%, 40%, or 50% greater than for subcutaneous fat. In one aspect, the methods result in a favorable fat distribution. In certain embodiments, favorable fat distribution is an increased ratio of subcutaneous fat to visceral fat, ectopic fat, or both. In one aspect, the method involves an increase in lean body mass, for example, as a result of an increase in muscle cell mass.

In other embodiments, methods for reducing the amount of subcutaneous fat in a subject are provided, wherein the method comprises administering, to a subject in need thereof, a combination of anti-obesity agents in amounts effective to reduce the amount of subcutaneous fat in the subject. In one instance, the amount of subcutaneous fat is reduced in a subject by at least about 5%. In other instances, the amount of subcutaneous fat is reduced by at least about 10%, 15%, 20%, 25%, 30% 40%, or 50% compared to the subject prior to administration of the anti-obesity agents.

The methods described herein can be used to reduce the amount of visceral fat in a subject. In one instance, the visceral fat is reduced in a subject by at least about 5%. In other instances, the visceral fat is reduced in the subject by at least about 10%, 15%, 20%, 25%, 30% 40%, or 50% compared to the subject prior to administration of the combination of anti-obesity agents. Visceral fat can be measured through any means available to determine the amount of visceral fat in a subject. Such methods include, for example, abdominal tomography by means of CT scanning and MRI. Other methods for determining visceral fat are described, for example, in U.S. Pat. Nos. 6,864,415, 6,850,797, and 6,487,445.

In certain embodiments, a method for preventing the accumulation of ectopic fat or reducing the amount of ectopic fat in a subject is provided, wherein the method comprises administering, to a subject in need thereof, a combination of anti-obesity agents in amounts effective to prevent accumulation of ectopic fat or to reduce the amount of ectopic fat in the subject. In one instance, the amount of ectopic fat is reduced in a subject by at least about 5% compared to the subject prior to administration of the combination of anti-obesity agents. In other instances, the amount of ectopic fat is reduced in a subject by at least about 10%, or by at least about 15%, 20%, 25%, 30% 40%, or 50%. Alternatively, the amount of ectopic fat is proportionally reduced 5%, 10%, 15%, 20%, 25%, 30%, 40%, 50%, 60%, 70%, 80%, 90%, or 100% in comparison to subcutaneous fat in a subject. Ectopic fat can be measured in a subject using any method available for measuring ectopic fat.

In other embodiments, methods are provided for producing a more favorable fat distribution in a subject, where the method comprises administering to a subject a combination of anti-obesity agents in amounts effective to produce a favorable fat distribution. In certain embodiments, administration of a combination of anti-obesity agents reduces the amount of visceral fat or ectopic fat, or both, in a subject. For example, administration of a combination of anti-obesity agents, where at least one anti-obesity agent that acts upon forebrain structures involved in food intake or body weight modulation or both in combination with administration of at least one anti-obesity agent that acts upon hindbrain structures involved in food intake or body weight modulation or both. In certain embodiments, the methods preferentially reduce the amount of visceral or ectopic fat, or a combination of both, over the reduction in subcutaneous fat. Such methods result in a higher ratio of subcutaneous fat to visceral fat or ectopic fat. Such improved ratios may result in a reduced risk of the development of cardiovascular diseases, polycystic ovary syndrome, metabolic syndrome, or any combinations thereof. In certain embodiments, ectopic or visceral fat is metabolized at a rate 5% greater than subcutaneous fat. In other embodiments, ectopic or visceral fat is metabolized at a rate at least 10% 15%, 20%, 25%, 30% 50%, 60%, 70%, 80%, 90%, or 100% greater than subcutaneous fat.

In another aspect, methods of the invention include the use of a therapeutically effective amount of a combination of anti-obesity agents administered in combination with glucocortico steroids. Glucocortico steroids have the adverse effect of increasing fat mass and decreasing lean mass. Accordingly, it is contemplated that the anti-obesity agent combination can be used in conjunction with glucocortico steroids under conditions where glucocortico steroid use is beneficial.

In still another aspect, methods of the invention include the use of a therapeutically effective amount of one anti-obesity agent or a combination of anti-obesity agents administered in combination with a therapeutic agent selected from orlistat, phentermine, topiramate, CONTRAVE, and QNEXA. In some embodiments, the methods of the invention include the use of a therapeutically effective amount of an engineered polypeptide of the invention in combination with a therapeutic agent selected from orlistat, phentermine, topiramate, CONTRAVE, and QNEXA. In other embodiments, the methods of the invention include the use of a therapeutically effective amount of an amylin, an amylin analog, an amylin agonist, or an amylin derivative in combination with a therapeutic agent selected from orlistat, phentermine, topiramate, CONTRAVE, and QNEXA. In other embodiments, the methods of the invention include the use of a therapeutically effective amount of an engineered compound of the invention in combination with an amylin, an amylin analog, an amylin agonist, or an amylin derivative and a therapeutic agent selected from orlistat, phentermine, topiramate, CONTRAVE, and QNEXA.

Also provided are methods to reduce weight in a morbidly obese subject by first reducing the subject's weight to a level below that of being morbidly obese, then administering to the subject a combination of anti-obesity agents in effective amounts to further reduce the subject's weight. Methods for reducing a subject's weight to below that of morbid obesity include reducing caloric intake, increasing physical activity, drug therapy, bariatric surgery, such as gastric bypass surgery, or any combinations of the preceeding methods. In one aspect, administering the combination of anti-obesity agents further reduces the weight of the subject. In other embodiments, methods are provided for reducing the body mass index in a subject having a body mass index of 40 or less by administering a combination of anti-obesity agents in effective amounts to further reduce the subject's weight.

By reducing weight it is meant that the subject loses a portion of his/her total body weight over the course of treatment, whether the course of treatment be days, weeks, months or years. Alternatively, reducing weight can be defined as a decrease in proportion of fat mass to lean mass (in other words, the subject has lost fat mass, but maintained or gained lean mass, without necessarily a corresponding loss in total body weight). An effective amount of the anti-obesity agents administered in combination in these embodiments is an amount effective to reduce a subject's body weight over the course of the treatment, or alternatively an amount effective to reduce the subject's percentage of fat mass over the course of the treatment. In certain embodiments, the subject's body weight is reduced, over the course of treatment, by at least about 1%, by at least about 5%, by at least about 10%, by at least about 15%, or by at least about 20%. Alternatively, the subject's percentage of fat mass is reduced, over the course of treatment, by at least 1%, at least 5%, at least 10%, at least 15%, at least 20%, or at least 25%.

In certain embodiments, methods of reducing weight include improved adherence to weight maintenance. Without wishing to be bound by any theory, the restoration of leptin responsiveness achieved by the administration of anti-obesity agents as described herein overcomes a critical challenge for obese subjects. In prior weight loss methods, leptin levels may still be higher than normal even at a reduced body weight, making it difficult for subjects to maintain the weight loss. The methods described herein include not only methods of reducing weight, but also the component of improved adherence to weight maintenance.

In certain embodiments, methods of reducing nutrient availability, e.g., reducing weight, in a subject comprise administering to the subject an effective amount of the anti-obesity agents in a bolus dose one or more times a day. A bolus dose is an intermittent dosage of medicine (as opposed to a continuous infusion). A subject can be administered one or more bolus doses per day. The bolus dose can be the same no matter when it is administered to the subject, or can be adjusted such that the subject is administered a larger bolus dose at certain times of the day as compared to others. Administration of an agent in certain formulations, e.g., sustained-release formulations, a bolus dose can be administered less frequently, for example, once every three days, once per week, twice a month, once every month. Furthermore, the time between bolus doses is preferably long enough to allow the drug administered in the previous bolus dose to clear the subject's blood stream.

In other embodiments, methods of reducing nutrient availability, e.g., reducing weight, in a subject comprise administering to the subject an effective amount of the anti-obesity agents in continuous doses. By continuous dose it is intended to mean the continuous infusion of the drug by, for example, intravenous injection or a transdermal patch. Alternatively, a continuous dose can be administered orally in the form of a controlled release capsule or tablet which releases the drug into the subject's system over a period of time. When administered by a continuous dose, the drug is released over a period of about 1 hour, in some cases the drug is released over a period of about 2, 3, 4, 5, 6, 7, 8, 9, 10, 11, 12, 18, or 24 hours.

By "administered in combination" is meant that the anti-obesity agents are administered as a single administration, simultaneously as separate doses, or as sequentially administered. Sequential administration refers to administering one of the anti-obesity agents either before or after an anti-obesity agent. In certain embodiments, the first anti-obesity agent is administered about 30 minutes before or after the at least one other anti-obesity agent, in other embodiments about 1, 2, 3, 4, 5, 6, 7, 8, 9, 10, 11, or 12 hours before or after the at least one other anti-obesity agents. Any of the administered anti-obesity agents can be administered as a bolus dose or as a continuous dose.

Furthermore, in certain embodiments, administration of the weight-inducing agents in combination results in a synergistic effect in any of the aspects of the invention. In addition, in certain embodiments, administration of the weight-inducing agents in combination results in a lower dosage requirement for at least one of the agents, with the same effect.

Accordingly, in one embodiment is a method of treating obesity or reducing body weight in a subject in need thereof, comprising peripherally administering therapeutically effective amounts of at least two different anti-obesity agents, wherein at least one anti-obesity agent is an amylin, an amylin analog, an amylin agonist, or an amylin derivative and at least one anti-obesity agent is an engineered polypeptide comprising: an albumin binding domain polypeptide (ABD); and a first peptide hormone domain (HD1) selected from a leptin, a leptin analog or an active fragment thereof, and the subject reduces body weight by least 10%, 12%, 15%, 20%, 30%, 40% or even 50%.

Further embodiments include the following.

Embodiment 1

A method of treating obesity in a subject comprising peripherally administering therapeutically effective amounts of at least two different anti-obesity agents, wherein at least one anti-obesity agent is an amylin, an amylin analog, an amylin agonist, or an amylin derivative (i.e. an amylin agent) and at least one anti-obesity agent is an engineered polypeptide comprising: an albumin binding domain polypeptide (ABD); and a first peptide hormone domain (HD1) selected from a leptin, a leptin analog or an active fragment thereof.

Embodiment 2

A method of reducing body weight in a subject comprising peripherally administering therapeutically effective amounts of at least two different anti-obesity agents, wherein at least one anti-obesity agent is an amylin, an amylin analog, an amylin agonist, or an amylin derivative (i.e. an amylin agent) and at least one anti-obesity agent is an engineered polypeptide comprising: an albumin binding domain polypeptide (ABD); and a first peptide hormone domain (HD1) selected from a leptin, a leptin analog or an active fragment thereof.

Embodiment 3

The method according to any one of embodiments 1 or 2 wherein the at least one anti-obesity amylin agent is an amylin agonist.

Embodiment 4

The method according to any one of embodiments 1 to 3 wherein the amylin agonist comprises an amylin analog or derivative.

Embodiment 5

The method according to any one of embodiments 1 to 4 wherein the amylin analog or derivative comprises pramlintide.

Embodiment 6

The method according to any one of embodiments 1 to 5 wherein the amylin analog or derivative comprises a compound disclosed in Table 4.

Embodiment 7

The method according to any one of embodiments 1 to 6 wherein the amylin analog or derivative comprises Des-Lys1-[Lys26(mPEG40K)]-Pramlintide (SEQ ID NO: 214).

Embodiment 8

The method according to any one of embodiments 1 to 7 wherein the ABD comprises any one of the peptides selected from the group consisting of:

```
                                         (SEQ ID NO: 38)
LAEAKVLANRELDKYGVSDFYKSYINRAKTVEGVHTLIGHILAALP, (SEQ ID NO: 39)
LAEAKVLANRELDKYGVSDFYKRLINKAKTVEGVNALTHHILAALP, (SEQ ID NO: 40)
LAEAKVLANRELDKYGVSDYYKNLINRARTVEGVHALIDHILAALP, (SEQ ID NO: 41)
LAEAKVLANRELDKYGVSDYYKNIINRAKTVEGVRALKLHILAALP, (SEQ ID NO: 42)
LAEAKVLANRELDKYGVSDFYKNLINRAKTVEGVSSLKGHILAALP, (SEQ ID NO: 43)
LAEAKVLANRELDKYGVSDYYKNLINKAKTVEGVEALTLHILAALP, (SEQ ID NO: 44)
LAEAKVLANRELDKYGVSDFYKNLINRAKTVEGVDALIAHILAALP, (SEQ ID NO: 45)
LAEAKVLANRELDKYGVSDFYKSLINRAKTVEGVDALTSHILAALP, (SEQ ID NO: 46)
LAEAKVLANRELDKYGVSDFYKNLINRAKTVEGVNSLTSHILAALP, (SEQ ID NO: 47)
LAEAKVLANRELDKYGVSDFYKNVINKAKTVEGVEALIADILAALP, (SEQ ID NO: 48)
LAEAKVLANRELDKYGVSDYYKNLINKAKTVEGVQALIAHILAALP, (SEQ ID NO: 49)
LAEAKVLANRELDKYGVSDFYKRLINKAKTVEGVEALKLHILAALP, (SEQ ID NO: 50)
LAEAKEDAIKELDKYGVSDYYKNLINKAKTVEGVEALTLHILAALP, (SEQ ID NO: 51)
LAEAKEDAIKELDKYGVSDYYKNLINKAKTVEGVEALISEILAALP,
and (SEQ ID NO: 52)
LAEAKEDAIKELDKYGVSDYYKRLISKAKTVEGVKALISEILAALP.
```

Embodiment 9

The method according to any one of embodiments 1 to 8 wherein the HD1 comprises an amino acid sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO: 26, SEQ ID NO:27, SEQ ID NO:28, SEQ ID NO:29, SEQ ID NO:30, SEQ ID NO:31, SEQ ID NO:32, SEQ ID NO:33, SEQ ID NO:143, SEQ ID NO:144, SEQ ID NO:145, SEQ ID NO:146, SEQ ID NO:664, SEQ ID NO:665, SEQ ID NO:666, SEQ ID NO:667, SEQ ID NO:668, SEQ ID NO:669, SEQ ID NO:670, SEQ ID NO:671, SEQ ID NO:672, SEQ ID NO:673, SEQ ID NO:674, SEQ ID NO:675, SEQ ID NO:676, and SEQ ID NO:677.

Embodiment 10

The method according to any one of embodiments 1 to 9, wherein the HD1 is SEQ ID NO:29.

Embodiment 11

The method according to any one of embodiments 1 to 10, wherein the engineered polypeptide comprises a compound disclosed in Table 2.

Embodiment 12

The method according to any one of embodiments 1 to 11, wherein the engineered polypeptide comprises an amino acid sequence selected from the group consisting of: SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85 SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, and SEQ ID NO:107.

Embodiment 13

The method according to any one of embodiments 1 to 12, wherein the engineered polypeptide comprises an amino acid sequence of SEQ ID NO:54.

Embodiment 14

The method according to any one of embodiments 1 to 12, wherein the engineered polypeptide comprises an amino acid sequence of SEQ ID NO:61.

Embodiment 15

The method according to any one of embodiments 1 to 14 wherein the effective amount of the amylin agent and the effective amount of the engineered polypeptide comprises an amount such that a greater amount of weight loss is achieved when the amylin agent is administered in combination with the engineered polypeptide to said subject than the amount of weight loss achieved when either agent is administered alone.

Embodiment 16

The method according to any one of embodiments 1 to 15 wherein the two agents are administered at the same time.

Embodiment 17

The method according to any one of embodiments 1 to 16 wherein the two agents are mixed together.

Embodiment 18

The method according to any one of embodiments 1 to 17 wherein the subject's BMI is greater than 25.

Embodiment 19

The method according to any one of embodiments 1 to 18 wherein the subject's BMI is 25 to 35.

Embodiment 20

The method according to any one of embodiments 1 to 19, wherein the subject's BMI is 25 to 40.

Embodiment 21

The method according to any one of embodiments 1 to 20, wherein the subject's BMI is 25 to 45.

Embodiment 22

The method according to any one of embodiments 1 to 21, wherein the subject's BMI is 35 to 45.

Embodiment 23

The method according to any one of embodiments 1 to 22, wherein the subject's BMI is reduced to less than 30.

Embodiment 24

The method according to any one of embodiments 1 to 23, wherein the subject's BMI is reduced to less than 25.

Embodiment 25

The method according to any one of embodiments 1 to 24, wherein the subject's BMI is reduced to normal.

Embodiment 26

The method according to any one of embodiments 1 to 25, wherein weight loss is achieved within 4 weeks of treatment.

Embodiment 27

The method according to any one of embodiments 1 to 26, wherein weight loss is achieved within 8 weeks of treatment.

Embodiment 28

The method according to any one of embodiments 1 to 27, wherein weight loss is achieved within 12 weeks of treatment.

Embodiment 29

The method according to any one of embodiments 1 to 28, wherein weight loss is achieved within 20 weeks of treatment.

Embodiment 30

The method according to any one of embodiments 1 to 29, wherein weight loss is achieved within 24 weeks of treatment.

Embodiment 31

The method according to any one of embodiments 1 to 30, wherein the subject is human.

Embodiment 32

The method according to any one of embodiments 1 to 31, wherein the subject is an obese human.

Embodiment 33

The method according to any one of embodiments 1 to 32, wherein the weight loss is reduced by at least 10%.

Embodiment 34

The method according to any one of embodiments 1 to 33, wherein the weight loss is reduced by at least 12%.

Embodiment 35

The method according to any one of embodiments 1 to 34, wherein the weight loss is reduced by at least 15%.

B. Formulations

The pharmaceutical compounds of the invention may be formulated with pharmaceutically acceptable carriers or diluents as well as any other known adjuvants and excipients in accordance with conventional techniques such as those disclosed in *Remington's Pharmaceutical Sciences* by E. W. Martin. See also Wang et al. (1988) *J. of Parenteral Sci.* and Tech., Technical Report No. 10, Supp. 42:2 S.

In general, the engineered polypeptides may be formulated into a stable, safe pharmaceutical composition for administration to a patient. Pharmaceutical formulations contemplated for use in the methods of the invention may comprise approximately 0.01 to 1.0% (w/v), in certain cases 0.05 to 1.0%, of the engineered polypeptide, approximately 0.02 to 0.5% (w/v) of an acetate, phosphate, citrate or glutamate buffer allowing a pH of the final composition of from about 3.0 to about 7.0; approximately 1.0 to 10% (w/v) of a carbohydrate or polyhydric alcohol tonicifier and, optionally, approximately 0.005 to 1.0% (w/v) of a preservative selected from the group consisting of m-cresol, benzyl alcohol, methyl, ethyl, propyl and butyl parabens and phenol. Such a preservative is generally included if the formulated peptide is to be included in a multiple use product.

In particular embodiments, a pharmaceutical formulation of the present engineered polypeptides may contain a range of concentrations of the compound(s), e.g., between about 0.01% to about 98% w/w, or between about 1 to about 98% w/w, or preferably between 80% and 90% w/w, or preferably between about 0.01% to about 50% w/w, or more preferably between about 10% to about 25% w/w in these embodiments. A sufficient amount of water for injection may be used to obtain the desired concentration of solution.

Additional tonicifying agents such as sodium chloride, as well as other known excipients, may also be present, if desired. In some cases, such excipients are useful in maintenance of the overall tonicity of the compound. An excipient may be included in the presently described formulations at various concentrations. For example, an excipient may be included in the concentration range from about 0.02% to about 20% w/w, preferably between about 0.02% and 0.5% w/w, about 0.02% to about 10% w/v, or about 1% to about 20% w/w. In addition, similar to the present formulations themselves, an excipient may be included in solid (including powdered), liquid, semi-solid or gel form.

The pharmaceutical formulations may be composed in various forms, e.g., solid, liquid, semisolid or liquid. The term "solid", as used herein, is meant to encompass all normal uses of this term including, for example, powders and lyophilized formulations. The presently described formulations may be lyophilized.

The terms buffer, buffer solution and buffered solution, when used with reference to hydrogen-ion concentration or pH, refer to the ability of a system, particularly an aqueous solution, to resist a change of pH on adding acid or alkali, or on dilution with a solvent. Characteristic of buffered solutions, which undergo small changes of pH on addition of acid or base, is the presence either of a weak acid and a salt of the weak acid, or a weak base and a salt of the weak base. An example of the former system is acetic acid and sodium acetate. The change of pH is slight as long as the amount of hydronium or hydroxyl ion added does not exceed the capacity of the buffer system to neutralize it.

As described herein, a variety of liquid vehicles are suitable for use in the formulations of engineered polypeptides, for example, water or an aqueous/organic solvent mixture or suspension.

The stability of a engineered polypeptide formulation for use as described herein is enhanced by maintaining the pH of the formulation in a range determined by methods known in the art. In certain embodiments, the pH of the formulation is maintained in the range of about 3.5 to 5.0, or about 3.5 to 6.5, in some embodiments from about 3.7 to 4.3, or about 3.8 to 4.2. In some embodiments, pH may be about 4.0, about 5.0, about 6.0, about 7.0, about 8.0, about 9.0, or even higher. In some embodiments, pH may be in the physiological range, pH 6-8, preferably pH 7-7.6.

In certain embodiments, the buffer with the engineered polypeptide is an acetate buffer (preferably at a final formulation concentration of from about 1-5 to about 60 mM), phosphate buffer (preferably at a final formulation concentration of from about 1-5 to about to about 30 mM) or glutamate buffer (preferably at a final formulation concentration of from about 1-5 to about to about 60 mM). In some embodiments, the buffer is acetate (preferably at a final formulation concentration of from about 5 to about 30 mM).

A stabilizer may be included in the formulations but is not necessarily needed. If included, however, a stabilizer useful in the practice of the present invention is a carbohydrate or a polyhydric alcohol. A suitable stabilizer useful in the practice of the present invention is approximately 1.0 to 10% (w/v) of a carbohydrate or polyhydric alcohol. The polyhydric alcohols and carbohydrates share the same feature in their backbones, i.e., —CHOH—CHOH—, which is responsible for stabilizing the proteins. The polyhydric alcohols include such compounds as sorbitol, mannitol, glycerol, and polyethylene glycols (PEGs). These compounds are straight-chain molecules. The carbohydrates, such as mannose, ribose, sucrose, fructose, trehalose, maltose, inositol, and lactose, on the other hand, are cyclic molecules that may contain a keto or aldehyde group. These two classes of compounds have been demonstrated to be effective in stabilizing protein against denaturation caused by elevated temperature and by freeze-thaw or freeze-drying processes. Suitable carbohydrates include: galactose, arabinose, lactose or any other carbohydrate which does not have an adverse affect on a diabetic patient, i.e., the carbohydrate is not metabolized to form unacceptably large concentrations of glucose in the blood. Such carbohydrates are well known in the art as suitable for diabetics. Sucrose and fructose are suitable for use with the compound in non-diabetic applications (e.g. treating obesity).

In certain embodiments, if a stabilizer is included, the compound is stabilized with a polyhydric alcohol such as sorbitol, mannitol, inositol, glycerol, xylitol, and polypropylene/ethylene glycol copolymer, as well as various polyethylene glycols (PEG) of molecular weight 200, 400, 1450, 3350, 4000, 6000, 8000 and even higher). Mannitol is the preferred polyhydric alcohol in some embodiments. Another useful feature of the lyophilized formulations of the present invention is the maintenance of the tonicity of the lyophilized formulations described herein with the same formulation component that serves to maintain their stability. In some embodiments, mannitol is the preferred polyhydric alcohol used for this purpose.

The United States Pharmacopeia (USP) states that antimicrobial agents in bacteriostatic or fungistatic concentrations must be added to preparations contained in multiple dose containers. They must be present in adequate concentration at the time of use to prevent the multiplication of microorganisms inadvertently introduced into the preparation while withdrawing a portion of the contents with a hypodermic needle and syringe, or using other invasive means for delivery, such as pen injectors. Antimicrobial agents should be evaluated to ensure compatibility with all other components of the formula, and their activity should be evaluated in the total formula to ensure that a particular agent that is effective in one formulation is not ineffective in another. It is not uncommon to find that a particular antimicrobial agent will be effective in one formulation but not effective in another formulation.

A preservative is, in the common pharmaceutical sense, a substance that prevents or inhibits microbial growth and may be added to pharmaceutical formulations for this purpose to avoid consequent spoilage of the formulation by microorganisms. While the amount of the preservative is not great, it may nevertheless affect the overall stability of the peptide.

While the preservative for use in the pharmaceutical compositions can range from 0.005 to 1.0% (w/v), in some embodiments range for each preservative, alone or in combination with others, is: benzyl alcohol (0.1-1.0%), or m-cresol (0.1-0.6%), or phenol (0.1-0.8%) or combination of methyl (0.05-0.25%) and ethyl or propyl or butyl (0.005%-0.03%) parabens. The parabens are lower alkyl esters of para-hydroxybenzoic acid. A detailed description of each preservative is set forth in Remington's Pharmaceutical Sciences (Id.)

Engineered polypeptides may not have a tendency to adsorb onto the glass in a glass container when in a liquid form, therefore, a surfactant may not be required to further stabilize the pharmaceutical formulation. However, with regard to compounds which do have such a tendency when in liquid form, a surfactant should be used in their formulation. These formulations may then be lyophilized. Surfactants frequently cause denaturation of protein, both of hydrophobic disruption and by salt bridge separation. Relatively low concentrations of surfactant may exert a potent denaturing activity, because of the strong interactions between surfactant moieties and the reactive sites on proteins. However, judicious use of this interaction can stabilize proteins against interfacial or surface denaturation. Surfactants which could further stabilize the engineered polypeptide may optionally be present in the range of about 0.001 to 0.3% (w/v) of the total formulation and include polysorbate 80 (i.e., polyoxyethylene(20) sorbitan monooleate), CHAPS® (i.e., 3-[(3-cholamidopropyl) dimethylammonio] l-propanesulfonate), Brij® (e.g., Brij® 35, which is (polyoxyethylene (23) lauryl ether), poloxamer, or another non-ionic surfactant.

It may also be desirable to add sodium chloride or other salt to adjust the tonicity of the pharmaceutical formulation, depending on the tonicifier selected. However, this is optional and depends on the particular formulation selected. Parenteral formulations preferably may be isotonic or substantially isotonic.

A preferred vehicle for parenteral products is water. Water of suitable quality for parenteral administration can be prepared either by distillation or by reverse osmosis. Water for injection is the preferred aqueous vehicle for use in the pharmaceutical formulations.

It is possible that other ingredients may be present in the pharmaceutical formulations. Such additional ingredients may include, e.g., wetting agents, emulsifiers, oils, antioxidants, bulking agents, tonicity modifiers, chelating agents, metal ions, oleaginous vehicles, proteins (e.g., human serum albumin, gelatin or proteins) and a zwitterion (e.g., an amino acid such as betaine, taurine, arginine, glycine, lysine and histidine). Additionally, polymer solutions, or mixtures with polymers provide the opportunity for controlled release of the peptide. Such additional ingredients, of course, should not adversely affect the overall stability of the pharmaceutical formulation of the present invention.

Containers are also an integral part of the formulation of an injection and may be considered a component, for there is no container that is totally inert, or does not in some way affect the liquid it contains, particularly if the liquid is aqueous. Therefore, the selection of a container for a particular injection must be based on a consideration of the composition of the container, as well as of the solution, and the treatment to which it will be subjected. Adsorption of the peptide to the glass surface of the vial can also be minimized, if necessary, by use of borosilicate glass, for example, Wheaton Type I borosilicate glass #33 (Wheaton Type 1-33) or its equivalent (Wheaton Glass Co.). Other vendors of similar borosilicate glass vials and cartridges acceptable for manufacture include Kimbel Glass Co., West Co., Bunder Glas GMBH and Form a Vitrum. The biological and chemical properties of the compound may be stabilized by formulation and lyophilization in a Wheaton Type 1-33 borosilicate serum vial to a final concentration of 0.1 mg/ml and 10 mg/ml of the compound in the presence of 5% mannitol, and 0.02% Tween 80.

For formulations to be delivered by injection, in order to permit introduction of a needle from a hypodermic syringe into a multiple-dose vial and provide for resealing as soon as the needle is withdrawn, the open end of each vial is preferably sealed with a rubber stopper closure held in place by an aluminum band.

Stoppers for glass vials, such as, West 4416/50, 4416/50 (Teflon faced) and 4406/40, Abbott 5139 or any equivalent stopper can be used as the closure for pharmaceutical for injection. For formulations comprising peptidic anti-obesity agents, these stoppers are compatible with the peptide as well as the other components of the formulation. The inventors have also discovered that these stoppers pass the stopper integrity test when tested using patient use patterns, e.g., the stopper can withstand at least about 100 injections. Alternatively, the peptide can be lyophilized in to vials, syringes or cartridges for subsequent reconstitution. Liquid formulations of the present invention can be filled into one or two chambered cartridges, or one or two chamber syringes.

Each of the components of the pharmaceutical formulation described above is known in the art and is described in PHARMACEUTICAL DOSAGE FORMS: PARENTERAL MEDICATIONS, Vol. 1, 2nd ed., Avis et al. Ed., Mercel Dekker, New York, N.Y. 1992, which is incorporated by reference in its entirety herein and for all purposes.

The manufacturing process for the above liquid formulations generally involves compounding, sterile filtration and filling steps. The compounding procedure involves dissolution of ingredients in a specific order (preservative followed by stabilizer/tonicity agents, buffers and peptide) or dissolving at the same time.

Alternative formulations, e.g., non-parenteral, may not require sterilization. However, if sterilization is desired or necessary, any suitable sterilization process can be used in developing the peptide pharmaceutical formulation of the present invention. Typical sterilization processes include filtration, steam (moist heat), dry heat, gases (e.g., ethylene oxide, formaldehyde, chlorine dioxide, propylene oxide, beta-propiolacctone, ozone, chloropicrin, peracetic acid methyl bromide and the like), exposure to a radiation source, and aseptic handling. Filtration is the preferred method of sterilization for liquid formulations of the present invention. The sterile filtration involves filtration through 0.45 um and 0.22 um (1 or 2) which may be connected in series. After filtration, the solution is filled into appropriate vials or containers.

In certain embodiments, the engineered polypeptides described herein are administered peripherally to the subjects. In some embodiments, the liquid pharmaceutical formulations of the present invention are intended for parenteral administration. Suitable routes of administration include intramuscular, intravenous, subcutaneous, intradermal, intraarticular, intrathecal and the like. In some embodiments, the subcutaneous route of administration is preferred. In certain embodiments, mucosal delivery is also preferred. These routes include, but are not limited to, oral, nasal, sublingual, pulmonary and buccal routes which may include administration of the peptide in liquid, semi-solid or solid form. For formulations comprising engineered polypeptides, administration via these routes can require substantially more compound to obtain the desired biological effects due to decreased bioavailability compared to parenteral delivery. In addition, parenteral controlled release delivery can be achieved by forming polymeric microcapsules, matrices, solutions, implants and devices and administering them parenterally or by surgical means. Examples of controlled release formulations are described in U.S. Pat. Nos. 6,368,630, 6,379,704, and 5,766,627, which are incorporated herein by reference. These dosage forms may have a lower bioavailability due to entrapment of some of the peptide in the polymer matrix or device. See e.g., U.S. Pat. Nos. 6,379,704, 6,379,703, and 6,296,842, each of which is incorporated herein by reference in its entirety and for all purposes.

The compounds may be provided in dosage unit form containing an amount of the engineered polypeptide that will be effective in one or multiple doses.

As will be recognized by those in the field, an effective amount of the engineered polypeptide will vary with many factors including the age and weight of the subject, the subject's physical condition, the condition to be treated, and other factors known in the art. An effective amount of the engineered polypeptides will also vary with the particular combination administered. As described herein, administration of the engineered polypeptides in combination may allow for a reduced amount of any of the administered engineered polypeptides to be an effective amount.

The long-duration of action of the engineered polypeptide can provide the extended duration of action desired, such as once daily or once weekly administration. The duration of action can be selected, for example, by choice of ABD and its affinity for albumin. While not wishing to be bound by theory, it is believed that higher affinity to albumin will yield longer circulation times providing longer duration of action. Either or both pharmacodynamic (therapeutic effects) and pharmacokinetic (drug properties) can be measured over time after delivery, such as drug plasma levels, acute or chronic glucose and/or HbA1 c lowering, insulin plasma levels, food intake inhibition or weight loss.

C. Effective Dosages

Pharmaceutical compositions provided herein include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat diabetes, such compositions will contain an amount of active ingredient effective to achieve the desired result (e.g. decreasing fasting blood glucose in a subject). When administered in methods to treat obesity, such compositions will contain an amount of active ingredient effective to achieve the desired result (e.g. decrease the body mass).

The dosage and frequency (single or multiple doses) of compound administered can vary depending upon a variety of factors, including route of administration; size, age, sex, health, body weight, body mass index, and diet of the recipient; nature and extent of symptoms of the disease being treated (e.g., the disease responsive to compounds described herein); presence of other diseases or other health-related problems; kind of concurrent treatment; and complications from any disease or treatment regimen. Other therapeutic regimens or agents can be used in conjunction with the methods and compounds of the invention.

Therapeutically effective amounts for use in humans may be determined from animal models. For example, a dose for humans can be formulated to achieve a concentration that has been found to be effective in animals. The dosage in humans can be adjusted by monitoring one or more physiological parameters, including but not limited to blood sugar and body mass, and adjusting the dosage upwards or downwards, as described above and known in the art.

Dosages may be varied depending upon the requirements of the patient and the compound being employed. The dose administered to a patient, in the context of the present invention, should be sufficient to affect a beneficial therapeutic response in the patient over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached. In one embodiment of the invention, the dosage range is 0.001% to 10% w/v. In another embodiment, the dosage range is 0.1% to 5% w/v.

However, typical doses may contain from a lower limit of about 0.1 mg to an upper limit of about 200 mg of the pharmaceutical compound per day. Also contemplated are other dose ranges such as 1 mg to 100 mg of the compound per dose, and 3 mg to 70 mg per dose. Typically, the dose of engineered polypeptides with long duration of action is administered, for example, daily and even once weekly. The doses per day may be delivered in discrete unit doses, provided continuously in a 24 hour period or any portion of that the 24 hours.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

The surprising dose-sparing property of the engineered polypeptides described herein, along with their surprisingly long plasma half-life and duration of pharmacological action, provides for a superior pharmaceutical agent. The superior properties including dose-sparing, allow for lower dosing, thus less or less severe side-effects and improved cost of goods, and/or more cost-effective and simpler formulations for once daily or once weekly administration not currently achieved by the parent compounds alone.

D. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p.1, 1975. The exact formulation, route of administration, and dosage can be chosen by the individual physician in view of the patient's condition and the particular method in which the compound is used.

Without wishing to be bound by any theory, it is believed that conjugation of an ABD albumin binding domain with a hormone domain as described herein, can provide decreased immunogenicity as judged by a reduction in immune response relative to the hormone domain without ABD conjugation. See e.g., WO 2009/016043, incorporated herein by reference in its entirety and for all purposes.

VII. Examples

Example 1: Engineered Polypeptide Recovery

Protein sequences were designed and back translated using commercial software to DNA sequence for cloning into an *E. coli* expression vector. Sequences were either obtained as oligonucleotides and stitched together using standard PCR amplification techniques, or they were digested from existing expression constructs using standard restriction enzymes and then ligated back together. Sequences expressing the protein of interest were placed in pET45 with a T7 promoter for inducible expression. After constructs were verified by sequencing, the vector DNA was purified and transformed into an expression host, typically BL21(DE3). A single colony was selected to grow a starter culture in 4 ml LB media for ~6 hrs. Glycerol stocks were prepared by adding 100 ul 80% glycerol to 900 ul stock and store at -80C. Optionally, 500 ul uninduced sample was retained for gel analysis. A 60 ml culture (magic media) was inoculated using 60 ul starter culture in a 125 ml Thompson flask and incubated @ 30C overnight. Remove 250 ul sample for analysis. Spin down and freeze cell pellet for later processing.

Bacterial cells were harvested and subsequently lysed to isolate inclusion bodies. Since the protein was present in the inclusion bodies, these were solubilized and the protein refolded at 4C. Proteins were then separated using size exclusion chromatography until only a single band remained and endotoxin levels were acceptable for in vivo testing. Analytical HPLC, RP-LC-MS and SDS-PAGE gel were run as quality control measures on the final protein. Protein was distributed to predetermined aliquots and stored at -80C.

Typical recoveries of engineered polypeptide for the methods described herein are provided in Table 5 following. Surprisingly, the recoveries observed for the compounds and production methods described above can be significantly higher than recoveries observed with previously reported conjugated species, e.g., Fc-leptin and the like. Furthermore, the foreign ABD domain did not adversely affect expression, recovery, re-folding, yield or solubility of the recovered engineered polypeptides, particularly for the leptin conjugates despite the generally recognized difficulties in recovering and handling leptin.

TABLE 5

Recoveries of engineered polypeptides

| Cmpd | Recovery, mg/50 mL culture |
| --- | --- |
| 1 | 26.2 |
| 2 | 53.5 |
| 3 | 11.2 |
| 4 | 33.6 |

Example 2: Leptin In Vitro Functional Activity

Method. This assay measures receptor signaling following treatment of cells expressing a modified Leptin receptor. Test samples were assumed at 100% purity and re-solvated to 10× assay concentration in stimulation buffer. A total of 90 ul of each 10× compound was transferred into a deep well pp plate and serially diluted (3-fold series) with Stimulation buffer using the Perkin Elmer Multiprobe® II and program "MSV_Lep_Func_3-Fold_Dil-Deepwell_96.MPT." The serially diluted plate was compounded into the 96-well stimulation plate containing 2.5×10A5 cell pellets of 18 hour leptin-weaned Keptin cells, as known in the art, using MultiMek test program "MSV_Lep_Func_200 ul_Transfer" that transfers 200 ul of each of the diluted compounds and mixes the cells. At this time, the plate was sealed with an adhesive plate cover and placed at 37C for 30 minutes to allow for stimulation of pSTAT5. See e.g., Crouse et al., 1998, *J. Biol. Chem.*, 273:18365-18373. After incubation, the stimulation plate was centrifuged to re-pellet the cells, the supernatant was removed and the remaining cell pellets were frozen at -80C (>30 minutes). Cell lysates were made by the addition of 100 ul of 1× lysate to the thawed cell pellets (Perkin Elmer pSTAT5 Assay kit) with rotation at ambient RT for 20 minutes. The lysates were clarified at 2500 rpm for 20 minutes and examined in the pSTAT5 Assay kit as 4 ul/well in a 384-well Proxiplate™ according to manufacturer instructions. The pSTAT5 signal (RFU) was determined using a Packard Fusion α-FP HT plate reader set to Alpha read parameters. Assay was completed in 384-well Proxiplate™ plates at 11 μl total volume with values representing mean of n=4 assay wells per dose point.

With reference to Table 6 following, Cmpds C1-C6 are exemplary leptins, leptin analogs and leptin derivatives, as described herein. Specifically, Cmpd C1 is SEQ ID NO:20 as described herein. Cmpd C2 is SEQ ID NO:30 (i.e., A200).

Cmpd C3 is SEQ ID NO:32, to which a single 20 kDa polyethyleneglycol (PEG) moiety has been attached via the cysteine residue at position 78. Methods for the conjugation of peptides and proteins with PEG as known in the art. Cmpd C4 is a PEGylated derivative of SEQ ID NO:20, in which a single 20 kDa PEG has been attached via the N-terminus of SEQ ID NO:20. Cmpd C5 is a dual PEGylated PEG derivative of SEQ ID NO:32, in which a single 20 kDa PEG moiety has been attached via the cysteine residue at position 78 and a single 20 kDa PEG moiety has been attached via the N-terminus. Cmpd C6 is a PEGylated derivative in which a single 40 kDa PEG has been attached via the N-terminus.

Results.

As set forth in Table 6 following, engineered polypeptides described herein (e.g., Cmpds 1-4) have comparable, and even superior, functional activity in the Obeca STATS assay, compared with a variety of conjugated leptins.

TABLE 6

In vitro Functional Activity for leptins

| Cmpd | Molecule or engineered polypeptide type | $EC_{50}$ nM (Obeca STAT5 assay) |
|---|---|---|
| C1 | SEQ ID NO:20 | 0.038 |
| C2 | SEQ ID NO: 30 | 0.855 |
| C3 | SEQ ID NO:32-single 20 kDa PEG via 78 C. | 0.319 |
| C4 | SEQ ID NO:20-single 20 kDa PEG via N-terminus | 0.275 |
| C5 | SEQ ID NO:32-dual PEGylated (20 kDa PEG via 78 C. and 20 kDa PEG via N-terminus) | 2.262 |
| C6 | SEQ ID NO:20-single PEG40 kDa via N-terminus | 0.355 |
| 1 | SEQ ID NO:53 | 0.628 |
| 2 | SEQ ID NO:54 | 0.530 |
| 3 | SEQ ID NO:55 | 0.095 |
| 4 | SEQ ID NO:56 | 0.103 |
| 9 | SEQ ID NO:57 | 0.185 |
| 12 | SEQ ID NO:58 | 1.052 |
| 13 | SEQ ID NO:59 | 0.116 |
| 14 | SEQ ID NO:60 | 0.406 |
| 15 | SEQ ID NO:61 | 0.427 |
| 16 | SEQ ID NO:62 | 0.411 |
| 17 | SEQ ID NO:63 | 0.468 |
| 18 | SEQ ID NO:64 | 0.322 |

Example 3: Change in Body Weight after Single Administration

Method.

Figure 1B:
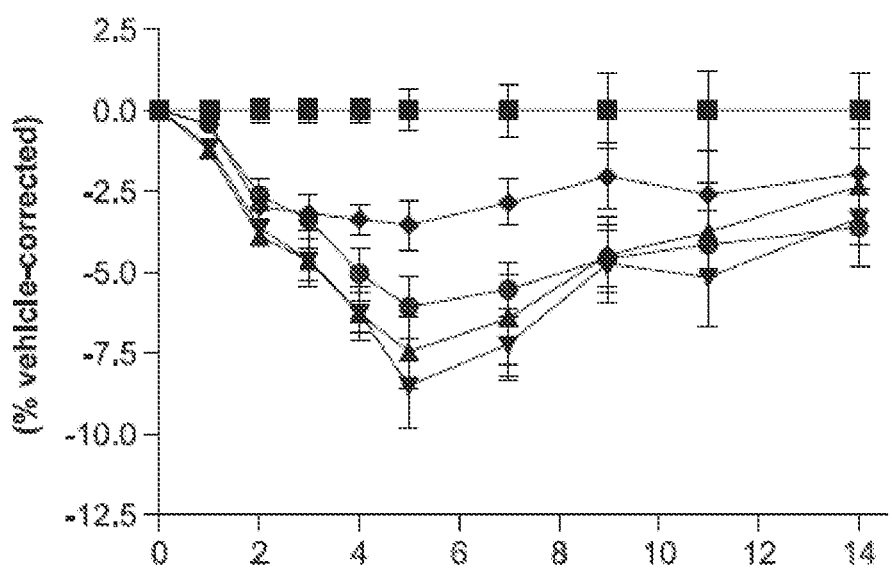

Lean Sprague Dawley rats were maintained on a low fat diet during the study. Mean body weight was 319 grams at beginning of study. Animals were divided into six groups (n=6/group). Each group was assigned to receive one of the following: vehicle; Cmpd 1 at 2.6 mg/kg in vehicle; Cmpd 2 at 2.7 mg/kg in vehicle; Cmpd 4 at 2.7 mg/kg in vehicle; Cmpd 2 at 10 mg/kg in vehicle. Each test animal received a single subcutaneous injection at time=0. Food intake and change in body weight (% vehicle corrected) were monitored for 14 days, and the results recorded as shown (FIG. 1A and FIG. 1B). Administered compounds: Vehicle (box); Cmpd 1 at 2.6 mg/kg (triangle tip up); Cmpd 2 at 2.7 mg/kg (triangle tip down); Cmpd 4 at 2.7 mg/kg (diamond); Cmpd C2 at 10 mg/kg (circle).

Results.

As depicted in FIG. 1A and FIG. 1B, administration of each engineered polypeptide resulted in reduced food intake and body weight. All compounds were given at an equimolar dose by total compound weight; compounds were all given at 120 nmol/kg (i.e., Cmpd 1 at 2.6 mg/kg; Cmpd 2 and Cmpd 4 at 2.7 mg/kg; Cmpd C2 at 10 mg/kg). It should be noted that Cmpd C2 (i.e., A200) is a dimer of two moieties, each moiety consisting of the FC region of IgG1 fused to human leptin. Cmpd 1 and Cmpd 2 have an activity similar to Cmpd C2 which, because it is a dimer, actually has two leptins per molecule. While the efficacy (lowest body weight) appears similar, it is clear that the trend favors both engineered polypeptides over Cmpd C2. When viewed on a per mole of leptin basis, the engineered polypeptides are superior for both inhibition of food intake and body weight, as Cmpd C2 has 2 moles of leptin for in each Fc-leptin dimeric complex, whereas each mole of ABD-leptin moiety has only 1 mole of leptin.

Previous results have shown that one needs approximately 500 ug/kg/day of an A500 compound to affect 9-10% weight loss at 7 days when given by continuous infusion to a lean rat. This results in 2.5 mg of A500 leptin compound at 5 days and 3.5 mg of compound at 7 days. Since an A500 compound itself is 16067.68 gm/mol and the molecular weight of Cmpd 2 is 22,510 gm/mol, one would anticipate needing 1.4× more of the ABD fusion protein over the 5 days. Instead only 1.08x (2.7 mg/2.5 mg) more compound was given which indicates a surprising dose-sparing property.

Example 4: Change in Body Weight after Single Administration of Cmpd 2

Method.

Figure 2A:
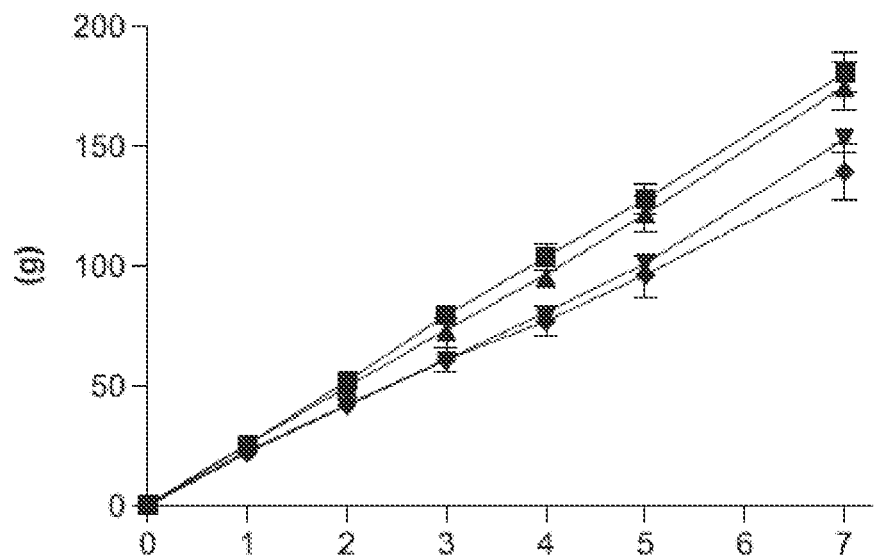
FIGS. 2A-2B depict the effects of a single administration of engineered polypeptides as described herein on food intake and body weight upon administration to lean rats as described in Example 4.
Figure 2B:
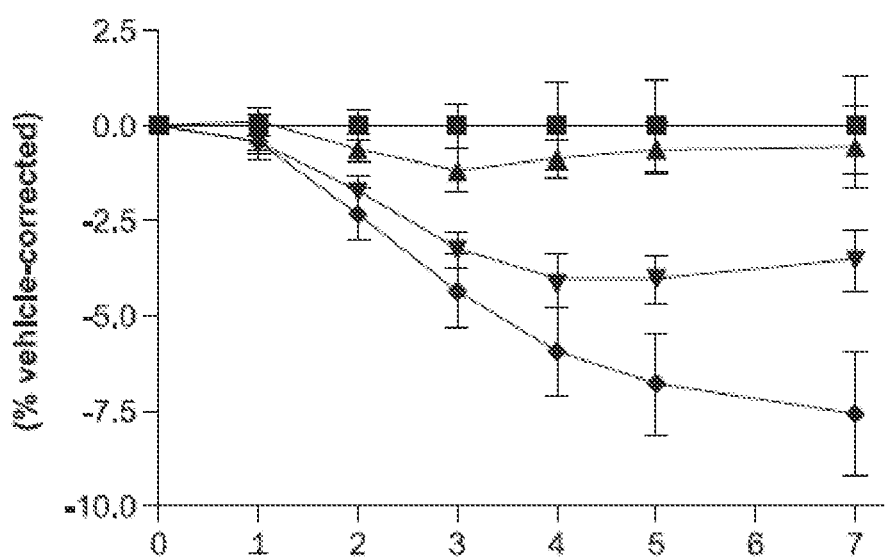

Lean Sprague Dawley rats were maintained on a low fat diet during the study. Mean body weight was 324 grams at beginning of study. Animals were divided into four groups (n=6/group). Each group was assigned to receive one of the following: vehicle; Cmpd 2 at 0.3 mg/kg in vehicle; Cmpd 2 at 1.0 mg/kg in vehicle; Cmpd 2 at 3.0 mg/kg in vehicle. Each test animal received a single subcutaneous injection at time=0. Food intake and change in body weight (% vehicle corrected) were monitored for 14 days, and the results recorded as shown (FIG. 2A and FIG. 2B). Administered compounds: Vehicle (box); Cmpd 2 at 0.3 mg/kg (triangle tip up); Cmpd 2 at 1.0 mg/kg (triangle tip down); Cmpd 2 at 3.0 mg/kg (diamond).

Results.

As depicted in FIG. 2A and FIG. 2B, administration at each concentration of engineered polypeptide Cmpd 2 resulted in reduced food intake and body weight. A dose response is observed in FIG. 2B.

Example 5: Change in Body Weight After Single Administration of Cmpd C2

Method.

Figure 3A:
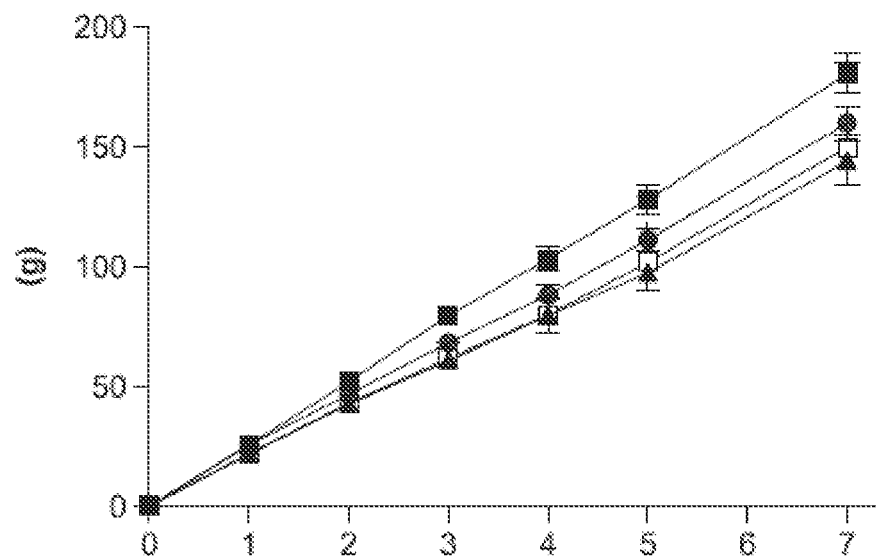
FIGS. 3A-3B depict the effects of a single administration of engineered polypeptides as described herein on food intake and body weight upon administration to lean rats as described in Example 5.
Figure 3B:
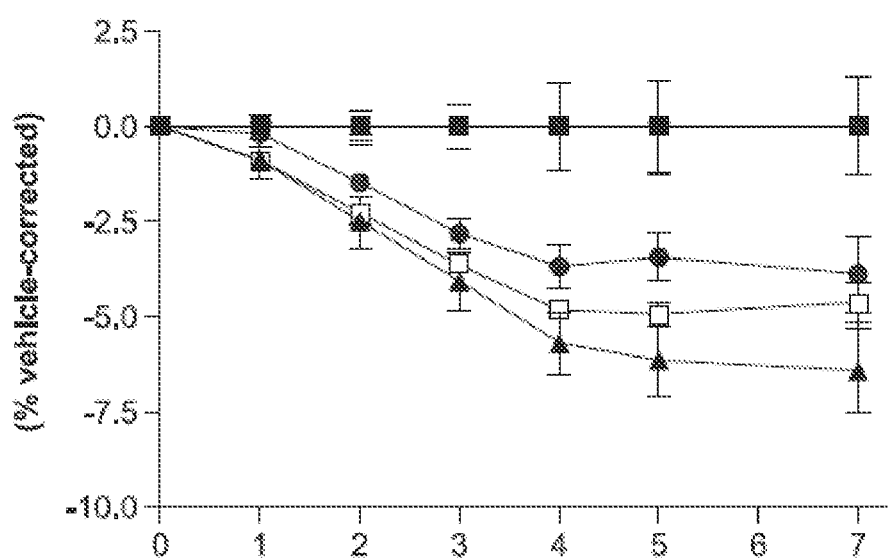

Lean Sprague Dawley rats were maintained on a low fat diet during the study. Mean body weight was 324 grams at beginning of study. Animals were divided into four groups (n=6/group). Each group was assigned to receive one of the following: vehicle; Cmpd C2 at 1.1 mg/kg in vehicle; Cmpd C2 at 3.3 mg/kg in vehicle; Cmpd C2 at 11.1 mg/kg in vehicle. Each test animal received a single subcutaneous injection at time=0. Food intake and change in body weight (% vehicle corrected) were monitored for 14 days, and the results recorded as shown (FIG. 3A and FIG. 3B). Administered compounds: Vehicle (box); Cmpd C2 at 1.1 mg/kg (circle); Cmpd C2 at 3.3 mg/kg (box); Cmpd C2 at 11.1 mg/kg (triangle tip up).

Results.

As depicted in FIG. 3A and FIG. 3B, administration at each concentration of control Cmpd C2 resulted in reduced food intake and body weight.

Example 6: Change in Body Weight after Single Administration of Cmpd C6

Method.

Figure 4A:
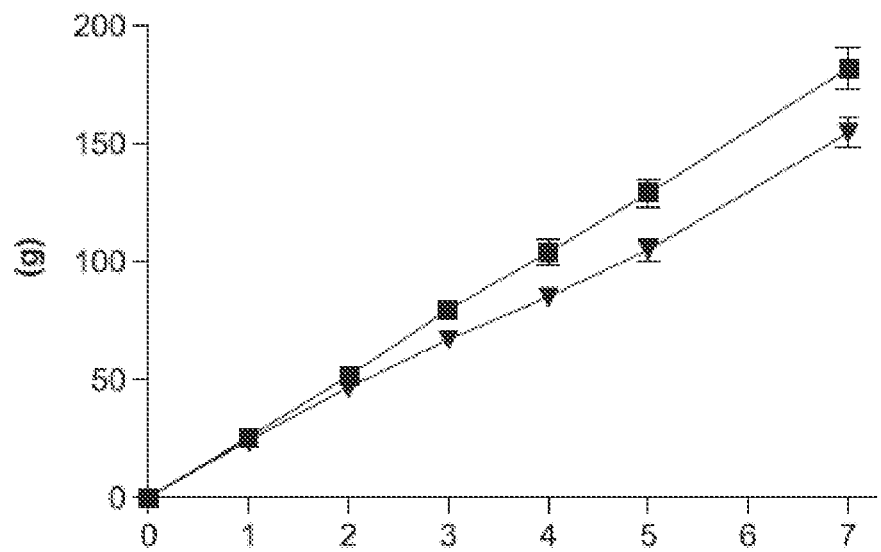
FIGS. 4A-4B depict the effects of a single administration of engineered polypeptides described herein, and of a control compound, on food intake and body weight upon administration to lean rats as described in Example 6.
Figure 4B:
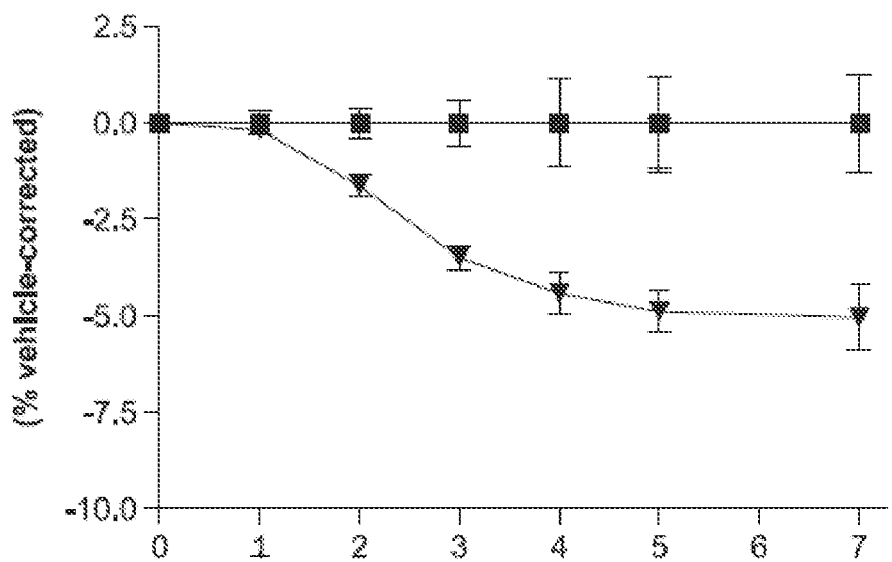

Lean Sprague Dawley rats were maintained on a low fat diet during the study. Mean body weight was 324 grams at beginning of study. Animals were divided into two groups (n=6/group). Each group was assigned to receive one of the following: vehicle; Cmpd C6 at 2.2 mg/kg in vehicle. Each test animal received a single subcutaneous injection at time=0. Food intake and change in body weight (% vehicle corrected) were monitored, and the results recorded as shown (FIG. 4A and FIG. 4B). Administered compounds: Vehicle (box); Cmpd C6 at 2.2 mg/kg (triangle tip down).

Results.

As depicted in FIG. 4A and FIG. 4B, administration at each concentration of control Cmpd C6 resulted in reduced food intake and body weight.

Example 7: Change in Body Weight in DIO Rats

Method.

Diet-induced obese (DIO) prone Sprague Dawley Rats averaging approximately 500 grams were injected IP with test and control compounds on day 0 and day 7 (n=6 per compound). The test compound was SEQ ID NO:54 given at 1.3 mg/kg/week in vehicle. Body weight and food intake were measured at multiple points (days 0, 4, 7, 12 and 14 d) during the study period. Administered compounds: Vehicle (box); SEQ ID NO:54 at 1.3 mg/kg in vehicle (triangle tip up).

Results.

Figure 5:
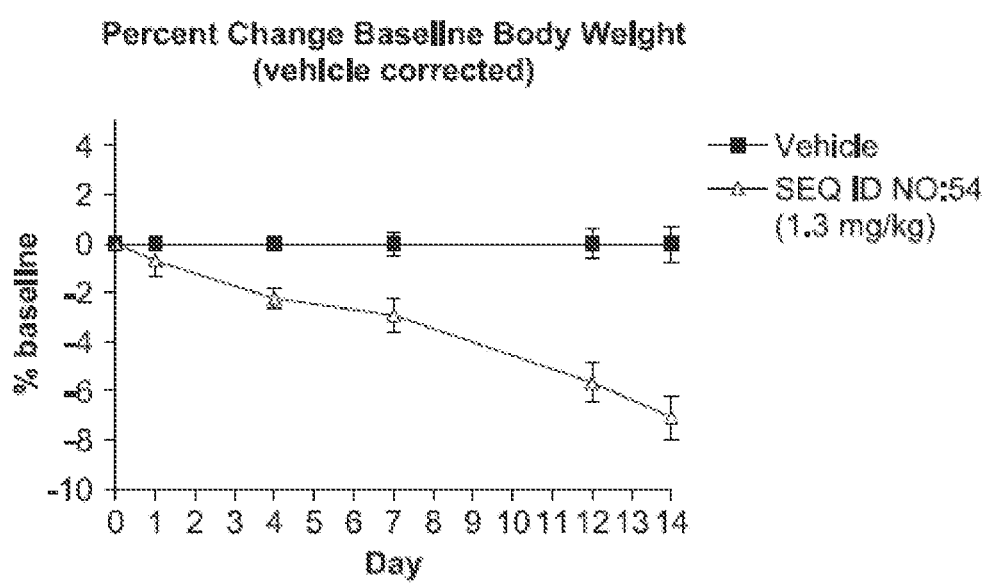
FIG. 5 depicts the effects of once weekly administration of SEQ ID NO:54 on body weight (% baseline) upon administration to DIO rats as described in Example 7. Legend: Vehicle (box); Cmpd 2 at 1.3 mg/kg per injection (triangle tip up).

The results, depicted in FIG. 5, demonstrate that IP injection at a once weekly interval results in a 3% weight loss after 7 days as seen previously at this dose. Upon a second injection, the rats continued to lose weight resulting in a cumulative vehicle corrected body weight loss of −7-8% at 14 days. In contrast and surprisingly, previous studies with FC-leptin (leptin A200) have only resulted in approximately 4% weight loss at 14 days after a 5 mg/kg/week dose with injections at day 0 and day 7 in a similar DIO model.

Example 8: Detection of Engineered Polypeptides in Plasma

Method.

Diet-induced obese (DIO) Sprague Dawley rats averaging approximately 483 grams were split into five groups, two of which were implanted with osmotic pumps. One of the two groups with osmotic pumps received a continuous subcutaneous infusion (CSI) of vehicle alone; the other received a CSI of SEQ ID NO:33 (i.e., A500) in vehicle at a dose of 250 µg/kg/day. The other three groups were treated as follows: one group received once-weekly subcutaneous injections of vehicle alone on days 0, 7, 14, and 21 of the study; another group received once-weekly subcutaneous injections of SEQ ID NO:54 (an ABD-A500 engineered polypeptide) at a dose of 1.3 mg/kg in vehicle on days 0, 7, 14, and 21 of the study; the remaining group received once-weekly subcutaneous injections of SEQ ID NO:54 at a dose of 3.0 mg/kg in vehicle on days 0, 7, 14, and 21 of the study. Blood samples were taken from each animal on Day 27, which was the day the study was terminated.

Figure 6A:
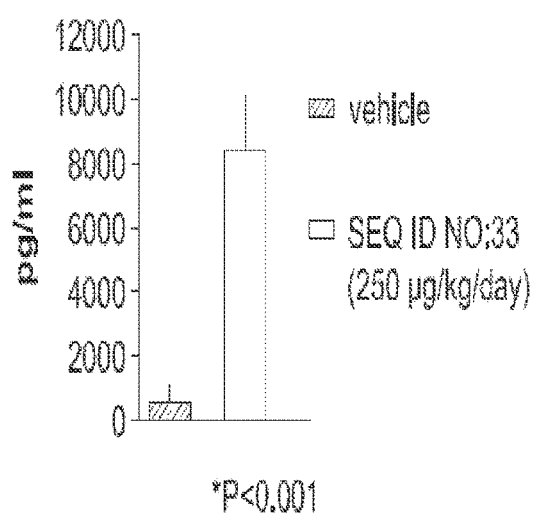
FIGS. 6A-6B depict detection and quantification of plasma levels of SEQ ID NO:33 (FIG. 6A) and SEQ ID NO:54 (FIG. 6B) upon administration to DIO rats as described in Example 8.
Figure 6B:
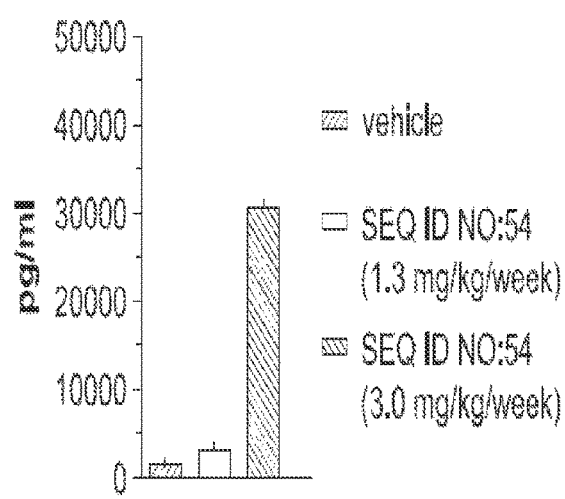

Results. The results, depicted in FIGS. 6A-6B, demonstrate that the once weekly injections of SEQ ID NO:54 at 1.3 mg/kg resulted in plasma levels that were slightly lower to that achieved by continuous infusion of SEQ ID NO:33, and once weekly injections of SEQ ID NO:54 at 3.0 mg/kg resulted in plasma levels that were significantly greater than that achieved with continuous infusion of SEQ ID NO:33 (compare FIG. 6A with FIG. 6B; note difference in scales of the Y-axis of each panel).

Example 9: Change in Body Weight After Single Administration of Engineered Polypeptides Method.

Lean Sprague Dawley rats were maintained on a low fat diet during the study. Mean body weight was 330 grams at beginning of study. Each test animal (n=5/group) received a single subcutaneous injection at time=0. Animals were divided into five groups. Each group was assigned to receive one of the following: vehicle; SEQ ID NO: 54 in vehicle; SEQ ID NO:56 in vehicle; SEQ ID NO: 58 in vehicle; SEQ ID NO: 59 in vehicle. SEQ ID NOS; 54, 56, 58, and 59 were each delivered at a dose of 120 nmol/kg. Percent change in body weight for each group was monitored for 14 days, and the results recorded as shown (FIG. 7).

Results.

Figure 7:
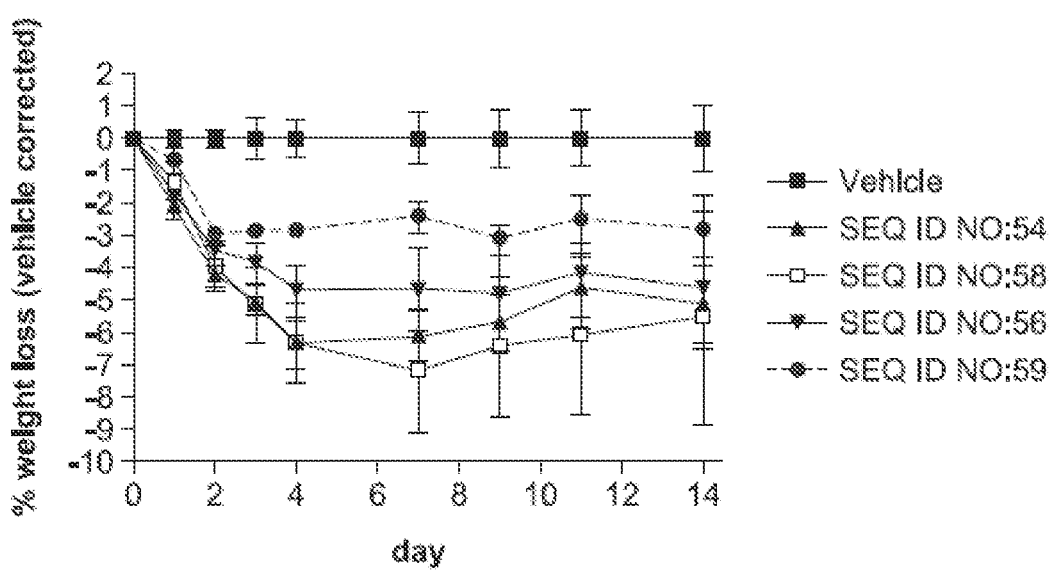
FIG. 7 depicts the effects the effects of a single administration of the indicated engineered polypeptides described herein on change in body weight (% vehicle-corrected) upon administration to lean rats as described in Example 9.

As depicted in FIG. 7, each group of animals that received a single injection of one of the SEQ ID NOS tested exhibited significant and sustained weight loss across the 14-day length of the study relative to the group that received vehicle alone.

Example 10: Change in Body Weight After Single Administration of Engineered Polypeptides Method.

Lean Sprague Dawley rats were maintained on a low fat diet during the study. Mean body weight was 330 grams at beginning of study. Animals were divided into six groups (n=5/group). Each test animal received a single subcutaneous injection at time=0. Each group was assigned to receive one of the following: vehicle; SEQ ID NO:54 in vehicle; SEQ ID NO:57 in vehicle; SEQ ID NO:60 in vehicle; SEQ ID NO:61 in vehicle; SEQ ID NO:62 in vehicle. SEQ ID NOS; 54, 57, 60, 61, and 62 were each delivered at a dose of 120 nmol/kg. Percent change in body weight for each group was monitored for 14 days, and the results recorded as shown (FIG. 8).

Results.

Figure 8:
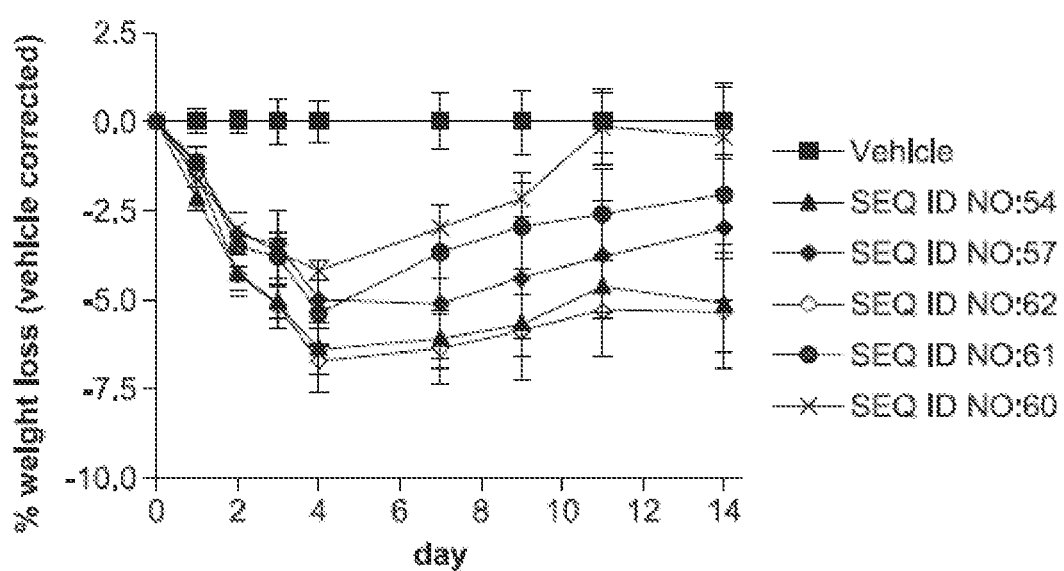
FIG. 8 depicts the effects of a single administration of the indicated engineered polypeptides described herein on change in body weight (% vehicle-corrected) upon administration to lean rats as described in Example 10.

As depicted in FIG. 8, each group of animals that received a single injection of one of the SEQ ID NOS tested exhibited significant and sustained reduction in body weight relative to the group that received vehicle alone.

Example 11: Change in Body Weight and Food Intake After Single Administration of Engineered Polypeptides Method.

Lean Sprague Dawley rats were maintained on a low fat diet during the study. Mean body weight was 317 grams at beginning of study. Each test animal (n=7/group) received a single subcutaneous injection at time=0. Animals were divided into four groups. Each group was assigned to receive one of the following: vehicle; SEQ ID NO: 54 in vehicle; SEQ ID NO:63 in vehicle; SEQ ID NO:64 in vehicle. SEQ ID NOS; 54, 63, and 64 were each delivered at a dose of 120 nmol/kg. Food intake and percent change in body weight for each group was monitored for 14 days, and the results recorded as shown (FIG. 9A and FIG. 9B, respectively).

Results.

Figure 9A:
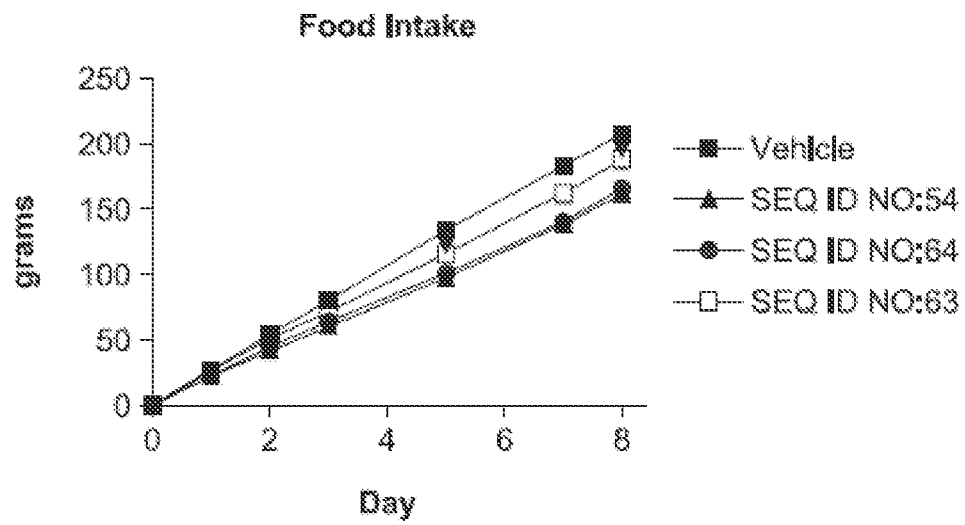
FIGS. 9A-9B depict the effects of a single administration of the indicated engineered polypeptides described herein on food intake and change in body weight (% vehicle-corrected) upon administration to rats as described in Example 11.
Figure 9B:
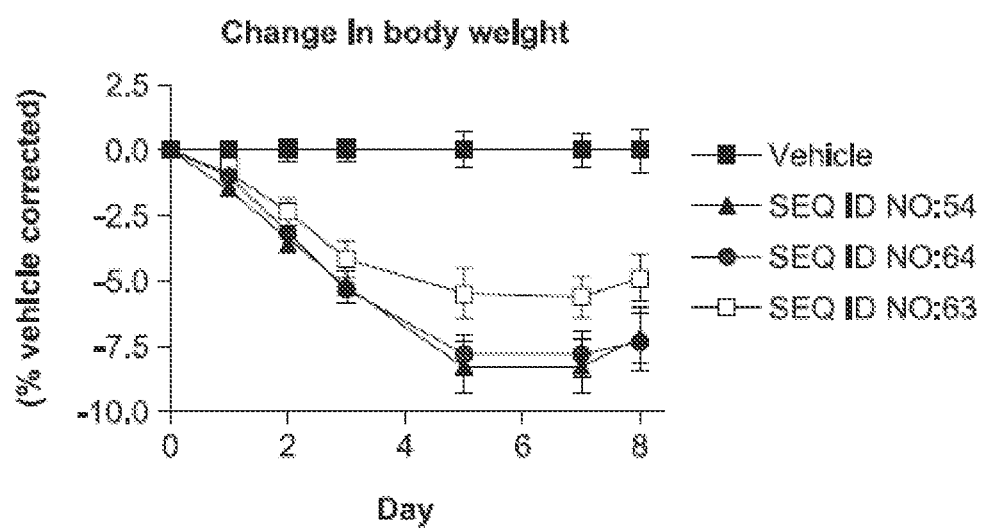

As depicted in FIG. 9A and FIG. 9B, each group of animals that received a single injection of one of the SEQ ID NOS tested exhibited significant and sustained reduction in food intake (FIG. 9A) and body weight (FIG. 9B) relative to vehicle alone.

Example 12: Change in Body Weight After Single Administration of Engineered Polypeptides Method.

Lean Sprague Dawley rats were maintained on a low fat diet during the study. Mean body weight was 330 g at beginning of study. Animals were divided into six groups. Each test animal (n=5/group) received a single subcutaneous injection at time=0. Each group was assigned to receive one of the following: vehicle; SEQ ID NO: 54 in vehicle; SEQ ID NO:67 in vehicle; SEQ ID NO: 68 in vehicle; and SEQ ID NO:69 in vehicle. SEQ ID NOS; 54, 67, 68, and 69 were each delivered at a dose of 120 nmol/kg. Percent change in body weight for each group was monitored for 10 days, and the results recorded as shown (FIG. 10).

Results.

Figure 10:
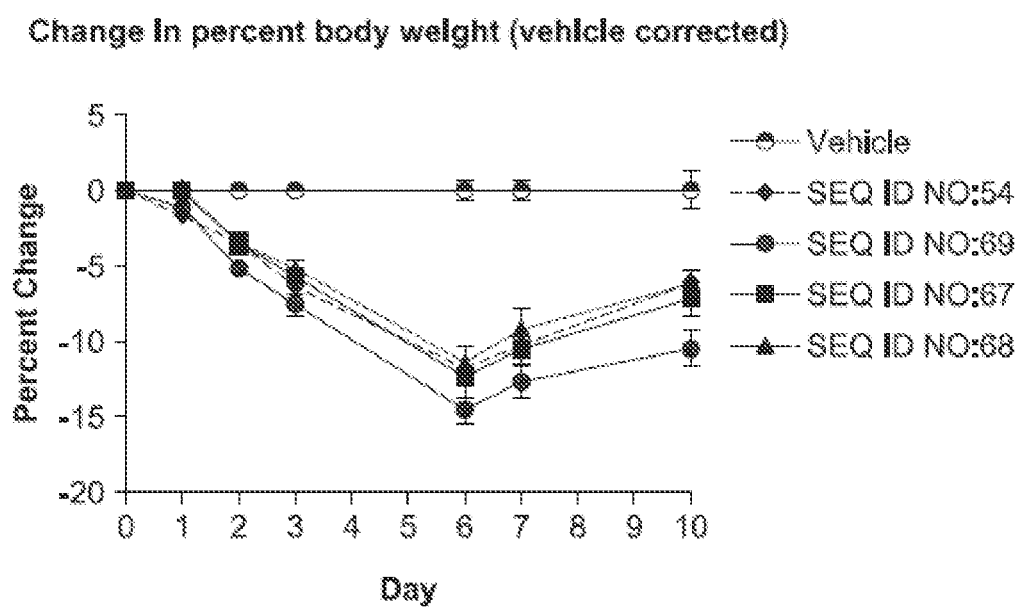
FIG. 10 depicts the effects of a single administration of the indicated engineered polypeptides described herein on food intake and change in body weight (% vehicle-corrected) upon administration to lean rats as described in Example 12.

As depicted in FIG. 10, each group of animals that received a single injection of one of the SEQ ID NOS tested exhibited significant and sustained reduction in body weight relative to the group that received vehicle alone.

Example 13: Change in Body Weight After Single Administration of Engineered Polypeptides Method.

Lean Sprague Dawley rats were maintained on a low fat diet during the study. Mean body weight was 320 grams at beginning of study. Animals were divided into six groups. Each test animal (n=5/group) received a single subcutaneous injection at time=0. Each group was assigned to receive one of the following: SEQ ID NO: 54 in vehicle; SEQ ID NO:104 in vehicle; SEQ ID NO:105 in vehicle; SEQ ID NO:106 in vehicle; and SEQ ID NO:107 in vehicle. SEQ ID NOS; 54, 104, 105, 106, and 107 were each delivered at a dose of 120 nmol/kg. Change in body weight for each group was monitored for 9 days, and the results recorded as shown (FIG. 11A through FIG. 11C).

Results.

Figure 11A:
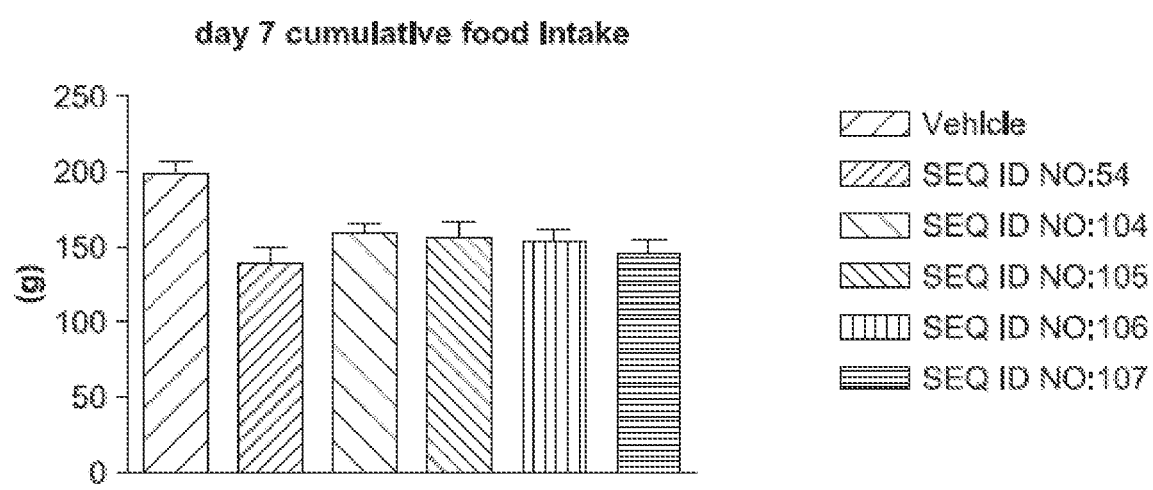
FIG. 11A through FIG. 11C depict the effects of a single administration of the indicated engineered polypeptides described herein on cumulative food intake (FIG. 11A) and percent change in body weight (FIG. 11B and FIG. 11C) upon administration to lean rats as described in Example 13.
Figure 11B:
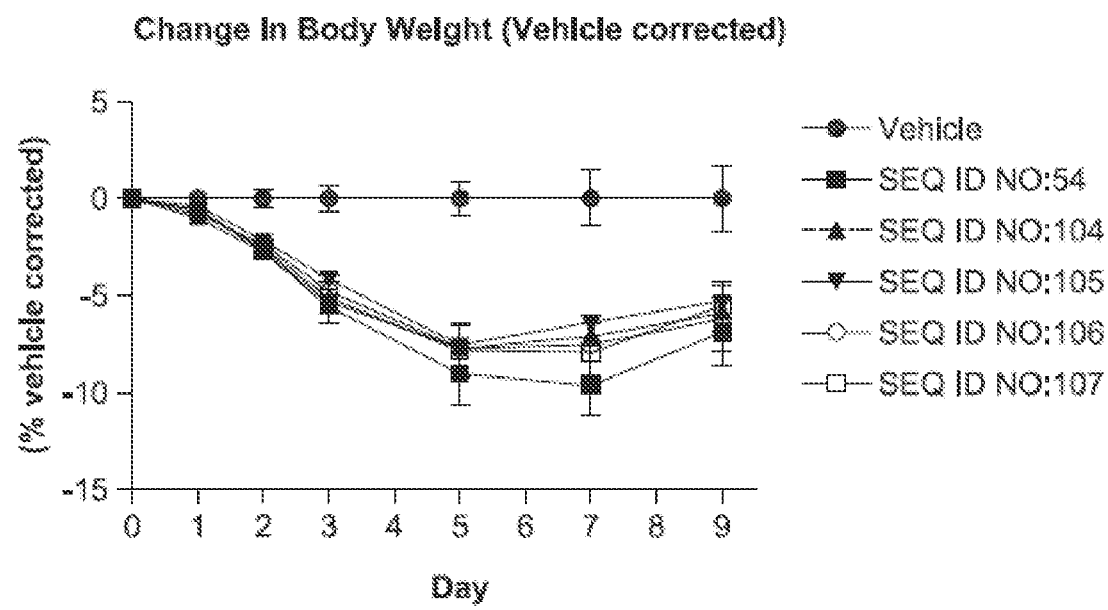
Figure 11C:
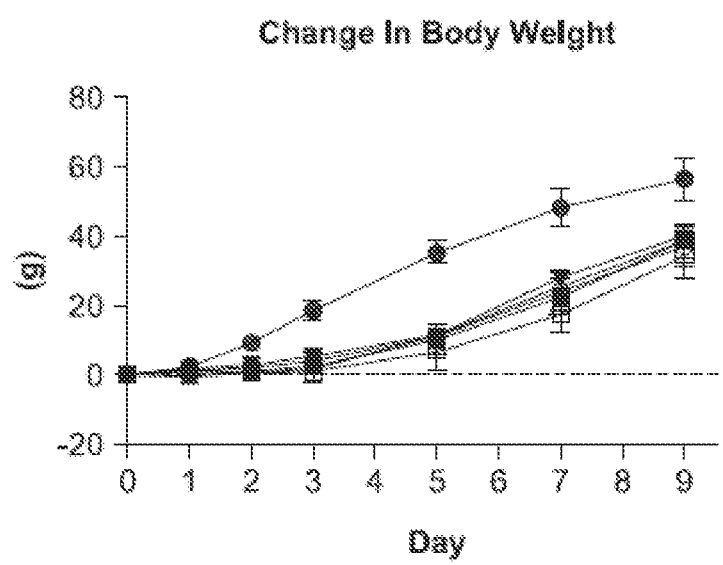

As depicted in FIGS. 11A-11C, each group of animals that received a single injection of one of the SEQ ID NOS tested exhibited significant and sustained reduction in food intake (FIG. 11A) and body weight (FIG. 11B and FIG. 11C) relative to vehicle alone.

Example 14: Affinity Determination for Albumin Binding Polypeptides

In this example, Compound 2 and Compound 15 were characterized for affinity to different variants of albumin.

Material and Methods

All studies were conducted on a BioRad ProteOn XPR36 system using a GLC sensor chip at 25 degrees C. For amine coupling the GLC chip was activated for 5 minutes using a 1:1 mixture of sulfo-NHS/EDC diluted 30-fold from the initial stock in water as shown below. Each albumin sample was diluted to 25 ug/ml in 10 mM Na Acetate pH 5.0 and injected for 5 minutes over separate sensor surfaces. Each surface was then blocked with 1 M ethanolamine pH 8.5. Each albumin was coupled at a density of 2000-5000 in resonance units.

The binding of an engineered polypeptide was tested using 5 nM as the highest concentration in a three-fold dilution series. The running buffer contained 10 mM HEPES pH 7.4, 150 mM NaCl, 3 mM EDTA and 0.005% tween-20. All samples were tested using a 3-fold dilution series. Each concentration series was tested in duplicate. The dissociation phase for the highest concentration was monitored for 3 hours.

Results

The relative $K_D$ measured for the engineered polypeptides are presented in Table 7 below. The results show that the albumin binding polypeptides associate with serum albumins (SA) with high affinity.

TABLE 7

$K_D$ of albumin binding polypeptides to albumin variants

| Compound name | Rat SA | Human SA | Monkey SA | Dog SA | Mouse SA | Units |
|---|---|---|---|---|---|---|
| ABD00239 (SEQ ID NO: 49) | 18 | 16 | 123 | 201 | 1,240 | pM |
| Cmpd 2 | 33 | 56 | 158 | 358 | 1,970 | |
| Cmpd 15 | <2 | 12 | 17 | 40 | 277 | |

Example 15: Leptin In Vitro Functional Activity in the Presence of Albumin

In this assay, the method described in Example 2 was used, except albumin was added to the stimulation buffer to test leptin function of Compound 2 in the presence of albumin. The albumins tested included 0.1% or 1% bovine serum albumin (BSA), 1% rat serum albumin (RSA), or 1% human serum albumin (HSA). The control sample was A100 leptin with 0.1% BSA.

Results.

Figure 12:
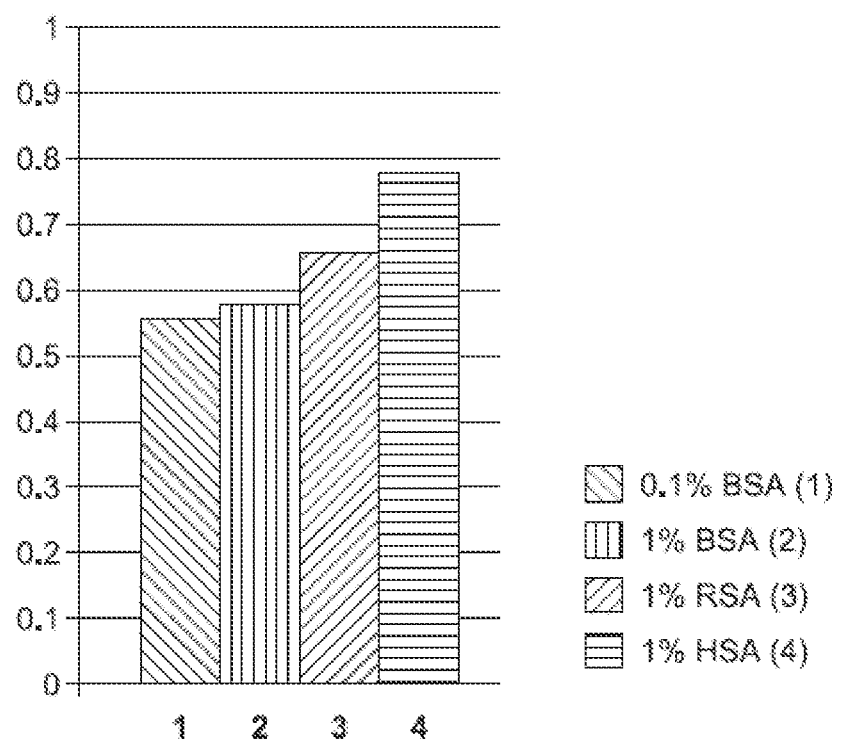
FIG. 12 depicts the leptin functional activity generated by Compound 2 in the presence of albumin, as described in Example 15.

As shown in FIG. 12, there were no effects of 1% Bovine/Rat/Human Albumin on the EC50 activity generated by Compound 2 in the Leptin Function Assay. The results are surprising and show that the therapeutic compounds are active even when bound to albumin.

Example 16: Prolonged Pharamacokinetic Profiles Delivered by Engineered Polypeptides Following Subcutaneous Injections in Rats This study was conducted to evaluate Compound 2 and Compound 15 in rats by comparing their blood concentration versus time profiles, i.e. pharamacokinetic profiles.

Rats were placed into treatment groups. Compound 2 was administered subcutaneously at 30 nmol/kg, 60 nmol/kg, or 120 nmol/kg. Blood samples were taken at pre, 12, 24, 48, 96, and 144 hr post-administration from the lateral tail vein. The concentration of Compound 2 in plasma was measured by an immunoenzymetric assay method.

Compound 15 was administered subcutaneously at 120 nmol/kg. Blood samples were taken at pre, 0.5, 1, 2, 4, 6, 24, 48, 72, 96, 120 and 144 hr post-administration from the lateral tail vein. The concentration of Compound 15 in plasma was measured by an immunoenzymetric assay method.

Figure 13:
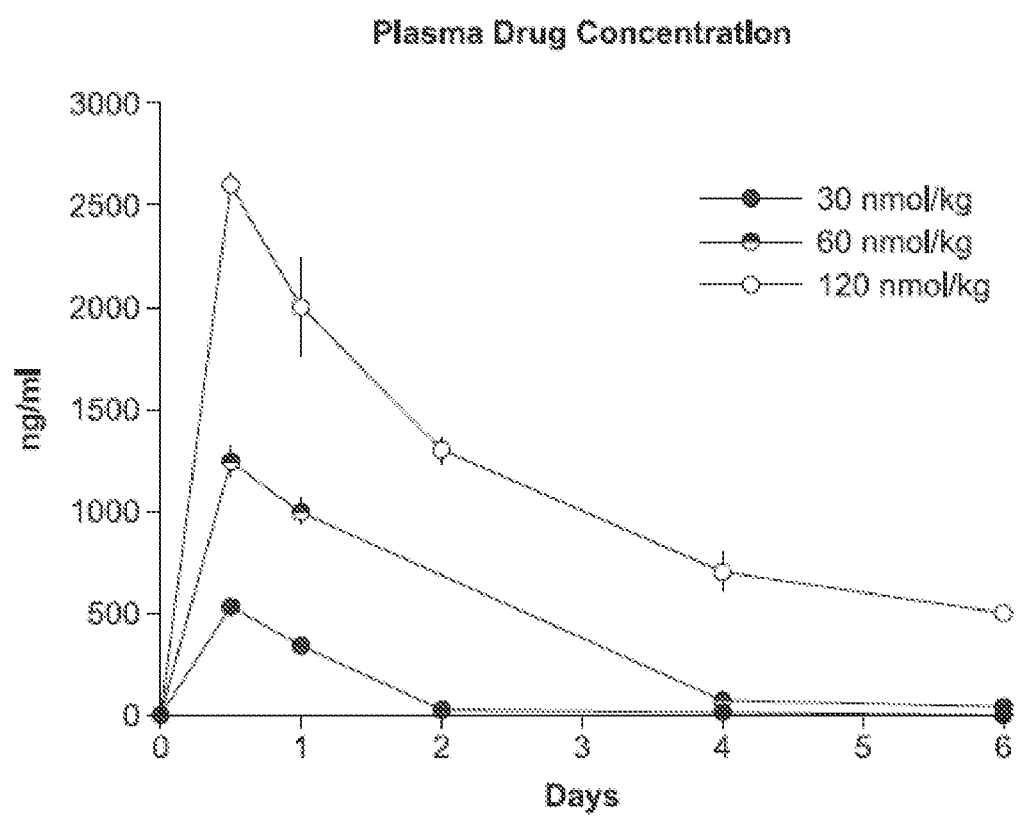
FIG. 13 illustrates a prolonged plasma concentration-versus-time profile Compound 2 in rats following a subcutaneous injection according to Example 16.
Figure 14A:
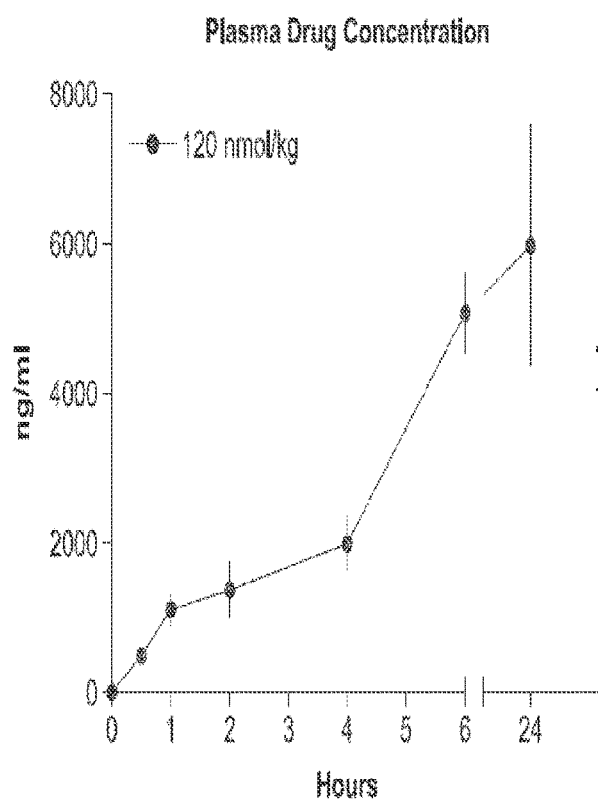
FIGS. 14A-14B illustrate a prolonged plasma concentration-versus-time profile Compound 15 in rats following a subcutaneous injection according to Example 16.
Figure 14B:
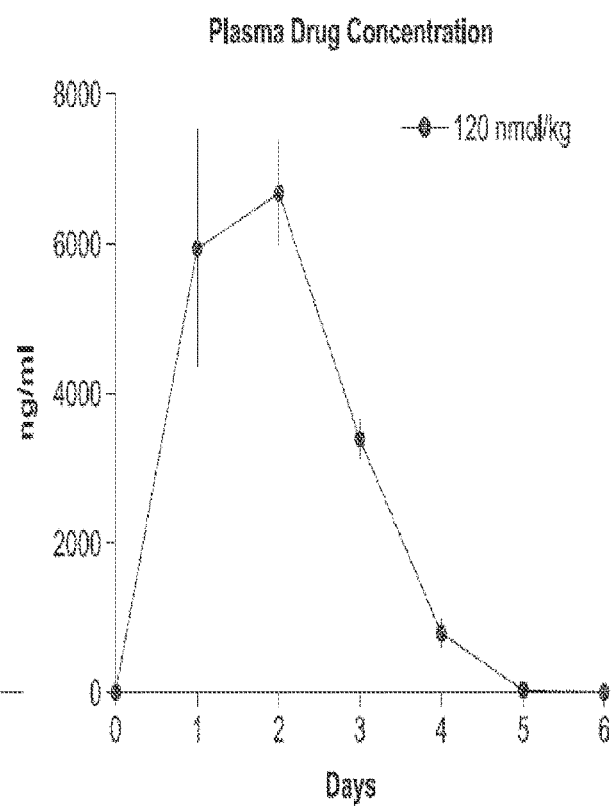

Both Compound 2 (FIG. 13) and Compound 15 (FIGS. 14A-14B) exhibited prolonged plasma-versus-time profiles.

Example 17: Effect of Engineered Polypeptides Mediated by Leptin Receptors

Method.

Figure 15A:
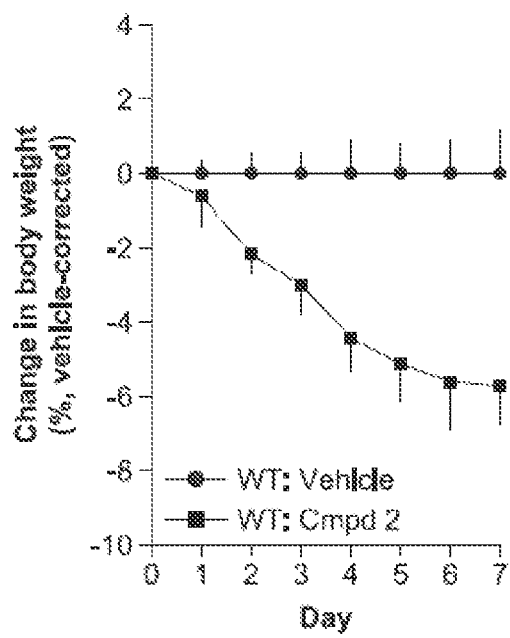
FIGS. 15A-15B depict the effects of a single administration of the indicated engineered polypeptides described herein on change in body weight (% vehicle-corrected) upon administration to lean rats (FIG. 15A) and ZDF rats (FIG. 15B) as described in Example 17.
Figure 15B:
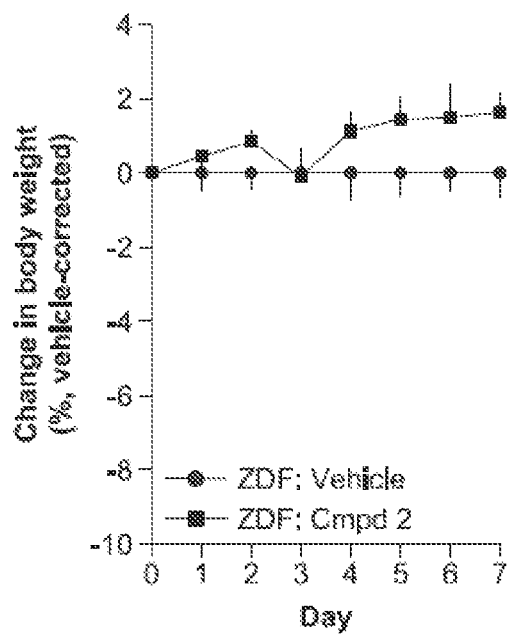

Lean Sprague Dawley rats and ZDF rats were used for this study. ZDF rats have a mutation (fa) which results in a shortened leptin receptor which does not effectively interact with leptin. Mean body weight was 225 grams at beginning of study. Animals were divided into two groups (n=5/group). Each group was assigned to receive one of the following: vehicle; Cmpd 2 at 2.7 mg/kg in vehicle. Each test animal received a single subcutaneous injection at time=0. Change in body weight (% vehicle corrected) was monitored, and the results recorded as shown (FIG. 15A, FIG. 15B). Administered compounds: Vehicle (filled circle); Cmpd 2 at 2.7 mg/kg (filled square).

Results.

As depicted in FIG. 15A and FIG. 15B, Compound 2 is not efficacious in ZDF rats, indicating its effects are mediated via leptin receptors.

Example 18: Dose Sparing with Engineered Polypeptides

Figure 16:
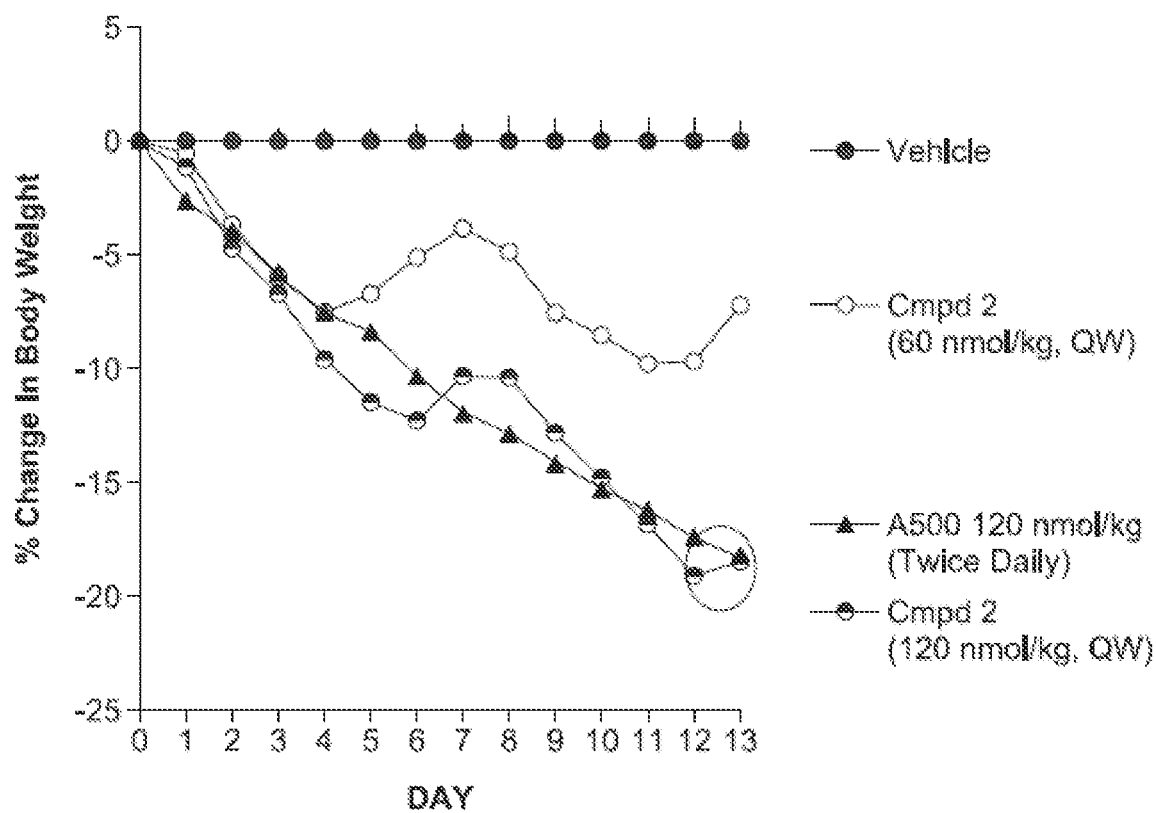
FIG. 16 depicts the dose sparing effects of once weekly administration of Compound 2 on body weight (% baseline) upon administration to lean rats as described in Example 18.

This study compared doses of A500 (SEQ ID NO:33) and Compound 2 (SEQ ID NO:54) required to achieve a similar amount of weight loss in lean leptin-sensitive rats. The results are shown in FIG. 16. Compound 2 dosed at 120 nmol/kg/week achieves ~18% vehicle corrected weight loss. To achieve the same amount of weight loss with A500 required a BID dose of 120 nmol/kg/d or 1680 nmol/kg (120 per injection x 2 for BID x 7 days) over the course of a week. Without wishing to be bound by any theory, this "dose sparing" may be at least partially attributable to the improved PK profile of Compound 2 over A-500.

Example 19: Solubility of Engineered Polypeptides

As set forth in Table 8 following, engineered polypeptides described herein have surprisingly high solubility in neutral pH.

Solubility was measured with the following assay: 6-10 mg of purified proteins were concentrated at 4° C. with centrifugal filter units (Amicon Ultra-15 or Ultra-4, with 3KDa MW cutoff; Millipore) to a volume of less than 0.5 ml. They were centrifuged at 14,000 rpm for 10 minutes at 4° C. to remove precipitates and the supernatant was transferred to a new tube. The proteins were allowed to equilibrate overnight at room temperature in the dark, then were filtered with 0.22 micron syringe filters (Milex GV; Millipore) to remove precipitates. The absorbance at OD280 was measured with a NanoDrop spectrophotometer and the concentration was calculated using the protein's theoretical molar extinction coefficient.

TABLE 8

Solubility of Engineered Polypeptides

| Compound | pI* | Net Charge at pH 7.4* | Solubility in PBS, pH 7.4 (mg/mL)** |
|---|---|---|---|
| A100 | 6.2 | −2.8 | 2.1 |
| ABD1-A100 (SEQ ID NO.:147) | 7.1 | −0.7 | 8 |
| A-500 | 6.2 | −2.8 | 42.9 |
| ABD1-A500 (Cmpd 2) | 7.1 | −0.7 | 10.8 |
| ABD1-HuSeal (Cmpd 15) | 10.0 | +9.1 | >80 |

Example 20: Stability of Engineered Polypeptides

As set forth in Table 9 following, engineered polypeptides described herein are chemically stabile. The compounds were formulated at 1 mg/mL in buffers of different pH. As shown in Table 9, the chimeric polypeptides have good potency (Table 9A) and purity (Table 9B) after two weeks at 40° C., as determined by reverse phase high performance liquid chromatography (HPLC).

TABLE 9A

Potency of Engineered Polypeptides

% Potency* by Reversed Phase HPLC, 14 days at 40° C.

| Compound | pH 3.0 | pH 4.0 | pH 5.0 | pH 6.0 | pH 7.0 | pH 8.0 | pH 9.0 | PBS, pH 7.4 |
|---|---|---|---|---|---|---|---|---|
| ABD1-HuSeal (Cmpd 15) | 102.7 | 107.2 | 104.9 | 108.5 | 107.3 | 100.1 | 90.7 | 104.5 |
| ABD1-A500 (Cmpd 2) | 95.9 | 95.9 | 97.3 | 91.7 | 87.3 | 90.8 | 72.1 | 92.0 |
| ABD1-A100 (SEQ ID NO: 147) | 72.3 | 82.0 | 88.8 | 86.1 | 83.3 | 85.8 | 69.6 | 89.2 |

*Potency = Main peak area/ref std area

TABLE 9B

Purity of Engineered Polypeptides

% Purity by Reversed Phase HPLC, 14 days at 40° C.

| Compound | pH 3.0 | pH 4.0 | pH 5.0 | pH 6.0 | pH 7.0 | pH 8.0 | pH 9.0 | PBS, pH 7.4 |
|---|---|---|---|---|---|---|---|---|
| ABD1-HuSeal | 96.7 | 98.0 | 98.5 | 99.8 | 97.6 | 93.8 | 95.1 | 97.1 |
| ABD1-A500 | 94.9 | 96.2 | 96.8 | 97.3 | 96.9 | 97.5 | 82.7 | 97.4 |
| ABD1-A100 | 70.0 | 79.4 | 85.4 | 86.5 | 86.8 | 86.8 | 70.9 | 87.8 |

Example 21: Stability of Engineered Polypeptides

As set forth in Table 10 following, engineered polypeptides described herein are chemically stabile. Compound 15 was formulated at three different concentrations in the following buffer: 10 mM glutamic acid, 2% glycine, 1% sucrose, 0.01% Tween 20, pH 4.25 and stored at 5° C., 15° C., or 25° C. As shown in Table 10, Compound 15 is chemically stable at 10, 20, and 30 mg/mL for at least 1 month at 5-25° C., as determined by HPLC.

TABLE 10

Stability of Engineered Polypeptides

| Concentration | Storage Condition | % Potency by RP-HPLC at Time Point (week) | | |
|---|---|---|---|---|
| (mg/mL) | (° C.) | 0 | 2 | 4 |
| 10 | 5 | 103.1 | 103.6 | 103.1 |
|  | 15 | 103.1 | 102.7 | 102.0 |
|  | 25 | 103.1 | 103.8 | 104.0 |
| 20 | 5 | 102.0 | 103.6 | 103.7 |
|  | 15 | 102.0 | 103.6 | 104.1 |
|  | 25 | 102.0 | 103.2 | 103.8 |
| 30 | 5 | 104.1 | 104.1 | 103.3 |
|  | 15 | 104.1 | 103.7 | 104.0 |
|  | 25 | 104.1 | 102.6 | 103.4 |

| Concentration | Storage Condition | % Purity by SCX-HPLC at Time Point (week) | | |
|---|---|---|---|---|
| (mg/mL) | (° C.) | 0 | 2 | 4 |
| 10 | 5 | 97.6 | 97.3 | 97.7 |
|  | 15 | 97.6 | 97.6 | 97.5 |
|  | 25 | 97.6 | 97.4 | 96.0 |
| 20 | 5 | 97.9 | 97.7 | 97.6 |
|  | 15 | 97.9 | 97.6 | 97.7 |
|  | 25 | 97.9 | 97.4 | 96.4 |
| 30 | 5 | 97.7 | 97.6 | 97.7 |
|  | 15 | 97.7 | 97.7 | 97.6 |
|  | 25 | 97.7 | 97.3 | 97.2 |

Example 22: Stability of Engineered Polypeptides

As set forth in Table 11 following, engineered polypeptides described herein are physically stabile. Compound 15 was formulated at three different concentrations in the following buffer: 10 mM glutamic acid, 2% glycine, 1% sucrose, 0.01% Tween 20, pH 4.25 and stored at 37° C. As shown in Table 11, Compound 15 is physically stable at 10, 20, and 30 mg/mL for at least 1 month, as determined by visual analysis.

TABLE 11

Stability of Engineered Polypeptides

| Concentration | Storage Condition | Appearance under FiberLite at Time Point (week) | | | |
|---|---|---|---|---|---|
| (mg/mL) | (° C.) | 0 | 2 | 4 | 8 |
| 10 | 5 | Clear | Clear | Clear | Clear |
|  | 15 | Clear | Clear | Clear | Clear |
|  | 25 | Clear | Clear | Clear | Clear |
| 20 | 5 | Clear | Clear | Clear | Clear |
|  | 15 | Clear | Clear | Clear | Clear |
|  | 25 | Clear | Clear | Clear | Clear |
| 30 | 5 | Clear | Clear | Clear | Clear |
|  | 15 | Clear | Clear | Clear | Clear |
|  | 25 | Clear | Clear | Clear | Slightly hazy |

Example 23: Stability of Engineered Polypeptides

Engineered polypeptides described herein are physically stable. Table 12 shows the results of size exclusion chromatography (SEC) performed on A100, ABD1-HuSeal, and ABD1-A500. The engineered polypeptides show little to no self-association to dimer/oligomer, compared to A100.

TABLE 12

Stability of Engineered Polypeptides

| Compound | Pk 1 (%) | Pk 2 (%) | Pk 3 (%) |
|---|---|---|---|
| ABD1-HuSeal | 99.22 | 0.78 | n/a |
| ABD1-A500 | 96.73 | 3.27 | n/a |
| A100 | 88.21 | 11.15 | 0.65 |

Pk1 = Monomer
Pk2 = Dimer
Pk3 = Oligomer (Trimner/Tetramer)

SEC Method:
Column—Tosoh TSK Gel G3000 SWx17.8 mm×30 cm (#08541)
Mobile Phase—10 mM Na Phosphate, pH 7.4+238 mM NaCl+2.7 mM KCl
Run Time—22 min
Flow Rate—0.8 mL/min
Column Temp—25° C.
Sample Temp—5° C.
Sample load—40 ug
Detection—214 nm

Example 24: Synergy of Amylin and Leptin is Absent in High BMI Subjects

Previous studies had described amylin/leptin synergy in rats weighing 500-550 grams. After an inverse relationship of efficacy and BMI was noted we assessed the effects of the combination in very obese rats (750 grams) and in very obese rats that were food restricted to the moderately obese range (500-550 g) range prior to initiating drug treatment.

Figure 17:
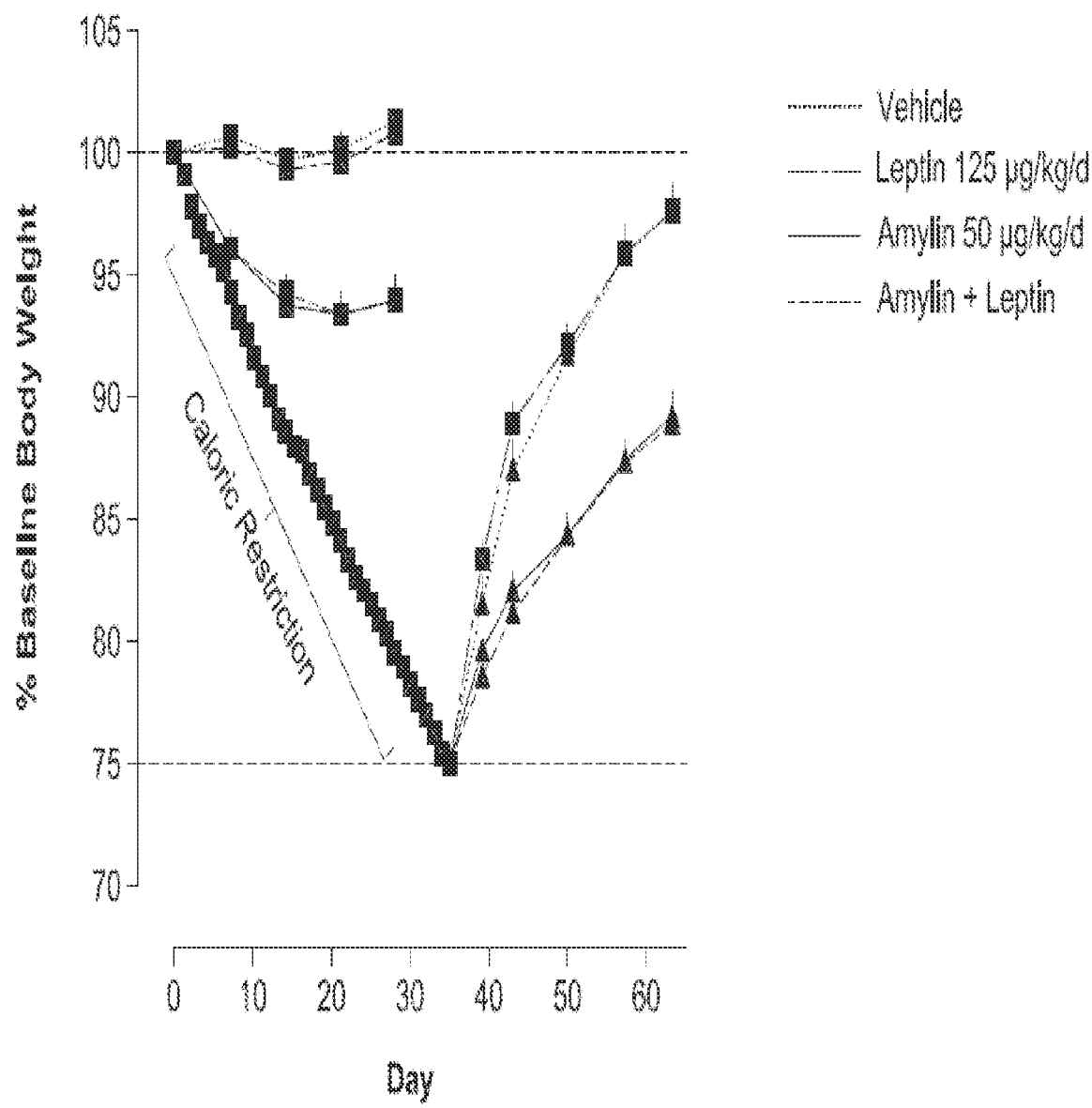
FIG. 17 is a graph depicting the effect on body weight of administration of leptin (125 µg/kg/day) and amylin (1500 µg/kg/day), either alone or in combination, in two groups of rats: one group of very obese rats and another group that was calorie restricted down to the range of moderate obesity.

In this study one group of very obese rats (750 g) were allowed to feed ad-libitum and were treated with amylin, leptin or the combination of amylin+leptin. Although amylin was effective, there was no synergy evident with the addition of leptin. A second group of very obese rats (750 g) was calorie restricted down to the 500-550 g range in which synergy was previously demonstrated. These animals then began amylin/leptin treatment and were allowed to feed ad-libitum. FIG. 17 shows the results of the study. Rapid weight regain was evident in vehicle and leptin monotherapy-treated rats. Some weight maintenance was achieved with amylin monotherapy. No further weight maintenance was achieved with the combination. These findings suggest that the lack of synergy in "high BMI" rodents cannot simply be rescued by a diet-lead in.

Example 25: Synergy of Engineered Polypeptides with Amylin Agonists

Figure 18A:
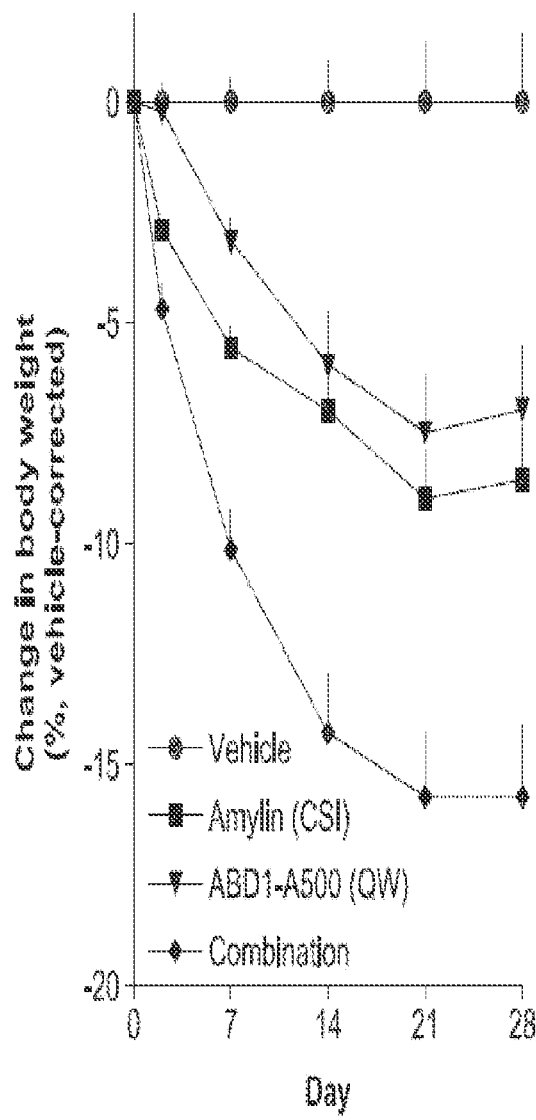
FIG. 18A is a graph depicting an effect on body weight of administration of Compound 2 (120 nmol/kg) and infused rat amylin (50 µg/kg/day), either alone or in combination over four weeks.
Figure 18B:
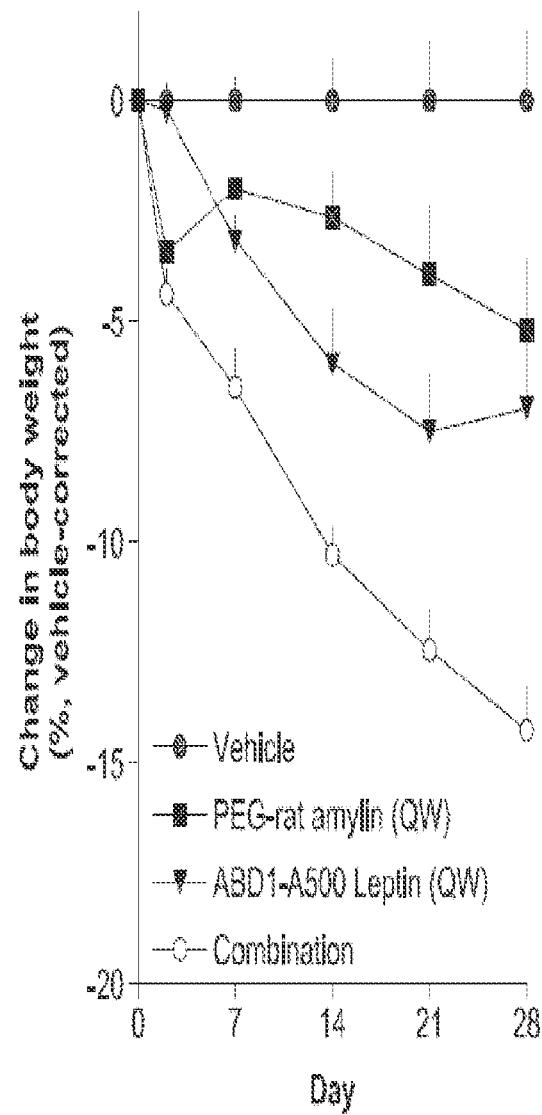
FIG. 18B is a graph depicting an effect on body weight of administration of Compound 2 (120 nmol/kg) and PEG-rat amylin (Des-Lys1-[Lys26(mPEG40K)]-Rat Amylin (SEQ ID NO: 148) (125 nmol/kg), either alone or in combination over four weeks.

This study examined whether a once weekly administration of PEG-rat amylin (Des-Lys1-[Lys26(mPEG40K)]-Rat Amylin (SEQ ID NO: 148), Compound 124) would be sufficient for synergy when co-administered with ABD1-A500 (Compound 2). For comparison, ABD1-A500 was also co-administered with infused rat amylin (FIG. 18A). FIG. 18B shows that although PEG-rat amylin induced weight loss is somewhat slower and of smaller magnitude, the overall amount of weight loss (and synergy) is qualitatively similar to that achieved by infused rat amylin. Amylin was administered at 50 μg/kg/d by SC osmotic minipump, PEG-rat amylin was administered at 125 nmol/kg once weekly, and ABD1-A500 was administered at 120 nmol/kg once weekly to male diet induced obese (DIO) Harlan Sprague Dawley (HSD) rats of 500 g average weight.

Example 26: Synergy of Engineered Polypeptides with Amylin Agonists

Figure 19A:
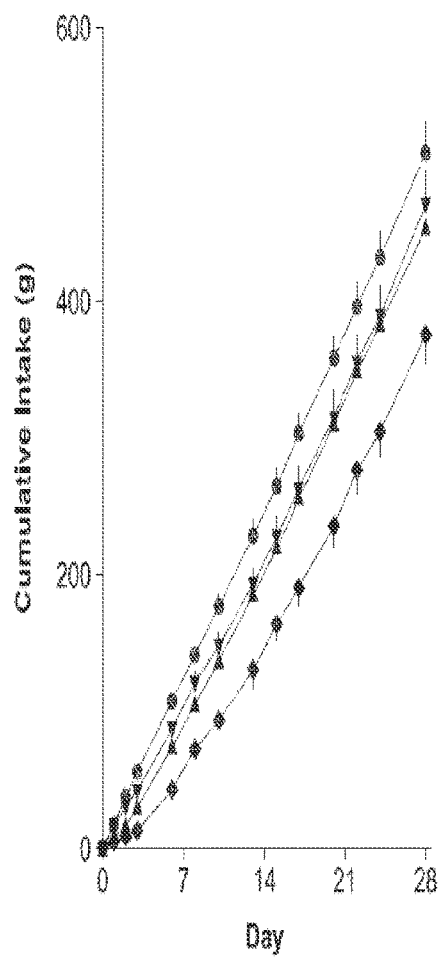
FIGS. 19A-19B depict an effect on food intake (FIG. 19A) and body weight (FIG. 19B) of administration of Compound 15 (120 nmol/kg) and amylin (50 µg/kg/day), either alone or in combination over four weeks.
Figure 19B:
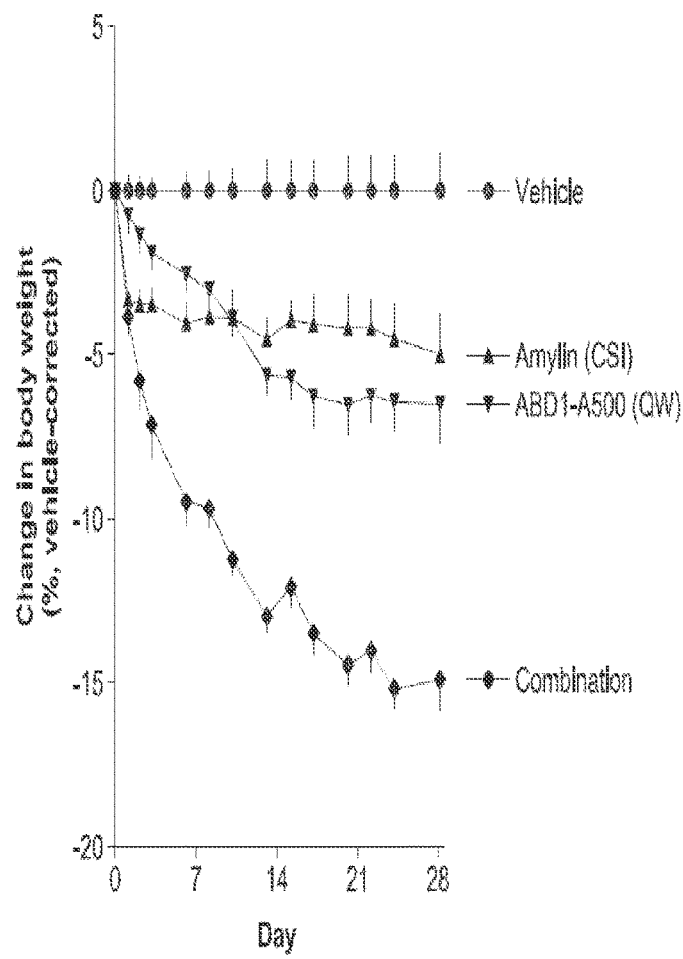

This study shows that a once weekly administration of ABD1-HuSeal (Compound 15) is sufficient for synergy when co-adminstered with infused rat amylin. FIGS. 19A-19B show that the combination of the engineered polypeptide and infused amylin resulted in lower food intake (FIG. 19A) and more weight loss (FIG. 19B) than the results observed for each agent alone. ABD1-HuSeal was administered at 120 nmol/kg and amylin was administered at 50 µg/kg/d by SC osmotic minipump to male DIO HSD rats of 500 g average weight.

Example 27: Synergy of Engineered Polypeptides with Amylin Agonists

Figure 20:
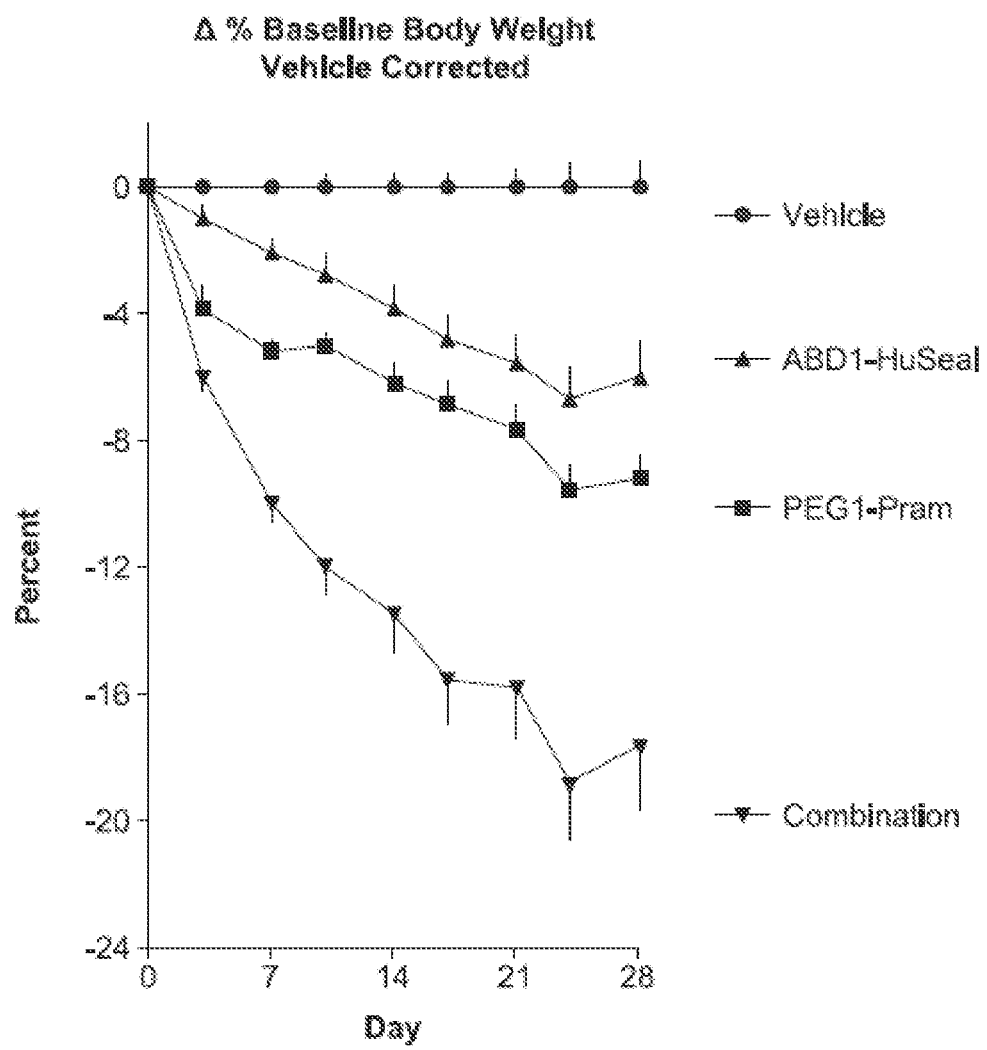
FIG. 20 is a graph depicting an effect on body weight of administration of Compound 15 (120 nmol/kg) and PEG-rat amylin (Des-Lys1-[Lys26(mPEG40K)]-Rat Amylin (SEQ ID NO: 148) (125 nmol/kg), either alone or in combination over four weeks.

This study shows that a once weekly administration of ABD1-HuSeal (Compound 15) is sufficient for synergy when co-adminstered with a twice weekly administration of PEG-rat amylin (Des-Lys1-[Lys26(mPEG40K)]-Rat Amylin (SEQ ID NO: 148), Compound 124). FIG. 20 shows that the combination of the engineered polypeptide and PEG-rat amylin resulted in more weight loss than the results observed for each agent alone. ABD1-HuSeal was administered at 120 nmol/kg and PEG-amylin was administered at 125 nmol/kg to male DIO HSD rats of 500 g average weight.

Example 28: Synergy of Engineered Polypeptides with Amylin Agonists in a High BMI Population FIG. 21A shows the results of previous studies, describing amylin/leptin synergy in rats weighing 500-550 grams. FIG. 21B shows that this synergy is not observed in a high BMI population of rats (average weight of 700 g). FIG. 21C shows once weekly administration of ABD1-A500 (Compound 15) is sufficient for synergy when co-adminstered with a twice weekly administration of PEG-rat amylin (Des-Lys1-[Lys26(mPEG40K)]-Rat Amylin (SEQ ID NO: 148), Compound 124) in high BMI rats. ABD1-A500 was administered at 120 nmol/kg and PEG-amylin was administered at 125 nmol/kg to male DIO HSD rats of 700 g average weight.

Figure 22A:
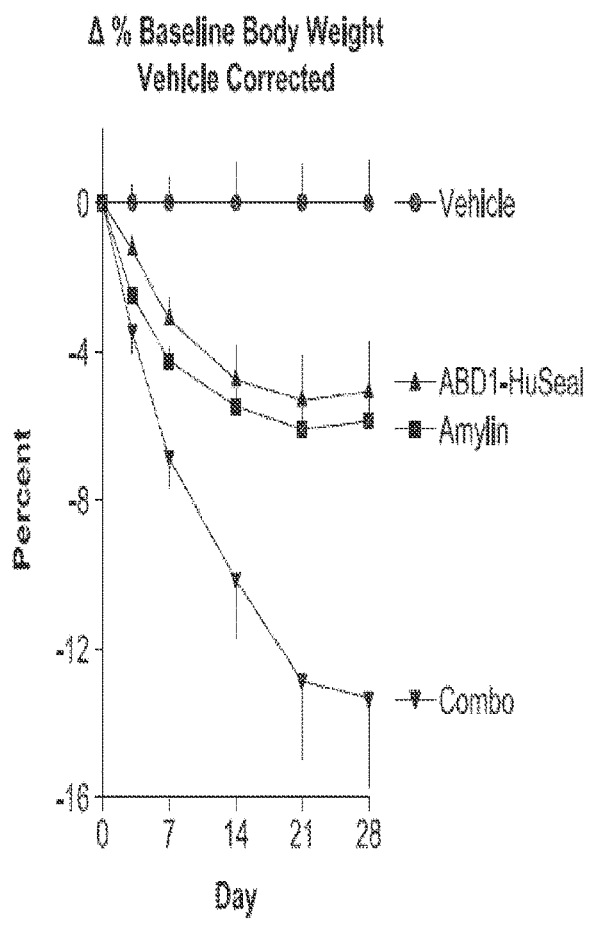
Figure 22B:
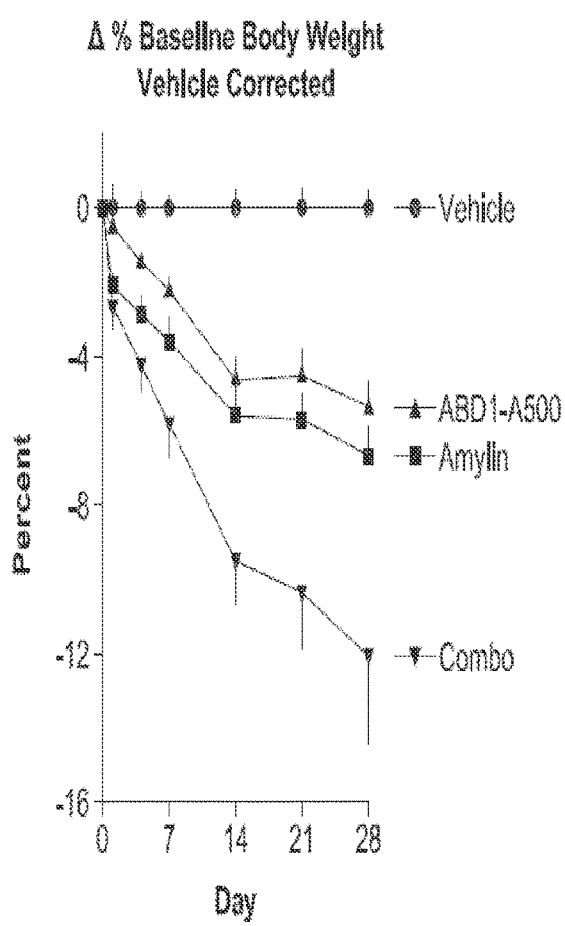

Example 29: Synergy of Engineered Polypeptides with Amylin Agonists in a High BMI Population This study shows that a once weekly administration of ABD1-HuSeal (Compound 15) or ABD1-A500 (Compound 2) is sufficient for synergy when co-adminstered with infused rat amylin to high BMI rats. ABD1-HuSeal (FIG. 22A) or ABD1-A500 (FIG. 22B) was administered at 120 nmol/kg and amylin was administered at 50 µg/kg/d by SC osmotic minipump to male DIO HSD rats of 700 g average weight.

Example 30: Anti-Diabetic Effects of Engineered Polypeptides in Non-Obese, Type 1 Diabetic Mice The purpose of this study was to evaluate the in vivo effects of engineered polypeptides on key diabetic and metabolic endpoints in a high-dose STZ mouse model of Type 1 diabetes mellitus (T1DM). C57 BL/6 male mice were given a single interperitoneal injection of STZ at 200 mg/kg to induce Type 1 diabetes. Compounds were administered twice a week subcutaneously at 120 nmol/kg for two weeks. Measured endpoints included HbA1c levels, glucose levels, body weight, and food intake.

Figure 23A:
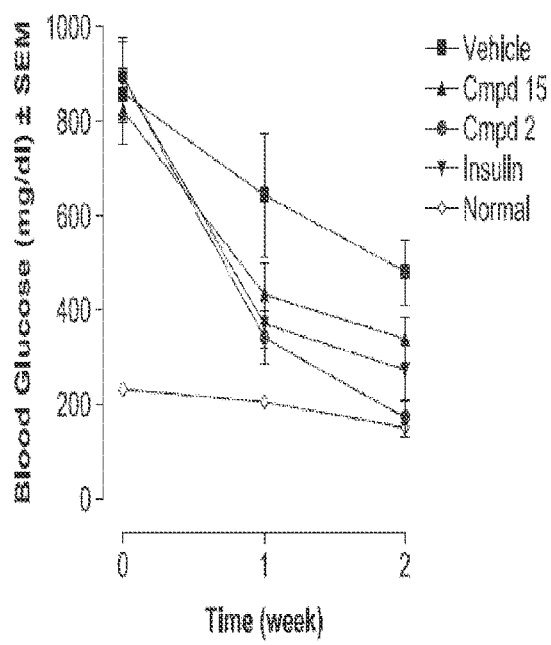
FIGS. 23A-23B depict the effects of the indicated engineered polypeptides described herein on blood glucose upon administration to STZ-induced T1DM mice as described in Example 30.
Figure 23B:
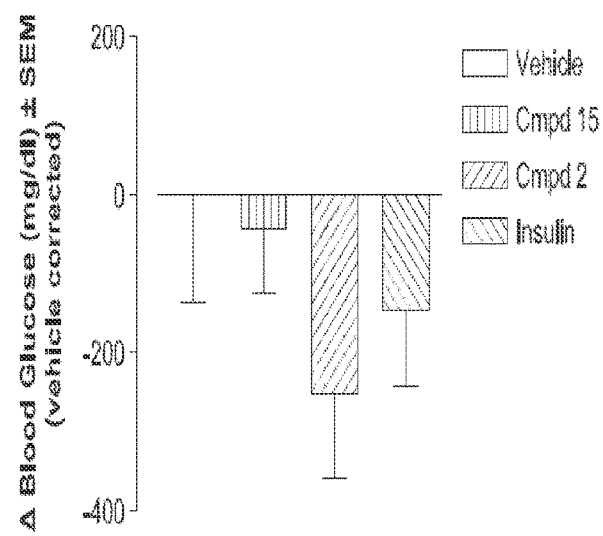
Figures 24A, 24B:
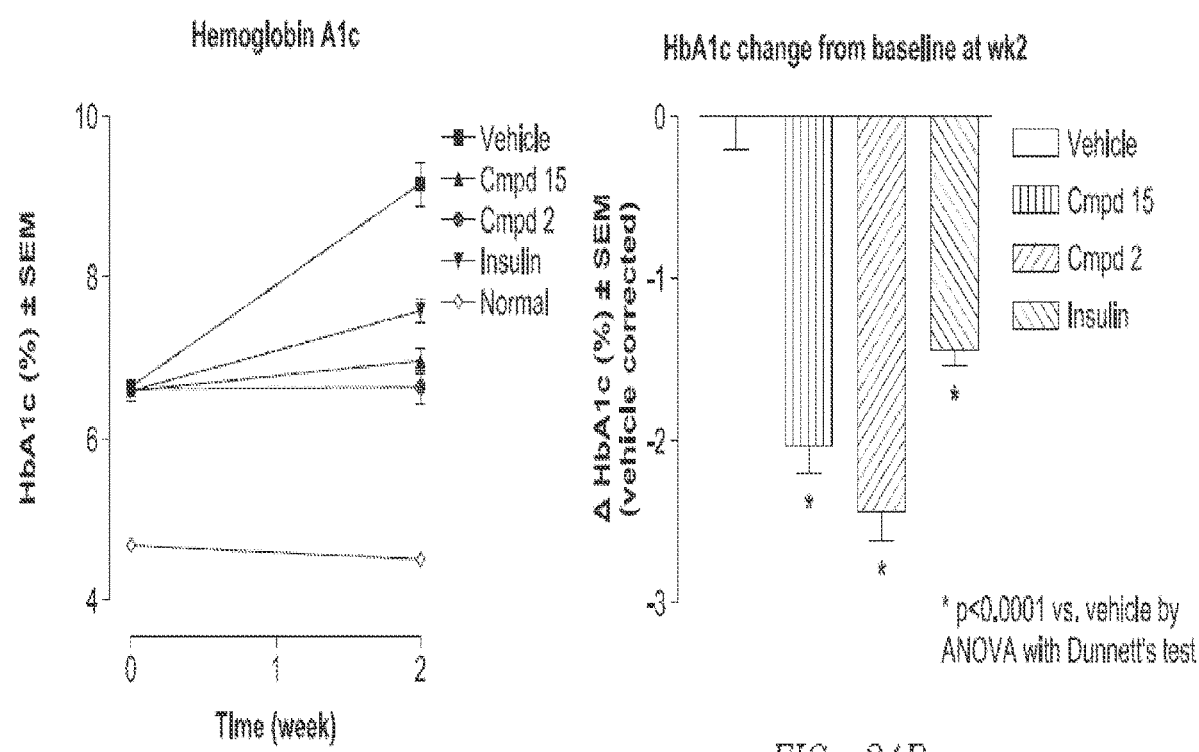
FIGS. 24A-24B depict the effects of the indicated engineered polypeptides described herein on Hemoglobin A1C upon administration to STZ-induced T1DM mice as described in Example 30.
Figure 25A:
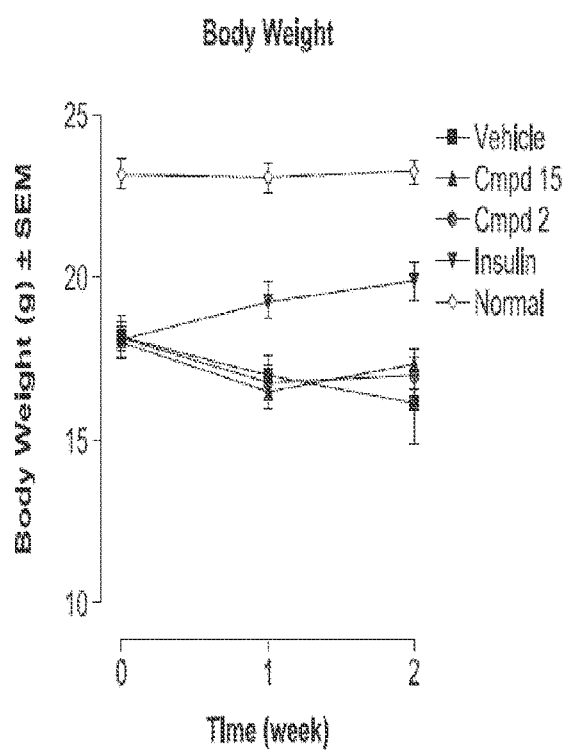
FIGS. 25A-25B depict the effects of the indicated engineered polypeptides described herein on food intake and body weight upon administration to STZ-induced T1DM mice as described in Example 30.
Figure 25B:
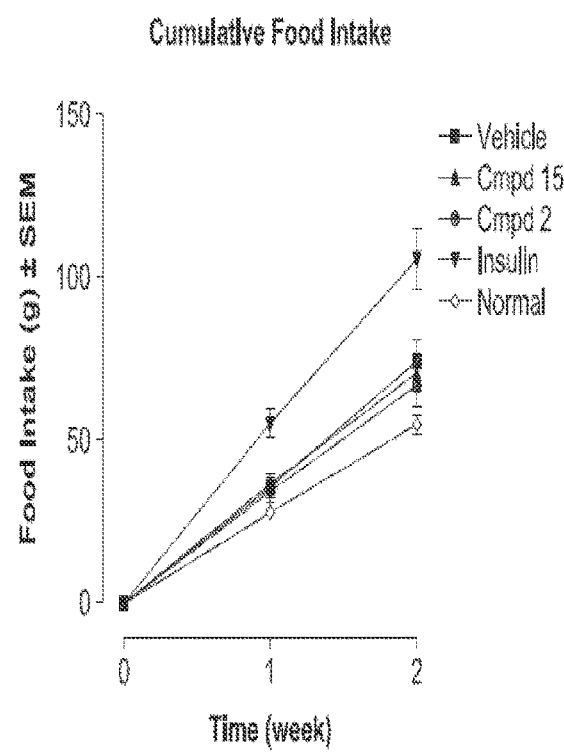

FIGS. 23A-23B show that both Compound 15 and Compound 2 normalized blood glucose in STZ-induced diabetic mice. Both engineered polypeptides also reduced Hemoglobin A1c levels, as shown in FIGS. 24A-24B, and reduced body weight and cumulative food intake, as shown in FIGS. 25A-25B.

In order to ensure that the glucose lowering effects of therapy are not due to insulin effects, another study was conducted to combine the leptin therapy with a low dose of insulin. Compound 15 was administered with or without the addition of a 0.05 U/day dose of insulin in a high-dose STZ mouse model of T1DM. C57 BL/6 male mice were given a single interperitoneal injection of STZ at 175 mg/kg to induce Type 1 diabetes. Compounds were administered twice a week subcutaneously at 60 nmol/kg for two weeks. Measured endpoints included HbA1c levels, glucose levels, body weight, and food intake.

Figures 26A, 26B:
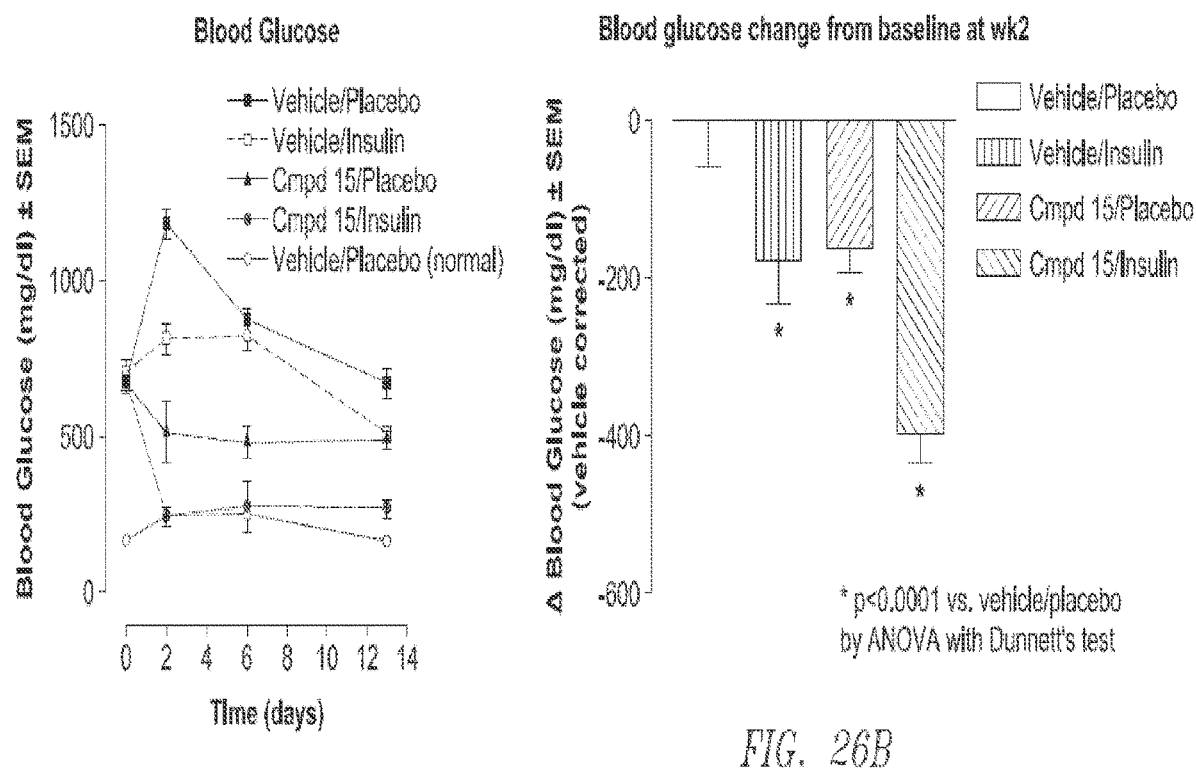
FIGS. 26A-26B depict the effects of the indicated engineered polypeptides described herein, with and without a low dose of insulin, on blood glucose upon administration to STZ-induced T1DM mice as described in Example 30.
Figures 27A, 27B:
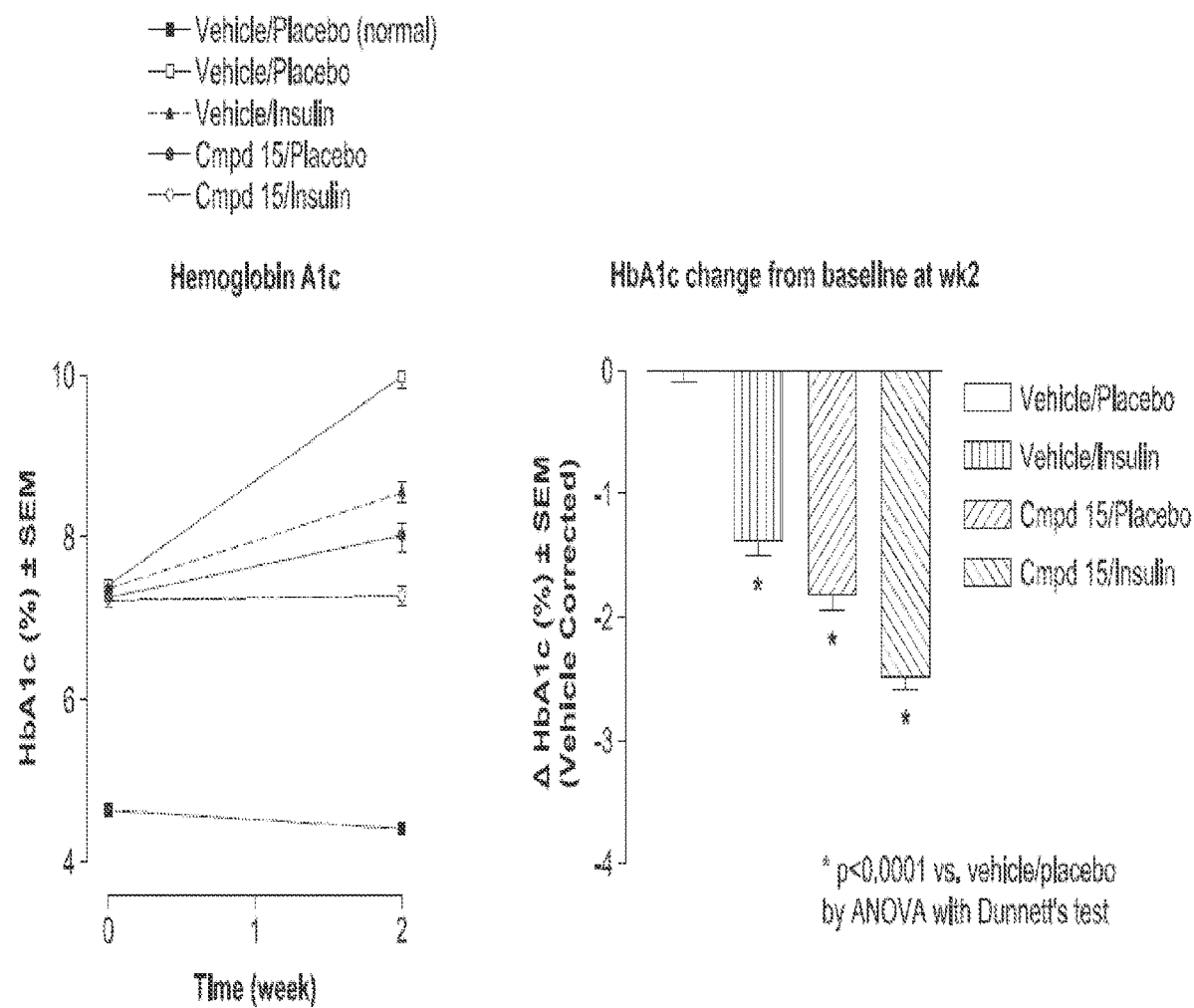
FIGS. 27A-27B depict the effects of the indicated engineered polypeptides described herein, with and without a low dose of insulin, on Hemoglobin A1C upon administration to STZ-induced T1DM mice as described in Example 30.
Figure 28A:
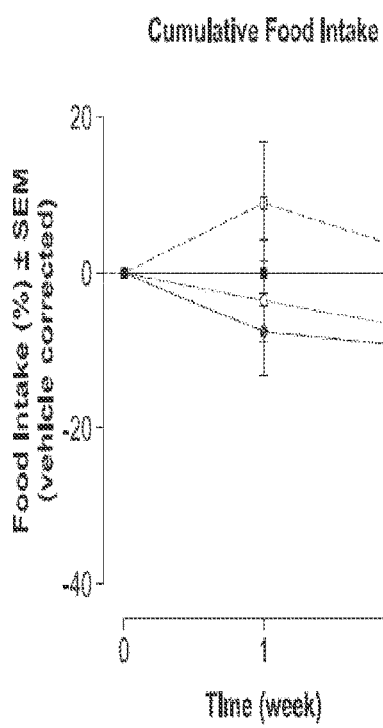
FIGS. 28A-28B depict the effects of the indicated engineered polypeptides described herein, with and without a low dose of insulin, on food intake (% vehicle-corrected) and change in body weight (% vehicle-corrected) upon administration to STZ-induced T1DM mice as described in Example 30.
Figure 28B:
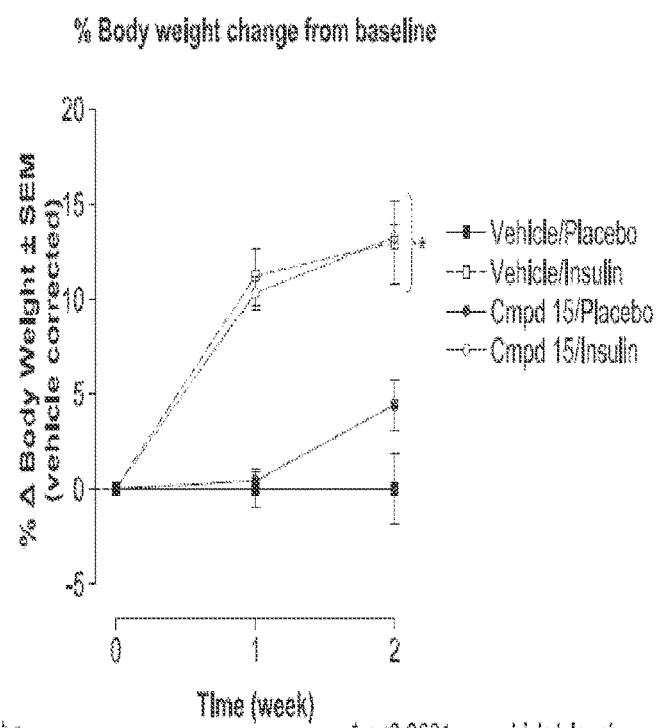

FIGS. 26A-26B show a glucose lowering effect potentiated with low dose of insulin in an additive fashion for Compound 15. It also reduced Hemoglobin A1c levels, as shown in FIGS. 27A-28B, and reduced body weight and cumulative food intake, as shown in FIGS. 28A-28B.

VIII. Embodiments

Additional embodiments of the engineered polypeptides, method of use thereof, and pharmaceuticals compositions described herein follow:

Embodiment 1

An engineered polypeptide comprising: an albumin binding domain polypeptide (ABD); and a first peptide hormone domain (HD1) selected from a leptin, a leptin analog or an active fragment thereof.

Embodiment 2

The engineered polypeptide according to Embodiment 1, further comprising a first linker (L1) covalently linked to said HD1.

Embodiment 3

The engineered polypeptide according to Embodiment 1 or 2, wherein said engineered polypeptide comprises said ABD as an N-terminal moiety and said HD1 as a C-terminal moiety.

Embodiment 4

The engineered polypeptide according to Embodiment 1 or 2, wherein said engineered polypeptide comprises said ABD as a C-terminal moiety and said HD1 as an N-terminal moiety.

Embodiment 5

The engineered polypeptide according to Embodiment 3, comprising the structure: ABD-HD1.

Embodiment 6

The engineered polypeptide according to Embodiment 3, comprising the structure: ABD-L1-HD1.

Embodiment 7

The engineered polypeptide according to Embodiment 4, comprising the structure: HD1-ABD.

Embodiment 8

The engineered polypeptide according to Embodiment 4, comprising the structure: HD1-L1-ABD.

Embodiment 9

The engineered polypeptide according to any one of Embodiments 1 to 8, wherein said HD1 is said a leptin, a leptin analog, a leptin active fragment, or a leptin derivative.

Embodiment 10

The engineered polypeptide according to any one of Embodiments 1 to 9, wherein said HD1 has at least 50% identity with an amino acid sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12.SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:143, SEQ ID NO:144, SEQ ID NO:145, and SEQ ID NO:146.

Embodiment 11

The engineered polypeptide according to any one of Embodiments 1 to 10, wherein said HD1 has at least 90% identity with an amino acid sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12.SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:143, SEQ ID NO:144, SEQ ID NO:145, and SEQ ID NO:146.

Embodiment 12

The engineered polypeptide according to any one of Embodiments 1 to 11, wherein said HD1 has at least 50% identity with a human leptin.

Embodiment 13

The engineered polypeptide according to any one of Embodiments 1 to 12, wherein said HD1 has at least 90% identity with a human leptin.

Embodiment 14

The engineered polypeptide according to any one of Embodiments 1 to 13, wherein said HD1 has at least 50% identity with SEQ ID NO: 20.

Embodiment 15

The engineered polypeptide according to any one of Embodiments 1 to 14, wherein said HD1 has at least 90% identity with SEQ ID NO: 20.

Embodiment 16

The engineered polypeptide according to any one of Embodiments 1 to 15, wherein said HD1 has at least 50% identity with a platypus leptin.

Embodiment 17

The engineered polypeptide according to any one of Embodiments 1 to 16, wherein said HD1 has at least 50% identity with a seal leptin.

Embodiment 18

The engineered polypeptide according to any one of Embodiments 1 to 17, wherein said HD1 has from 1 to 5 amino acid modifications selected independently from any one or combination of an insertion, deletion, addition and substitution.

Embodiment 19

The engineered polypeptide according to any one of Embodiments 1 to 18, wherein said HD1 comprises an amino acid sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO: 26, SEQ ID NO:27, SEQ ID NO:28, SEQ ID NO: SEQ ID NO:29, SEQ ID NO:30, SEQ ID NO:31, SEQ ID NO:32, SEQ ID NO:33, SEQ ID NO:143, SEQ ID NO:144, SEQ ID NO:145, and SEQ ID NO:146.

Embodiment 20

The engineered polypeptide according to any one of Embodiments 1 to 19, wherein said HD1 comprises an amino acid sequence that is selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO: 26, SEQ ID NO:27, SEQ ID NO:28, SEQ ID NO: SEQ ID NO:29, SEQ ID NO:30, SEQ ID NO:31, SEQ ID NO:32, and SEQ ID NO:33, SEQ ID NO:143, SEQ ID NO:144, SEQ ID NO:145, and SEQ ID NO:146.

Embodiment 21

The engineered polypeptide according to any one of Embodiments 1 to 20, wherein said HD1 is SEQ ID NO:1.

Embodiment 22

The engineered polypeptide according to any one of Embodiments 1 to 20, wherein said HD1 is SEQ ID NO:2.

Embodiment 23

The engineered polypeptide according to any one of Embodiments 1 to 20, wherein said HD1 is SEQ ID NO:3.

Embodiment 24

The engineered polypeptide according to any one of Embodiments 1 to 20, wherein said HD1 is SEQ ID NO:4.

Embodiment 25

The engineered polypeptide according to any one of Embodiments 1 to 20, wherein said HD1 is: SEQ ID NO:5.

Embodiment 26

The engineered polypeptide according to any one of Embodiments 1 to 20, wherein said HD1 is SEQ ID NO:6.

Embodiment 27

The engineered polypeptide according to any one of Embodiments 1 to 20, wherein said HD1 is SEQ ID NO:7.

Embodiment 28

The engineered polypeptide according to any one of Embodiments 1 to 20, wherein said HD1 is SEQ ID NO:8.

Embodiment 29

The engineered polypeptide according to any one of Embodiments 1 to 20, wherein said HD1 is SEQ ID NO:9.

Embodiment 30

The engineered polypeptide according to any one of Embodiments 1 to 20, wherein said HD1 is SEQ ID NO:10.

Embodiment 31

The engineered polypeptide according to any one of Embodiments 1 to 20, wherein said HD1 is SEQ ID NO:11.

Embodiment 32

The engineered polypeptide according to any one of Embodiments 1 to 20, wherein said HD1 is SEQ ID NO:12.

Embodiment 33

The engineered polypeptide according to any one of Embodiments 1 to 20, wherein said HD1 is SEQ ID NO:13.

Embodiment 34

The engineered polypeptide according to any one of Embodiments 1 to 20, wherein said HD1 is SEQ ID NO:14.

Embodiment 35

The engineered polypeptide according to any one of Embodiments 1 to 20, wherein said HD1 is SEQ ID NO:15.

Embodiment 36

The engineered polypeptide according to any one of Embodiments 1 to 20, wherein said HD1 is SEQ ID NO:16.

Embodiment 37

The engineered polypeptide according to any one of Embodiments 1 to 20, wherein said HD1 is SEQ ID NO:17.

Embodiment 38

The engineered polypeptide according to any one of Embodiments 1 to 20, wherein said HD1 is SEQ ID NO:18.

Embodiment 39

The engineered polypeptide according to any one of Embodiments 1 to 20, wherein said HD1 is SEQ ID NO:19.

Embodiment 40

The engineered polypeptide according to any one of Embodiments 1 to 20, wherein said HD1 is SEQ ID NO:20.

Embodiment 41

The engineered polypeptide according to any one of Embodiments 1 to 20, wherein said HD1 is SEQ ID NO:21.

Embodiment 42

The engineered polypeptide according to any one of Embodiments 1 to 20, wherein said HD1 is SEQ ID NO:22.

Embodiment 43

The engineered polypeptide according to any one of Embodiments 1 to 20, wherein said HD1 is SEQ ID NO:23.

Embodiment 44

The engineered polypeptide according to any one of Embodiments 1 to 20, wherein said HD1 is SEQ ID NO:24.

Embodiment 45

The engineered polypeptide according to any one of Embodiments 1 to 20, wherein said HD1 is SEQ ID NO:25.

Embodiment 46

The engineered polypeptide according to any one of Embodiments 1 to 20, wherein said HD1 is SEQ ID NO: 26.

Embodiment 47

The engineered polypeptide according to any one of Embodiments 1 to 20, wherein said HD1 is SEQ ID NO:27.

Embodiment 48

The engineered polypeptide according to any one of Embodiments 1 to 20, wherein said HD1 is SEQ ID NO:28.

Embodiment 49

The engineered polypeptide according to any one of Embodiments 1 to 20, wherein said HD1 is SEQ ID NO:29.

Embodiment 50

The engineered polypeptide according to any one of Embodiments 1 to 20, wherein said HD1 is SEQ ID NO:30.

Embodiment 51

The engineered polypeptide according to any one of Embodiments 1 to 20, wherein said HD1 is SEQ ID NO:31.

Embodiment 52

The engineered polypeptide according to any one of Embodiments 1 to 20, wherein said HD1 is SEQ ID NO:32.

Embodiment 53

The engineered polypeptide according to any one of Embodiments 1 to 20, wherein said HD1 is SEQ ID NO:33.

Embodiment 54

The engineered polypeptide according to any one of Embodiments 1 to 53, wherein said ABD comprises an albumin binding motif (ABM) that consists of the amino acid sequence:

```
                                       (SEQ ID NO: 34)
GVSD X5 YK X8 X9 I X11 X12 A X14 TVEGV X20 AL X23 X24
X25 I
``` wherein, independently of each other,
  $X_5$ is selected from Y and F;
  $X_8$ is selected from N, R and S;
  $X_9$ is selected from V, I, L, M, F and Y;
  $X_{11}$ is selected from N, S, E and D;
  $X_{12}$ is selected from R, K and N;
  $X_{14}$ is selected from K and R;
  $X_{20}$ is selected from D, N, Q, E, H, S, R and K;
  $X_{23}$ is selected from K, I and T;
  $X_{24}$ is selected from A, S, T, G, H, L and D; and
  $X_{25}$ is selected from H, E and D.

Embodiment 55

The engineered polypeptide according to any one of Embodiments 1 to 54, wherein, independently of each other,
  $X_5$ is Y;
  $X_8$ is N;
  $X_{23}$ is T or I;
  $X_{24}$ is S or L; and
  $X_{25}$ is E or H.

Embodiment 56

The engineered polypeptide according to any one of Embodiments 1 to 55, wherein the albumin binding motif comprises an amino acid sequence that is selected from the group consisting of: GVSDYYKNLINKAKTVEGVEALTLHI (SEQ ID NO:114) and GVSDYYKNLINKAKTVEGVEALISEI (SEQ ID NO:115).

Embodiment 57

The engineered polypeptide according to any one of Embodiments 1 to 56, wherein said ABD comprises an albumin binding motif (ABM) that is not GVSDYYKNLINNAKTVEGVKALIDEI (SEQ ID NO:35).

Embodiment 58

The engineered polypeptide according to any one of Embodiments 1 to 57, wherein said ABD comprises an ABM disclosed in Table 1.

Embodiment 59

The engineered polypeptide according to any one of Embodiments 1 to 58, wherein said ABD comprises the amino acid sequence:

```
                                       (SEQ ID NO: 36)
LAEAK Xa Xb A Xc Xd EL Xe KY -[ABM]- LAALP
``` wherein
  [ABM] is an albumin binding motif, and,
  independently of each other,
  $X_a$ is selected from V and E;
  $X_b$ is selected from L, E and D;
  $X_c$ is selected from N, L and I;
  $X_d$ is selected from R and K;
  $X_e$ is selected from D and K;
  the leucine at position 45 is present or absent; and
  the proline at position 46 is present or absent.

Embodiment 60

The engineered polypeptide according to any one of Embodiments 1 to 59, wherein, independently of each other,
  $X_a$ is E;
  $X_b$ is D;
  $X_c$ is I; and
  $X_d$ is K.

Embodiment 61

The engineered polypeptide according to any one of Embodiments 1 to 60, wherein the albumin binding domain polypeptide (ABD) comprises an amino acid sequence that is selected from the group consisting of:

```
                                       (SEQ ID NO: 50)
LAEAKEDAIKELDKYGVSDYYKNLINKAKTVEGVEALTLHILAALP;
and (SEQ ID NO: 51)
LAEAKEDAIKELDKYGVSDYYKNLINKAKTVEGVEALISEILAALP.
```

Embodiment 62

The engineered polypeptide according to any one of Embodiments 1 to 61, wherein said ABD comprises the amino acid sequence:

(SEQ ID NO: 36)
LAEAK $X_a$ $X_b$ A $X_c$ $X_d$ EL $X_e$ KY -[ABM]- LAALP wherein
[ABM] is an albumin binding motif, and, independently of each other,
$X_a$ is selected from V and E;
$X_b$ is selected from L, E and D;
$X_c$ is selected from N, L and I;
$X_d$ is selected from R and K;
$X_e$ is selected from D and K;
the leucine at position 45 is present or absent;
the proline at position 46 is present or absent; and
wherein ABM consists of the amino acid sequence:

(SEQ ID NO: 34)
GVSD $X_5$ YK $X_8$ $X_9$ I $X_{11}$ $X_{12}$ A $X_{14}$ TVEGV $X_{20}$ AL $X_{23}$ $X_{24}$ $X_{25}$ I wherein, independently of each other,
$X_5$ is selected from Y and F;
$X_8$ is selected from N, R and S;
$X_9$ is selected from V, I, L, M, F and Y;
$X_{11}$ is selected from N, S, E and D;
$X_{12}$ is selected from R, K and N;
$X_{14}$ is selected from K and R;
$X_{20}$ is selected from D, N, Q, E, H, S, R and K;
$X_{23}$ is selected from K, I and T;
$X_{24}$ is selected from A, S, T, G, H, L and D; and
$X_{25}$ is selected from H, E and D.

Embodiment 63

The engineered polypeptide according to any one of the Embodiments 1 to 62, wherein said ABD comprises an amino acid sequence having at least 85% identity with an amino acid sequence that is selected from the group consisting of SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, and SEQ ID NO:52.

Embodiment 64

The engineered polypeptide according to any one of Embodiments 1 to 63, wherein said ABD comprises any one of the peptides selected from the group consisting of:

(SEQ ID NO: 38)
LAEAKVLANRELDKYGVSDFYKSYINRAKTVEGVHTLIGHILAALP, (SEQ ID NO: 39)
LAEAKVLANRELDKYGVSDFYKRLINKAKTVEGVNALTHHILAALP, (SEQ ID NO: 40)
LAEAKVLANRELDKYGVSDYYKNLINRARTVEGVHALIDHILAALP, (SEQ ID NO: 41)
LAEAKVLANRELDKYGVSDYYKNIINRAKTVEGVRALKLHILAALP, (SEQ ID NO: 42)
LAEAKVLANRELDKYGVSDFYKNLINRAKTVEGVSSLKGHILAALP, (SEQ ID NO: 43)
LAEAKVLANRELDKYGVSDYYKNLINKAKTVEGVEALTLHILAALP, (SEQ ID NO: 44)
LAEAKVLANRELDKYGVSDFYKNLINRAKTVEGVDALIAHILAALP, (SEQ ID NO: 45)
LAEAKVLANRELDKYGVSDFYKSLINRAKTVEGVDALTSHILAALP, (SEQ ID NO: 46)
LAEAKVLANRELDKYGVSDFYKNLINRAKTVEGVNSLTSHILAALP, (SEQ ID NO: 47)
LAEAKVLANRELDKYGVSDFYKNVINKAKTVEGVEALIADILAALP, (SEQ ID NO: 48)
LAEAKVLANRELDKYGVSDYYKNLINKAKTVEGVQALIAHILAALP, (SEQ ID NO: 49)
LAEAKVLANRELDKYGVSDFYKRLINKAKTVEGVEALKLHILAALP, (SEQ ID NO: 50)
LAEAKEDAIKELDKYGVSDYYKNLINKAKTVEGVEALTLHILAALP, (SEQ ID NO: 51)
LAEAKEDAIKELDKYGVSDYYKNLINKAKTVEGVEALISEILAALP,
and (SEQ ID NO: 52)
LAEAKEDAIKELDKYGVSDYYKRLISKAKTVEGVKALISEILAALP.

Embodiment 65

The engineered polypeptide according to any one of Embodiments 1 to 64, wherein said linker L1 is a peptide of from 1 to 30 amino acids or less than 30 amino acids.

Embodiment 66

The engineered polypeptide according to any one of Embodiments 1 to 65, wherein said linker L1 is selected from the 20 naturally occurring amino acids.

Embodiment 67

The engineered polypeptide according to any one of Embodiments 1 to 66, wherein said linker L1 is a non-natural amino acids incorporated by chemical synthesis, post-translational chemical modification or by in vivo incorporation by recombinant expression in a host cell.

Embodiment 68

The engineered polypeptide according to any one of Embodiments 1 to 67, wherein said linker L1 amino acids are selected from serine, glycine, alanine, proline, asparagine, glutamine, glutamate, aspartate, and lysine.

Embodiment 69

The engineered polypeptide according to any one of Embodiments 1 to 68, wherein said linker L1 comprises a majority of amino acids that are sterically unhindered.

Embodiment 70

The engineered polypeptide according to any one of Embodiments 1 to 69, wherein said linker L1 comprises one or more of the following: an acidic linker, a basic linker, and a structural motif.

Embodiment 71

The engineered polypeptide according to any one of Embodiments 1 to 70, wherein said linker L1 comprises polyglycine, polyalanines, poly(Gly-Ala), or poly(Gly-Ser).

Embodiment 72

The engineered polypeptide according to any one of Embodiments 1 to 71, wherein said linker L1 comprises a polyglycine of (Gly)$_3$, (Gly)$_4$ (SEQ ID NO: 116), or (Gly)$_5$ (SEQ ID NO: 117).

Embodiment 73

The engineered polypeptide according to any one of Embodiments 1 to 72, wherein said linker L1 comprises (Gly)$_3$Lys(Gly)$_4$ (SEQ ID NO: 118); (Gly)$_3$AsnGlySer(Gly)$_2$ (SEQ ID NO: 119); (Gly)$_3$Cys(Gly)$_4$ (SEQ ID NO: 120); and GlyProAsnGlyGly (SEQ ID NO: 121).

Embodiment 74

The engineered polypeptide according to any one of Embodiments 1 to 73, wherein said linker L1 comprises a combination of Gly and Ala.

Embodiment 75

The engineered polypeptide according to any one of Embodiments 1 to 74, wherein said linker L1 comprises a combination of Gly and Ser.

Embodiment 76

The engineered polypeptide according to any one of Embodiments 1 to 75, wherein said linker L1 comprises a combination of Gly and Glu.

Embodiment 77

The engineered polypeptide according to any one of Embodiments 1 to 76, wherein said linker L1 comprises a combination of Gly and Lys.

Embodiment 78

The engineered polypeptide according to any one of Embodiments 1 to 77, wherein said linker L1 comprises a sequence selected from group consisting of: [Gly-Ser]$_n$ (SEQ ID NO: 122), [Gly-Gly-Ser]$_n$ (SEQ ID NO: 123), [Gly-Gly-Gly-Ser]$_n$ (SEQ ID NO: 124) and [Gly-Gly-Gly-Gly-Ser]$_n$ (SEQ ID NO: 125); where n is 1, 2, 3, 4, 5, 6, 7, 8, 9, or 10.

Embodiment 79

The engineered polypeptide according to any one of Embodiments 1 to 78, wherein said linker L1 comprises a sequence selected from the group consisting of: [Gly-Glu]$_n$ (SEQ ID NO: 126); [Gly-Gly-Glu]$_n$ (SEQ ID NO: 127); [Gly-Gly-Gly-Glu]$_n$ (SEQ ID NO: 128); [Gly-Gly-Gly-Gly-Glu]$_n$ (SEQ ID NO: 129), [Gly-Asp]$_n$ (SEQ ID NO: 130); [Gly-Gly-Asp]$_n$ (SEQ ID NO: 131); [Gly-Gly-Gly-Asp]$_n$ (SEQ ID NO: 132); [Gly-Gly-Gly-Gly-Asp]$_n$ (SEQ ID NO: 133) where n is 1, 2, 3, 4, 5, 6, 7, 8, 9, 10.

Embodiment 80

The engineered polypeptide according to any one of Embodiments 1 to 79, wherein said linker L1 comprises a sequence selected from the group consisting of: [Gly-Glu]$_n$ (SEQ ID NO: 126); [Gly-Gly-Glu]$_n$ (SEQ ID NO: 127); [Gly-Gly-Gly-Glu]$_n$ (SEQ ID NO: 128); [Gly-Gly-Gly-Gly-Glu]$_n$ (SEQ ID NO: 129), [Gly-Asp]$_n$ (SEQ ID NO: 130); [Gly-Gly-Asp]$_n$ (SEQ ID NO: 131); [Gly-Gly-Gly-Asp]$_n$ (SEQ ID NO: 132); [Gly-Gly-Gly-Gly-Asp]$_n$ (SEQ ID NO: 133) where n is 1, 2, 3, 4, 5, 6, 7, 8, 9, 10.

Embodiment 81

The engineered polypeptide according to any one of Embodiments 1 to 80, wherein said linker L1 comprises a sequence selected from the group consisting of: [Gly-Lys]$_n$ (SEQ ID NO: 134); [Gly-Gly-Lys]$_n$ (SEQ ID NO: 135); [Gly-Gly-Gly-Lys]$_n$ (SEQ ID NO: 136); [Gly-Gly-Gly-Gly-Lys]$_n$ (SEQ ID NO: 137), [Gly-Arg]$_n$ (SEQ ID NO: 138); [Gly-Gly-Arg]$_n$ (SEQ ID NO: 139); [Gly-Gly-Gly-Arg]$_n$ (SEQ ID NO: 140); [Gly-Gly-Gly-Gly-Arg]$_n$ (SEQ ID NO: 141) where n is 1, 2, 3, 4, 5, 6, 7, 8, 9, 10.

Embodiment 82

The engineered polypeptide according to any one of Embodiments 1 to 81, wherein said linker L1 comprises a sequence selected from the group consisting of: [Glu-Ala-Ala-Ala-Lys]$_n$ (SEQ ID NO: 142), where n is 1, 2, 3, 4, 5, 6, 7, 8, 9, 10.

Embodiment 83

The engineered polypeptide according to any one of Embodiments 1 to 81, wherein said linker L1 comprises a sequence selected from the group consisting of: [Gly-Gly-Glu]$_6$ (SEQ ID NO: 153) [Gly-Gly-Lys]$_6$ (SEQ ID NO: 154). [Glu-Ala-Ala-Ala-Lys]$_3$ (SEQ ID NO: 155), [Glu-Ala-Ala-Ala-Lys]$_4$ (SEQ ID NO: 156), or [Glu-Ala-Ala-Ala-Lys]$_5$ (SEQ ID NO: 157).

Embodiment 84

The engineered polypeptide according to any one of Embodiments 1 to 83, wherein said linker L1 comprises a N-terminal TG dipeptide.

Embodiment 85

The engineered polypeptide according to any one of Embodiments 1 to 84, wherein said linker L1 comprises a C-terminal AS dipeptide.

Embodiment 86

The engineered polypeptide according to any one of Embodiments 1 to 85, wherein said linker L1 comprises an N-terminal TG dipeptide and a C-terminal AS dipeptide.

Embodiment 87

The engineered polypeptide according to any one of Embodiments 1 to 86, wherein said linker L1 comprises an amino acids sequence that is selected from the group consisting of TG-(GGGS)$_1$ (SEQ ID NO: 215), TG-(GGGS)$_2$ (SEQ ID NO: 216), TG-(GGGS)$_3$ (SEQ ID NO: 217), TG-(GGGS)$_4$ (SEQ ID NO: 218), TG-(GGGS)$_5$ (SEQ ID NO: 219), (GGGS)$_1$-AS (SEQ ID NO: 220), (GGGS)$_2$-AS (SEQ ID NO: 221), (GGGS)$_3$-AS (SEQ ID NO: 222), (GGGS)$_4$-AS (SEQ ID NO: 223), (GGGS)$_5$-AS (SEQ ID NO: 224), TG-(GGGS)$_1$-AS (SEQ ID NO: 225), TG-(GGGS)$_2$-AS (SEQ ID NO: 226), TG-(GGGS)$_3$-AS (SEQ ID NO: 227), TG-(GGGS)$_4$-AS (SEQ ID NO: 228), and TG-(GGGS)$_5$-AS (SEQ ID NO: 229).

Embodiment 88

The engineered polypeptide according to any one of Embodiments 1 to 87, wherein said TG dipeptide TG and/or said dipeptide AS are absent or are replaced by a pair of amino acids selected from T, A, S, and G.

Embodiment 89

The engineered polypeptide according to any one of Embodiments 1 to 88, wherein said polypeptide further comprises one or more additional linkers.

Embodiment 90

The engineered polypeptide according to any one of Embodiments 1 to 89, wherein said engineered polypeptide comprises an amino acid sequence selected from the group consisting of: SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85 SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, and SEQ ID NO:107.

Embodiment 91

The engineered polypeptide according to any one of Embodiments 1 to 90, wherein said engineered polypeptide comprises the amino acid sequence selected set out in SEQ ID NO:53.

Embodiment 92

The engineered polypeptide according to any one of Embodiments 1 to 90, wherein said engineered polypeptide comprises the amino acid sequence selected set out in SEQ ID NO:54.

Embodiment 93

The engineered polypeptide according to any one of Embodiments 1 to 90, wherein said engineered polypeptide comprises the amino acid sequence selected set out in SEQ ID NO:55.

Embodiment 94

The engineered polypeptide according to any one of Embodiments 1 to 90, wherein said engineered polypeptide comprises the amino acid sequence selected set out in SEQ ID NO:56.

Embodiment 95

The engineered polypeptide according to any one of Embodiments 1 to 90, wherein said engineered polypeptide comprises the amino acid sequence selected set out in SEQ ID NO:57.

Embodiment 96

The engineered polypeptide according to any one of Embodiments 1 to 90, wherein said engineered polypeptide comprises the amino acid sequence selected set out in SEQ ID NO:58.

Embodiment 97

The engineered polypeptide according to any one of Embodiments 1 to 90, wherein said engineered polypeptide comprises the amino acid sequence selected set out in SEQ ID NO:59.

Embodiment 98

The engineered polypeptide according to any one of Embodiments 1 to 90, wherein said engineered polypeptide comprises the amino acid sequence selected set out in SEQ ID NO:60.

Embodiment 99

The engineered polypeptide according to any one of Embodiments 1 to 90, wherein said engineered polypeptide comprises the amino acid sequence selected set out in SEQ ID NO:61.

Embodiment 100

The engineered polypeptide according to any one of Embodiments 1 to 90, wherein said engineered polypeptide comprises the amino acid sequence selected set out in SEQ ID NO:62.

Embodiment 101

The engineered polypeptide according to any one of Embodiments 1 to 90, wherein said engineered polypeptide comprises the amino acid sequence selected set out in SEQ ID NO:63.

Embodiment 102

The engineered polypeptide according to any one of Embodiments 1 to 90, wherein said engineered polypeptide comprises the amino acid sequence selected set out in SEQ ID NO:64.

Embodiment 103

The engineered polypeptide according to any one of Embodiments 1 to 90, wherein said engineered polypeptide comprises the amino acid sequence selected set out in SEQ ID NO:65.

Embodiment 104

The engineered polypeptide according to any one of Embodiments 1 to 90, wherein said engineered polypeptide comprises the amino acid sequence selected set out in SEQ ID NO:66.

Embodiment 105

The engineered polypeptide according to any one of Embodiments 1 to 90, wherein said engineered polypeptide comprises the amino acid sequence selected set out in SEQ ID NO:67.

Embodiment 106

The engineered polypeptide according to any one of Embodiments 1 to 90, wherein said engineered polypeptide comprises the amino acid sequence selected set out in SEQ ID NO:68.

Embodiment 107

The engineered polypeptide according to any one of Embodiments 1 to 90, wherein said engineered polypeptide comprises the amino acid sequence selected set out in SEQ ID NO:69.

Embodiment 108

The engineered polypeptide according to any one of Embodiments 1 to 90, wherein said engineered polypeptide comprises the amino acid sequence selected set out in SEQ ID NO:70.

Embodiment 109

The engineered polypeptide according to any one of Embodiments 1 to 90, wherein said engineered polypeptide comprises the amino acid sequence selected set out in SEQ ID NO:71.

Embodiment 110

The engineered polypeptide according to any one of Embodiments 1 to 90, wherein said engineered polypeptide comprises the amino acid sequence selected set out in SEQ ID NO:72.

Embodiment 111

The engineered polypeptide according to any one of Embodiments 1 to 90, wherein said engineered polypeptide comprises the amino acid sequence selected set out in SEQ ID NO:73.

Embodiment 112

The engineered polypeptide according to any one of Embodiments 1 to 90, wherein said engineered polypeptide comprises the amino acid sequence selected set out in SEQ ID NO:74.

Embodiment 113

The engineered polypeptide according to any one of Embodiments 1 to 90, wherein said engineered polypeptide comprises the amino acid sequence selected set out in SEQ ID NO:75.

Embodiment 114

The engineered polypeptide according to any one of Embodiments 1 to 90, wherein said engineered polypeptide comprises the amino acid sequence selected set out in SEQ ID NO:76.

Embodiment 115

The engineered polypeptide according to any one of Embodiments 1 to 90, wherein said engineered polypeptide comprises the amino acid sequence selected set out in SEQ ID NO:77.

Embodiment 116

The engineered polypeptide according to any one of Embodiments 1 to 90, wherein said engineered polypeptide comprises the amino acid sequence selected set out in SEQ ID NO:78.

Embodiment 117

The engineered polypeptide according to any one of Embodiments 1 to 90, wherein said engineered polypeptide comprises the amino acid sequence selected set out in SEQ ID NO:79.

Embodiment 118

The engineered polypeptide according to any one of Embodiments 1 to 90, wherein said engineered polypeptide comprises the amino acid sequence selected set out in SEQ ID NO:80.

Embodiment 119

The engineered polypeptide according to any one of Embodiments 1 to 90, wherein said engineered polypeptide comprises the amino acid sequence selected set out in SEQ ID NO:81.

Embodiment 120

The engineered polypeptide according to any one of Embodiments 1 to 90, wherein said engineered polypeptide comprises the amino acid sequence selected set out in SEQ ID NO:82.

Embodiment 121

The engineered polypeptide according to any one of Embodiments 1 to 90, wherein said engineered polypeptide comprises the amino acid sequence selected set out in SEQ ID NO:83.

Embodiment 122

The engineered polypeptide according to any one of Embodiments 1 to 90, wherein said engineered polypeptide comprises the amino acid sequence selected set out in SEQ ID NO:84.

Embodiment 123

The engineered polypeptide according to any one of Embodiments 1 to 90, wherein said engineered polypeptide comprises the amino acid sequence selected set out in SEQ ID NO:85.

Embodiment 124

The engineered polypeptide according to any one of Embodiments 1 to 90, wherein said engineered polypeptide comprises the amino acid sequence selected set out in SEQ ID NO:86.

Embodiment 125

The engineered polypeptide according to any one of Embodiments 1 to 90, wherein said engineered polypeptide comprises the amino acid sequence selected set out in SEQ ID NO:87.

Embodiment 126

The engineered polypeptide according to any one of Embodiments 1 to 90, wherein said engineered polypeptide comprises the amino acid sequence selected set out in SEQ ID NO:88.

Embodiment 127

The engineered polypeptide according to any one of Embodiments 1 to 90, wherein said engineered polypeptide comprises the amino acid sequence selected set out in SEQ ID NO:89.

Embodiment 128

The engineered polypeptide according to any one of Embodiments 1 to 90, wherein said engineered polypeptide comprises the amino acid sequence selected set out in SEQ ID NO:90.

Embodiment 129

The engineered polypeptide according to any one of Embodiments 1 to 90, wherein said engineered polypeptide comprises the amino acid sequence selected set out in SEQ ID NO:91.

Embodiment 130

The engineered polypeptide according to any one of Embodiments 1 to 90, wherein said engineered polypeptide comprises the amino acid sequence selected set out in SEQ ID NO:92.

Embodiment 131

The engineered polypeptide according to any one of Embodiments 1 to 90, wherein said engineered polypeptide comprises the amino acid sequence selected set out in SEQ ID NO:93.

Embodiment 132

The engineered polypeptide according to any one of Embodiments 1 to 90, wherein said engineered polypeptide comprises the amino acid sequence selected set out in SEQ ID NO:94.

Embodiment 133

The engineered polypeptide according to any one of Embodiments 1 to 90, wherein said engineered polypeptide comprises the amino acid sequence selected set out in SEQ ID NO:95.

Embodiment 134

The engineered polypeptide according to any one of Embodiments 1 to 90, wherein said engineered polypeptide comprises the amino acid sequence selected set out in SEQ ID NO:96.

Embodiment 135

The engineered polypeptide according to any one of Embodiments 1 to 90, wherein said engineered polypeptide comprises the amino acid sequence selected set out in SEQ ID NO:97.

Embodiment 136

The engineered polypeptide according to any one of Embodiments 1 to 90, wherein said engineered polypeptide comprises the amino acid sequence selected set out in SEQ ID NO:98.

Embodiment 137

The engineered polypeptide according to any one of Embodiments 1 to 90, wherein said engineered polypeptide comprises the amino acid sequence selected set out in SEQ ID NO:99.

Embodiment 138

The engineered polypeptide according to any one of Embodiments 1 to 90, wherein said engineered polypeptide comprises the amino acid sequence selected set out in SEQ ID NO:100.

Embodiment 139

The engineered polypeptide according to any one of Embodiments 1 to 90, wherein said engineered polypeptide comprises the amino acid sequence selected set out in SEQ ID NO:102.

Embodiment 140

The engineered polypeptide according to any one of Embodiments 1 to 90, wherein said engineered polypeptide comprises the amino acid sequence selected set out in SEQ ID NO:102.

Embodiment 141

The engineered polypeptide according to any one of Embodiments 1 to 90, wherein said engineered polypeptide comprises the amino acid sequence selected set out in SEQ ID NO:103.

Embodiment 142

The engineered polypeptide according to any one of Embodiments 1 to 90, wherein said engineered polypeptide comprises the amino acid sequence selected set out in SEQ ID NO:104.

Embodiment 143

The engineered polypeptide according to any one of Embodiments 1 to 90, wherein said engineered polypeptide comprises the amino acid sequence selected set out in SEQ ID NO:105.

Embodiment 144

The engineered polypeptide according to any one of Embodiments 1 to 90, wherein said engineered polypeptide comprises the amino acid sequence selected set out in SEQ ID NO:106.

Embodiment 145

The engineered polypeptide according to any one of Embodiments 1 to 90, wherein said engineered polypeptide comprises the amino acid sequence selected set out in SEQ ID NO:107.

Embodiment 146

The engineered polypeptide according to any one of Embodiments 1 to 145, having affinity for serum albumin with a dissociation constant less than about $10^{-6}$ mol/L.

Embodiment 147

The engineered polypeptide according to any one of Embodiments 1 to 146, having affinity for serum albumin with a dissociation constant less than about $10^{-9}$ mol/L.

Embodiment 148

The engineered polypeptide according to any one of Embodiments 1 to 147, having affinity for serum albumin with a dissociation constant less than about $10^{-12}$ mol/L.

Embodiment 149

The engineered polypeptide according to any one of Embodiments 1 to 148, wherein the polypeptide has a duration of action of at least 1 day.

Embodiment 150

The engineered polypeptide according to any one of Embodiments 1 to 149, wherein the polypeptide has a duration of action of at least 3 days.

Embodiment 151

The engineered polypeptide according to any one of Embodiments 1 to 150, wherein the polypeptide has a duration of action of at least 5 days.

Embodiment 152

The engineered polypeptide according to any one of Embodiments 1 to 151, wherein the polypeptide has a duration of action of at least 5 days in a human subject.

Embodiment 153

A method for treating a disease or disorder in a subject, comprising administering a engineered polypeptide according to any one of Embodiments 1 to 152 and 170 to 192 to a subject in need thereof in an amount effective to treat said disease or disorder.

Embodiment 154

The method according to Embodiment 153, wherein said disease or disorder is disease or disorder can be lipodystrophy, dyslipidemia, hyperlipidemia, overweight, obesity, hypothalamic amenorrhea, Alzheimer's disease, leptin deficiency, fatty liver disease, diabetes (including type I and type II), nonalcoholic steatohepatitis (NASH), nonalcoholic fatty liver disease (NAFLD) and metabolic syndrome X.

Embodiment 155

The method according to Embodiment 153 or Embodiment 154, wherein said disease or disorder is lipodystrophy, dyslipidemia, hyperlipidemia, overweight, obesity, hypothalamic amenorrhea, Alzheimer's disease, leptin deficiency, fatty liver disease or diabetes.

Embodiment 156

The method according to any one of Embodiments 153 to 155, wherein said disease or disorder is type I diabetes or type II diabetes.

Embodiment 157

The method according to any one of Embodiments 153 to 155, wherein said disease or disorder is obesity.

Embodiment 158

The method according to any one of Embodiments 153 to 155, wherein said disease or disorder is lipodystrophy or leptin deficiency.

Embodiment 159

A pharmaceutical composition comprising an engineered polypeptide according to any one of Embodiments 1 to 152 and a pharmaceutically acceptable excipient.

Embodiment 160

The pharmaceutical composition according to Embodiment 159, wherein said pharmaceutical composition is an injectable pharmaceutical composition.

Embodiment 161

The pharmaceutical composition according to any one of Embodiments 159 to 160, wherein said pharmaceutical composition is a sustained release or long lasting pharmaceutical composition.

Embodiment 162

The pharmaceutical composition according to any one of Embodiments 159 to 161, wherein said pharmaceutical composition is a once daily pharmaceutical composition.

Embodiment 163

The pharmaceutical composition according to any one of Embodiments 159 to 161, wherein said pharmaceutical composition is a once weekly pharmaceutical composition.

Embodiment 164

A pharmaceutical composition of any one of Embodiments 159 to 163 for treating a disease or disorder in a subject.

Embodiment 165

The pharmaceutical composition according to any one of Embodiments 159 to 164 wherein the disease or disorder is lipodystrophy, dyslipidemia, hyperlipidemia, overweight, obesity, hypothalamic amenorrhea, Alzheimer's disease, leptin deficiency, fatty liver disease, diabetes (including type I and type II), nonalcoholic steatohepatitis (NASH), nonalcoholic fatty liver disease (NAFLD) and metabolic syndrome X.

Embodiment 166

The pharmaceutical composition of Embodiment 164 or Embodiment 165 wherein said disease or disorder is lipodystrophy, dyslipidemia, hyperlipidemia, overweight, obesity, hypothalamic amenorrhea, Alzheimer's disease, leptin deficiency, fatty liver disease or diabetes.

Embodiment 167

The method according to any one of Embodiments 164 to 166, wherein said disease or disorder is type I diabetes or type II diabetes.

Embodiment 168

The method according to any one of Embodiments 164 to 166, wherein said disease or disorder is obesity.

Embodiment 169

The method according to any one of Embodiments 164 to 166, wherein said disease or disorder is lipodystrophy or leptin deficiency.

Embodiment 170

The engineered polypeptide according to any one of embodiments 1 to 18, wherein said HD1 is selected from the group consisting of:
(a) the amino acid sequence 1-146 of a leptin selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:143, SEQ ID NO:144, SEQ ID NO:145, and SEQ ID NO:146; in which a different amino acid is substituted in one or more of the following positions and retaining the same numbering (even in the absence of a glutaminyl residue at position 28): 4, 32, 33, 35, 50, 64, 68, 71, 74, 77, 78, 89, 97, 100, 102, 105, 106, 107, 108, 111, 118, 136, 138, 142, and 145;
(b) the amino acid sequence of subpart (a) in which the glutaminyl residue at position 28 is absent;
(c) the amino acid sequence of subparts (a) or (b) in which a methionyl residue is added at the N-terminus;
(d) a leptin consisting of a fragment of the amino acid sequence of (a), (b), or (c) selected from the group consisting of:
(i) amino acids 98-146;
(ii) amino acids 1-32;
(iii) amino acids 40-116;
(iv) amino acids 1-99 and 112-146;
(v) amino acids 1-99 and 112-146 in which one or more of amino acids 100-111 is placed between amino acids 99 and 112;
(vi) the amino acid sequence of subpart (i) wherein one or more of amino acids 100, 102, 105, 106, 107, 108, 111, 118, 136, 138, 142, and 145 is substituted with another amino acid;
(vii) the amino acid sequence of subpart (ii) wherein one or more of amino acids 4, 8 and 32 is substituted with another amino acid;
(viii) the amino acid sequence of subpart (iii) wherein one or more of amino acids 50, 53, 60, 64, 66, 67, 68, 71, 74, 77, 78, 89, 97, 100, 102, 105, 106, 107, 108, 111 and 112 is replaced with another amino acid;
(ix) the amino acid sequence of subpart (iv) wherein one or more of amino acids 4, 8, 32, 33, 35, 48, 50, 53, 60, 64, 66, 67, 68, 71, 74, 77, 78, 89, 97, 112, 118, 136, 138, 142, and 145 is replaced with another amino acid; and
(x) the amino acid sequence of subpart (v) wherein one or more of amino acids 4, 32, 33, 35, 50, 64, 68, 71, 74, 77, 78, 89, 97, 100, 102, 105, 106, 107, 108, 111, 118, 136, 138, 142, and 145 is replaced with another amino acid;

(xi) the amino acid sequence of any of subparts (i)-(x) wherein a methionine has been added at the N-terminus;
(e) the amino acid sequence of any of subparts (a) through (d) wherein said amino acid sequence is attached to a chemical moiety;
(f) the amino acid sequence of subpart (e) wherein said chemical moiety is a water soluble polymer moiety;
(g) the amino acid sequence of subpart (f) wherein said water soluble polymer moiety is selected from the group consisting of: polyethylene glycol, an ethylene glycol/propylene glycol copolymer, a carboxymethylcellulose, a dextran, a polyvinyl alcohol, a polyvinyl pyrolidone, a poly-1,3-dioxolane, a poly-1,3,6-trioxane, an ethylene/maleic anhydride copolymer, a polyaminoacid homopolymer, a polyaminoacid random copolymer, an albumin, an Fc protein, a poly(n-vinyl pyrolidone)polyethylene glycol, a propylene glycol homopolymer, a polypropylene oxide/ethylene oxide copolymer, a polyoxyethylated polyol, a polyvinyl alcohol, a polyethylene glycol propionadehyde, a succinate, and a styrene;
(h) the amino acid sequence of subpart (g) wherein said water soluble polymer moiety is a polyethylene glycol; and
(i) the amino acid sequence of subpart (g) wherein said water soluble polymer is a polyamino acid selected from the group consisting of: an albumin, an antibody, an Fc protein, and a polylysine moiety.

Embodiment 171

The engineered polypeptide according to any one of embodiments 1 to 18 and 170, wherein said HD1 comprises an amino acid sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:143, SEQ ID NO:144, SEQ ID NO:145, and SEQ ID NO:146; wherein one or more amino acid substitutions have been made.

Embodiment 172

The engineered polypeptide according to any one of embodiments 1 to 18 and 171, wherein said HD1 comprises an amino acid sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:143, SEQ ID NO:144, SEQ ID NO:145, and SEQ ID NO:146; wherein one amino acid substitution has been made.

Embodiment 173

The engineered polypeptide according to any one of embodiments 1 to 18 and 171, wherein said HD1 comprises an amino acid sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:143, SEQ ID NO:144, SEQ ID NO:145, and SEQ ID NO:146; wherein two amino acid substitutions have been made.

Embodiment 174

The engineered polypeptide according to any one of embodiments 1 to 18 and 171, wherein said HD1 comprises an amino acid sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:143, SEQ ID NO:144, SEQ ID NO:145, and SEQ ID NO:146; wherein three amino acid substitutions have been made.

Embodiment 175

The engineered polypeptide according to any one of embodiments 1 to 18 and 171, wherein said HD1 comprises an amino acid sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:143, SEQ ID NO:144, SEQ ID NO:145, and SEQ ID NO:146; wherein four amino acid substitutions have been made.

Embodiment 176

The engineered polypeptide according to any one of embodiments 1 to 18 and 171, wherein said HD1 comprises an amino acid sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:143, SEQ ID NO:144, SEQ ID NO:145, and SEQ ID NO:146; wherein five amino acid substitutions have been made.

Embodiment 177

The engineered polypeptide according to any one of embodiments 1 to 18 and 171, wherein said HD1 comprises an amino acid sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:143, SEQ ID NO:144, SEQ ID NO:145, and SEQ ID NO:146; wherein six amino acid substitutions have been made.

Embodiment 178

The engineered polypeptide according to any one of embodiments 1 to 18 and 171, wherein said HD1 comprises an amino acid sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:143, SEQ ID NO:144, SEQ ID NO:145, and SEQ ID NO:146; wherein seven amino acid substitutions have been made.

Embodiment 179

The engineered polypeptide according to any one of embodiments 1 to 18 and 171, wherein said HD1 comprises an amino acid sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:143, SEQ ID NO:144, SEQ ID NO:145, and SEQ ID NO:146; wherein eight amino acid substitutions have been made.

Embodiment 180

The engineered polypeptide according to any one of embodiments 1 to 18 and 171, wherein said HD1 comprises an amino acid sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:143, SEQ ID NO:144, SEQ ID NO:145, and SEQ ID NO:146; wherein nine amino acid substitutions have been made.

Embodiment 181

The engineered polypeptide according to any one of embodiments 1 to 18 and 171, wherein said HD1 comprises an amino acid sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:143, SEQ ID NO:144, SEQ ID NO:145, and SEQ ID NO:146; wherein ten amino acid substitutions have been made.

Embodiment 182

The engineered polypeptide according to any one of embodiments 1 to 18 and 171, wherein said HD1 comprises an amino acid sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:143, SEQ ID NO:144, SEQ ID NO:145, and SEQ ID NO:146; wherein 11 amino acid substitutions have been made.

Embodiment 183

The engineered polypeptide according to any one of embodiments 1 to 18 and 171, wherein said HD1 comprises an amino acid sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:143, SEQ ID NO:144, SEQ ID NO:145, and SEQ ID NO:146; wherein 12 amino acid substitutions have been made.

Embodiment 184

The engineered polypeptide according to any one of embodiments 1 to 18 and 171, wherein said HD1 comprises an amino acid sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:143, SEQ ID NO:144, SEQ ID NO:145, and SEQ ID NO:146; wherein 13 amino acid substitutions have been made.

Embodiment 185

The engineered polypeptide according to any one of embodiments 1 to 18 and 171, wherein said HD1 comprises an amino acid sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:143, SEQ ID NO:144, SEQ ID NO:145, and SEQ ID NO:146; wherein 14 amino acid substitutions have been made.

Embodiment 186

The engineered polypeptide according to any one of embodiments 1 to 18 and 171, wherein said HD1 comprises an amino acid sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:143, SEQ ID NO:144, SEQ ID NO:145, and SEQ ID NO:146; wherein 15 amino acid substitutions have been made.

Embodiment 187

The engineered polypeptide according to any one of embodiments 1 to 18 and 171, wherein said HD1 comprises an amino acid sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:143, SEQ ID NO:144, SEQ ID NO:145, and SEQ ID NO:146; wherein 16 amino acid substitutions have been made.

Embodiment 188

The engineered polypeptide according to any one of embodiments 1 to 18 and 171, wherein said HD1 comprises an amino acid sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:143, SEQ ID NO:144, SEQ ID NO:145, and SEQ ID NO:146; wherein 17 amino acid substitutions have been made.

Embodiment 189

The engineered polypeptide according to any one of embodiments 1 to 18 and 171, wherein said HD1 comprises an amino acid sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:143, SEQ ID NO:144, SEQ ID NO:145, and SEQ ID NO:146; wherein 18 amino acid substitutions have been made.

Embodiment 190

The engineered polypeptide according to any one of embodiments 1 to 18 and 171, wherein said HD1 comprises an amino acid sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:143, SEQ ID NO:144, SEQ ID NO:145, and SEQ ID NO:146; wherein 19 amino acid substitutions have been made.

Embodiment 191

The engineered polypeptide according to any one of embodiments 1 to 18 and 171, wherein said HD1 comprises an amino acid sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:143, SEQ ID NO:144, SEQ ID NO:145, and SEQ ID NO:146; wherein 20 amino acid substitutions have been made.

Embodiment 192

The engineered polypeptide according to any one of embodiments 1 to 18 and 171, wherein said HD1 comprises an amino acid sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:143, SEQ ID NO:144, SEQ ID NO:145, and SEQ ID NO:146; wherein 21 amino acid substitutions have been made.

Embodiment 193

The engineered polypeptide according to any one of embodiments 1 to 20, wherein said HD1 is SEQ ID NO:143.

Embodiment 194

The engineered polypeptide according to any one of embodiments 1 to 20, wherein said HD1 is SEQ ID NO:144.

Embodiment 195

The engineered polypeptide according to any one of embodiments 1 to 20, wherein said HD1 is SEQ ID NO:145.

Embodiment 196

The engineered polypeptide according to any one of embodiments 1 to 20, wherein said HD1 is SEQ ID NO:146.

While the foregoing description discloses the present invention, with examples provided for the purpose of illustration, it will be understood that the practice of the present invention encompasses all of the usual variations, adaptations, or modifications as being within the scope of the claimed invention. Therefore, descriptions and examples should not be construed as limiting the scope of the invention, which is delineated by the appended claims.

IX. Informal Sequence Listing

An informal listing of sequences disclosed herein follows:

```
                                                          (SEQ ID NO: 1)
VPIQKVQDDTKTLIKTIVTRINDISHT-Xaa-SVSSKQKVTGLDFIPGLHPILTLSKMDQTLAVYQQILTSMPSRNVIQ

ISNDLENLRDLLHVLAFSKSCHLPQASGLETLESLGGVLEASGYSTEVVALSRLQGSLQDMLQQLDLSPGC, wherein Xaa at position 28 is Q or absent;

(SEQ ID NO: 2)
MVPIQKVQDDTKTLIKTIVTRINDISHT-Xaa-SVSSKQKVTGLDFIPGLHPILTLSKMDQTLAVYQQILTSMPSRNVI

QISNDLENLRDLLHVLAFSKSCHLPQASGLETLESLGGVLEASGYSTEVVALSRLQGSLQDMLQQLDLSPGC, wherein Xaa at position 29 is Q or absent;

(SEQ ID NO: 3)
VPIWRVQDDTKTLIKTIVTRISDISHMQSVSSKQRVTGLDFIPGLHPVLSLSKMDQTLAIYQQILTSLPSRNVIQISND

LENLRDLLHLLASSKSCPLPQARALETLESLGGVLEASLYSTEVVALSRLQGALQDMLRQLDLSPGC;

(SEQ ID NO: 4)
MVPIWRVQDDTKTLIKTIVTRISDISHMQSVSSKQRVTGLDFIPGLHPVLSLSKMDQTLAIYQQILTSLPSRNVIQISN

DLENLRDLLHLLASSKSCPLPQARALETLESLGGVLEASLYSTEVVALSRLQGALQDMLRQLDLSPGC;

(SEQ ID NO: 5)
VPICKVQDDTKTLIKTIVTRINDISHT-Xaa-SVSSKQRVTGLDFIPGLHPLLSLSKMDQTLAIYQQILTSLPSRNVVQ

ISNDLENLRDLLHLLAASKSCPLPQVRALESLESLGVVLEASLYSTEVVALSRLQGSLQDMLRQLDLSPGC, wherein Xaa at position 28 is Q or absent;

(SEQ ID NO: 6)
MVPICKVQDDTKTLIKTIVTRINDISHT-Xaa-SVSSKQRVTGLDFIPGLHPLLSLSKMDQTLAIYQQILTSLPSRNVV

QISNDLENLRDLLHLLAASKSCPLPQVRALESLESLGVVLEASLYSTEVVALSRLQGSLQDMLRQLDLSPGC, wherein Xaa at position 29 is Q or absent;

(SEQ ID NO: 7)
MHWGTLCGFLWLWPYLFYVQAVPIQKVQDDTKTLIKTIVTRINDISHTQSVSSKQKVTGLDFIPGLHPILTLSKMDQTL

AVYQQILTSMPSRNVIQISNDLENLRDLLHVLAFSKSCHLPWASGLETLDSLGGVLEASGYSTEVVALSRLQGSLQDML

WQLDLSPGC;
```

```
                                                                      (SEQ ID NO: 8)
VPIQKVQDDTKTLIKTIVTRINDISH-Xaa-Xaa-SVSSKQKVTGLDFIPGLHPILTLSKMDQTLAVYQQILTSMPSRN

VIQISNDLENLRDLLHVLAFSKSCHLPWASGLETLDSLGGVLEASGYSTEVVALSRLQGSLQDMLWQLDLSPGC, wherein: Xaa at position 27 is T or A; and Xaa at position 28 is Q or absent;

(SEQ ID NO: 9)
MVPIQKVQDDTKTLIKTIVTRINDISH-Xaa-Xaa-SVSSKQKVTGLDFIPGLHPILTLSKMDQTLAVYQQILTSMPSR

NVIQISNDLENLRDLLHVLAFSKSCHLPWASGLETLDSLGGVLEASGYSTEVVALSRLQGSLQDMLWQLDLSPGC, wherein: Xaa at position 28 is T or A, and Xaa at position 29 is Q or absent;

(SEQ ID NO: 10)
VPIQKVQSDTKTLIKTIVTRINDISHTQSVSSKQRVTGLDFIPGLHPVLTLSQMDQTLAIYQQILINLPSRNVIQISND

LENLRDLLHLLAFSKSCHLPLASGLETLESLGDVLEASLYSTEVVALSRLQGSLQDMLWQLDLSPGC;

(SEQ ID NO: 11)
MVPIQKVQSDTKTLIKTIVTRINDISHTQSVSSKQRVTGLDFIPGLHPVLTLSQMDQTLAIYQQILINLPSRNVIQISN

DLENLRDLLHLLAFSKSCHLPLASGLETLESLGDVLEASLYSTEVVALSRLQGSLQDMLWQLDLSPGC;

(SEQ ID NO: 12)
VPIHKVQDDTKTLIKTIVTRINDISHTQSVSARQRVTGLDFIPGLHPILSLSKMDQTLAVYQQILTSLPSQNVLQIAHD

LENLRDLLHLLAFSKSCSLPQTRGLQKPESLDGVLEASLYSTEVVALSRLQGSLQDILQQLDLSPEC;

(SEQ ID NO: 13)
MVPIHKVQDDTKTLIKTIVTRINDISHTQSVSARQRVTGLDFIPGLHPILSLSKMDQTLAVYQQILTSLPSQNVLQIAH

DLENLRDLLHLLAFSKSCSLPQTRGLQKPESLDGVLEASLYSTEVVALSRLQGSLQDILQQLDLSPEC;

(SEQ ID NO: 14)
ISIEKIQADTKTLTKTIITRIIQLSTQNGVSTDQRVSGLDFIPGNQQFQNLADMDQTLAVYQQILSSLPMPDRTQISND

LENLRSLFALLATLKNCPFTRSDGLDTMEIWGGIVEESLYSTEVVTLDRLRKSLKNIEKQLDHIQG;

(SEQ ID NO: 15)
MRCILLYGFLCVWQHLYYSHPISIEKIQADTKTLTKTIITRIIQLSTQNGVSTDQRVSGLDFIPGNQQFQNLADMDQTL

AVYQQILSSLPMPDRTQISNDLENRSLFALLATLKNCPFTRSDGLDTMEIWGGIVEESLYSTEVVTLDRLRKSLKNIE

KQLDHIQG;

(SEQ ID NO: 16)
VPIQKVQDDTKTLIKTIVTRINDISHTQSVSSKQKVTGLDFIPGLHPILTLSKMDQTLAVYQQILTSMPSRNVIQISND

LENRDLLHVLAFSKSCHLPWASGLETLDSLGGVLEASGYSTEVVALSRLQGSLQDMLWQLDLSPGC;

(SEQ ID NO: 17)
VPIQKVQDDTKTLIKTIVTRINDISHAQSVSSKQKVTGLDFIPGLHPILTLSKMDQTLAVYQQILTSMPSRNVIQISND

LENLRDLLHVLAFSKSCHLPWASGLETLDSLGGVLEASGYSTEVVALSRLQGSLQDMLWQLDLSPGC;

(SEQ ID NO: 18)
VPIQKVQDDTKTLIKTIVTRINDISHTSVSSKQKVTGLDFIPGLHPILTLSKMDQTLAVYQQILTSMPSRNVIQISNDL

ENLRDLLHVLAFSKSCHLPWASGLETLDSLGGVLEASGYSTEVVALSRLQGSLQDMLWQLDLSPGC;

(SEQ ID NO: 19)
VPIQKVQDDTKTLIKTIVTRINDISHASVSSKQKVTGLDFIPGLHPILTLSKMDQTLAVYQQILTSMPSRNVIQISNDL

ENLRDLLHVLAFSKSCHLPWASGLETLDSLGGVLEASGYSTEVVALSRLQGSLQDMLWQLDLSPGC;

(SEQ ID NO: 20)
MVPIQKVQDDTKTLIKTIVTRINDISHTQSVSSKQKVTGLDFIPGLHPILTLSKMDQTLAVYQQILTSMPSRNVIQISN

DLENLRDLLHVLAFSKSCHLPWASGLETLDSLGGVLEASGYSTEVVALSRLQGSLQDMLWQLDLSPGC;

(SEQ ID NO: 21)
MVPIQKVQDDTKTLIKTIVTRINDISHAQSVSSKQKVTGLDFIPGLHPILTLSKMDQTLAVYQQILTSMPSRNVIQISN

DLENLRDLLHVLAFSKSCHLPWASGLETLDSLGGVLEASGYSTEVVALSRLQGSLQDMLWQLDLSPGC;

(SEQ ID NO: 22)
MVPIQKVQDDTKTLIKTIVTRINDISHTSVSSKQKVTGLDFIPGLHPILTLSKMDQTLAVYQQILTSMPSRNVIQISND

LENLRDLLHVLAFSKSCHLPWASGLETLDSLGGVLEASGYSTEVVALSRLQGSLQDMLWQLDLSPGC;
```

-continued (SEQ ID NO: 23)
MVPIQKVQDDTKTLIKTIVTRINDISHASVSSKQKVTGLDFIPGLHPILTLSKMDQTLAVYQQILTSMPSRNVIQISND
LENLRDLLHVLAFSKSCHLPWASGLETLDSLGGVLEASGYSTEVVALSRLQGSLQDMLWQLDLSPGC;

(SEQ ID NO: 24)
PIQRVQDDTKTLIKTIITRINDISPPQGVCSRPRVAGLDFIPRVQSVRTLSGMDQILATYQQILTSLQSRSVVQIANDL
ANLRALLRLLASAKSCPVPRARGSDTIKGLGNVLRASVHSTEVVALSRLKAALQDMLRQLDRNPGC;

(SEQ ID NO: 25)
PIQRVQDDTKTLIKTIITRINDISPPQGVCSRPRVAGLDFIPRVQSVRTLSGMDQILATYQQILTSLQSRNVIQISNDL
ENLRDLLHVLAFSKSCPVPRARGSDTIKGLGNVLRASVHSTEVVALSRLKAALQDMLRQLDRNPGC;

(SEQ ID NO: 26)
PIQRVQDDTKTLIKTIITRINDISPPQGVSSRPRVAGLDFIPRVQSVRTLSGMDQILATYQQILTSLQSRNVIQISNDL
ENLRDLLHVLAFSKSCPVPRARGSDTIKGLGNVLRASVHSTEVVALSRLKAALQDMLRQLDRNPGC;

(SEQ ID NO: 27)
MPIQRVQDDTKTLIKTIITRINDISPPQGVCSRPRVAGLDFIPRVQSVRTLSGMDQILATYQQILTSLQSRSVVQIAND
LANLRALLRLLASAKSCPVPRARGSDTIKGLGNVLRASVHSTEVVALSRLKAALQDMLRQLDRNPGC;

(SEQ ID NO: 28)
MPIQRVQDDTKTLIKTIITRINDISPPQGVCSRPRVAGLDFIPRVQSVRTLSGMDQILATYQQILTSLQSRNVIQISND
LENLRDLLHVLAFSKSCPVPRARGSDTIKGLGNVLRASVHSTEVVALSRLKAALQDMLRQLDRNPGC;

(SEQ ID NO: 29)
MPIQRVQDDTKTLIKTIITRINDISPPQGVSSRPRVAGLDFIPRVQSVRTLSGMDQILATYQQILTSLQSRNVIQISND
LENLRDLLHVLAFSKSCPVPRARGSDTIKGLGNVLRASVHSTEVVALSRLKAALQDMLRQLDRNPGC;

(SEQ ID NO: 30)
MDKTHTCPPCPAPELLGGPSVFLFPPKPKDTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQVYTLPPSRDELTKNQVSLTCLVKGFYPSDI
AVEWESNGQPENNYKTTPPVLDSDGSFFLYSKLTVDKSRWQQGNVFSCSVMHEALHNHYTQKSLSLSPGKVPIQKVQDD
TKTLIKTIVTRINDISHTQSVSSKQKVTGLDFIPGLHPILTLSKMDQTLAVYQQILTSMPSRNVIQISNDLENLRDLLH
VLAFSKSCHLPWASGLETLDSLGGVLEASGYSTEVVALSRLQGSLQDMLWQLDLSPGC;

(SEQ ID NO: 31)
MVPIQKVQDDTKTLIKTIVTRINDISHTQSVSSKQKVTGLDFIPGLHPILTLSKMDQTLAVYQQILTSMPSRNVIQISN
DLENLRDLLHVLAFSKSCHLPQASGLETLDSLGGVLEASGYSTEVVALSRLQGSLQDMLQQLDLSPGC;

(SEQ ID NO: 32)
MVPIQKVQDDTKTLIKTIVTRINDISHTQSVSSKQKVTGLDFIPGLHPILTLSKMDQTLAVYQQILTSMPSRNVIQICN
DLENLRDLLHVLAFSKSCHLPWASGLETLDSLGGVLEASGYSTEVVALSRLQGSLQDMLWQLDLSPGC;
to which a 20 kilodalton (kDa) PEG moiety has been attached via the cysteine
residue at position 78;

(SEQ ID NO: 33)
MVPIQKVQDDTKTLIKTIVTRINDISHTQSVSSKQKVTGLEFIPGLHPILTLSKMDQTLAVYQQILTSMPSRNVIQISN
DLENLRDLLHVLAFSKSCHLPQASGLETLESLGGVLEASGYSTEVVALSRLQGSLQDMLQQLDLSPGC;

(SEQ ID NO: 34)
GVSD $X_5$ YK $X_8$ $X_9$ I $X_{11}$ $X_{12}$ A $X_{14}$ TVEGV $X_{20}$ AL $X_{23}$ $X_{24}$ $X_{25}$ I,
wherein $X_5$, $X_8$, $X_9$, $X_{11}$, $X_{12}$, $X_{14}$, $X_{20}$, $X_{23}$, $X_{24}$ and $X_{25}$ are as described herein;

(SEQ ID NO: 35)
GVSDYYKNLINNAKTVEGVKALIDEI;

(SEQ ID NO: 36)
LAEAK $X_a$ $X_b$ A $X_c$ $X_d$ EL $X_e$ KY -[ABM]- LAALP,
wherein ABM, $X_a$, $X_b$, $X_c$, $X_d$ and $X_e$ are as described herein;

(SEQ ID NO: 37)
LAEAKVLANRELDKYGVSDYYKNLINNAKTVEGVKALIDEILAALP;

(SEQ ID NO: 38)
LAEAKVLANRELDKYGVSDFYKSYINRAKTVEGVHTLIGHILAALP;

-continued (SEQ ID NO: 39)
LAEAKVLANRELDKYGVSDFYKRLINKAKTVEGVNALTHHILAALP;

(SEQ ID NO: 40)
LAEAKVLANRELDKYGVSDYYKNLINRARTVEGVHALIDHILAALP;

(SEQ ID NO: 41)
LAEAKVLANRELDKYGVSDYYKNIINRAKTVEGVRALKLHILAALP;

(SEQ ID NO: 42)
LAEAKVLANRELDKYGVSDFYKNLINRAKTVEGVSSLKGHILAALP;

(SEQ ID NO: 43)
LAEAKVLANRELDKYGVSDYYKNLINKAKTVEGVEALTLHILAALP;

(SEQ ID NO: 44)
LAEAKVLANRELDKYGVSDFYKNLINRAKTVEGVDALIAHILAALP;

(SEQ ID NO: 45)
LAEAKVLANRELDKYGVSDFYKSLINRAKTVEGVDALTSHILAALP;

(SEQ ID NO: 46)
LAEAKVLANRELDKYGVSDFYKNLINRAKTVEGVNSLTSHILAALP;

(SEQ ID NO: 47)
LAEAKVLANRELDKYGVSDFYKNVINKAKTVEGVEALIADILAALP;

(SEQ ID NO: 48)
LAEAKVLANRELDKYGVSDYYKNLINKAKTVEGVQALIAHILAALP;

(SEQ ID NO: 49)
LAEAKVLANRELDKYGVSDFYKRLINKAKTVEGVEALKLHILAALP;

(SEQ ID NO: 50)
LAEAKEDAIKELDKYGVSDYYKNLINKAKTVEGVEALTLHILAALP;

(SEQ ID NO: 51)
LAEAKEDAIKELDKYGVSDYYKNLINKAKTVEGVEALiseILAALP;

(SEQ ID NO: 52)
LAEAKEDAIKELDKYGVSDYYKRLISKAKTVEGVKALISEILAALP;

(SEQ ID NO: 53)
MLAEAKVLANRELDKYGVSDFYKRLINKAKTVEGVEALKLHILAALPTGGGGASVPIQKVQDDTKTLIKTIVTRINDIS
HTQSVSSKQKVTGLEFIPGLHPILTLSKMDQTLAVYQQILTSMPSRNVIQISNDLENLRDLLHVLAFSKSCHLPQASGL
ETLESLGGVLEASGYSTEVVALSRLQGSLQDMLQQLDLSPGC;

(SEQ ID NO: 54)
MLAEAKVLANRELDKYGVSDFYKRLINKAKTVEGVEALKLHILAALPTGGGGSGGGGSGGGGSGGGSASVPIQKVQDDTKT
LIKTIVTRINDISHTQSVSSKQKVTGLEFIPGLHPILTLSKMDQTLAVYQQILTSMPSRNVIQISNDLENLRDLLHVLA
FSKSCHLPQASGLETLESLGGVLEASGYSTEVVALSRLQGSLQDMLQQLDLSPGC;

(SEQ ID NO: 55)
MVPIQKVQDDTKTLIKTIVTRINDISHTQSVSSKQKVTGLEFIPGLHPILTLSKMDQTLAVYQQILTSMPSRNVIQISN
DLENLRDLLHVLAFSKSCHLPQASGLETLESLGGVLEASGYSTEVVALSRLQGSLQDMLQQLDLSPGCTGGGGSASLAE
AKVLANRELDKYGVSDFYKRLINKAKTVEGVEALKLHILAALP;

(SEQ ID NO: 56)
MVPIQKVQDDTKTLIKTIVTRINDISHTQSVSSKQKVTGLEFIPGLHPILTLSKMDQTLAVYQQILTSMPSRNVIQISN
DLENLRDLLHVLAFSKSCHLPQASGLETLESLGGVLEASGYSTEVVALSRLQGSLQDMLQQLDLSPGCTGGGGSGGGSG
GGSGGGSASLAEAKVLANRELDKYGVSDFYKRLINKAKTVEGVEALKLHILAALP;

(SEQ ID NO: 57)
MLAEAKVLANRELDKYGVSDFYKRLINKAKTVEGVEALKLHILAALPTGGGGSGGGGSGGGGSGGGSASISIEKIQADTKT
LTKTIITRIIQLSTQNGVSTDQRVSGLDFIPGNQQFQNLADMDQTLAVYQQILSSLPMPDRTQISNDLENLRSLFALLA
TLKNCPFTRSDGLDTMEIWGGIVEESLYSTEVVTLDRLRKSLKNIEKQLDHIQGC;

```
                                                              (SEQ ID NO: 58)
MLAEAKVLANRELDKYGVSDFYKRLINKAKTVEGVEALKLHILAALPTGGGGSGGGSGGGSGGGSASVPIQKVQDDTKT

LIKTIVTRINDISHTQSVSSKQKVTGLDFIPGLHPILTLSKMDQTLAVYQQILTSMPSRNVIQISNDLENLRDLLHVLA

FSKSCHLPWASGLETLDSLGGVLEASGYSTEVVALSRLQGSLQDMLWQLDLSPGC;

(SEQ ID NO: 59)
MVPIQKVQDDTKTLIKTIVTRINDISHTQSVSSKQKVTGLDFIPGLHPILTLSKMDQTLAVYQQILTSMPSRNVIQISN

DLENLRDLLHVLAFSKSCHLPWASGLETLDSLGGVLEASGYSTEVVALSRLQGSLQDMLWQLDLSPGCTGGGGSGGGSG

GGSGGGSASLAEAKVLANRELDKYGVSDFYKRLINKAKTVEGVEALKLHILAALP;

(SEQ ID NO: 60)
MLAEAKVLANRELDKYGVSDFYKRLINKAKTVEGVEALKLHILAALPTGGGGSGGGSGGGSGGGSASPIQRVQDDTKTL

IKTIITRINDISPPQGVCSRPRVAGLDFIPRVQSVRTLSGMDQILATYQQILTSLQSRNVIQISNDLENLRDLLHVLAF

SKSCPVPRARGSDTIKGLGNVLRASVHSTEVVALSRLKAALQDMLRQLDRNPGC;

(SEQ ID NO: 61)
MLAEAKVLANRELDKYGVSDFYKRLINKAKTVEGVEALKLHILAALPTGGGGSGGGSGGGSGGGSASPIQRVQDDTKTL

IKTIITRINDISPPQGVSSRPRVAGLDFIPRVQSVRTLSGMDQILATYQQILTSLQSRNVIQISNDLENLRDLLHVLAF

SKSCPVPRARGSDTIKGLGNVLRASVHSTEVVALSRLKAALQDMLRQLDRNPGC;

(SEQ ID NO: 62)
MLAEAKVLANRELDKYGVSDFYKRLINKAKTVEGVEALKLHILAALPTGPIQRVQDDTKTLIKTIITRINDISPPQGVC

SPRVAGLDFIPRVQSVRTLSGMDQILATYQQILTSLQSRNVIQISNDLENLRDLLHVLAFSKSCPVPRARGSDTIKGLG

NVLRASVHSTEVVALSRLKAALQDMLRQLDRNPGC;

(SEQ ID NO: 63)
MLAEAKVLANRELDKYGVSDYYKNIINRAKTVEGVRALKLHILAALPTGGGGSGGGSGGGSGGGSASVPIQKVQDDTKT

LIKTIVTRINDISHTQSVSSKQKVTGLDFIPGLHPILTLSKMDQTLAVYQQILTSMPSRNVIQISNDLENLRDLLHVLA

FSKSCHLPWASGLETLDSLGGVLEASGYSTEVVALSRLQGSLQDMLWQLDLSPGC;

(SEQ ID NO: 64)
MLAEAKVLANRELDKYGVSDYYKNIINRAKTVEGVRALKLHILAALPTGGGGSGGGSGGGSGGGSASVPIQKVQDDTKT

LIKTIVTRINDISHTQSVSSKQKVTGLEFIPGLHPILTLSKMDQTLAVYQQILTSMPSRNVIQISNDLENLRDLLHVLA

FSKSCHLPQASGLETLESLGGVLEASGYSTEVVALSRLQGSLQDMLQQLDLSPGC;

(SEQ ID NO: 65)
MLAEAKVLANRELDKYGVSDFYKRLINKAKTVEGVEALKLHILAALPTGGGGSGGGSGGGSGGGSASVPIQKVQDDTKT

LIKTIVTRINDISHTQSVSSKQKVTGLDFIPGLHPILTLSKMDQTLAVYQQILTSMPSRNVIQISNDLENLRDLLHVLA

FSKSCHLPQASGLETLDSLGGVLEASGYSTEVVALSRLQGSLQDMLQQLDLSPGC;

(SEQ ID NO: 66)
MLAEAKVLANRELDKYGVSDFYKRLINKAKTVEGVEALKLHILAALPTGLAEAAAKEAAAKEAAAKEAAAKEAAAKAAA

ASVPIQKVQDDTKTLIKTIVTRINDISHTQSVSSKQKVTGLEFIPGLHPILTLSKMDQTLAVYQQILTSMPSRNVIQIS

NDLENLRDLLHVLAFSKSCHLPQASGLETLESLGGVLEASGYSTEVVALSRLQGSLQDMLQQLDLSPGC;

(SEQ ID NO: 67)
MLAEAKVLANRELDKYGVSDFYKRLINKAKTVEGVEALKLHILAALPTGGEGGEGGEGGEGGEGGEASVPIQKVQDDTK

TLIKTIVTRINDISHTQSVSSKQKVTGLEFIPGLHPILTLSKMDQTLAVYQQILTSMPSRNVIQISNDLENLRDLLHVL

AFSKSCHLPQASGLETLESLGGVLEASGYSTEVVALSRLQGSLQDMLQQLDLSPGC;

(SEQ ID NO: 68)
MLAEAKVLANRELDKYGVSDFYKRLINKAKTVEGVEALKLHILAALPTGGKGGKGGKGGKGGKGGKASVPIQKVQDDTK

TLIKTIVTRINDISHTQSVSSKQKVTGLEFIPGLHPILTLSKMDQTLAVYQQILTSMPSRNVIQISNDLENLRDLLHVL

AFSKSCHLPQASGLETLESLGGVLEASGYSTEVVALSRLQGSLQDMLQQLDLSPGC;
```

-continued (SEQ ID NO: 69)
MLAEAKVLANRELDKYGVSDFYKRLINKAKTVEGVEALKLHILAALPTGGGGSGGGSGGGSGGGSASVPIQKVQDDTKT
LIKTIVTRINDISHTQSVSSKQKVTGLEFIPGLHPILTLSKMDQTLAVYQQILTSMPSRNVIQISNDLENLRDLLHVLA
FSKSCSLPQASGLETLESLGEVLEASGYSTEVVALSRLQGSLQDILQQLDLSPEC;

(SEQ ID NO: 70)
MLAEAKEDAIKELDKYGVSDYYKNLINKAKTVEGVEALTLHILAALPTGGGGASVPIQKVQDDTKTLIKTIVTRINDIS
HTQSVSSKQKVTGLEFIPGLHPILTLSKMDQTLAVYQQILTSMPSRNVIQISNDLENLRDLLHVLAFSKSCHLPQASGL
ETLESLGGVLEASGYSTEVVALSRLQGSLQDMLQQLDLSPGC;

(SEQ ID NO: 71)
MLAEAKEDAIKELDKYGVSDYYKNLINKAKTVEGVEALTLHILAALPTGGGGSGGGSGGGSGGGSASVPIQKVQDDTKT
LIKTIVTRINDISHTQSVSSKQKVTGLEFIPGLHPILTLSKMDQTLAVYQQILTSMPSRNVIQISNDLENLRDLLHVLA
FSKSCHLPQASGLETLESLGGVLEASGYSTEVVALSRLQGSLQDMLQQLDLSPGC;

(SEQ ID NO: 72)
MVPIQKVQDDTKTLIKTIVTRINDISHTQSVSSKQKVTGLEFIPGLHPILTLSKMDQTLAVYQQILTSMPSRNVIQISN
DLENLRDLLHVLAFSKSCHLPQASGLETLESLGGVLEASGYSTEVVALSRLQGSLQDMLQQLDLSPGCTGGGGSASLAE
AKEDAIKELDKYGVSDYYKNLINKAKTVEGVEALTLHILAALP;

(SEQ ID NO: 73)
MVPIQKVQDDTKTLIKTIVTRINDISHTQSVSSKQKVTGLEFIPGLHPILTLSKMDQTLAVYQQILTSMPSRNVIQISN
DLENLRDLLHVLAFSKSCHLPQASGLETLESLGGVLEASGYSTEVVALSRLQGSLQDMLQQLDLSPGCTGGGGSGGGSG
GGSGGGSASLAEAKEDAIKELDKYGVSDYYKNLINKAKTVEGVEALTLHILAALP;

(SEQ ID NO: 74)
MLAEAKEDAIKELDKYGVSDYYKNLINKAKTVEGVEALTLHILAALPTGGGGSGGGSGGGSGGGSASISIEKIQADTKT
LTKTIITRIIQLSTQNGVSTDQRVSGLDFIPGNQQFQNLADMDQTLAVYQQILSSLPMPDRTQISNDLENLRSLFALLA
TLKNCPFTRSDGLDTMEIWGGIVEESLYSTEVVTLDRLRKSLKNIEKQLDHIQGC;

(SEQ ID NO: 75)
MLAEAKEDAIKELDKYGVSDYYKNLINKAKTVEGVEALTLHILAALPTGGGGSGGGSGGGSGGGSASVPIQKVQDDTKT
LIKTIVTRINDISHTQSVSSKQKVTGLDFIPGLHPILTLSKMDQTLAVYQQILTSMPSRNVIQISNDLENLRDLLHVLA
FSKSCHLPWASGLETLDSLGGVLEASGYSTEVVALSRLQGSLQDMLWQLDLSPGC;

(SEQ ID NO: 76)
MVPIQKVQDDTKTLIKTIVTRINDISHTQSVSSKQKVTGLDFIPGLHPILTLSKMDQTLAVYQQILTSMPSRNVIQISN
DLENLRDLLHVLAFSKSCHLPWASGLETLDSLGGVLEASGYSTEVVALSRLQGSLQDMLWQLDLSPGCTGGGGSGGGSG
GGSGGGSASLAEAKEDAIKELDKYGVSDYYKNLINKAKTVEGVEALTLHILAALP;

(SEQ ID NO: 77)
MLAEAKEDAIKELDKYGVSDYYKNLINKAKTVEGVEALTLHILAALPTGGGGSGGGSGGGSGGGSASPIQRVQDDTKTL
IKTIITRINDISPPQGVCSRPRVAGLDFIPRVQSVRTLSGMDQILATYQQILTSLQSRNVIQISNDLENLRDLLHVLAF
SKSCPVPRARGSDTIKGLGNVLRASVHSTEVVALSRLKAALQDMLRQLDRNPGC;

(SEQ ID NO: 78)
MLAEAKEDAIKELDKYGVSDYYKNLINKAKTVEGVEALTLHILAALPTGGGGSGGGSGGGSGGGSASPIQRVQDDTKTL
IKTIITRINDISPPQGVSSRPRVAGLDFIPRVQSVRTLSGMDQILATYQQILTSLQSRNVIQISNDLENLRDLLHVLAF
SKSCPVPRARGSDTIKGLGNVLRASVHSTEVVALSRLKAALQDMLRQLDRNPGC;

(SEQ ID NO: 79)
MLAEAKEDAIKELDKYGVSDYYKNLINKAKTVEGVEALTLHILAALPTGPIQRVQDDTKTLIKTIITRINDISPPQGVC
SPRVAGLDFIPRVQSVRTLSGMDQILATYQQILTSLQSRNVIQISNDLENLRDLLHVLAFSKSCPVPRARGSDTIKGLG
NVLRASVHSTEVVALSRLKAALQDMLRQLDRNPGC;

```
                                                           (SEQ ID NO: 80)
MLAEAKEDAIKELDKYGVSDYYKNLINKAKTVEGVEALTLHILAALPTGGGGSGGGSGGGSGGGSASVPIQKVQDDTKT

LIKTIVTRINDISHTQSVSSKQKVTGLDFIPGLHPILTLSKMDQTLAVYQQILTSMPSRNVIQISNDLENLRDLLHVLA

FSKSCHLPWASGLETLDSLGGVLEASGYSTEVVALSRLQGSLQDMLWQLDLSPGC;

(SEQ ID NO: 81)
MLAEAKEDAIKELDKYGVSDYYKNLINKAKTVEGVEALTLHILAALPTGGGGSGGGSGGGSGGGSASVPIQKVQDDTKT

LIKTIVTRINDISHTQSVSSKQKVTGLEFIPGLHPILTLSKMDQTLAVYQQILTSMPSRNVIQISNDLENLRDLLHVLA

FSKSCHLPQASGLETLESLGGVLEASGYSTEVVALSRLQGSLQDMLQQLDLSPGC;

(SEQ ID NO: 82)
MLAEAKEDAIKELDKYGVSDYYKNLINKAKTVEGVEALTLHILAALPTGGGGSGGGSGGGSGGGSASVPIQKVQDDTKT

LIKTIVTRINDISHTQSVSSKQKVTGLDFIPGLHPILTLSKMDQTLAVYQQILTSMPSRNVIQISNDLENLRDLLHVLA

FSKSCHLPQASGLETLDSLGGVLEASGYSTEVVALSRLQGSLQDMLQQLDLSPGC;

(SEQ ID NO: 83)
MLAEAKEDAIKELDKYGVSDYYKNLINKAKTVEGVEALTLHILAALPTGLAEAAAKEAAAKEAAAKEAAAKEAAAKAAA

ASVPIQKVQDDTKTLIKTIVTRINDISHTQSVSSKQKVTGLEFIPGLHPILTLSKMDQTLAVYQQILTSMPSRNVIQIS

NDLENLRDLLHVLAFSKSCHLPQASGLETLESLGGVLEASGYSTEVVALSRLQGSLQDMLQQLDLSPGC;

(SEQ ID NO: 84)
MLAEAKEDAIKELDKYGVSDYYKNLINKAKTVEGVEALTLHILAALPTGGEGGEGGEGGEGGEGGEASVPIQKVQDDTK

TLIKTIVTRINDISHTQSVSSKQKVTGLEFIPGLHPILTLSKMDQTLAVYQQILTSMPSRNVIQISNDLENLRDLLHVL

AFSKSCHLPQASGLETLESLGGVLEASGYSTEVVALSRLQGSLQDMLQQLDLSPGC;

(SEQ ID NO: 85)
MLAEAKEDAIKELDKYGVSDYYKNLINKAKTVEGVEALTLHILAALPTGGKGGKGGKGGKGGKGGKASVPIQKVQDDTK

TLIKTIVTRINDISHTQSVSSKQKVTGLEFIPGLHPILTLSKMDQTLAVYQQILTSMPSRNVIQISNDLENLRDLLHVL

AFSKSCHLPQASGLETLESLGGVLEASGYSTEVVALSRLQGSLQDMLQQLDLSPGC;

(SEQ ID NO: 86)
MLAEAKEDAIKELDKYGVSDYYKNLINKAKTVEGVEALTLHILAALPTGGGGSGGGSGGGSGGGSASVPIQKVQDDTKT

LIKTIVTRINDISHTQSVSSKQKVTGLEFIPGLHPILTLSKMDQTLAVYQQILTSMPSRNVIQISNDLENLRDLLHVLA

FSKSCSLPQASGLETLESLGEVLEASGYSTEVVALSRLQGSLQDILQQLDLSPEC;

(SEQ ID NO: 87)
MLAEAKEDAIKELDKYGVSDYYKNLINKAKTVEGVEALiseILAALPTGGGGASVPIQKVQDDTKTLIKTIVTRINDIS

HTQSVSSKQKVTGLEFIPGLHPILTLSKMDQTLAVYQQILTSMPSRNVIQISNDLENLRDLLHVLAFSKSCHLPQASGL

ETLESLGGVLEASGYSTEVVALSRLQGSLQDMLQQLDLSPGC;

(SEQ ID NO: 88)
MLAEAKEDAIKELDKYGVSDYYKNLINKAKTVEGVEALiseILAALPTGGGGSGGGSGGGSGGGSASVPIQKVQDDTKT

LIKTIVTRINDISHTQSVSSKQKVTGLEFIPGLHPILTLSKMDQTLAVYQQILTSMPSRNVIQISNDLENLRDLLHVLA

FSKSCHLPQASGLETLESLGGVLEASGYSTEVVALSRLQGSLQDMLQQLDLSPGC;

(SEQ ID NO: 89)
MVPIQKVQDDTKTLIKTIVTRINDISHTQSVSSKQKVTGLEFIPGLHPILTLSKMDQTLAVYQQILTSMPSRNVIQISN

DLENLRDLLHVLAFSKSCHLPQASGLETLESLGGVLEASGYSTEVVALSRLQGSLQDMLQQLDLSPGCTGGGGSASLAE

AKEDAIKELDKYGVSDYYKNLINKAKTVEGVEALiseILAALP;

(SEQ ID NO: 90)
MVPIQKVQDDTKTLIKTIVTRINDISHTQSVSSKQKVTGLEFIPGLHPILTLSKMDQTLAVYQQILTSMPSRNVIQISN

DLENLRDLLHVLAFSKSCHLPQASGLETLESLGGVLEASGYSTEVVALSRLQGSLQDMLQQLDLSPGCTGGGGSGGGSG

GGSGGGSASLAEAKEDAIKELDKYGVSDYYKNLINKAKTVEGVEALiseILAALP;
```

```
                                                          (SEQ ID NO: 91)
MLAEAKEDAIKELDKYGVSDYYKNLINKAKTVEGVEALISEILAALPTGGGGSGGGSGGGSGGGSASISIEKIQADTKT

LTKTIITRIIQLSTQNGVSTDQRVSGLDFIPGNQQFQNLADMDQTLAVYQQILSSLPMPDRTQISNDLENLRSLFALLA

TLKNCPFTRSDGLDTMEIWGGIVEESLYSTEVVTLDRLRKSLKNIEKQLDHIQGC;

(SEQ ID NO: 92)
MLAEAKEDAIKELDKYGVSDYYKNLINKAKTVEGVEALiseILAALPTGGGGSGGGSGGGSGGGSASVPIQKVQDDTKT

LIKTIVTRINDISHTQSVSSKQKVTGLDFIPGLHPILTLSKMDQTLAVYQQILTSMPSRNVIQISNDLENLRDLLHVLA

FSKSCHLPWASGLETLDSLGGVLEASGYSTEVVALSRLQGSLQDMLWQLDLSPGC;

(SEQ ID NO: 93)
MVPIQKVQDDTKTLIKTIVTRINDISHTQSVSSKQKVTGLDFIPGLHPILTLSKMDQTLAVYQQILTSMPSRNVIQISN

DLENLRDLLHVLAFSKSCHLPWASGLETLDSLGGVLEASGYSTEVVALSRLQGSLQDMLWQLDLSPGCTGGGGSGGGSG

GGSGGGSASLAEAKEDAIKELDKYGVSDYYKNLINKAKTVEGVEALiseILAALP;

(SEQ ID NO: 94)
MLAEAKEDAIKELDKYGVSDYYKNLINKAKTVEGVEALiseILAALPTGGGGSGGGSGGGSGGGSASPIQRVQDDTKTL

IKTIITRINDISPPQGVCSRPRVAGLDFIPRVQSVRTLSGMDQILATYQQILTSLQSRNVIQISNDLENLRDLLHVLAF

SKSCPVPRARGSDTIKGLGNVLRASVHSTEVVALSRLKAALQDMLRQLDRNPGC;

(SEQ ID NO: 95)
MLAEAKEDAIKELDKYGVSDYYKNLINKAKTVEGVEALiseILAALPTGGGGSGGGSGGGSGGGSASPIQRVQDDTKTL

IKTIITRINDISPPQGVSSRPRVAGLDFIPRVQSVRTLSGMDQILATYQQILTSLQSRNVIQISNDLENLRDLLHVLAF

SKSCPVPRARGSDTIKGLGNVLRASVHSTEVVALSRLKAALQDMLRQLDRNPGC;

(SEQ ID NO: 96)
MLAEAKEDAIKELDKYGVSDYYKNLINKAKTVEGVEALiseILAALPTGPIQRVQDDTKTLIKTIITRINDISPPQGVC

SPRVAGLDFIPRVQSVRTLSGMDQILATYQQILTSLQSRNVIQISNDLENLRDLLHVLAFSKSCPVPRARGSDTIKGLG

NVLRASVHSTEVVALSRLKAALQDMLRQLDRNPGC;

(SEQ ID NO: 97)
MLAEAKEDAIKELDKYGVSDYYKNLINKAKTVEGVEALiseILAALPTGGGGSGGGSGGGSGGGSASVPIQKVQDDTKT

LIKTIVTRINDISHTQSVSSKQKVTGLDFIPGLHPILTLSKMDQTLAVYQQILTSMPSRNVIQISNDLENLRDLLHVLA

FSKSCHLPWASGLETLDSLGGVLEASGYSTEVVALSRLQGSLQDMLWQLDLSPGC;

(SEQ ID NO: 98)
MLAEAKEDAIKELDKYGVSDYYKNLINKAKTVEGVEALiseILAALPTGGGGSGGGSGGGSGGGSASVPIQKVQDDTKT

LIKTIVTRINDISHTQSVSSKQKVTGLEFIPGLHPILTLSKMDQTLAVYQQILTSMPSRNVIQISNDLENLRDLLHVLA

FSKSCHLPQASGLETLESLGGVLEASGYSTEVVALSRLQGSLQDMLQQLDLSPGC;

(SEQ ID NO: 99)
MLAEAKEDAIKELDKYGVSDYYKNLINKAKTVEGVEALiseILAALPTGGGGSGGGSGGGSGGGSASVPIQKVQDDTKT

LIKTIVTRINDISHTQSVSSKQKVTGLDFIPGLHPILTLSKMDQTLAVYQQILTSMPSRNVIQISNDLENLRDLLHVLA

FSKSCHLPQASGLETLDSLGGVLEASGYSTEVVALSRLQGSLQDMLQQLDLSPGC;

(SEQ ID NO: 100)
MLAEAKEDAIKELDKYGVSDYYKNLINKAKTVEGVEALiseILAALPTGLAEAAAKEAAAKEAAAKEAAAKEAAAKAAA

ASVPIQKVQDDTKTLIKTIVTRINDISHTQSVSSKQKVTGLEFIPGLHPILTLSKMDQTLAVYQQILTSMPSRNVIQIS

NDLENLRDLLHVLAFSKSCHLPQASGLETLESLGGVLEASGYSTEVVALSRLQGSLQDMLQQLDLSPGC;

(SEQ ID NO: 101)
MLAEAKEDAIKELDKYGVSDYYKNLINKAKTVEGVEALiseILAALPTGGEGGEGGEGGEGGEGGEASVPIQKVQDDTK

TLIKTIVTRINDISHTQSVSSKQKVTGLEFIPGLHPILTLSKMDQTLAVYQQILTSMPSRNVIQISNDLENLRDLLHVL

AFSKSCHLPQASGLETLESLGGVLEASGYSTEVVALSRLQGSLQDMLQQLDLSPGC;
```

-continued

```
                                                        (SEQ ID NO: 102)
MLAEAKEDAIKELDKYGVSDYYKNLINKAKTVEGVEALiseILAALPTGGKGGKGGKGGKGGKGGKASVPIQKVQDDTK

TLIKTIVTRINDISHTQSVSSKQKVTGLEFIPGLHPILTLSKMDQTLAVYQQILTSMPSRNVIQISNDLENLRDLLHVL

AFSKSCHLPQASGLETLESLGGVLEASGYSTEVVALSRLQGSLQDMLQQLDLSPGC;

(SEQ ID NO: 103)
MLAEAKEDAIKELDKYGVSDYYKNLINKAKTVEGVEALiseILAALPTGGGSGGGSGGGSGGGSASVPIQKVQDDTKT

LIKTIVTRINDISHTQSVSSKQKVTGLEFIPGLHPILTLSKMDQTLAVYQQILTSMPSRNVIQISNDLENLRDLLHVLA

FSKSCSLPQASGLETLESLGEVLEASGYSTEVVALSRLQGSLQDILQQLDLSPEC;

(SEQ ID NO: 104)
MLAEAKVLANRELDKYGVSDYYKNLINKAKTVEGVEALTLHILAALPTGGGSGGGSGGGSGGGSASVPIQKVQDDTKT

LIKTIVTRINDISHTQSVSSKQKVTGLEFIPGLHPILTLSKMDQTLAVYQQILTSMPSRNVIQISNDLENLRDLLHVLA

FSKSCHLPQASGLETLESLGGVLEASGYSTEVVALSRLQGSLQDMLQQLDLSPGC;

(SEQ ID NO: 105)
MLAEAKEDAIKELDKYGVSDYYKRLISKAKTVEGVKALISEILAALPTGGGSGGGSGGGSGGGSASVPIQKVQDDTKT

LIKTIVTRINDISHTQSVSSKQKVTGLEFIPGLHPILTLSKMDQTLAVYQQILTSMPSRNVIQISNDLENLRDLLHVLA

FSKSCHLPQASGLETLESLGGVLEASGYSTEVVALSRLQGSLQDMLQQLDLSPGC;

(SEQ ID NO: 106)
MLAEAKEDAIKELDKYGVSDYYKNLINKAKTVEGVEALTLHILAALPTGGGSGGGSGGGSGGGSASVPIQKVQDDTKT

LIKTIVTRINDISHTQSVSSKQKVTGLEFIPGLHPILTLSKMDQTLAVYQQILTSMPSRNVIQISNDLENLRDLLHVLA

FSKSCHLPQASGLETLESLGGVLEASGYSTEVVALSRLQGSLQDMLQQLDLSPGC;

(SEQ ID NO: 107)
MLAEAKEDAIKELDKYGVSDYYKNLINKAKTVEGVEALISEILAALPTGGGSGGGSGGGSGGGSASVPIQKVQDDTKT

LIKTIVTRINDISHTQSVSSKQKVTGLEFIPGLHPILTLSKMDQTLAVYQQILTSMPSRNVIQISNDLENLRDLLHVLA

FSKSCHLPQASGLETLESLGGVLEASGYSTEVVALSRLQGSLQDMLQQLDLSPGC;

(SEQ ID NO: 108)
KCNTATCATQRLANFLVRSSNNLGPVLPPTNVGSNTY;

(SEQ ID NO: 109)
KCNTATCATQRLANFLVHSSNNFGAILSSTNVGSNTY;

(SEQ ID NO: 110)
KCNTATCATQRLANFLVHSSNNFGPILPPTNVGSNTY.

(SEQ ID NO: 111)
CGNLSTCMLGTYTQDFNKFHTFPQTAIGVGAP;

(SEQ ID NO: 112)
CSNLSTCVLGKLSQELHKLQTYPRTNTGSGTP;

(SEQ ID NO: 113)
KCNTATCVLGRLSQELHRLQTYPRTNTGSNTY.

(SEQ ID NO: 114)
GVSDYYKNLINKAKTVEGVEALTLHI;

(SEQ ID NO: 115)
GVSDYYKNLINKAKTVEGVEALISEI;

(SEQ ID NO: 116)
GGGG;

(SEQ ID NO: 117)
GGGGG;

(SEQ ID NO: 118)
GGGKGGGG;

(SEQ ID NO: 119)
GGGNGSGG;

(SEQ ID NO: 120)
GGGCGGGG;
```

-continued

GPNGG; (SEQ ID NO: 121)

[GS]$_n$, where n is 1-10; (SEQ ID NO: 122)

[GGS]$_n$, where n is 1-10; (SEQ ID NO: 123)

[GGGS]$_n$, where n is 1-10; (SEQ ID NO: 124)

[GGGGS]$_n$, where n is 1-10; (SEQ ID NO: 125)

[GE]$_n$, where n is 1-10; (SEQ ID NO: 126)

[GGE]$_n$, where n is 1-10; (SEQ ID NO: 127)

[GGGE]$_n$, wherein n is 1-10; (SEQ ID NO: 128)

[GGGGE]$_n$, wherein n is 1-10; (SEQ ID NO: 129)

[GD]$_n$, wherein n is 1-10; (SEQ ID NO: 130)

[GGD]$_n$, wherein n is 1-10; (SEQ ID NO: 131)

[GGGD]$_n$, wherein n is 1-10; (SEQ ID NO: 132)

[GGGGD]$_n$, where n is 1-10; (SEQ ID NO: 133)

[GK]$_n$, where n is 1-10; (SEQ ID NO: 134)

[GGK]$_n$, where n is 1-10; (SEQ ID NO: 135)

[GGGK]$_n$, where n is 1-10; (SEQ ID NO: 136)

[GGGGK]$_n$, where n is 1-10; (SEQ ID NO: 137)

[GR]$_n$, where n is 1-10; (SEQ ID NO: 138)

[GGR]$_n$, where n is 1-10; (SEQ ID NO: 139)

[GGGR]$_n$, where n is 1-10; (SEQ ID NO: 140)

[GGGGR]$_n$, where n is 1-10; (SEQ ID NO: 141)

[GAAAK]$_n$, where n is 1-10; (SEQ ID NO: 142)

(SEQ ID NO: 143)
VPIQKVQDDTKTLIKTIVTRINDISHTQSVSAKQRVTGLDFIPGLHPILSLSKMDQTLAVYQQVLTSLPSQNVLQIAND
LENLRDLLHLLAFSKSCSLPQTSGLQKPESLDGVLEASLYSTEVVALSRLQGSLQDILQQLDVSPEC;

(SEQ ID NO: 144)
VPIQKVQDDTKTLIKTIVTRINDISHTSVSAKQRVTGLDFIPGLHPILSLSKMDQTLAVYQQVLTSLPSQNVLQIANDL
ENLRDLLHLLAFSKSCSLPQTSGLQKPESLDGVLEASLYSTEVVALSRLQGSLQDILQQLDVSPEC;

(SEQ ID NO: 145)
MVPIQKVQDDTKTLIKTIVTRINDISHTQSVSAKQRVTGLDFIPGLHPILSLSKMDQTLAVYQQVLTSLPSQNVLQIAN
DLENLRDLLHLLAFSKSCSLPQTSGLQKPESLDGVLEASLYSTEVVALSRLQGSLQDILQQLDVSPEC;
and -continued (SEQ ID NO: 146)
MVPIQKVQDDTKTLIKTIVTRINDISHTSVSAKQRVTGLDFIPGLHPILSLSKMDQTLAVYQQVLTSLPSQNVLQIAND
LENLRDLLHLLAFSKSCSLPQTSGLQKPESLDGVLEASLYSTEVVALSRLQGSLQDILQQLDVSPEC.

(SEQ ID NO: 147)
MLAEAKVLANRELDKYGVSDFYKRLINKAKTVEGVEALKLHILAALPTGGGGSGGGSGGGSGGGSASVPIQKVQDDTKT
LIKTIVTRINDISHTQSVSSKQKVTGLDFIPGLHPILTLSKMDQTLAVYQQILTSMPSRNVIQISNDLENLRDLLHVLA
FSKSCHLPWASGLETLDSLGGVLEASGYSTEVVALSRLQGSLQDMLWQLDLSPGC.

(SEQ ID NO: 664)
MVPIQKVQDDTKTLIKTIVTRINDISHTQSVSSKQKVTGLEFIPGLHPILTLSKMDQTLAVYQQILTSMPSRNVIQISN
DLENLRDLLHVLAFSKSCSLPQASGLETLESLGEVLEASGYSTEVVALSRLQGSLQDILQQLDLSPEC.

(SEQ ID NO: 665)
MVPIQKVQDDTKTLIKTIVTRINDISHTQSVSSKQKVTGLDFIPGLHPILTLSKMDQTLAVYQQILTSMPSRNVIQISN
DLENLRDLLHVLAFSKSCSLPQASGLETLDSLGGVLEASGYSTEVVALSRLQGSLQDILQQLDLSPEC.

(SEQ ID NO: 666)
MVPIQKVQDDTKTLIKTIVTRINDISHTQSVSSKQKVTGLDFIPGLHPILTLSKMDQTLAVYQQILTSMPSRNVIQISN
DLENLRDLLHVLAFSKSCSLPQASGLETLDSLGEVLEASGYSTEVVALSRLQGSLQDILQQLDLSPEC.

(SEQ ID NO: 667)
MVPIQKVQDDTKTLIKTIVTRINDISHTQSVSSKQKVTGLDFIPGLHPILTLSKMDQTLAVYQQILTSMPSRNVIQISN
DLENLRDLLHVLAFSKSCHLPQASGLETLDSLGEVLEASGYSTEVVALSRLQGSLQDILQQLDLSPEC.

(SEQ ID NO: 668)
MVPIQKVQDDTKTLIKTIVTRINDISHTQSVSSKQKVTGLDFIPGLHPILTLSKMDQTLAVYQQILTSMPSRNVIQISN
DLENLRDLLHVLAFSKSCSLPQASGLETLDSLGGVLEASGYSTEVVALSRLQGSLQDILQQLDLSPEC.

(SEQ ID NO: 669)
MVPIQKVQDDTKTLIKTIVTRINDISHTQSVSSKQKVTGLDFIPGLHPILTLSKMDQTLAVYQQILTSMPSRNVIQISN
DLENLRDLLHVLAFSKSCHLPQASGLETLDSLGEVLEASGYSTEVVALSRLQGSLQDILQQLDVSPEC.

(SEQ ID NO: 670)
MVPIQKVQDDTKTLIKTIVTRINDISHTQSVSSKQKVTGLDFIPGLHPILTLSKMDQTLAVYQQILTSMPSRNVIQISN
DLENLRDLLHVLAFSKSCSLPQTSGLETLDSLGGVLEASGYSTEVVALSRLQGSLQDILQQLDLSPEC.

(SEQ ID NO: 671)
MVPIQKVQDDTKTLIKTIVTRINDISHTQSVSSKQKVTGLDFIPGLHPILTLSKMDQTLAVYQQILTSMPSRNVIQISN
DLENLRDLLHVLAFSKSCSLPQASGLETLESLGEVLEASGYSTEVVALSRLQGSLQDMLWQLDLSPEC.

(SEQ ID NO: 672)
MVPIQKVQDDTKTLIKTIVTRINDISHTQSVSSKQKVTGLDFIPGLHPILTLSKMDQTLAVYQQILTSMPSRNVIQISN
DLENLRDLLHVLAFSKSCHLPQASGLETLDSLGGVLEASGYSTEVVALSRLQGSLQDILQQLDLSPEC.

(SEQ ID NO: 673)
MVPIQKVQDDTKTLIKTIVTRINDISHTQSVSSKQKVTGLDFIPGLHPILTLSKMDQTLAVYQQILTSMPSRNVIQISN
DLENLRDLLHVLAFSKSCHLPQASGLETLDSLGGVLEASGYSTEVVALSRLQGSLQDILQQLDVSPEC.

(SEQ ID NO: 674)
MVPIQKVQDDTKTLIKTIVTRINDISHTQSVSSKQKVTGLDFIPGLHPILTLSKMDQTLAVYQQILTSMPSRNVIQISN
DLENLRDLLHVLAFSKSCSLPQTSGLETLDSLGGVLEASGYSTEVVALSRLQGSLQDILQQLDVSPEC.

(SEQ ID NO: 675)
MVPIQKVQDDTKTLIKTIVTRINDISHTQSVSSKQKVTGLDFIPGLHPILTLSKMDQTLAVYQQILTSMPSRNVIQISN
DLENLRDLLHVLAFSKSCSLPQTSGLETLDSLGEVLEASGYSTEVVALSRLQGSLQDMLWQLDLSPEC.

(SEQ ID NO: 676)
MVPIQKVQDDTKTLIKTIVTRINDISHTQSVSSKQKVTGLDFIPGLHPILTLSKMDQTLAVYQQILTSMPSRNVIQISN
DLENLRDLLHVLAFSKSCHLPQASGLETLDSLGEVLEASGYSTEVVALSRLQGSLQDMLQQLDLSPGC.

```
                                                                   (SEQ ID NO: 677)
MVPIQKVQDDTKTLIKTIVTRINDISHTQSVSSKQKVTGLDFIPGLHPILTLSKMDQTLAVYQQILTSMPSRNVIQISN

DLENLRDLLHVLAFSKSCHLPQASGLETLDSLGEVLEASGYSTEVVALSRLQGSLQDMLQQLDLSPEC.
```

(SEQ ID NO: 800)

X'-Xaa$^1$-Cys$^2$-Asn$^3$-Thr$^4$-Ala$^5$-Thr$^6$-Cys$^7$-Ala$^8$-Thr$^9$-Gln$^{10}$-Arg$^{11}$-Leu$^{12}$-Ala$^{13}$-Asn$^{14}$-Phe$^{15}$-Leu$^{16}$-Val$^{17}$-His$^{18}$-Ser$^{19}$-Ser$^{20}$-Xaa$^{21}$-Asn$^{22}$-Phe$^{23}$-Xaa$^{24}$-Xaa$^{25}$-Xaa$^{26}$-Xaa$^{27}$-Xaa$^{28}$-Xaa$^{29}$-Thr$^{30}$-Xaa$^{31}$-Val$^{32}$-Gly$^{33}$-Ser$^{34}$-Asn$^{35}$-Thr$^{36}$-Tyr$^{37}$-X

```
                                                                   (SEQ ID NO: 801)
CNTATCATQRLANFLVRSSNNLGPVLPPTNVGSNTY-NH2

(SEQ ID NO: 802)
KCNTATCATQRLANFLVRSSKNLGPVLPPTNVGSNTY-NH2

(SEQ ID NO: 803)
CNTATCATQRLANFLVRSSKNLGPVLPPTNVGSNTY-NH2

(SEQ ID NO: 804)
KCNTATCATQRLANFLVRSSNNLGPKLPPTNVGSNTY-NH2

(SEQ ID NO: 805)
CNTATCATQRLANFLVRSSNNLGPKLPPTNVGSNTY-NH2

(SEQ ID NO: 806)
KCNTATCATQRLANFLVRSSNNLGPVLPPTKVGSNTY-NH2

(SEQ ID NO: 807)
CNTATCATQRLANFLVRSSNNLGPVLPPTKVGSNTY-NH2

(SEQ ID NO: 808)
KCNTATCATQRLANFLVHSSNNFGPILPPTNVGSNTY-NH2

(SEQ ID NO: 809)
CNTATCATQRLANFLVHSSNNFGPILPPTNVGSNTY-NH2

(SEQ ID NO: 810)
CNTATCATQRLANFLVHSSKNFGPILPPTNVGSNTY-NH2

(SEQ ID NO: 811)
CNTATCATQRLANFLVHSSNNFGPKLPPTNVGSNTY-NH2

(SEQ ID NO: 812)
CNTATCATQRLANFLVHSSNNFGPILPPTKVGSNTY-NH2

(SEQ ID NO: 813)
CNTATCATQRLANFLVHSSNNFKPILPPTNVGSNTY-NH2

(SEQ ID NO: 814)
CNTATCATQRLANFLVHSSNNFGKILPPTNVGSNTY-NH2

(SEQ ID NO: 815)
CNTATCATQRLANFLVHSSNNFGPIKPPTNVGSNTY-NH2

(SEQ ID NO: 816)
CNTATCATQRLANFLVHSSNNFGPILKPTNVGSNTY-NH2

(SEQ ID NO: 817)
CNTATCATQRLANFLVHSSNNFGPILPKTNVGSNTY-NH2
```

What is claimed is:

1. An engineered polypeptide comprising: an albumin binding domain polypeptide (ABD) having the sequence of SEQ ID NO: 114, a first peptide hormone domain (HD1) having the sequence of SEQ ID NO: 20, and a linker L1 having the sequence of SEQ ID NO: 215.

2. The engineered polypeptide according to claim 1, wherein the ABD is located N-terminal to the HD1.

3. The engineered polypeptide according to claim 1, wherein the HD1 is located N-terminal to the ABD.

4. A method for treating a disease or disorder in a subject, comprising administering a engineered polypeptide according to claim 1 to a subject in need thereof in an amount effective to treat said disease or disorder.

5. The method according to claim 4, wherein said disease or disorder is disease or disorder can be lipodystrophy, dyslipidemia, hyperlipidemia, overweight, obesity, hypothalamic amenorrhea, Alzheimer's disease, leptin deficiency, fatty liver disease, diabetes, type I diabetes, type II diabetes, nonalcoholic steatohepatitis (NASH), nonalcoholic fatty liver disease (NAFLD), metabolic syndrome X and Huntington's Disease.

6. A pharmaceutical composition comprising an engineered polypeptide according to claim 1 and a pharmaceutically acceptable excipient.

7. A method of treating obesity in a subject in need thereof comprising peripherally administering therapeutically effective amounts of at least two different anti-obesity agents, wherein at least one anti-obesity agent is an amylin, an amylin analog, an amylin agonist, or an amylin derivative; and at least one anti-obesity agent is the engineered polypeptide of claim 1.

8. A method of reducing body weight in a subject in need thereof comprising peripherally administering therapeutically effective amounts of at least two different anti-obesity agents, wherein at least one anti-obesity agent is an amylin, an amylin analog, an amylin agonist, or an amylin derivative; and at least one anti-obesity agent is the engineered polypeptide of claim 1.

* * * * *

SEQUENCE LISTING

<160> NUMBER OF SEQ ID NOS: 817

<210> SEQ ID NO 1
<211> LENGTH: 146
<212> TYPE: PRT
<213> ORGANISM: Unknown
<220> FEATURE:
<223> OTHER INFORMATION: Polypeptide from unknown Mus species
<220> FEATURE:
<221> NAME/KEY: MOD_RES
<222> LOCATION: (28)..(28)
<223> OTHER INFORMATION: May or may not be present

<400> SEQUENCE: 1

Val Pro Ile Gln Lys Val Gln Asp Asp Thr Lys Thr Leu Ile Lys Thr
1               5                   10                  15

Ile Val Thr Arg Ile Asn Asp Ile Ser His Thr Gln Ser Val Ser Ser
            20                  25                  30

Lys Gln Lys Val Thr Gly Leu Asp Phe Ile Pro Gly Leu His Pro Ile
        35                  40                  45

Leu Thr Leu Ser Lys Met Asp Gln Thr Leu Ala Val Tyr Gln Gln Ile
    50                  55                  60

Leu Thr Ser Met Pro Ser Arg Asn Val Ile Gln Ile Ser Asn Asp Leu
65                  70                  75                  80

Glu Asn Leu Arg Asp Leu Leu His Val Leu Ala Phe Ser Lys Ser Cys
                85                  90                  95

His Leu Pro Gln Ala Ser Gly Leu Glu Thr Leu Glu Ser Leu Gly Gly
            100                 105                 110

Val Leu Glu Ala Ser Gly Tyr Ser Thr Glu Val Val Ala Leu Ser Arg
        115                 120                 125

Leu Gln Gly Ser Leu Gln Asp Met Leu Gln Gln Leu Asp Leu Ser Pro
130                 135                 140

Gly Cys
145

<210> SEQ ID NO 2
<211> LENGTH: 147
<212> TYPE: PRT
<213> ORGANISM: Unknown
<220> FEATURE:
<223> OTHER INFORMATION: Polypeptide from unknown Mus species
<220> FEATURE:
<221> NAME/KEY: MOD_RES
<222> LOCATION: (29)..(29)
<223> OTHER INFORMATION: May or may not be present

<400> SEQUENCE: 2

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Lys Val Thr Gly Leu Asp Phe Ile Pro Gly Leu His Pro
        35                  40                  45

Ile Leu Thr Leu Ser Lys Met Asp Gln Thr Leu Ala Val Tyr Gln Gln
    50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys His Leu Pro Gln Ala Ser Gly Leu Glu Thr Leu Glu Ser Leu Gly
            100                 105                 110

Gly Val Leu Glu Ala Ser Gly Tyr Ser Thr Glu Val Val Ala Leu Ser
        115                 120                 125

Arg Leu Gln Gly Ser Leu Gln Asp Met Leu Gln Gln Leu Asp Leu Ser
130                 135                 140

Pro Gly Cys
145

<210> SEQ ID NO 3

```
<211> LENGTH: 146
<212> TYPE: PRT
<213> ORGANISM: Unknown
<220> FEATURE:
<223> OTHER INFORMATION: Polypeptide from unknown Sus species

<400> SEQUENCE: 3

Val Pro Ile Trp Arg Val Gln Asp Asp Thr Lys Thr Leu Ile Lys Thr
1               5                   10                  15
Ile Val Thr Arg Ile Ser Asp Ile Ser His Met Gln Ser Val Ser Ser
            20                  25                  30
Lys Gln Arg Val Thr Gly Leu Asp Phe Ile Pro Gly Leu His Pro Val
        35                  40                  45
Leu Ser Leu Ser Lys Met Asp Gln Thr Leu Ala Ile Tyr Gln Gln Ile
    50                  55                  60
Leu Thr Ser Leu Pro Ser Arg Asn Val Ile Gln Ile Ser Asn Asp Leu
65                  70                  75                  80
Glu Asn Leu Arg Asp Leu Leu His Leu Leu Ala Ser Ser Lys Ser Cys
                85                  90                  95
Pro Leu Pro Gln Ala Arg Ala Leu Glu Thr Leu Glu Ser Leu Gly Gly
            100                 105                 110
Val Leu Glu Ala Ser Leu Tyr Ser Thr Glu Val Val Ala Leu Ser Arg
        115                 120                 125
Leu Gln Gly Ala Leu Gln Asp Met Leu Arg Gln Leu Asp Leu Ser Pro
    130                 135                 140
Gly Cys
145

<210> SEQ ID NO 4
<211> LENGTH: 147
<212> TYPE: PRT
<213> ORGANISM: Unknown
<220> FEATURE:
<223> OTHER INFORMATION: Polypeptide from unknown Sus species

<400> SEQUENCE: 4

Met Val Pro Ile Trp Arg Val Gln Asp Asp Thr Lys Thr Leu Ile Lys
1               5                   10                  15
Thr Ile Val Thr Arg Ile Ser Asp Ile Ser His Met Gln Ser Val Ser
            20                  25                  30
Ser Lys Gln Arg Val Thr Gly Leu Asp Phe Ile Pro Gly Leu His Pro
        35                  40                  45
Val Leu Ser Leu Ser Lys Met Asp Gln Thr Leu Ala Ile Tyr Gln Gln
    50                  55                  60
Ile Leu Thr Ser Leu Pro Ser Arg Asn Val Ile Gln Ile Ser Asn Asp
65                  70                  75                  80
Leu Glu Asn Leu Arg Asp Leu Leu His Leu Leu Ala Ser Ser Lys Ser
                85                  90                  95
Cys Pro Leu Pro Gln Ala Arg Ala Leu Glu Thr Leu Glu Ser Leu Gly
            100                 105                 110
Gly Val Leu Glu Ala Ser Leu Tyr Ser Thr Glu Val Val Ala Leu Ser
        115                 120                 125
Arg Leu Gln Gly Ala Leu Gln Asp Met Leu Arg Gln Leu Asp Leu Ser
    130                 135                 140
Pro Gly Cys
145
```

```
<210> SEQ ID NO 5
<211> LENGTH: 146
<212> TYPE: PRT
<213> ORGANISM: Unknown
<220> FEATURE:
<223> OTHER INFORMATION: Polypeptide from unknown Bos species
<220> FEATURE:
<221> NAME/KEY: MOD_RES
<222> LOCATION: (28)..(28)
<223> OTHER INFORMATION: May or may not be present

<400> SEQUENCE: 5

Val Pro Ile Cys Lys Val Gln Asp Asp Thr Lys Thr Leu Ile Lys Thr
1               5                   10                  15

Ile Val Thr Arg Ile Asn Asp Ile Ser His Thr Gln Ser Val Ser Ser
            20                  25                  30

Lys Gln Arg Val Thr Gly Leu Asp Phe Ile Pro Gly Leu His Pro Leu
        35                  40                  45

Leu Ser Leu Ser Lys Met Asp Gln Thr Leu Ala Ile Tyr Gln Gln Ile
    50                  55                  60

Leu Thr Ser Leu Pro Ser Arg Asn Val Val Gln Ile Ser Asn Asp Leu
65                  70                  75                  80

Glu Asn Leu Arg Asp Leu Leu His Leu Leu Ala Ala Ser Lys Ser Cys
                85                  90                  95

Pro Leu Pro Gln Val Arg Ala Leu Glu Ser Leu Glu Ser Leu Gly Val
            100                 105                 110

Val Leu Glu Ala Ser Leu Tyr Ser Thr Glu Val Val Ala Leu Ser Arg
        115                 120                 125

Leu Gln Gly Ser Leu Gln Asp Met Leu Arg Gln Leu Asp Leu Ser Pro
    130                 135                 140

Gly Cys
145

<210> SEQ ID NO 6
<211> LENGTH: 147
<212> TYPE: PRT
<213> ORGANISM: Unknown
<220> FEATURE:
<223> OTHER INFORMATION: Polypeptide from unknown Bos species
<220> FEATURE:
<221> NAME/KEY: MOD_RES
<222> LOCATION: (29)..(29)
<223> OTHER INFORMATION: May or may not be present

<400> SEQUENCE: 6

Met Val Pro Ile Cys Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Arg Val Thr Gly Leu Asp Phe Ile Pro Gly Leu His Pro
        35                  40                  45

Leu Leu Ser Leu Ser Lys Met Asp Gln Thr Leu Ala Ile Tyr Gln Gln
    50                  55                  60

Ile Leu Thr Ser Leu Pro Ser Arg Asn Val Val Gln Ile Ser Asn Asp
65                  70                  75                  80

Leu Glu Asn Leu Arg Asp Leu Leu His Leu Leu Ala Ala Ser Lys Ser
                85                  90                  95

Cys Pro Leu Pro Gln Val Arg Ala Leu Glu Ser Leu Glu Ser Leu Gly
            100                 105                 110

Val Val Leu Glu Ala Ser Leu Tyr Ser Thr Glu Val Val Ala Leu Ser
```

```
                115                 120                 125
Arg Leu Gln Gly Ser Leu Gln Asp Met Leu Arg Gln Leu Asp Leu Ser
    130                 135                 140

Pro Gly Cys
145

<210> SEQ ID NO 7
<211> LENGTH: 167
<212> TYPE: PRT
<213> ORGANISM: Homo sapiens

<400> SEQUENCE: 7

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
            20                  25                  30

Thr Leu Ile Lys Thr Ile Val Thr Arg Ile Asn Asp Ile Ser His Thr
        35                  40                  45

Gln Ser Val Ser Ser Lys Gln Lys Val Thr Gly Leu Asp Phe Ile Pro
    50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asn Val Ile Gln
                85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
        115                 120                 125

Asp Ser Leu Gly Gly Val Leu Glu Ala Ser Gly Tyr Ser Thr Glu Val
    130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 8
<211> LENGTH: 146
<212> TYPE: PRT
<213> ORGANISM: Homo sapiens
<220> FEATURE:
<221> NAME/KEY: MOD_RES
<222> LOCATION: (27)..(27)
<223> OTHER INFORMATION: Thr or Ala
<220> FEATURE:
<221> NAME/KEY: MOD_RES
<222> LOCATION: (28)..(28)
<223> OTHER INFORMATION: May or may not be present

<400> SEQUENCE: 8

Val Pro Ile Gln Lys Val Gln Asp Asp Thr Lys Thr Leu Ile Lys Thr
1               5                   10                  15

Ile Val Thr Arg Ile Asn Asp Ile Ser His Xaa Gln Ser Val Ser Ser
            20                  25                  30

Lys Gln Lys Val Thr Gly Leu Asp Phe Ile Pro Gly Leu His Pro Ile
        35                  40                  45

Leu Thr Leu Ser Lys Met Asp Gln Thr Leu Ala Val Tyr Gln Gln Ile
    50                  55                  60

Leu Thr Ser Met Pro Ser Arg Asn Val Ile Gln Ile Ser Asn Asp Leu
65                  70                  75                  80
```

-continued

```
Glu Asn Leu Arg Asp Leu Leu His Val Leu Ala Phe Ser Lys Ser Cys
                85                  90                  95

His Leu Pro Trp Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
        115                 120                 125

Leu Gln Gly Ser Leu Gln Asp Met Leu Trp Gln Leu Asp Leu Ser Pro
    130                 135                 140

Gly Cys
145

<210> SEQ ID NO 9
<211> LENGTH: 147
<212> TYPE: PRT
<213> ORGANISM: Homo sapiens
<220> FEATURE:
<221> NAME/KEY: MOD_RES
<222> LOCATION: (28)..(28)
<223> OTHER INFORMATION: Thr or Ala
<220> FEATURE:
<221> NAME/KEY: MOD_RES
<222> LOCATION: (29)..(29)
<223> OTHER INFORMATION: May or may not be present

<400> SEQUENCE: 9

Met Val Pro Ile Gln Lys Val Gln Asp Asp Thr Lys Thr Leu Ile Lys
1               5                   10                  15

Thr Ile Val Thr Arg Ile Asn Asp Ile Ser His Xaa Gln Ser Val Ser
            20                  25                  30

Ser Lys Gln Lys Val Thr Gly Leu Asp Phe Ile Pro Gly Leu His Pro
        35                  40                  45

Ile Leu Thr Leu Ser Lys Met Asp Gln Thr Leu Ala Val Tyr Gln Gln
    50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys His Leu Pro Trp Ala Ser Gly Leu Glu Thr Leu Asp Ser Leu Gly
            100                 105                 110

Gly Val Leu Glu Ala Ser Gly Tyr Ser Thr Glu Val Val Ala Leu Ser
        115                 120                 125

Arg Leu Gln Gly Ser Leu Gln Asp Met Leu Trp Gln Leu Asp Leu Ser
    130                 135                 140

Pro Gly Cys
145

<210> SEQ ID NO 10
<211> LENGTH: 146
<212> TYPE: PRT
<213> ORGANISM: Macaca mulatta

<400> SEQUENCE: 10

Val Pro Ile Gln Lys Val Gln Ser Asp Thr Lys Thr Leu Ile Lys Thr
1               5                   10                  15

Ile Val Thr Arg Ile Asn Asp Ile Ser His Thr Gln Ser Val Ser Ser
            20                  25                  30

Lys Gln Arg Val Thr Gly Leu Asp Phe Ile Pro Gly Leu His Pro Val
        35                  40                  45
```

```
Leu Thr Leu Ser Gln Met Asp Gln Thr Leu Ala Ile Tyr Gln Gln Ile
    50                  55                  60

Leu Ile Asn Leu Pro Ser Arg Asn Val Ile Gln Ile Ser Asn Asp Leu
65                  70                  75                  80

Glu Asn Leu Arg Asp Leu Leu His Leu Leu Ala Phe Ser Lys Ser Cys
                85                  90                  95

His Leu Pro Leu Ala Ser Gly Leu Glu Thr Leu Glu Ser Leu Gly Asp
            100                 105                 110

Val Leu Glu Ala Ser Leu Tyr Ser Thr Glu Val Val Ala Leu Ser Arg
            115                 120                 125

Leu Gln Gly Ser Leu Gln Asp Met Leu Trp Gln Leu Asp Leu Ser Pro
        130                 135                 140

Gly Cys
145

<210> SEQ ID NO 11
<211> LENGTH: 147
<212> TYPE: PRT
<213> ORGANISM: Macaca mulatta

<400> SEQUENCE: 11

Met Val Pro Ile Gln Lys Val Gln Ser Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Arg Val Thr Gly Leu Asp Phe Ile Pro Gly Leu His Pro
        35                  40                  45

Val Leu Thr Leu Ser Gln Met Asp Gln Thr Leu Ala Ile Tyr Gln Gln
    50                  55                  60

Ile Leu Ile Asn Leu Pro Ser Arg Asn Val Ile Gln Ile Ser Asn Asp
65                  70                  75                  80

Leu Glu Asn Leu Arg Asp Leu Leu His Leu Leu Ala Phe Ser Lys Ser
                85                  90                  95

Cys His Leu Pro Leu Ala Ser Gly Leu Glu Thr Leu Glu Ser Leu Gly
            100                 105                 110

Asp Val Leu Glu Ala Ser Leu Tyr Ser Thr Glu Val Val Ala Leu Ser
            115                 120                 125

Arg Leu Gln Gly Ser Leu Gln Asp Met Leu Trp Gln Leu Asp Leu Ser
        130                 135                 140

Pro Gly Cys
145

<210> SEQ ID NO 12
<211> LENGTH: 146
<212> TYPE: PRT
<213> ORGANISM: Unknown
<220> FEATURE:
<223> OTHER INFORMATION: Polypeptide from unknown Rattus species

<400> SEQUENCE: 12

Val Pro Ile His Lys Val Gln Asp Asp Thr Lys Thr Leu Ile Lys Thr
1               5                   10                  15

Ile Val Thr Arg Ile Asn Asp Ile Ser His Thr Gln Ser Val Ser Ala
            20                  25                  30

Arg Gln Arg Val Thr Gly Leu Asp Phe Ile Pro Gly Leu His Pro Ile
        35                  40                  45

Leu Ser Leu Ser Lys Met Asp Gln Thr Leu Ala Val Tyr Gln Gln Ile
```

```
                    50                  55                  60
Leu Thr Ser Leu Pro Ser Gln Asn Val Leu Gln Ile Ala His Asp Leu
 65                  70                  75                  80

Glu Asn Leu Arg Asp Leu Leu His Leu Leu Ala Phe Ser Lys Ser Cys
                 85                  90                  95

Ser Leu Pro Gln Thr Arg Gly Leu Gln Lys Pro Glu Ser Leu Asp Gly
            100                 105                 110

Val Leu Glu Ala Ser Leu Tyr Ser Thr Glu Val Val Ala Leu Ser Arg
        115                 120                 125

Leu Gln Gly Ser Leu Gln Asp Ile Leu Gln Gln Leu Asp Leu Ser Pro
    130                 135                 140

Glu Cys
145

<210> SEQ ID NO 13
<211> LENGTH: 147
<212> TYPE: PRT
<213> ORGANISM: Unknown
<220> FEATURE:
<223> OTHER INFORMATION: Polypeptide from unknown Rattus species

<400> SEQUENCE: 13

Met Val Pro Ile His Lys Val Gln Asp Asp Thr Lys Thr Leu Ile Lys
 1               5                  10                  15

Thr Ile Val Thr Arg Ile Asn Asp Ile Ser His Thr Gln Ser Val Ser
                20                  25                  30

Ala Arg Gln Arg Val Thr Gly Leu Asp Phe Ile Pro Gly Leu His Pro
            35                  40                  45

Ile Leu Ser Leu Ser Lys Met Asp Gln Thr Leu Ala Val Tyr Gln Gln
        50                  55                  60

Ile Leu Thr Ser Leu Pro Ser Gln Asn Val Leu Gln Ile Ala His Asp
 65                  70                  75                  80

Leu Glu Asn Leu Arg Asp Leu Leu His Leu Leu Ala Phe Ser Lys Ser
                 85                  90                  95

Cys Ser Leu Pro Gln Thr Arg Gly Leu Gln Lys Pro Glu Ser Leu Asp
            100                 105                 110

Gly Val Leu Glu Ala Ser Leu Tyr Ser Thr Glu Val Val Ala Leu Ser
        115                 120                 125

Arg Leu Gln Gly Ser Leu Gln Asp Ile Leu Gln Gln Leu Asp Leu Ser
    130                 135                 140

Pro Glu Cys
145

<210> SEQ ID NO 14
<211> LENGTH: 145
<212> TYPE: PRT
<213> ORGANISM: Ornithorhynchus anatinus

<400> SEQUENCE: 14

Ile Ser Ile Glu Lys Ile Gln Ala Asp Thr Lys Thr Leu Thr Lys Thr
 1               5                  10                  15

Ile Ile Thr Arg Ile Ile Gln Leu Ser Thr Gln Asn Gly Val Ser Thr
                20                  25                  30

Asp Gln Arg Val Ser Gly Leu Asp Phe Ile Pro Gly Asn Gln Gln Phe
            35                  40                  45

Gln Asn Leu Ala Asp Met Asp Gln Thr Leu Ala Val Tyr Gln Gln Ile
        50                  55                  60
```

```
Leu Ser Ser Leu Pro Met Pro Asp Arg Thr Gln Ile Ser Asn Asp Leu
 65                  70                  75                  80

Glu Asn Leu Arg Ser Leu Phe Ala Leu Leu Ala Thr Leu Lys Asn Cys
                 85                  90                  95

Pro Phe Thr Arg Ser Asp Gly Leu Asp Thr Met Glu Ile Trp Gly Gly
            100                 105                 110

Ile Val Glu Glu Ser Leu Tyr Ser Thr Glu Val Val Thr Leu Asp Arg
        115                 120                 125

Leu Arg Lys Ser Leu Lys Asn Ile Glu Lys Gln Leu Asp His Ile Gln
    130                 135                 140

Gly
145

<210> SEQ ID NO 15
<211> LENGTH: 166
<212> TYPE: PRT
<213> ORGANISM: Ornithorhynchus anatinus

<400> SEQUENCE: 15

Met Arg Cys Ile Leu Leu Tyr Gly Phe Leu Cys Val Trp Gln His Leu
  1               5                  10                  15

Tyr Tyr Ser His Pro Ile Ser Ile Glu Lys Ile Gln Ala Asp Thr Lys
             20                  25                  30

Thr Leu Thr Lys Thr Ile Ile Thr Arg Ile Ile Gln Leu Ser Thr Gln
         35                  40                  45

Asn Gly Val Ser Thr Asp Gln Arg Val Ser Gly Leu Asp Phe Ile Pro
 50                  55                  60

Gly Asn Gln Gln Phe Gln Asn Leu Ala Asp Met Asp Gln Thr Leu Ala
 65                  70                  75                  80

Val Tyr Gln Gln Ile Leu Ser Ser Leu Pro Met Pro Asp Arg Thr Gln
                 85                  90                  95

Ile Ser Asn Asp Leu Glu Asn Leu Arg Ser Leu Phe Ala Leu Leu Ala
            100                 105                 110

Thr Leu Lys Asn Cys Pro Phe Thr Arg Ser Asp Gly Leu Asp Thr Met
        115                 120                 125

Glu Ile Trp Gly Gly Ile Val Glu Glu Ser Leu Tyr Ser Thr Glu Val
    130                 135                 140

Val Thr Leu Asp Arg Leu Arg Lys Ser Leu Lys Asn Ile Glu Lys Gln
145                 150                 155                 160

Leu Asp His Ile Gln Gly
                165

<210> SEQ ID NO 16
<211> LENGTH: 146
<212> TYPE: PRT
<213> ORGANISM: Homo sapiens

<400> SEQUENCE: 16

Val Pro Ile Gln Lys Val Gln Asp Asp Thr Lys Thr Leu Ile Lys Thr
  1               5                  10                  15

Ile Val Thr Arg Ile Asn Asp Ile Ser His Thr Gln Ser Val Ser Ser
             20                  25                  30

Lys Gln Lys Val Thr Gly Leu Asp Phe Ile Pro Gly Leu His Pro Ile
         35                  40                  45

Leu Thr Leu Ser Lys Met Asp Gln Thr Leu Ala Val Tyr Gln Gln Ile
 50                  55                  60
```

```
Leu Thr Ser Met Pro Ser Arg Asn Val Ile Gln Ile Ser Asn Asp Leu
 65                  70                  75                  80

Glu Asn Leu Arg Asp Leu Leu His Val Leu Ala Phe Ser Lys Ser Cys
             85                  90                  95

His Leu Pro Trp Ala Ser Gly Leu Glu Thr Leu Asp Ser Leu Gly Gly
        100                 105                 110

Val Leu Glu Ala Ser Gly Tyr Ser Thr Glu Val Val Ala Leu Ser Arg
            115                 120                 125

Leu Gln Gly Ser Leu Gln Asp Met Leu Trp Gln Leu Asp Leu Ser Pro
        130                 135                 140

Gly Cys
145

<210> SEQ ID NO 17
<211> LENGTH: 146
<212> TYPE: PRT
<213> ORGANISM: Homo sapiens

<400> SEQUENCE: 17

Val Pro Ile Gln Lys Val Gln Asp Asp Thr Lys Thr Leu Ile Lys Thr
  1               5                  10                  15

Ile Val Thr Arg Ile Asn Asp Ile Ser His Ala Gln Ser Val Ser Ser
             20                  25                  30

Lys Gln Lys Val Thr Gly Leu Asp Phe Ile Pro Gly Leu His Pro Ile
         35                  40                  45

Leu Thr Leu Ser Lys Met Asp Gln Thr Leu Ala Val Tyr Gln Gln Ile
 50                  55                  60

Leu Thr Ser Met Pro Ser Arg Asn Val Ile Gln Ile Ser Asn Asp Leu
 65                  70                  75                  80

Glu Asn Leu Arg Asp Leu Leu His Val Leu Ala Phe Ser Lys Ser Cys
             85                  90                  95

His Leu Pro Trp Ala Ser Gly Leu Glu Thr Leu Asp Ser Leu Gly Gly
        100                 105                 110

Val Leu Glu Ala Ser Gly Tyr Ser Thr Glu Val Val Ala Leu Ser Arg
            115                 120                 125

Leu Gln Gly Ser Leu Gln Asp Met Leu Trp Gln Leu Asp Leu Ser Pro
        130                 135                 140

Gly Cys
145

<210> SEQ ID NO 18
<211> LENGTH: 145
<212> TYPE: PRT
<213> ORGANISM: Homo sapiens

<400> SEQUENCE: 18

Val Pro Ile Gln Lys Val Gln Asp Asp Thr Lys Thr Leu Ile Lys Thr
  1               5                  10                  15

Ile Val Thr Arg Ile Asn Asp Ile Ser His Thr Ser Val Ser Ser Lys
             20                  25                  30

Gln Lys Val Thr Gly Leu Asp Phe Ile Pro Gly Leu His Pro Ile Leu
         35                  40                  45

Thr Leu Ser Lys Met Asp Gln Thr Leu Ala Val Tyr Gln Gln Ile Leu
 50                  55                  60

Thr Ser Met Pro Ser Arg Asn Val Ile Gln Ile Ser Asn Asp Leu Glu
 65                  70                  75                  80
```

-continued

```
Asn Leu Arg Asp Leu Leu His Val Leu Ala Phe Ser Lys Ser Cys His
                85                  90                  95

Leu Pro Trp Ala Ser Gly Leu Glu Thr Leu Asp Ser Leu Gly Gly Val
            100                 105                 110

Leu Glu Ala Ser Gly Tyr Ser Thr Glu Val Val Ala Leu Ser Arg Leu
        115                 120                 125

Gln Gly Ser Leu Gln Asp Met Leu Trp Gln Leu Asp Leu Ser Pro Gly
    130                 135                 140

Cys
145

<210> SEQ ID NO 19
<211> LENGTH: 145
<212> TYPE: PRT
<213> ORGANISM: Homo sapiens

<400> SEQUENCE: 19

Val Pro Ile Gln Lys Val Gln Asp Asp Thr Lys Thr Leu Ile Lys Thr
1               5                   10                  15

Ile Val Thr Arg Ile Asn Asp Ile Ser His Ala Ser Val Ser Ser Lys
            20                  25                  30

Gln Lys Val Thr Gly Leu Asp Phe Ile Pro Gly Leu His Pro Ile Leu
        35                  40                  45

Thr Leu Ser Lys Met Asp Gln Thr Leu Ala Val Tyr Gln Gln Ile Leu
    50                  55                  60

Thr Ser Met Pro Ser Arg Asn Val Ile Gln Ile Ser Asn Asp Leu Glu
65                  70                  75                  80

Asn Leu Arg Asp Leu Leu His Val Leu Ala Phe Ser Lys Ser Cys His
                85                  90                  95

Leu Pro Trp Ala Ser Gly Leu Glu Thr Leu Asp Ser Leu Gly Gly Val
            100                 105                 110

Leu Glu Ala Ser Gly Tyr Ser Thr Glu Val Val Ala Leu Ser Arg Leu
        115                 120                 125

Gln Gly Ser Leu Gln Asp Met Leu Trp Gln Leu Asp Leu Ser Pro Gly
    130                 135                 140

Cys
145

<210> SEQ ID NO 20
<211> LENGTH: 147
<212> TYPE: PRT
<213> ORGANISM: Homo sapiens

<400> SEQUENCE: 20

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Lys Val Thr Gly Leu Asp Phe Ile Pro Gly Leu His Pro
        35                  40                  45

Ile Leu Thr Leu Ser Lys Met Asp Gln Thr Leu Ala Val Tyr Gln Gln
    50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95
```

-continued

```
Cys His Leu Pro Trp Ala Ser Gly Leu Glu Thr Leu Asp Ser Leu Gly
            100                 105                 110

Gly Val Leu Glu Ala Ser Gly Tyr Ser Thr Glu Val Ala Leu Ser
        115                 120                 125

Arg Leu Gln Gly Ser Leu Gln Asp Met Leu Trp Gln Leu Asp Leu Ser
    130                 135                 140

Pro Gly Cys
145

<210> SEQ ID NO 21
<211> LENGTH: 147
<212> TYPE: PRT
<213> ORGANISM: Homo sapiens

<400> SEQUENCE: 21

Met Val Pro Ile Gln Lys Val Gln Asp Asp Thr Lys Thr Leu Ile Lys
1               5                   10                  15

Thr Ile Val Thr Arg Ile Asn Asp Ile Ser His Ala Gln Ser Val Ser
            20                  25                  30

Ser Lys Gln Lys Val Thr Gly Leu Asp Phe Ile Pro Gly Leu His Pro
        35                  40                  45

Ile Leu Thr Leu Ser Lys Met Asp Gln Thr Leu Ala Val Tyr Gln Gln
    50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys His Leu Pro Trp Ala Ser Gly Leu Glu Thr Leu Asp Ser Leu Gly
            100                 105                 110

Gly Val Leu Glu Ala Ser Gly Tyr Ser Thr Glu Val Ala Leu Ser
        115                 120                 125

Arg Leu Gln Gly Ser Leu Gln Asp Met Leu Trp Gln Leu Asp Leu Ser
    130                 135                 140

Pro Gly Cys
145

<210> SEQ ID NO 22
<211> LENGTH: 146
<212> TYPE: PRT
<213> ORGANISM: Homo sapiens

<400> SEQUENCE: 22

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Ser Val Ser Ser
            20                  25                  30

Lys Gln Lys Val Thr Gly Leu Asp Phe Ile Pro Gly Leu His Pro Ile
        35                  40                  45

Leu Thr Leu Ser Lys Met Asp Gln Thr Leu Ala Val Tyr Gln Gln Ile
    50                  55                  60

Leu Thr Ser Met Pro Ser Arg Asn Val Ile Gln Ile Ser Asn Asp Leu
65                  70                  75                  80

Glu Asn Leu Arg Asp Leu Leu His Val Leu Ala Phe Ser Lys Ser Cys
                85                  90                  95

His Leu Pro Trp Ala Ser Gly Leu Glu Thr Leu Asp Ser Leu Gly Gly
            100                 105                 110
```

```
Val Leu Glu Ala Ser Gly Tyr Ser Thr Glu Val Val Ala Leu Ser Arg
            115                 120                 125

Leu Gln Gly Ser Leu Gln Asp Met Leu Trp Gln Leu Asp Leu Ser Pro
        130                 135                 140

Gly Cys
145

<210> SEQ ID NO 23
<211> LENGTH: 146
<212> TYPE: PRT
<213> ORGANISM: Homo sapiens

<400> SEQUENCE: 23

Met Val Pro Ile Gln Lys Val Gln Asp Asp Thr Lys Thr Leu Ile Lys
1               5                   10                  15

Thr Ile Val Thr Arg Ile Asn Asp Ile Ser His Ala Ser Val Ser Ser
            20                  25                  30

Lys Gln Lys Val Thr Gly Leu Asp Phe Ile Pro Gly Leu His Pro Ile
        35                  40                  45

Leu Thr Leu Ser Lys Met Asp Gln Thr Leu Ala Val Tyr Gln Gln Ile
    50                  55                  60

Leu Thr Ser Met Pro Ser Arg Asn Val Ile Gln Ile Ser Asn Asp Leu
65                  70                  75                  80

Glu Asn Leu Arg Asp Leu Leu His Val Leu Ala Phe Ser Lys Ser Cys
                85                  90                  95

His Leu Pro Trp Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
        115                 120                 125

Leu Gln Gly Ser Leu Gln Asp Met Leu Trp Gln Leu Asp Leu Ser Pro
    130                 135                 140

Gly Cys
145

<210> SEQ ID NO 24
<211> LENGTH: 145
<212> TYPE: PRT
<213> ORGANISM: Unknown
<220> FEATURE:
<223> OTHER INFORMATION: Description of Unknown: Seal leptin polypeptide

<400> SEQUENCE: 24

Pro Ile Gln Arg Val Gln Asp Asp Thr Lys Thr Leu Ile Lys Thr Ile
1               5                   10                  15

Ile Thr Arg Ile Asn Asp Ile Ser Pro Pro Gln Gly Val Cys Ser Arg
            20                  25                  30

Pro Arg Val Ala Gly Leu Asp Phe Ile Pro Arg Val Gln Ser Val Arg
        35                  40                  45

Thr Leu Ser Gly Met Asp Gln Ile Leu Ala Thr Tyr Gln Gln Ile Leu
    50                  55                  60

Thr Ser Leu Gln Ser Arg Ser Val Val Gln Ile Ala Asn Asp Leu Ala
65                  70                  75                  80

Asn Leu Arg Ala Leu Leu Arg Leu Leu Ala Ser Ala Lys Ser Cys Pro
                85                  90                  95

Val Pro Arg Ala Arg Gly Ser Asp Thr Ile Lys Gly Leu Gly Asn Val
            100                 105                 110
```

```
Leu Arg Ala Ser Val His Ser Thr Glu Val Val Ala Leu Ser Arg Leu
            115                 120                 125

Lys Ala Ala Leu Gln Asp Met Leu Arg Gln Leu Asp Arg Asn Pro Gly
        130                 135                 140

Cys
145

<210> SEQ ID NO 25
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Pro Ile Gln Arg Val Gln Asp Asp Thr Lys Thr Leu Ile Lys Thr Ile
1               5                   10                  15

Ile Thr Arg Ile Asn Asp Ile Ser Pro Pro Gln Gly Val Cys Ser Arg
            20                  25                  30

Pro Arg Val Ala Gly Leu Asp Phe Ile Pro Arg Val Gln Ser Val Arg
        35                  40                  45

Thr Leu Ser Gly Met Asp Gln Ile Leu Ala Thr Tyr Gln Gln Ile Leu
    50                  55                  60

Thr Ser Leu Gln Ser Arg Asn Val Ile Gln Ile Ser Asn Asp Leu Glu
65                  70                  75                  80

Asn Leu Arg Asp Leu Leu His Val Leu Ala Phe Ser Lys Ser Cys Pro
                85                  90                  95

Val Pro Arg Ala Arg Gly Ser Asp Thr Ile Lys Gly Leu Gly Asn Val
            100                 105                 110

Leu Arg Ala Ser Val His Ser Thr Glu Val Val Ala Leu Ser Arg Leu
            115                 120                 125

Lys Ala Ala Leu Gln Asp Met Leu Arg Gln Leu Asp Arg Asn Pro Gly
        130                 135                 140

Cys
145

<210> SEQ ID NO 26
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Pro Ile Gln Arg Val Gln Asp Asp Thr Lys Thr Leu Ile Lys Thr Ile
1               5                   10                  15

Ile Thr Arg Ile Asn Asp Ile Ser Pro Pro Gln Gly Val Ser Ser Arg
            20                  25                  30

Pro Arg Val Ala Gly Leu Asp Phe Ile Pro Arg Val Gln Ser Val Arg
        35                  40                  45

Thr Leu Ser Gly Met Asp Gln Ile Leu Ala Thr Tyr Gln Gln Ile Leu
    50                  55                  60

Thr Ser Leu Gln Ser Arg Asn Val Ile Gln Ile Ser Asn Asp Leu Glu
65                  70                  75                  80

Asn Leu Arg Asp Leu Leu His Val Leu Ala Phe Ser Lys Ser Cys Pro
                85                  90                  95
```

```
Val Pro Arg Ala Arg Gly Ser Asp Thr Ile Lys Gly Leu Gly Asn Val
            100                 105                 110

Leu Arg Ala Ser Val His Ser Thr Glu Val Val Ala Leu Ser Arg Leu
        115                 120                 125

Lys Ala Ala Leu Gln Asp Met Leu Arg Gln Leu Asp Arg Asn Pro Gly
    130                 135                 140

Cys
145

<210> SEQ ID NO 27
<211> LENGTH: 146
<212> TYPE: PRT
<213> ORGANISM: Unknown
<220> FEATURE:
<223> OTHER INFORMATION: Description of Unknown: Seal leptin polypeptide

<400> SEQUENCE: 27

Met Pro Ile Gln Arg Val Gln Asp Asp Thr Lys Thr Leu Ile Lys Thr
1               5                   10                  15

Ile Ile Thr Arg Ile Asn Asp Ile Ser Pro Pro Gln Gly Val Cys Ser
            20                  25                  30

Arg Pro Arg Val Ala Gly Leu Asp Phe Ile Pro Arg Val Gln Ser Val
        35                  40                  45

Arg Thr Leu Ser Gly Met Asp Gln Ile Leu Ala Thr Tyr Gln Gln Ile
    50                  55                  60

Leu Thr Ser Leu Gln Ser Arg Ser Val Val Gln Ile Ala Asn Asp Leu
65                  70                  75                  80

Ala Asn Leu Arg Ala Leu Leu Arg Leu Leu Ala Ser Ala Lys Ser Cys
                85                  90                  95

Pro Val Pro Arg Ala Arg Gly Ser Asp Thr Ile Lys Gly Leu Gly Asn
            100                 105                 110

Val Leu Arg Ala Ser Val His Ser Thr Glu Val Val Ala Leu Ser Arg
        115                 120                 125

Leu Lys Ala Ala Leu Gln Asp Met Leu Arg Gln Leu Asp Arg Asn Pro
    130                 135                 140

Gly Cys
145

<210> SEQ ID NO 28
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Pro Ile Gln Arg Val Gln Asp Asp Thr Lys Thr Leu Ile Lys Thr
1               5                   10                  15

Ile Ile Thr Arg Ile Asn Asp Ile Ser Pro Gln Gly Val Cys Ser
            20                  25                  30

Arg Pro Arg Val Ala Gly Leu Asp Phe Ile Pro Arg Val Gln Ser Val
        35                  40                  45

Arg Thr Leu Ser Gly Met Asp Gln Ile Leu Ala Thr Tyr Gln Gln Ile
    50                  55                  60

Leu Thr Ser Leu Gln Ser Arg Asn Val Ile Gln Ile Ser Asn Asp Leu
65                  70                  75                  80

Glu Asn Leu Arg Asp Leu Leu His Val Leu Ala Phe Ser Lys Ser Cys
```

```
                      85                  90                  95

Pro Val Pro Arg Ala Arg Gly Ser Asp Thr Ile Lys Gly Leu Gly Asn
            100                 105                 110

Val Leu Arg Ala Ser Val His Ser Thr Glu Val Val Ala Leu Ser Arg
        115                 120                 125

Leu Lys Ala Ala Leu Gln Asp Met Leu Arg Gln Leu Asp Arg Asn Pro
    130                 135                 140

Gly Cys
145

<210> SEQ ID NO 29
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Pro Ile Gln Arg Val Gln Asp Asp Thr Lys Thr Leu Ile Lys Thr
1               5                   10                  15

Ile Ile Thr Arg Ile Asn Asp Ile Ser Pro Gln Gly Val Ser Ser
            20                  25                  30

Arg Pro Arg Val Ala Gly Leu Asp Phe Ile Pro Arg Val Gln Ser Val
        35                  40                  45

Arg Thr Leu Ser Gly Met Asp Gln Ile Leu Ala Thr Tyr Gln Gln Ile
    50                  55                  60

Leu Thr Ser Leu Gln Ser Arg Asn Val Ile Gln Ile Ser Asn Asp Leu
65                  70                  75                  80

Glu Asn Leu Arg Asp Leu Leu His Val Leu Ala Phe Ser Lys Ser Cys
                85                  90                  95

Pro Val Pro Arg Ala Arg Gly Ser Asp Thr Ile Lys Gly Leu Gly Asn
            100                 105                 110

Val Leu Arg Ala Ser Val His Ser Thr Glu Val Val Ala Leu Ser Arg
        115                 120                 125

Leu Lys Ala Ala Leu Gln Asp Met Leu Arg Gln Leu Asp Arg Asn Pro
    130                 135                 140

Gly Cys
145

<210> SEQ ID NO 30
<211> LENGTH: 374
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
```

```
            65                  70                  75                  80
Tyr Arg Val Val Ser Val Leu Thr Val Leu His Gln Asp Trp Leu Asn
                85                  90                  95
Gly Lys Glu Tyr Lys Cys Lys Val Ser Asn Lys Ala Leu Pro Ala Pro
            100                 105                 110
Ile Glu Lys Thr Ile Ser Lys Ala Lys Gly Gln Pro Arg Glu Pro Gln
            115                 120                 125
Val Tyr Thr Leu Pro Pro Ser Arg Asp Glu Leu Thr Lys Asn Gln Val
        130                 135                 140
Ser Leu Thr Cys Leu Val Lys Gly Phe Tyr Pro Ser Asp Ile Ala Val
145                 150                 155                 160
Glu Trp Glu Ser Asn Gly Gln Pro Glu Asn Asn Tyr Lys Thr Thr Pro
                165                 170                 175
Pro Val Leu Asp Ser Asp Gly Ser Phe Phe Leu Tyr Ser Lys Leu Thr
            180                 185                 190
Val Asp Lys Ser Arg Trp Gln Gln Gly Asn Val Phe Ser Cys Ser Val
            195                 200                 205
Met His Glu Ala Leu His Asn His Tyr Thr Gln Lys Ser Leu Ser Leu
        210                 215                 220
Ser Pro Gly Lys Val Pro Ile Gln Lys Val Gln Asp Asp Thr Lys Thr
225                 230                 235                 240
Leu Ile Lys Thr Ile Val Thr Arg Ile Asn Asp Ile Ser His Thr Gln
                245                 250                 255
Ser Val Ser Ser Lys Gln Lys Val Thr Gly Leu Asp Phe Ile Pro Gly
            260                 265                 270
Leu His Pro Ile Leu Thr Leu Ser Lys Met Asp Gln Thr Leu Ala Val
        275                 280                 285
Tyr Gln Gln Ile Leu Thr Ser Met Pro Ser Arg Asn Val Ile Gln Ile
        290                 295                 300
Ser Asn Asp Leu Glu Asn Leu Arg Asp Leu Leu His Val Leu Ala Phe
305                 310                 315                 320
Ser Lys Ser Cys His Leu Pro Trp Ala Ser Gly Leu Glu Thr Leu Asp
                325                 330                 335
Ser Leu Gly Gly Val Leu Glu Ala Ser Gly Tyr Ser Thr Glu Val Val
            340                 345                 350
Ala Leu Ser Arg Leu Gln Gly Ser Leu Gln Asp Met Leu Trp Gln Leu
            355                 360                 365
Asp Leu Ser Pro Gly Cys
    370

<210> SEQ ID NO 31
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Val Pro Ile Gln Lys Val Gln Asp Asp Thr Lys Thr Leu Ile Lys
1               5                   10                  15
Thr Ile Val Thr Arg Ile Asn Asp Ile Ser His Thr Gln Ser Val Ser
            20                  25                  30
Ser Lys Gln Lys Val Thr Gly Leu Asp Phe Ile Pro Gly Leu His Pro
        35                  40                  45
```

```
Ile Leu Thr Leu Ser Lys Met Asp Gln Thr Leu Ala Val Tyr Gln Gln
         50                  55                  60

Ile Leu Thr Ser Met Pro Ser Arg Asn Val Ile Gln Ile Ser Asn Asp
 65                  70                  75                  80

Leu Glu Asn Leu Arg Asp Leu Leu His Val Leu Ala Phe Ser Lys Ser
                 85                  90                  95

Cys His Leu Pro Gln Ala Ser Gly Leu Glu Thr Leu Asp Ser Leu Gly
                100                 105                 110

Gly Val Leu Glu Ala Ser Gly Tyr Ser Thr Glu Val Val Ala Leu Ser
            115                 120                 125

Arg Leu Gln Gly Ser Leu Gln Asp Met Leu Gln Leu Asp Leu Ser
130                 135                 140

Pro Gly Cys
145

<210> SEQ ID NO 32
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (78)..(78)
<223> OTHER INFORMATION: Cys-PEG20K

<400> SEQUENCE: 32

Met Val Pro Ile Gln Lys Val Gln Asp Asp Thr Lys Thr Leu Ile Lys
 1               5                  10                  15

Thr Ile Val Thr Arg Ile Asn Asp Ile Ser His Thr Gln Ser Val Ser
                 20                  25                  30

Ser Lys Gln Lys Val Thr Gly Leu Asp Phe Ile Pro Gly Leu His Pro
             35                  40                  45

Ile Leu Thr Leu Ser Lys Met Asp Gln Thr Leu Ala Val Tyr Gln Gln
         50                  55                  60

Ile Leu Thr Ser Met Pro Ser Arg Asn Val Ile Gln Ile Cys Asn Asp
 65                  70                  75                  80

Leu Glu Asn Leu Arg Asp Leu Leu His Val Leu Ala Phe Ser Lys Ser
                 85                  90                  95

Cys His Leu Pro Trp Ala Ser Gly Leu Glu Thr Leu Asp Ser Leu Gly
                100                 105                 110

Gly Val Leu Glu Ala Ser Gly Tyr Ser Thr Glu Val Val Ala Leu Ser
            115                 120                 125

Arg Leu Gln Gly Ser Leu Gln Asp Met Leu Trp Gln Leu Asp Leu Ser
130                 135                 140

Pro Gly Cys
145

<210> SEQ ID NO 33
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met Val Pro Ile Gln Lys Val Gln Asp Asp Thr Lys Thr Leu Ile Lys
 1               5                  10                  15
```

```
Thr Ile Val Thr Arg Ile Asn Asp Ile Ser His Thr Gln Ser Val Ser
            20                  25                  30

Ser Lys Gln Lys Val Thr Gly Leu Glu Phe Ile Pro Gly Leu His Pro
        35                  40                  45

Ile Leu Thr Leu Ser Lys Met Asp Gln Thr Leu Ala Val Tyr Gln Gln
 50                  55                  60

Ile Leu Thr Ser Met Pro Ser Arg Asn Val Ile Gln Ile Ser Asn Asp
 65                  70                  75                  80

Leu Glu Asn Leu Arg Asp Leu Leu His Val Leu Ala Phe Ser Lys Ser
                85                  90                  95

Cys His Leu Pro Gln Ala Ser Gly Leu Glu Thr Leu Glu Ser Leu Gly
            100                 105                 110

Gly Val Leu Glu Ala Ser Gly Tyr Ser Thr Glu Val Val Ala Leu Ser
        115                 120                 125

Arg Leu Gln Gly Ser Leu Gln Asp Met Leu Gln Gln Leu Asp Leu Ser
    130                 135                 140

Pro Gly Cys
145

<210> SEQ ID NO 34
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Tyr or Phe
<220> FEATURE:
<221> NAME/KEY: MOD_RES
<222> LOCATION: (8)..(8)
<223> OTHER INFORMATION: Asn, Arg or Ser
<220> FEATURE:
<221> NAME/KEY: MOD_RES
<222> LOCATION: (9)..(9)
<223> OTHER INFORMATION: Val, Ile, Leu, Met, Phe or Tyr
<220> FEATURE:
<221> NAME/KEY: MOD_RES
<222> LOCATION: (11)..(11)
<223> OTHER INFORMATION: Asn, Ser, Glu or Asp
<220> FEATURE:
<221> NAME/KEY: MOD_RES
<222> LOCATION: (12)..(12)
<223> OTHER INFORMATION: Arg, Lys or Asn
<220> FEATURE:
<221> NAME/KEY: MOD_RES
<222> LOCATION: (14)..(14)
<223> OTHER INFORMATION: Lys or Arg
<220> FEATURE:
<221> NAME/KEY: MOD_RES
<222> LOCATION: (20)..(20)
<223> OTHER INFORMATION: Asp, Asn, Gln, Glu, His, Ser, Arg or Lys
<220> FEATURE:
<221> NAME/KEY: MOD_RES
<222> LOCATION: (23)..(23)
<223> OTHER INFORMATION: Lys, Ile or Thr
<220> FEATURE:
<221> NAME/KEY: MOD_RES
<222> LOCATION: (24)..(24)
<223> OTHER INFORMATION: Ala, Ser, Thr, Gly, His, Leu or Asp
<220> FEATURE:
<221> NAME/KEY: MOD_RES
<222> LOCATION: (25)..(25)
<223> OTHER INFORMATION: His, Glu or Asp

<400> SEQUENCE: 34
```

```
Gly Val Ser Asp Xaa Tyr Lys Xaa Xaa Ile Xaa Xaa Ala Xaa Thr Val
1               5                   10                  15

Glu Gly Val Xaa Ala Leu Xaa Xaa Xaa Ile
            20                  25

<210> SEQ ID NO 35
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Val Ser Asp Tyr Tyr Lys Asn Leu Ile Asn Asn Ala Lys Thr Val
1               5                   10                  15

Glu Gly Val Lys Ala Leu Ile Asp Glu Ile
            20                  25

<210> SEQ ID NO 36
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Val or Glu
<220> FEATURE:
<221> NAME/KEY: MOD_RES
<222> LOCATION: (7)..(7)
<223> OTHER INFORMATION: Leu, Glu or Asp
<220> FEATURE:
<221> NAME/KEY: MOD_RES
<222> LOCATION: (9)..(9)
<223> OTHER INFORMATION: Asn, Leu or Ile
<220> FEATURE:
<221> NAME/KEY: MOD_RES
<222> LOCATION: (10)..(10)
<223> OTHER INFORMATION: Arg or Lys
<220> FEATURE:
<221> NAME/KEY: MOD_RES
<222> LOCATION: (13)..(13)
<223> OTHER INFORMATION: Asp or Lys
<220> FEATURE:
<221> NAME/KEY: MOD_RES
<222> LOCATION: (20)..(20)
<223> OTHER INFORMATION: Tyr or Phe
<220> FEATURE:
<221> NAME/KEY: MOD_RES
<222> LOCATION: (23)..(23)
<223> OTHER INFORMATION: Asn, Arg or Ser
<220> FEATURE:
<221> NAME/KEY: MOD_RES
<222> LOCATION: (24)..(24)
<223> OTHER INFORMATION: Val, Ile, Leu, Met, Phe or Tyr
<220> FEATURE:
<221> NAME/KEY: MOD_RES
<222> LOCATION: (26)..(26)
<223> OTHER INFORMATION: Asn, Ser, Glu or Asp
<220> FEATURE:
<221> NAME/KEY: MOD_RES
<222> LOCATION: (27)..(27)
<223> OTHER INFORMATION: Arg, Lys or Asn
<220> FEATURE:
<221> NAME/KEY: MOD_RES
<222> LOCATION: (29)..(29)
<223> OTHER INFORMATION: Lys or Arg
<220> FEATURE:
<221> NAME/KEY: MOD_RES
<222> LOCATION: (35)..(35)
<223> OTHER INFORMATION: Asp, Asn, Gln, Glu, His, Ser, Arg or Lys
```

```
<220> FEATURE:
<221> NAME/KEY: MOD_RES
<222> LOCATION: (38)..(38)
<223> OTHER INFORMATION: Lys, Ile or Thr
<220> FEATURE:
<221> NAME/KEY: MOD_RES
<222> LOCATION: (39)..(39)
<223> OTHER INFORMATION: Ala, Ser, Thr, Gly, His, Leu or Asp
<220> FEATURE:
<221> NAME/KEY: MOD_RES
<222> LOCATION: (40)..(40)
<223> OTHER INFORMATION: His, Glu or Asp

<400> SEQUENCE: 36

Leu Ala Glu Ala Lys Xaa Xaa Ala Xaa Xaa Glu Leu Xaa Lys Tyr Gly
1               5                  10                  15

Val Ser Asp Xaa Tyr Lys Xaa Xaa Ile Xaa Xaa Ala Xaa Thr Val Glu
            20                  25                  30

Gly Val Xaa Ala Leu Xaa Xaa Xaa Ile Leu Ala Ala Leu Pro
        35                  40                  45

<210> SEQ ID NO 37
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Leu Ala Glu Ala Lys Val Leu Ala Asn Arg Glu Leu Asp Lys Tyr Gly
1               5                  10                  15

Val Ser Asp Tyr Tyr Lys Asn Leu Ile Asn Asn Ala Lys Thr Val Glu
            20                  25                  30

Gly Val Lys Ala Leu Ile Asp Glu Ile Leu Ala Ala Leu Pro
        35                  40                  45

<210> SEQ ID NO 38
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Leu Ala Glu Ala Lys Val Leu Ala Asn Arg Glu Leu Asp Lys Tyr Gly
1               5                  10                  15

Val Ser Asp Phe Tyr Lys Ser Tyr Ile Asn Arg Ala Lys Thr Val Glu
            20                  25                  30

Gly Val His Thr Leu Ile Gly His Ile Leu Ala Ala Leu Pro
        35                  40                  45

<210> SEQ ID NO 39
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Leu Ala Glu Ala Lys Val Leu Ala Asn Arg Glu Leu Asp Lys Tyr Gly
1               5                  10                  15

Val Ser Asp Phe Tyr Lys Arg Leu Ile Asn Lys Ala Lys Thr Val Glu
```

-continued

```
                20                  25                  30

Gly Val Asn Ala Leu Thr His His Ile Leu Ala Ala Leu Pro
            35                  40                  45

<210> SEQ ID NO 40
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asn Arg Ala Arg Thr Val Glu
            20                  25                  30

Gly Val His Ala Leu Ile Asp His Ile Leu Ala Ala Leu Pro
            35                  40                  45

<210> SEQ ID NO 41
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Leu Ala Glu Ala Lys Val Leu Ala Asn Arg Glu Leu Asp Lys Tyr Gly
1               5                   10                  15

Val Ser Asp Tyr Tyr Lys Asn Ile Ile Asn Arg Ala Lys Thr Val Glu
            20                  25                  30

Gly Val Arg Ala Leu Lys Leu His Ile Leu Ala Ala Leu Pro
            35                  40                  45

<210> SEQ ID NO 42
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Ser Ser Leu Lys Gly His Ile Leu Ala Ala Leu Pro
            35                  40                  45

<210> SEQ ID NO 43
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Leu Ala Glu Ala Lys Val Leu Ala Asn Arg Glu Leu Asp Lys Tyr Gly
1               5                   10                  15
```

Val Ser Asp Tyr Tyr Lys Asn Leu Ile Asn Lys Ala Lys Thr Val Glu
            20                  25                  30

Gly Val Glu Ala Leu Thr Leu His Ile Leu Ala Ala Leu Pro
        35                  40                  45

<210> SEQ ID NO 44
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Asp Ala Leu Ile Ala His Ile Leu Ala Ala Leu Pro
        35                  40                  45

<210> SEQ ID NO 45
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Leu Ala Glu Ala Lys Val Leu Ala Asn Arg Glu Leu Asp Lys Tyr Gly
1               5                   10                  15

Val Ser Asp Phe Tyr Lys Ser Leu Ile Asn Arg Ala Lys Thr Val Glu
            20                  25                  30

Gly Val Asp Ala Leu Thr Ser His Ile Leu Ala Ala Leu Pro
        35                  40                  45

<210> SEQ ID NO 46
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Asn Ser Leu Thr Ser His Ile Leu Ala Ala Leu Pro
        35                  40                  45

<210> SEQ ID NO 47
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Leu Ala Glu Ala Lys Val Leu Ala Asn Arg Glu Leu Asp Lys Tyr Gly
1               5                   10                  15

```
Val Ser Asp Phe Tyr Lys Asn Val Ile Asn Lys Ala Lys Thr Val Glu
            20                  25                  30

Gly Val Glu Ala Leu Ile Ala Asp Ile Leu Ala Ala Leu Pro
        35                  40                  45

<210> SEQ ID NO 48
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asn Lys Ala Lys Thr Val Glu
            20                  25                  30

Gly Val Gln Ala Leu Ile Ala His Ile Leu Ala Ala Leu Pro
        35                  40                  45

<210> SEQ ID NO 49
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Lys Ala Lys Thr Val Glu
            20                  25                  30

Gly Val Glu Ala Leu Lys Leu His Ile Leu Ala Ala Leu Pro
        35                  40                  45

<210> SEQ ID NO 50
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Leu Ala Glu Ala Lys Glu Asp Ala Ile Lys Glu Leu Asp Lys Tyr Gly
1               5                   10                  15

Val Ser Asp Tyr Tyr Lys Asn Leu Ile Asn Lys Ala Lys Thr Val Glu
            20                  25                  30

Gly Val Glu Ala Leu Thr Leu His Ile Leu Ala Ala Leu Pro
        35                  40                  45

<210> SEQ ID NO 51
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Leu Ala Glu Ala Lys Glu Asp Ala Ile Lys Glu Leu Asp Lys Tyr Gly
```

```
                1               5                  10                 15
Val Ser Asp Tyr Tyr Lys Asn Leu Ile Asn Lys Ala Lys Thr Val Glu
                20                 25                 30

Gly Val Glu Ala Leu Ile Ser Glu Ile Leu Ala Ala Leu Pro
        35                 40                 45

<210> SEQ ID NO 52
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Leu Ala Glu Ala Lys Glu Asp Ala Ile Lys Glu Leu Asp Lys Tyr Gly
1               5                  10                 15

Val Ser Asp Tyr Tyr Lys Arg Leu Ile Ser Lys Ala Lys Thr Val Glu
                20                 25                 30

Gly Val Lys Ala Leu Ile Ser Glu Ile Leu Ala Ala Leu Pro
        35                 40                 45

<210> SEQ ID NO 53
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Leu Ala Glu Ala Lys Val Leu Ala Asn Arg Glu Leu Asp Lys Tyr
1               5                  10                 15

Gly Val Ser Asp Phe Tyr Lys Arg Leu Ile Asn Lys Ala Lys Thr Val
                20                 25                 30

Glu Gly Val Glu Ala Leu Lys Leu His Ile Leu Ala Ala Leu Pro Thr
        35                 40                 45

Gly Gly Gly Gly Ala Ser Val Pro Ile Gln Lys Val Gln Asp Thr
50                  55                 60

Lys Thr Leu Ile Lys Thr Ile Val Thr Arg Ile Asn Asp Ile Ser His
65                  70                 75                 80

Thr Gln Ser Val Ser Ser Lys Gln Lys Val Thr Gly Leu Glu Phe Ile
                85                 90                 95

Pro Gly Leu His Pro Ile Leu Thr Leu Ser Lys Met Asp Gln Thr Leu
            100                105                110

Ala Val Tyr Gln Gln Ile Leu Thr Ser Met Pro Ser Arg Asn Val Ile
            115                120                125

Gln Ile Ser Asn Asp Leu Glu Asn Leu Arg Asp Leu Leu His Val Leu
        130                135                140

Ala Phe Ser Lys Ser Cys His Leu Pro Gln Ala Ser Gly Leu Glu Thr
145                150                155                160

Leu Glu Ser Leu Gly Gly Val Leu Glu Ala Ser Gly Tyr Ser Thr Glu
                165                170                175

Val Val Ala Leu Ser Arg Leu Gln Gly Ser Leu Gln Asp Met Leu Gln
            180                185                190

Gln Leu Asp Leu Ser Pro Gly Cys
        195                200
```

```
<210> SEQ ID NO 54
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Met Leu Ala Glu Ala Lys Val Leu Ala Asn Arg Glu Leu Asp Lys Tyr
1               5                   10                  15

Gly Val Ser Asp Phe Tyr Lys Arg Leu Ile Asn Lys Ala Lys Thr Val
                20                  25                  30

Glu Gly Val Glu Ala Leu Lys Leu His Ile Leu Ala Ala Leu Pro Thr
            35                  40                  45

Gly Gly Gly Gly Ser Gly Gly Gly Ser Gly Gly Gly Ser Gly Gly Gly
        50                  55                  60

Ser Ala Ser Val Pro Ile Gln Lys Val Gln Asp Asp Thr Lys Thr Leu
65                  70                  75                  80

Ile Lys Thr Ile Val Thr Arg Ile Asn Asp Ile Ser His Thr Gln Ser
                85                  90                  95

Val Ser Ser Lys Gln Lys Val Thr Gly Leu Glu Phe Ile Pro Gly Leu
                100                 105                 110

His Pro Ile Leu Thr Leu Ser Lys Met Asp Gln Thr Leu Ala Val Tyr
            115                 120                 125

Gln Gln Ile Leu Thr Ser Met Pro Ser Arg Asn Val Ile Gln Ile Ser
        130                 135                 140

Asn Asp Leu Glu Asn Leu Arg Asp Leu Leu His Val Leu Ala Phe Ser
145                 150                 155                 160

Lys Ser Cys His Leu Pro Gln Ala Ser Gly Leu Glu Thr Leu Glu Ser
                165                 170                 175

Leu Gly Gly Val Leu Glu Ala Ser Gly Tyr Ser Thr Glu Val Val Ala
                180                 185                 190

Leu Ser Arg Leu Gln Gly Ser Leu Gln Asp Met Leu Gln Gln Leu Asp
            195                 200                 205

Leu Ser Pro Gly Cys
        210

<210> SEQ ID NO 55
<211> LENGTH: 201
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
                20                  25                  30

Ser Lys Gln Lys Val Thr Gly Leu Glu Phe Ile Pro Gly Leu His Pro
            35                  40                  45

Ile Leu Thr Leu Ser Lys Met Asp Gln Thr Leu Ala Val Tyr Gln Gln
        50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
```

85                  90                  95
Cys His Leu Pro Gln Ala Ser Gly Leu Glu Thr Leu Glu Ser Leu Gly
                100                 105                 110

Gly Val Leu Glu Ala Ser Gly Tyr Ser Thr Glu Val Ala Leu Ser
            115                 120                 125

Arg Leu Gln Gly Ser Leu Gln Asp Met Leu Gln Gln Leu Asp Leu Ser
            130                 135                 140

Pro Gly Cys Thr Gly Gly Gly Ser Ala Ser Leu Ala Glu Ala Lys
145                 150                 155                 160

Val Leu Ala Asn Arg Glu Leu Asp Lys Tyr Gly Val Ser Asp Phe Tyr
                165                 170                 175

Lys Arg Leu Ile Asn Lys Ala Lys Thr Val Glu Gly Val Glu Ala Leu
                180                 185                 190

Lys Leu His Ile Leu Ala Ala Leu Pro
                195                 200

<210> SEQ ID NO 56
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
                20                  25                  30

Ser Lys Gln Lys Val Thr Gly Leu Glu Phe Ile Pro Gly Leu His Pro
            35                  40                  45

Ile Leu Thr Leu Ser Lys Met Asp Gln Thr Leu Ala Val Tyr Gln Gln
        50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys His Leu Pro Gln Ala Ser Gly Leu Glu Thr Leu Glu Ser Leu Gly
                100                 105                 110

Gly Val Leu Glu Ala Ser Gly Tyr Ser Thr Glu Val Val Ala Leu Ser
            115                 120                 125

Arg Leu Gln Gly Ser Leu Gln Asp Met Leu Gln Gln Leu Asp Leu Ser
            130                 135                 140

Pro Gly Cys Thr Gly Gly Gly Ser Gly Gly Gly Ser Gly Gly Gly
145                 150                 155                 160

Ser Gly Gly Ser Ala Ser Leu Ala Glu Ala Lys Val Leu Ala Asn
                165                 170                 175

Arg Glu Leu Asp Lys Tyr Gly Val Ser Asp Phe Tyr Lys Arg Leu Ile
                180                 185                 190

Asn Lys Ala Lys Thr Val Glu Gly Val Glu Ala Leu Lys Leu His Ile
            195                 200                 205

Leu Ala Ala Leu Pro
        210

<210> SEQ ID NO 57
<211> LENGTH: 213

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Met Leu Ala Glu Ala Lys Val Leu Ala Asn Arg Glu Leu Asp Lys Tyr
1               5                   10                  15

Gly Val Ser Asp Phe Tyr Lys Arg Leu Ile Asn Lys Ala Lys Thr Val
                20                  25                  30

Glu Gly Val Glu Ala Leu Lys Leu His Ile Leu Ala Ala Leu Pro Thr
            35                  40                  45

Gly Gly Gly Gly Ser Gly Gly Gly Ser Gly Gly Ser Gly Gly Gly
        50                  55                  60

Ser Ala Ser Ile Ser Ile Glu Lys Ile Gln Ala Asp Thr Lys Thr Leu
65                  70                  75                  80

Thr Lys Thr Ile Ile Thr Arg Ile Ile Gln Leu Ser Thr Gln Asn Gly
                85                  90                  95

Val Ser Thr Asp Gln Arg Val Ser Gly Leu Asp Phe Ile Pro Gly Asn
            100                 105                 110

Gln Gln Phe Gln Asn Leu Ala Asp Met Asp Gln Thr Leu Ala Val Tyr
        115                 120                 125

Gln Gln Ile Leu Ser Ser Leu Pro Met Pro Asp Arg Thr Gln Ile Ser
130                 135                 140

Asn Asp Leu Glu Asn Leu Arg Ser Leu Phe Ala Leu Leu Ala Thr Leu
145                 150                 155                 160

Lys Asn Cys Pro Phe Thr Arg Ser Asp Gly Leu Asp Thr Met Glu Ile
                165                 170                 175

Trp Gly Gly Ile Val Glu Glu Ser Leu Tyr Ser Thr Glu Val Val Thr
            180                 185                 190

Leu Asp Arg Leu Arg Lys Ser Leu Lys Asn Ile Glu Lys Gln Leu Asp
        195                 200                 205

His Ile Gln Gly Cys
    210

<210> SEQ ID NO 58
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Met Leu Ala Glu Ala Lys Val Leu Ala Asn Arg Glu Leu Asp Lys Tyr
1               5                   10                  15

Gly Val Ser Asp Phe Tyr Lys Arg Leu Ile Asn Lys Ala Lys Thr Val
                20                  25                  30

Glu Gly Val Glu Ala Leu Lys Leu His Ile Leu Ala Ala Leu Pro Thr
            35                  40                  45

Gly Gly Gly Gly Ser Gly Gly Gly Ser Gly Gly Ser Gly Gly Gly
        50                  55                  60

Ser Ala Ser Val Pro Ile Gln Lys Val Gln Asp Asp Thr Lys Thr Leu
65                  70                  75                  80

Ile Lys Thr Ile Val Thr Arg Ile Asn Asp Ile Ser His Thr Gln Ser
                85                  90                  95

Val Ser Ser Lys Gln Lys Val Thr Gly Leu Asp Phe Ile Pro Gly Leu
            100                 105                 110

His Pro Ile Leu Thr Leu Ser Lys Met Asp Gln Thr Leu Ala Val Tyr
        115                 120                 125

Gln Gln Ile Leu Thr Ser Met Pro Ser Arg Asn Val Ile Gln Ile Ser
    130                 135                 140

Asn Asp Leu Glu Asn Leu Arg Asp Leu Leu His Val Leu Ala Phe Ser
145                 150                 155                 160

Lys Ser Cys His Leu Pro Trp Ala Ser Gly Leu Glu Thr Leu Asp Ser
                165                 170                 175

Leu Gly Gly Val Leu Glu Ala Ser Gly Tyr Ser Thr Glu Val Val Ala
            180                 185                 190

Leu Ser Arg Leu Gln Gly Ser Leu Gln Asp Met Leu Trp Gln Leu Asp
        195                 200                 205

Leu Ser Pro Gly Cys
    210

<210> SEQ ID NO 59
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Lys Val Thr Gly Leu Asp Phe Ile Pro Gly Leu His Pro
        35                  40                  45

Ile Leu Thr Leu Ser Lys Met Asp Gln Thr Leu Ala Val Tyr Gln Gln
    50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys His Leu Pro Trp Ala Ser Gly Leu Glu Thr Leu Asp Ser Leu Gly
            100                 105                 110

Gly Val Leu Glu Ala Ser Gly Tyr Ser Thr Glu Val Val Ala Leu Ser
        115                 120                 125

Arg Leu Gln Gly Ser Leu Gln Asp Met Leu Trp Gln Leu Asp Leu Ser
    130                 135                 140

Pro Gly Cys Thr Gly Gly Gly Ser Gly Gly Ser Gly Gly Gly
145                 150                 155                 160

Ser Gly Gly Gly Ser Ala Ser Leu Ala Glu Ala Lys Val Leu Ala Asn
                165                 170                 175

Arg Glu Leu Asp Lys Tyr Gly Val Ser Asp Phe Tyr Lys Arg Leu Ile
            180                 185                 190

Asn Lys Ala Lys Thr Val Glu Gly Val Glu Ala Leu Lys Leu His Ile
        195                 200                 205

Leu Ala Ala Leu Pro
    210

<210> SEQ ID NO 60

```
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Met Leu Ala Glu Ala Lys Val Leu Ala Asn Arg Glu Leu Asp Lys Tyr
1               5                   10                  15

Gly Val Ser Asp Phe Tyr Lys Arg Leu Ile Asn Lys Ala Lys Thr Val
                20                  25                  30

Glu Gly Val Glu Ala Leu Lys Leu His Ile Leu Ala Ala Leu Pro Thr
            35                  40                  45

Gly Gly Gly Gly Ser Gly Gly Ser Gly Gly Gly Ser Gly Gly Gly
        50                  55                  60

Ser Ala Ser Pro Ile Gln Arg Val Gln Asp Asp Thr Lys Thr Leu Ile
65                  70                  75                  80

Lys Thr Ile Ile Thr Arg Ile Asn Asp Ile Ser Pro Pro Gln Gly Val
                85                  90                  95

Cys Ser Arg Pro Arg Val Ala Gly Leu Asp Phe Ile Pro Arg Val Gln
                100                 105                 110

Ser Val Arg Thr Leu Ser Gly Met Asp Gln Ile Leu Ala Thr Tyr Gln
            115                 120                 125

Gln Ile Leu Thr Ser Leu Gln Ser Arg Asn Val Ile Gln Ile Ser Asn
        130                 135                 140

Asp Leu Glu Asn Leu Arg Asp Leu Leu His Val Leu Ala Phe Ser Lys
145                 150                 155                 160

Ser Cys Pro Val Pro Arg Ala Arg Gly Ser Asp Thr Ile Lys Gly Leu
                165                 170                 175

Gly Asn Val Leu Arg Ala Ser Val His Ser Thr Glu Val Val Ala Leu
                180                 185                 190

Ser Arg Leu Lys Ala Ala Leu Gln Asp Met Leu Arg Gln Leu Asp Arg
            195                 200                 205

Asn Pro Gly Cys
    210

<210> SEQ ID NO 61
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Met Leu Ala Glu Ala Lys Val Leu Ala Asn Arg Glu Leu Asp Lys Tyr
1               5                   10                  15

Gly Val Ser Asp Phe Tyr Lys Arg Leu Ile Asn Lys Ala Lys Thr Val
                20                  25                  30

Glu Gly Val Glu Ala Leu Lys Leu His Ile Leu Ala Ala Leu Pro Thr
            35                  40                  45

Gly Gly Gly Gly Ser Gly Gly Ser Gly Gly Gly Ser Gly Gly Gly
        50                  55                  60

Ser Ala Ser Pro Ile Gln Arg Val Gln Asp Asp Thr Lys Thr Leu Ile
65                  70                  75                  80

Lys Thr Ile Ile Thr Arg Ile Asn Asp Ile Ser Pro Pro Gln Gly Val
                85                  90                  95
```

Ser Ser Arg Pro Arg Val Ala Gly Leu Asp Phe Ile Pro Arg Val Gln
            100                 105                 110

Ser Val Arg Thr Leu Ser Gly Met Asp Gln Ile Leu Ala Thr Tyr Gln
        115                 120                 125

Gln Ile Leu Thr Ser Leu Gln Ser Arg Asn Val Ile Gln Ile Ser Asn
    130                 135                 140

Asp Leu Glu Asn Leu Arg Asp Leu Leu His Val Leu Ala Phe Ser Lys
145                 150                 155                 160

Ser Cys Pro Val Pro Arg Ala Arg Gly Ser Asp Thr Ile Lys Gly Leu
                165                 170                 175

Gly Asn Val Leu Arg Ala Ser Val His Ser Thr Glu Val Ala Leu
                180                 185                 190

Ser Arg Leu Lys Ala Ala Leu Gln Asp Met Leu Arg Gln Leu Asp Arg
    195                 200                 205

Asn Pro Gly Cys
    210

<210> SEQ ID NO 62
<211> LENGTH: 193
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Met Leu Ala Glu Ala Lys Val Leu Ala Asn Arg Glu Leu Asp Lys Tyr
1               5                   10                  15

Gly Val Ser Asp Phe Tyr Lys Arg Leu Ile Asn Lys Ala Lys Thr Val
            20                  25                  30

Glu Gly Val Glu Ala Leu Lys Leu His Ile Leu Ala Ala Leu Pro Thr
        35                  40                  45

Gly Pro Ile Gln Arg Val Gln Asp Asp Thr Lys Thr Leu Ile Lys Thr
    50                  55                  60

Ile Ile Thr Arg Ile Asn Asp Ile Ser Pro Pro Gln Gly Val Cys Ser
65                  70                  75                  80

Pro Arg Val Ala Gly Leu Asp Phe Ile Pro Arg Val Gln Ser Val Arg
                85                  90                  95

Thr Leu Ser Gly Met Asp Gln Ile Leu Ala Thr Tyr Gln Gln Ile Leu
            100                 105                 110

Thr Ser Leu Gln Ser Arg Asn Val Ile Gln Ile Ser Asn Asp Leu Glu
        115                 120                 125

Asn Leu Arg Asp Leu Leu His Val Leu Ala Phe Ser Lys Ser Cys Pro
    130                 135                 140

Val Pro Arg Ala Arg Gly Ser Asp Thr Ile Lys Gly Leu Gly Asn Val
145                 150                 155                 160

Leu Arg Ala Ser Val His Ser Thr Glu Val Ala Leu Ser Arg Leu
                165                 170                 175

Lys Ala Ala Leu Gln Asp Met Leu Arg Gln Leu Asp Arg Asn Pro Gly
            180                 185                 190

Cys

<210> SEQ ID NO 63
<211> LENGTH: 213
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 63
```

| | | | | | | | | | | | | | | |
|---|---|---|---|---|---|---|---|---|---|---|---|---|---|---|
|Met|Leu|Ala|Glu|Ala|Lys|Val|Leu|Ala|Asn|Arg|Glu|Leu|Asp|Lys|Tyr|
|1| | | |5| | | | |10| | | | |15|

| | | | | | | | | | | | |
|---|---|---|---|---|---|---|---|---|---|---|---|
|Gly|Val|Ser|Asp|Tyr|Tyr|Lys|Asn|Ile|Ile|Asn|Arg|Ala|Lys|Thr|Val|
| | | |20| | | | |25| | | | |30| | |

Glu Gly Val Arg Ala Leu Lys Leu His Ile Leu Ala Ala Leu Pro Thr
            35                  40                  45

Gly Gly Gly Gly Ser Gly Gly Ser Gly Gly Ser Gly Gly Gly
50                  55                  60

Ser Ala Ser Val Pro Ile Gln Lys Val Gln Asp Asp Thr Lys Thr Leu
65                  70                  75                  80

Ile Lys Thr Ile Val Thr Arg Ile Asn Asp Ile Ser His Thr Gln Ser
                85                  90                  95

Val Ser Ser Lys Gln Lys Val Thr Gly Leu Asp Phe Ile Pro Gly Leu
                100                 105                 110

His Pro Ile Leu Thr Leu Ser Lys Met Asp Gln Thr Leu Ala Val Tyr
            115                 120                 125

Gln Gln Ile Leu Thr Ser Met Pro Ser Arg Asn Val Ile Gln Ile Ser
130                 135                 140

Asn Asp Leu Glu Asn Leu Arg Asp Leu Leu His Val Leu Ala Phe Ser
145                 150                 155                 160

Lys Ser Cys His Leu Pro Trp Ala Ser Gly Leu Glu Thr Leu Asp Ser
                165                 170                 175

Leu Gly Gly Val Leu Glu Ala Ser Gly Tyr Ser Thr Glu Val Val Ala
            180                 185                 190

Leu Ser Arg Leu Gln Gly Ser Leu Gln Asp Met Leu Trp Gln Leu Asp
            195                 200                 205

Leu Ser Pro Gly Cys
            210

```
<210> SEQ ID NO 64
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64
```

Met Leu Ala Glu Ala Lys Val Leu Ala Asn Arg Glu Leu Asp Lys Tyr
1               5                   10                  15

Gly Val Ser Asp Tyr Tyr Lys Asn Ile Ile Asn Arg Ala Lys Thr Val
                20                  25                  30

Glu Gly Val Arg Ala Leu Lys Leu His Ile Leu Ala Ala Leu Pro Thr
            35                  40                  45

Gly Gly Gly Gly Ser Gly Gly Gly Ser Gly Gly Ser Gly Gly Gly
50                  55                  60

Ser Ala Ser Val Pro Ile Gln Lys Val Gln Asp Asp Thr Lys Thr Leu
65                  70                  75                  80

Ile Lys Thr Ile Val Thr Arg Ile Asn Asp Ile Ser His Thr Gln Ser
                85                  90                  95

Val Ser Ser Lys Gln Lys Val Thr Gly Leu Glu Phe Ile Pro Gly Leu
                100                 105                 110

His Pro Ile Leu Thr Leu Ser Lys Met Asp Gln Thr Leu Ala Val Tyr
            115                 120                 125

Gln Gln Ile Leu Thr Ser Met Pro Ser Arg Asn Val Ile Gln Ile Ser
        130                 135                 140

Asn Asp Leu Glu Asn Leu Arg Asp Leu Leu His Val Leu Ala Phe Ser
145                 150                 155                 160

Lys Ser Cys His Leu Pro Gln Ala Ser Gly Leu Glu Thr Leu Glu Ser
                165                 170                 175

Leu Gly Gly Val Leu Glu Ala Ser Gly Tyr Ser Thr Glu Val Val Ala
            180                 185                 190

Leu Ser Arg Leu Gln Gly Ser Leu Gln Asp Met Leu Gln Gln Leu Asp
        195                 200                 205

Leu Ser Pro Gly Cys
        210

<210> SEQ ID NO 65
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Met Leu Ala Glu Ala Lys Val Leu Ala Asn Arg Glu Leu Asp Lys Tyr
1               5                   10                  15

Gly Val Ser Asp Phe Tyr Lys Arg Leu Ile Asn Lys Ala Lys Thr Val
            20                  25                  30

Glu Gly Val Glu Ala Leu Lys Leu His Ile Leu Ala Ala Leu Pro Thr
        35                  40                  45

Gly Gly Gly Gly Ser Gly Gly Gly Ser Gly Gly Gly Ser Gly Gly Gly
    50                  55                  60

Ser Ala Ser Val Pro Ile Gln Lys Val Gln Asp Asp Thr Lys Thr Leu
65                  70                  75                  80

Ile Lys Thr Ile Val Thr Arg Ile Asn Asp Ile Ser His Thr Gln Ser
                85                  90                  95

Val Ser Ser Lys Gln Lys Val Thr Gly Leu Asp Phe Ile Pro Gly Leu
            100                 105                 110

His Pro Ile Leu Thr Leu Ser Lys Met Asp Gln Thr Leu Ala Val Tyr
        115                 120                 125

Gln Gln Ile Leu Thr Ser Met Pro Ser Arg Asn Val Ile Gln Ile Ser
    130                 135                 140

Asn Asp Leu Glu Asn Leu Arg Asp Leu Leu His Val Leu Ala Phe Ser
145                 150                 155                 160

Lys Ser Cys His Leu Pro Gln Ala Ser Gly Leu Glu Thr Leu Asp Ser
                165                 170                 175

Leu Gly Gly Val Leu Glu Ala Ser Gly Tyr Ser Thr Glu Val Val Ala
            180                 185                 190

Leu Ser Arg Leu Gln Gly Ser Leu Gln Asp Met Leu Gln Gln Leu Asp
        195                 200                 205

Leu Ser Pro Gly Cys
        210

<210> SEQ ID NO 66
<211> LENGTH: 227
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 66

Met Leu Ala Glu Ala Lys Val Leu Ala Asn Arg Glu Leu Asp Lys Tyr
1               5                   10                  15

Gly Val Ser Asp Phe Tyr Lys Arg Leu Ile Asn Lys Ala Lys Thr Val
            20                  25                  30

Glu Gly Val Glu Ala Leu Lys Leu His Ile Leu Ala Ala Leu Pro Thr
        35                  40                  45

Gly Leu Ala Glu Ala Ala Ala Lys Glu Ala Ala Ala Lys Glu Ala Ala
    50                  55                  60

Ala Lys Glu Ala Ala Ala Lys Glu Ala Ala Ala Lys Ala Ala Ala Ala
65                  70                  75                  80

Ser Val Pro Ile Gln Lys Val Gln Asp Asp Thr Lys Thr Leu Ile Lys
                85                  90                  95

Thr Ile Val Thr Arg Ile Asn Asp Ile Ser His Thr Gln Ser Val Ser
            100                 105                 110

Ser Lys Gln Lys Val Thr Gly Leu Glu Phe Ile Pro Gly Leu His Pro
        115                 120                 125

Ile Leu Thr Leu Ser Lys Met Asp Gln Thr Leu Ala Val Tyr Gln Gln
130                 135                 140

Ile Leu Thr Ser Met Pro Ser Arg Asn Val Ile Gln Ile Ser Asn Asp
145                 150                 155                 160

Leu Glu Asn Leu Arg Asp Leu Leu His Val Leu Ala Phe Ser Lys Ser
                165                 170                 175

Cys His Leu Pro Gln Ala Ser Gly Leu Glu Thr Leu Glu Ser Leu Gly
            180                 185                 190

Gly Val Leu Glu Ala Ser Gly Tyr Ser Thr Glu Val Val Ala Leu Ser
        195                 200                 205

Arg Leu Gln Gly Ser Leu Gln Asp Met Leu Gln Gln Leu Asp Leu Ser
    210                 215                 220

Pro Gly Cys
225

<210> SEQ ID NO 67
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Met Leu Ala Glu Ala Lys Val Leu Ala Asn Arg Glu Leu Asp Lys Tyr
1               5                   10                  15

Gly Val Ser Asp Phe Tyr Lys Arg Leu Ile Asn Lys Ala Lys Thr Val
            20                  25                  30

Glu Gly Val Glu Ala Leu Lys Leu His Ile Leu Ala Ala Leu Pro Thr
        35                  40                  45

Gly Gly Glu Gly Gly Glu Gly Gly Glu Gly Gly Glu Gly Gly Glu Gly
    50                  55                  60

Gly Glu Ala Ser Val Pro Ile Gln Lys Val Gln Asp Asp Thr Lys Thr
65                  70                  75                  80

Leu Ile Lys Thr Ile Val Thr Arg Ile Asn Asp Ile Ser His Thr Gln 85                  90                  95
Ser Val Ser Ser Lys Gln Lys Val Thr Gly Leu Glu Phe Ile Pro Gly
                100                 105                 110

Leu His Pro Ile Leu Thr Leu Ser Lys Met Asp Gln Thr Leu Ala Val
            115                 120                 125

Tyr Gln Gln Ile Leu Thr Ser Met Pro Ser Arg Asn Val Ile Gln Ile
        130                 135                 140

Ser Asn Asp Leu Glu Asn Leu Arg Asp Leu Leu His Val Leu Ala Phe
145                 150                 155                 160

Ser Lys Ser Cys His Leu Pro Gln Ala Ser Gly Leu Glu Thr Leu Glu
                165                 170                 175

Ser Leu Gly Gly Val Leu Glu Ala Ser Gly Tyr Ser Thr Glu Val Val
            180                 185                 190

Ala Leu Ser Arg Leu Gln Gly Ser Leu Gln Asp Met Leu Gln Gln Leu
        195                 200                 205

Asp Leu Ser Pro Gly Cys
    210

<210> SEQ ID NO 68
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Met Leu Ala Glu Ala Lys Val Leu Ala Asn Arg Glu Leu Asp Lys Tyr
1               5                   10                  15

Gly Val Ser Asp Phe Tyr Lys Arg Leu Ile Asn Lys Ala Lys Thr Val
            20                  25                  30

Glu Gly Val Glu Ala Leu Lys Leu His Ile Leu Ala Ala Leu Pro Thr
        35                  40                  45

Gly Gly Lys Gly Gly Lys Gly Gly Lys Gly Gly Lys Gly Gly Lys Gly
    50                  55                  60

Gly Lys Ala Ser Val Pro Ile Gln Lys Val Gln Asp Asp Thr Lys Thr
65                  70                  75                  80

Leu Ile Lys Thr Ile Val Thr Arg Ile Asn Asp Ile Ser His Thr Gln
                85                  90                  95

Ser Val Ser Ser Lys Gln Lys Val Thr Gly Leu Glu Phe Ile Pro Gly
                100                 105                 110

Leu His Pro Ile Leu Thr Leu Ser Lys Met Asp Gln Thr Leu Ala Val
            115                 120                 125

Tyr Gln Gln Ile Leu Thr Ser Met Pro Ser Arg Asn Val Ile Gln Ile
        130                 135                 140

Ser Asn Asp Leu Glu Asn Leu Arg Asp Leu Leu His Val Leu Ala Phe
145                 150                 155                 160

Ser Lys Ser Cys His Leu Pro Gln Ala Ser Gly Leu Glu Thr Leu Glu
                165                 170                 175

Ser Leu Gly Gly Val Leu Glu Ala Ser Gly Tyr Ser Thr Glu Val Val
            180                 185                 190

Ala Leu Ser Arg Leu Gln Gly Ser Leu Gln Asp Met Leu Gln Gln Leu
        195                 200                 205

Asp Leu Ser Pro Gly Cys
    210

<210> SEQ ID NO 69
<211> LENGTH: 213
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 69

Met Leu Ala Glu Ala Lys Val Leu Ala Asn Arg Glu Leu Asp Lys Tyr
1               5                   10                  15

Gly Val Ser Asp Phe Tyr Lys Arg Leu Ile Asn Lys Ala Lys Thr Val
                20                  25                  30

Glu Gly Val Glu Ala Leu Lys Leu His Ile Leu Ala Ala Leu Pro Thr
            35                  40                  45

Gly Gly Gly Gly Ser Gly Gly Ser Gly Gly Ser Gly Gly Gly
        50                  55                  60

Ser Ala Ser Val Pro Ile Gln Lys Val Gln Asp Asp Thr Lys Thr Leu
65                  70                  75                  80

Ile Lys Thr Ile Val Thr Arg Ile Asn Asp Ile Ser His Thr Gln Ser
                85                  90                  95

Val Ser Ser Lys Gln Lys Val Thr Gly Leu Glu Phe Ile Pro Gly Leu
                100                 105                 110

His Pro Ile Leu Thr Leu Ser Lys Met Asp Gln Thr Leu Ala Val Tyr
            115                 120                 125

Gln Gln Ile Leu Thr Ser Met Pro Ser Arg Asn Val Ile Gln Ile Ser
        130                 135                 140

Asn Asp Leu Glu Asn Leu Arg Asp Leu Leu His Val Leu Ala Phe Ser
145                 150                 155                 160

Lys Ser Cys Ser Leu Pro Gln Ala Ser Gly Leu Glu Thr Leu Glu Ser
                165                 170                 175

Leu Gly Glu Val Leu Glu Ala Ser Gly Tyr Ser Thr Glu Val Val Ala
            180                 185                 190

Leu Ser Arg Leu Gln Gly Ser Leu Gln Asp Ile Leu Gln Gln Leu Asp
        195                 200                 205

Leu Ser Pro Glu Cys
    210

<210> SEQ ID NO 70
<211> LENGTH: 200
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 70

Met Leu Ala Glu Ala Lys Glu Asp Ala Ile Lys Glu Leu Asp Lys Tyr
1               5                   10                  15

Gly Val Ser Asp Tyr Tyr Lys Asn Leu Ile Asn Lys Ala Lys Thr Val
                20                  25                  30

Glu Gly Val Glu Ala Leu Thr Leu His Ile Leu Ala Ala Leu Pro Thr
            35                  40                  45

Gly Gly Gly Gly Ala Ser Val Pro Ile Gln Lys Val Gln Asp Asp Thr
        50                  55                  60

Lys Thr Leu Ile Lys Thr Ile Val Thr Arg Ile Asn Asp Ile Ser His
65                  70                  75                  80

```
Thr Gln Ser Val Ser Ser Lys Gln Lys Val Thr Gly Leu Glu Phe Ile
                85                  90                  95

Pro Gly Leu His Pro Ile Leu Thr Leu Ser Lys Met Asp Gln Thr Leu
            100                 105                 110

Ala Val Tyr Gln Gln Ile Leu Thr Ser Met Pro Ser Arg Asn Val Ile
        115                 120                 125

Gln Ile Ser Asn Asp Leu Glu Asn Leu Arg Asp Leu Leu His Val Leu
    130                 135                 140

Ala Phe Ser Lys Ser Cys His Leu Pro Gln Ala Ser Gly Leu Glu Thr
145                 150                 155                 160

Leu Glu Ser Leu Gly Gly Val Leu Glu Ala Ser Gly Tyr Ser Thr Glu
                165                 170                 175

Val Val Ala Leu Ser Arg Leu Gln Gly Ser Leu Gln Asp Met Leu Gln
            180                 185                 190

Gln Leu Asp Leu Ser Pro Gly Cys
        195                 200

<210> SEQ ID NO 71
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Met Leu Ala Glu Ala Lys Glu Asp Ala Ile Lys Glu Leu Asp Lys Tyr
1               5                   10                  15

Gly Val Ser Asp Tyr Tyr Lys Asn Leu Ile Asn Lys Ala Lys Thr Val
            20                  25                  30

Glu Gly Val Glu Ala Leu Thr Leu His Ile Leu Ala Ala Leu Pro Thr
        35                  40                  45

Gly Gly Gly Gly Ser Gly Gly Gly Ser Gly Gly Gly Ser Gly Gly Gly
    50                  55                  60

Ser Ala Ser Val Pro Ile Gln Lys Val Gln Asp Asp Thr Lys Thr Leu
65                  70                  75                  80

Ile Lys Thr Ile Val Thr Arg Ile Asn Asp Ile Ser His Thr Gln Ser
                85                  90                  95

Val Ser Ser Lys Gln Lys Val Thr Gly Leu Glu Phe Ile Pro Gly Leu
            100                 105                 110

His Pro Ile Leu Thr Leu Ser Lys Met Asp Gln Thr Leu Ala Val Tyr
        115                 120                 125

Gln Gln Ile Leu Thr Ser Met Pro Ser Arg Asn Val Ile Gln Ile Ser
    130                 135                 140

Asn Asp Leu Glu Asn Leu Arg Asp Leu Leu His Val Leu Ala Phe Ser
145                 150                 155                 160

Lys Ser Cys His Leu Pro Gln Ala Ser Gly Leu Glu Thr Leu Glu Ser
                165                 170                 175

Leu Gly Gly Val Leu Glu Ala Ser Gly Tyr Ser Thr Glu Val Val Ala
            180                 185                 190

Leu Ser Arg Leu Gln Gly Ser Leu Gln Asp Met Leu Gln Gln Leu Asp
        195                 200                 205

Leu Ser Pro Gly Cys
    210

<210> SEQ ID NO 72
```

<211> LENGTH: 201
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Lys Val Thr Gly Leu Glu Phe Ile Pro Gly Leu His Pro
        35                  40                  45

Ile Leu Thr Leu Ser Lys Met Asp Gln Thr Leu Ala Val Tyr Gln Gln
    50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys His Leu Pro Gln Ala Ser Gly Leu Glu Thr Leu Glu Ser Leu Gly
            100                 105                 110

Gly Val Leu Glu Ala Ser Gly Tyr Ser Thr Glu Val Val Ala Leu Ser
        115                 120                 125

Arg Leu Gln Gly Ser Leu Gln Asp Met Leu Gln Gln Leu Asp Leu Ser
    130                 135                 140

Pro Gly Cys Thr Gly Gly Gly Ser Ala Ser Leu Ala Glu Ala Lys
145                 150                 155                 160

Glu Asp Ala Ile Lys Glu Leu Asp Lys Tyr Gly Val Ser Asp Tyr Tyr
                165                 170                 175

Lys Asn Leu Ile Asn Lys Ala Lys Thr Val Glu Gly Val Glu Ala Leu
            180                 185                 190

Thr Leu His Ile Leu Ala Ala Leu Pro
        195                 200

<210> SEQ ID NO 73
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Lys Val Thr Gly Leu Glu Phe Ile Pro Gly Leu His Pro
        35                  40                  45

Ile Leu Thr Leu Ser Lys Met Asp Gln Thr Leu Ala Val Tyr Gln Gln
    50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys His Leu Pro Gln Ala Ser Gly Leu Glu Thr Leu Glu Ser Leu Gly
            100                 105                 110

```
Gly Val Leu Glu Ala Ser Gly Tyr Ser Thr Glu Val Ala Leu Ser
            115                 120                 125

Arg Leu Gln Gly Ser Leu Gln Asp Met Leu Gln Gln Leu Asp Leu Ser
130                 135                 140

Pro Gly Cys Thr Gly Gly Gly Ser Gly Gly Gly Ser Gly Gly Gly
145                 150                 155                 160

Ser Gly Gly Gly Ser Ala Ser Leu Ala Glu Ala Lys Glu Asp Ala Ile
                165                 170                 175

Lys Glu Leu Asp Lys Tyr Gly Val Ser Asp Tyr Tyr Lys Asn Leu Ile
            180                 185                 190

Asn Lys Ala Lys Thr Val Glu Gly Val Glu Ala Leu Thr Leu His Ile
            195                 200                 205

Leu Ala Ala Leu Pro
            210
```

<210> SEQ ID NO 74
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

```
Met Leu Ala Glu Ala Lys Glu Asp Ala Ile Lys Glu Leu Asp Lys Tyr
1               5                   10                  15

Gly Val Ser Asp Tyr Tyr Lys Asn Leu Ile Asn Lys Ala Lys Thr Val
            20                  25                  30

Glu Gly Val Glu Ala Leu Thr Leu His Ile Leu Ala Ala Leu Pro Thr
            35                  40                  45

Gly Gly Gly Gly Ser Gly Gly Gly Ser Gly Gly Gly Ser Gly Gly Gly
        50                  55                  60

Ser Ala Ser Ile Ser Ile Glu Lys Ile Gln Ala Asp Thr Lys Thr Leu
65                  70                  75                  80

Thr Lys Thr Ile Ile Thr Arg Ile Ile Gln Leu Ser Thr Gln Asn Gly
                85                  90                  95

Val Ser Thr Asp Gln Arg Val Ser Gly Leu Asp Phe Ile Pro Gly Asn
            100                 105                 110

Gln Gln Phe Gln Asn Leu Ala Asp Met Asp Gln Thr Leu Ala Val Tyr
            115                 120                 125

Gln Gln Ile Leu Ser Ser Leu Pro Met Pro Asp Arg Thr Gln Ile Ser
            130                 135                 140

Asn Asp Leu Glu Asn Leu Arg Ser Leu Phe Ala Leu Leu Ala Thr Leu
145                 150                 155                 160

Lys Asn Cys Pro Phe Thr Arg Ser Asp Gly Leu Asp Thr Met Glu Ile
                165                 170                 175

Trp Gly Gly Ile Val Glu Glu Ser Leu Tyr Ser Thr Glu Val Val Thr
            180                 185                 190

Leu Asp Arg Leu Arg Lys Ser Leu Lys Asn Ile Glu Lys Gln Leu Asp
            195                 200                 205

His Ile Gln Gly Cys
        210
```

<210> SEQ ID NO 75
<211> LENGTH: 213
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 75

Met Leu Ala Glu Ala Lys Glu Asp Ala Ile Lys Glu Leu Asp Lys Tyr
1               5                   10                  15

Gly Val Ser Asp Tyr Tyr Lys Asn Leu Ile Asn Lys Ala Lys Thr Val
                20                  25                  30

Glu Gly Val Glu Ala Leu Thr Leu His Ile Leu Ala Ala Leu Pro Thr
            35                  40                  45

Gly Gly Gly Gly Ser Gly Gly Gly Ser Gly Gly Ser Gly Gly Gly
        50                  55                  60

Ser Ala Ser Val Pro Ile Gln Lys Val Gln Asp Asp Thr Lys Thr Leu
65                  70                  75                  80

Ile Lys Thr Ile Val Thr Arg Ile Asn Asp Ile Ser His Thr Gln Ser
                85                  90                  95

Val Ser Ser Lys Gln Lys Val Thr Gly Leu Asp Phe Ile Pro Gly Leu
            100                 105                 110

His Pro Ile Leu Thr Leu Ser Lys Met Asp Gln Thr Leu Ala Val Tyr
        115                 120                 125

Gln Gln Ile Leu Thr Ser Met Pro Ser Arg Asn Val Ile Gln Ile Ser
    130                 135                 140

Asn Asp Leu Glu Asn Leu Arg Asp Leu Leu His Val Leu Ala Phe Ser
145                 150                 155                 160

Lys Ser Cys His Leu Pro Trp Ala Ser Gly Leu Glu Thr Leu Asp Ser
                165                 170                 175

Leu Gly Gly Val Leu Glu Ala Ser Gly Tyr Ser Thr Glu Val Val Ala
            180                 185                 190

Leu Ser Arg Leu Gln Gly Ser Leu Gln Asp Met Leu Trp Gln Leu Asp
        195                 200                 205

Leu Ser Pro Gly Cys
    210

<210> SEQ ID NO 76
<211> LENGTH: 213
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 76

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
                20                  25                  30

Ser Lys Gln Lys Val Thr Gly Leu Asp Phe Ile Pro Gly Leu His Pro
            35                  40                  45

Ile Leu Thr Leu Ser Lys Met Asp Gln Thr Leu Ala Val Tyr Gln Gln
        50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys His Leu Pro Trp Ala Ser Gly Leu Glu Thr Leu Asp Ser Leu Gly

```
                100             105             110
Gly Val Leu Glu Ala Ser Gly Tyr Ser Thr Glu Val Ala Leu Ser
            115                 120                 125
Arg Leu Gln Gly Ser Leu Gln Asp Met Leu Trp Gln Leu Asp Leu Ser
        130                 135                 140
Pro Gly Cys Thr Gly Gly Gly Ser Gly Gly Ser Gly Gly Gly
145                 150                 155                 160
Ser Gly Gly Gly Ser Ala Ser Leu Ala Glu Ala Lys Glu Asp Ala Ile
                165                 170                 175
Lys Glu Leu Asp Lys Tyr Gly Val Ser Asp Tyr Tyr Lys Asn Leu Ile
            180                 185                 190
Asn Lys Ala Lys Thr Val Glu Gly Val Glu Ala Leu Thr Leu His Ile
        195                 200                 205
Leu Ala Ala Leu Pro
    210

<210> SEQ ID NO 77
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Met Leu Ala Glu Ala Lys Glu Asp Ala Ile Lys Glu Leu Asp Lys Tyr
1               5                   10                  15
Gly Val Ser Asp Tyr Tyr Lys Asn Leu Ile Asn Lys Ala Lys Thr Val
            20                  25                  30
Glu Gly Val Glu Ala Leu Thr Leu His Ile Leu Ala Ala Leu Pro Thr
        35                  40                  45
Gly Gly Gly Gly Ser Gly Gly Gly Ser Gly Gly Gly Ser Gly Gly Gly
    50                  55                  60
Ser Ala Ser Pro Ile Gln Arg Val Gln Asp Asp Thr Lys Thr Leu Ile
65                  70                  75                  80
Lys Thr Ile Ile Thr Arg Ile Asn Asp Ile Ser Pro Pro Gln Gly Val
                85                  90                  95
Cys Ser Arg Pro Arg Val Ala Gly Leu Asp Phe Ile Pro Arg Val Gln
            100                 105                 110
Ser Val Arg Thr Leu Ser Gly Met Asp Gln Ile Leu Ala Thr Tyr Gln
        115                 120                 125
Gln Ile Leu Thr Ser Leu Gln Ser Arg Asn Val Ile Gln Ile Ser Asn
    130                 135                 140
Asp Leu Glu Asn Leu Arg Asp Leu Leu His Val Leu Ala Phe Ser Lys
145                 150                 155                 160
Ser Cys Pro Val Pro Arg Ala Arg Gly Ser Asp Thr Ile Lys Gly Leu
                165                 170                 175
Gly Asn Val Leu Arg Ala Ser Val His Ser Thr Glu Val Val Ala Leu
            180                 185                 190
Ser Arg Leu Lys Ala Ala Leu Gln Asp Met Leu Arg Gln Leu Asp Arg
        195                 200                 205
Asn Pro Gly Cys
    210

<210> SEQ ID NO 78
<211> LENGTH: 212
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Met Leu Ala Glu Ala Lys Glu Asp Ala Ile Lys Glu Leu Asp Lys Tyr
1               5                   10                  15

Gly Val Ser Asp Tyr Tyr Lys Asn Leu Ile Asn Lys Ala Lys Thr Val
            20                  25                  30

Glu Gly Val Glu Ala Leu Thr Leu His Ile Leu Ala Ala Leu Pro Thr
        35                  40                  45

Gly Gly Gly Gly Ser Gly Gly Ser Gly Gly Ser Gly Gly Gly
    50                  55                  60

Ser Ala Ser Pro Ile Gln Arg Val Gln Asp Asp Thr Lys Thr Leu Ile
65                  70                  75                  80

Lys Thr Ile Ile Thr Arg Ile Asn Asp Ile Ser Pro Pro Gln Gly Val
                85                  90                  95

Ser Ser Arg Pro Arg Val Ala Gly Leu Asp Phe Ile Pro Arg Val Gln
            100                 105                 110

Ser Val Arg Thr Leu Ser Gly Met Asp Gln Ile Leu Ala Thr Tyr Gln
            115                 120                 125

Gln Ile Leu Thr Ser Leu Gln Ser Arg Asn Val Ile Gln Ile Ser Asn
        130                 135                 140

Asp Leu Glu Asn Leu Arg Asp Leu Leu His Val Leu Ala Phe Ser Lys
145                 150                 155                 160

Ser Cys Pro Val Pro Arg Ala Arg Gly Ser Asp Thr Ile Lys Gly Leu
                165                 170                 175

Gly Asn Val Leu Arg Ala Ser Val His Ser Thr Glu Val Val Ala Leu
            180                 185                 190

Ser Arg Leu Lys Ala Ala Leu Gln Asp Met Leu Arg Gln Leu Asp Arg
            195                 200                 205

Asn Pro Gly Cys
    210

<210> SEQ ID NO 79
<211> LENGTH: 193
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Met Leu Ala Glu Ala Lys Glu Asp Ala Ile Lys Glu Leu Asp Lys Tyr
1               5                   10                  15

Gly Val Ser Asp Tyr Tyr Lys Asn Leu Ile Asn Lys Ala Lys Thr Val
            20                  25                  30

Glu Gly Val Glu Ala Leu Thr Leu His Ile Leu Ala Ala Leu Pro Thr
        35                  40                  45

Gly Pro Ile Gln Arg Val Gln Asp Asp Thr Lys Thr Leu Ile Lys Thr
    50                  55                  60

Ile Ile Thr Arg Ile Asn Asp Ile Ser Pro Pro Gln Gly Val Cys Ser
65                  70                  75                  80

Pro Arg Val Ala Gly Leu Asp Phe Ile Pro Arg Val Gln Ser Val Arg
                85                  90                  95
```

Thr Leu Ser Gly Met Asp Gln Ile Leu Ala Thr Tyr Gln Gln Ile Leu
            100                 105                 110

Thr Ser Leu Gln Ser Arg Asn Val Ile Gln Ile Ser Asn Asp Leu Glu
        115                 120                 125

Asn Leu Arg Asp Leu Leu His Val Leu Ala Phe Ser Lys Ser Cys Pro
    130                 135                 140

Val Pro Arg Ala Arg Gly Ser Asp Thr Ile Lys Gly Leu Gly Asn Val
145                 150                 155                 160

Leu Arg Ala Ser Val His Ser Thr Glu Val Val Ala Leu Ser Arg Leu
                165                 170                 175

Lys Ala Ala Leu Gln Asp Met Leu Arg Gln Leu Asp Arg Asn Pro Gly
            180                 185                 190

Cys

<210> SEQ ID NO 80
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Met Leu Ala Glu Ala Lys Glu Asp Ala Ile Lys Glu Leu Asp Lys Tyr
1               5                   10                  15

Gly Val Ser Asp Tyr Tyr Lys Asn Leu Ile Asn Lys Ala Lys Thr Val
            20                  25                  30

Glu Gly Val Glu Ala Leu Thr Leu His Ile Leu Ala Ala Leu Pro Thr
        35                  40                  45

Gly Gly Gly Gly Ser Gly Gly Ser Gly Gly Gly Ser Gly Gly Gly
    50                  55                  60

Ser Ala Ser Val Pro Ile Gln Lys Val Gln Asp Asp Thr Lys Thr Leu
65                  70                  75                  80

Ile Lys Thr Ile Val Thr Arg Ile Asn Asp Ile Ser His Thr Gln Ser
                85                  90                  95

Val Ser Ser Lys Gln Lys Val Thr Gly Leu Asp Phe Ile Pro Gly Leu
            100                 105                 110

His Pro Ile Leu Thr Leu Ser Lys Met Asp Gln Thr Leu Ala Val Tyr
        115                 120                 125

Gln Gln Ile Leu Thr Ser Met Pro Ser Arg Asn Val Ile Gln Ile Ser
    130                 135                 140

Asn Asp Leu Glu Asn Leu Arg Asp Leu Leu His Val Leu Ala Phe Ser
145                 150                 155                 160

Lys Ser Cys His Leu Pro Trp Ala Ser Gly Leu Glu Thr Leu Asp Ser
                165                 170                 175

Leu Gly Gly Val Leu Glu Ala Ser Gly Tyr Ser Thr Glu Val Val Ala
            180                 185                 190

Leu Ser Arg Leu Gln Gly Ser Leu Gln Asp Met Leu Trp Gln Leu Asp
        195                 200                 205

Leu Ser Pro Gly Cys
    210

<210> SEQ ID NO 81
<211> LENGTH: 213
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 81

Met Leu Ala Glu Ala Lys Glu Asp Ala Ile Lys Glu Leu Asp Lys Tyr
1               5                   10                  15

Gly Val Ser Asp Tyr Tyr Lys Asn Leu Ile Asn Lys Ala Lys Thr Val
                20                  25                  30

Glu Gly Val Glu Ala Leu Thr Leu His Ile Leu Ala Ala Leu Pro Thr
            35                  40                  45

Gly Gly Gly Gly Ser Gly Gly Ser Gly Gly Ser Gly Gly Gly
        50                  55                  60

Ser Ala Ser Val Pro Ile Gln Lys Val Gln Asp Asp Thr Lys Thr Leu
65                  70                  75                  80

Ile Lys Thr Ile Val Thr Arg Ile Asn Asp Ile Ser His Thr Gln Ser
                85                  90                  95

Val Ser Ser Lys Gln Lys Val Thr Gly Leu Glu Phe Ile Pro Gly Leu
            100                 105                 110

His Pro Ile Leu Thr Leu Ser Lys Met Asp Gln Thr Leu Ala Val Tyr
        115                 120                 125

Gln Gln Ile Leu Thr Ser Met Pro Ser Arg Asn Val Ile Gln Ile Ser
    130                 135                 140

Asn Asp Leu Glu Asn Leu Arg Asp Leu Leu His Val Leu Ala Phe Ser
145                 150                 155                 160

Lys Ser Cys His Leu Pro Gln Ala Ser Gly Leu Glu Thr Leu Glu Ser
                165                 170                 175

Leu Gly Gly Val Leu Glu Ala Ser Gly Tyr Ser Thr Glu Val Val Ala
            180                 185                 190

Leu Ser Arg Leu Gln Gly Ser Leu Gln Asp Met Leu Gln Gln Leu Asp
        195                 200                 205

Leu Ser Pro Gly Cys
    210

<210> SEQ ID NO 82
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Met Leu Ala Glu Ala Lys Glu Asp Ala Ile Lys Glu Leu Asp Lys Tyr
1               5                   10                  15

Gly Val Ser Asp Tyr Tyr Lys Asn Leu Ile Asn Lys Ala Lys Thr Val
                20                  25                  30

Glu Gly Val Glu Ala Leu Thr Leu His Ile Leu Ala Ala Leu Pro Thr
            35                  40                  45

Gly Gly Gly Gly Ser Gly Gly Ser Gly Gly Ser Gly Gly Gly
        50                  55                  60

Ser Ala Ser Val Pro Ile Gln Lys Val Gln Asp Asp Thr Lys Thr Leu
65                  70                  75                  80

Ile Lys Thr Ile Val Thr Arg Ile Asn Asp Ile Ser His Thr Gln Ser
                85                  90                  95

Val Ser Ser Lys Gln Lys Val Thr Gly Leu Asp Phe Ile Pro Gly Leu
            100                 105                 110

```
His Pro Ile Leu Thr Leu Ser Lys Met Asp Gln Thr Leu Ala Val Tyr
        115                 120                 125

Gln Gln Ile Leu Thr Ser Met Pro Ser Arg Asn Val Ile Gln Ile Ser
    130                 135                 140

Asn Asp Leu Glu Asn Leu Arg Asp Leu Leu His Val Leu Ala Phe Ser
145                 150                 155                 160

Lys Ser Cys His Leu Pro Gln Ala Ser Gly Leu Glu Thr Leu Asp Ser
                165                 170                 175

Leu Gly Gly Val Leu Glu Ala Ser Gly Tyr Ser Thr Glu Val Val Ala
            180                 185                 190

Leu Ser Arg Leu Gln Gly Ser Leu Gln Asp Met Leu Gln Gln Leu Asp
        195                 200                 205

Leu Ser Pro Gly Cys
    210

<210> SEQ ID NO 83
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Met Leu Ala Glu Ala Lys Glu Asp Ala Ile Lys Glu Leu Asp Lys Tyr
1               5                   10                  15

Gly Val Ser Asp Tyr Tyr Lys Asn Leu Ile Asn Lys Ala Lys Thr Val
            20                  25                  30

Glu Gly Val Glu Ala Leu Thr Leu His Ile Leu Ala Ala Leu Pro Thr
        35                  40                  45

Gly Leu Ala Glu Ala Ala Ala Lys Glu Ala Ala Lys Glu Ala Ala
    50                  55                  60

Ala Lys Glu Ala Ala Lys Glu Ala Ala Lys Ala Ala Ala
65                  70                  75                  80

Ser Val Pro Ile Gln Lys Val Gln Asp Asp Thr Lys Thr Leu Ile Lys
                85                  90                  95

Thr Ile Val Thr Arg Ile Asn Asp Ile Ser His Thr Gln Ser Val Ser
            100                 105                 110

Ser Lys Gln Lys Val Thr Gly Leu Glu Phe Ile Pro Gly Leu His Pro
        115                 120                 125

Ile Leu Thr Leu Ser Lys Met Asp Gln Thr Leu Ala Val Tyr Gln Gln
    130                 135                 140

Ile Leu Thr Ser Met Pro Ser Arg Asn Val Ile Gln Ile Ser Asn Asp
145                 150                 155                 160

Leu Glu Asn Leu Arg Asp Leu Leu His Val Leu Ala Phe Ser Lys Ser
                165                 170                 175

Cys His Leu Pro Gln Ala Ser Gly Leu Glu Thr Leu Glu Ser Leu Gly
            180                 185                 190

Gly Val Leu Glu Ala Ser Gly Tyr Ser Thr Glu Val Val Ala Leu Ser
        195                 200                 205

Arg Leu Gln Gly Ser Leu Gln Asp Met Leu Gln Gln Leu Asp Leu Ser
    210                 215                 220

Pro Gly Cys
225

<210> SEQ ID NO 84
```

-continued

<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Met Leu Ala Glu Ala Lys Glu Asp Ala Ile Lys Glu Leu Asp Lys Tyr
1               5                   10                  15

Gly Val Ser Asp Tyr Tyr Lys Asn Leu Ile Asn Lys Ala Lys Thr Val
            20                  25                  30

Glu Gly Val Glu Ala Leu Thr Leu His Ile Leu Ala Ala Leu Pro Thr
        35                  40                  45

Gly Gly Glu Gly Gly Glu Gly Gly Glu Gly Gly Glu Gly Gly Glu Gly
    50                  55                  60

Gly Glu Ala Ser Val Pro Ile Gln Lys Val Gln Asp Asp Thr Lys Thr
65                  70                  75                  80

Leu Ile Lys Thr Ile Val Thr Arg Ile Asn Asp Ile Ser His Thr Gln
                85                  90                  95

Ser Val Ser Ser Lys Gln Lys Val Thr Gly Leu Glu Phe Ile Pro Gly
            100                 105                 110

Leu His Pro Ile Leu Thr Leu Ser Lys Met Asp Gln Thr Leu Ala Val
        115                 120                 125

Tyr Gln Gln Ile Leu Thr Ser Met Pro Ser Arg Asn Val Ile Gln Ile
    130                 135                 140

Ser Asn Asp Leu Glu Asn Leu Arg Asp Leu Leu His Val Leu Ala Phe
145                 150                 155                 160

Ser Lys Ser Cys His Leu Pro Gln Ala Ser Gly Leu Glu Thr Leu Glu
                165                 170                 175

Ser Leu Gly Gly Val Leu Glu Ala Ser Gly Tyr Ser Thr Glu Val Val
            180                 185                 190

Ala Leu Ser Arg Leu Gln Gly Ser Leu Gln Asp Met Leu Gln Gln Leu
        195                 200                 205

Asp Leu Ser Pro Gly Cys
    210

<210> SEQ ID NO 85
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Met Leu Ala Glu Ala Lys Glu Asp Ala Ile Lys Glu Leu Asp Lys Tyr
1               5                   10                  15

Gly Val Ser Asp Tyr Tyr Lys Asn Leu Ile Asn Lys Ala Lys Thr Val
            20                  25                  30

Glu Gly Val Glu Ala Leu Thr Leu His Ile Leu Ala Ala Leu Pro Thr
        35                  40                  45

Gly Gly Lys Gly Gly Lys Gly Gly Lys Gly Gly Lys Gly Gly Lys Gly
    50                  55                  60

Gly Lys Ala Ser Val Pro Ile Gln Lys Val Gln Asp Asp Thr Lys Thr
65                  70                  75                  80

Leu Ile Lys Thr Ile Val Thr Arg Ile Asn Asp Ile Ser His Thr Gln
                85                  90                  95

Ser Val Ser Ser Lys Gln Lys Val Thr Gly Leu Glu Phe Ile Pro Gly
                100                 105                 110

Leu His Pro Ile Leu Thr Leu Ser Lys Met Asp Gln Thr Leu Ala Val
            115                 120                 125

Tyr Gln Gln Ile Leu Thr Ser Met Pro Ser Arg Asn Val Ile Gln Ile
    130                 135                 140

Ser Asn Asp Leu Glu Asn Leu Arg Asp Leu Leu His Val Leu Ala Phe
145                 150                 155                 160

Ser Lys Ser Cys His Leu Pro Gln Ala Ser Gly Leu Glu Thr Leu Glu
                165                 170                 175

Ser Leu Gly Gly Val Leu Glu Ala Ser Gly Tyr Ser Thr Glu Val Val
            180                 185                 190

Ala Leu Ser Arg Leu Gln Gly Ser Leu Gln Asp Met Leu Gln Gln Leu
        195                 200                 205

Asp Leu Ser Pro Gly Cys
    210

<210> SEQ ID NO 86
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Met Leu Ala Glu Ala Lys Glu Asp Ala Ile Lys Glu Leu Asp Lys Tyr
1               5                   10                  15

Gly Val Ser Asp Tyr Tyr Lys Asn Leu Ile Asn Lys Ala Lys Thr Val
            20                  25                  30

Glu Gly Val Glu Ala Leu Thr Leu His Ile Leu Ala Ala Leu Pro Thr
        35                  40                  45

Gly Gly Gly Gly Ser Gly Gly Ser Gly Gly Ser Gly Gly Gly
    50                  55                  60

Ser Ala Ser Val Pro Ile Gln Lys Val Gln Asp Asp Thr Lys Thr Leu
65                  70                  75                  80

Ile Lys Thr Ile Val Thr Arg Ile Asn Asp Ile Ser His Thr Gln Ser
                85                  90                  95

Val Ser Ser Lys Gln Lys Val Thr Gly Leu Glu Phe Ile Pro Gly Leu
                100                 105                 110

His Pro Ile Leu Thr Leu Ser Lys Met Asp Gln Thr Leu Ala Val Tyr
            115                 120                 125

Gln Gln Ile Leu Thr Ser Met Pro Ser Arg Asn Val Ile Gln Ile Ser
    130                 135                 140

Asn Asp Leu Glu Asn Leu Arg Asp Leu Leu His Val Leu Ala Phe Ser
145                 150                 155                 160

Lys Ser Cys Ser Leu Pro Gln Ala Ser Gly Leu Glu Thr Leu Glu Ser
                165                 170                 175

Leu Gly Glu Val Leu Glu Ala Ser Gly Tyr Ser Thr Glu Val Val Ala
            180                 185                 190

Leu Ser Arg Leu Gln Gly Ser Leu Gln Asp Ile Leu Gln Gln Leu Asp
        195                 200                 205

Leu Ser Pro Glu Cys
    210

```
<210> SEQ ID NO 87
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Met Leu Ala Glu Ala Lys Glu Asp Ala Ile Lys Glu Leu Asp Lys Tyr
1               5                   10                  15

Gly Val Ser Asp Tyr Tyr Lys Asn Leu Ile Asn Lys Ala Lys Thr Val
            20                  25                  30

Glu Gly Val Glu Ala Leu Ile Ser Glu Ile Leu Ala Ala Leu Pro Thr
        35                  40                  45

Gly Gly Gly Gly Ala Ser Val Pro Ile Gln Lys Val Gln Asp Thr
    50                  55                  60

Lys Thr Leu Ile Lys Thr Ile Val Thr Arg Ile Asn Asp Ile Ser His
65                  70                  75                  80

Thr Gln Ser Val Ser Ser Lys Gln Lys Val Thr Gly Leu Glu Phe Ile
                85                  90                  95

Pro Gly Leu His Pro Ile Leu Thr Leu Ser Lys Met Asp Gln Thr Leu
            100                 105                 110

Ala Val Tyr Gln Gln Ile Leu Thr Ser Met Pro Ser Arg Asn Val Ile
        115                 120                 125

Gln Ile Ser Asn Asp Leu Glu Asn Leu Arg Asp Leu Leu His Val Leu
    130                 135                 140

Ala Phe Ser Lys Ser Cys His Leu Pro Gln Ala Ser Gly Leu Glu Thr
145                 150                 155                 160

Leu Glu Ser Leu Gly Gly Val Leu Glu Ala Ser Gly Tyr Ser Thr Glu
                165                 170                 175

Val Val Ala Leu Ser Arg Leu Gln Gly Ser Leu Gln Asp Met Leu Gln
            180                 185                 190

Gln Leu Asp Leu Ser Pro Gly Cys
        195                 200

<210> SEQ ID NO 88
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Met Leu Ala Glu Ala Lys Glu Asp Ala Ile Lys Glu Leu Asp Lys Tyr
1               5                   10                  15

Gly Val Ser Asp Tyr Tyr Lys Asn Leu Ile Asn Lys Ala Lys Thr Val
            20                  25                  30

Glu Gly Val Glu Ala Leu Ile Ser Glu Ile Leu Ala Ala Leu Pro Thr
        35                  40                  45

Gly Gly Gly Gly Ser Gly Gly Ser Gly Gly Ser Gly Gly Gly
    50                  55                  60

Ser Ala Ser Val Pro Ile Gln Lys Val Gln Asp Thr Lys Thr Leu
65                  70                  75                  80

Ile Lys Thr Ile Val Thr Arg Ile Asn Asp Ile Ser His Thr Gln Ser
                85                  90                  95

Val Ser Ser Lys Gln Lys Val Thr Gly Leu Glu Phe Ile Pro Gly Leu
```

```
              100                 105                 110
His Pro Ile Leu Thr Leu Ser Lys Met Asp Gln Thr Leu Ala Val Tyr
            115                 120                 125

Gln Gln Ile Leu Thr Ser Met Pro Ser Arg Asn Val Ile Gln Ile Ser
        130                 135                 140

Asn Asp Leu Glu Asn Leu Arg Asp Leu Leu His Val Leu Ala Phe Ser
145                 150                 155                 160

Lys Ser Cys His Leu Pro Gln Ala Ser Gly Leu Glu Thr Leu Glu Ser
                165                 170                 175

Leu Gly Gly Val Leu Glu Ala Ser Gly Tyr Ser Thr Glu Val Val Ala
            180                 185                 190

Leu Ser Arg Leu Gln Gly Ser Leu Gln Asp Met Leu Gln Gln Leu Asp
        195                 200                 205

Leu Ser Pro Gly Cys
        210

<210> SEQ ID NO 89
<211> LENGTH: 201
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Lys Val Thr Gly Leu Glu Phe Ile Pro Gly Leu His Pro
        35                  40                  45

Ile Leu Thr Leu Ser Lys Met Asp Gln Thr Leu Ala Val Tyr Gln Gln
    50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys His Leu Pro Gln Ala Ser Gly Leu Glu Thr Leu Glu Ser Leu Gly
            100                 105                 110

Gly Val Leu Glu Ala Ser Gly Tyr Ser Thr Glu Val Val Ala Leu Ser
        115                 120                 125

Arg Leu Gln Gly Ser Leu Gln Asp Met Leu Gln Gln Leu Asp Leu Ser
    130                 135                 140

Pro Gly Cys Thr Gly Gly Gly Ser Ala Ser Leu Ala Glu Ala Lys
145                 150                 155                 160

Glu Asp Ala Ile Lys Glu Leu Asp Lys Tyr Gly Val Ser Asp Tyr Tyr
                165                 170                 175

Lys Asn Leu Ile Asn Lys Ala Lys Thr Val Glu Gly Val Glu Ala Leu
            180                 185                 190

Ile Ser Glu Ile Leu Ala Ala Leu Pro
        195                 200

<210> SEQ ID NO 90
<211> LENGTH: 213
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 90

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Lys Val Thr Gly Leu Glu Phe Ile Pro Gly Leu His Pro
        35                  40                  45

Ile Leu Thr Leu Ser Lys Met Asp Gln Thr Leu Ala Val Tyr Gln Gln
    50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys His Leu Pro Gln Ala Ser Gly Leu Glu Thr Leu Glu Ser Leu Gly
            100                 105                 110

Gly Val Leu Glu Ala Ser Gly Tyr Ser Thr Glu Val Val Ala Leu Ser
        115                 120                 125

Arg Leu Gln Gly Ser Leu Gln Asp Met Leu Gln Gln Leu Asp Leu Ser
    130                 135                 140

Pro Gly Cys Thr Gly Gly Gly Ser Gly Gly Gly Ser Gly Gly Gly Gly
145                 150                 155                 160

Ser Gly Gly Gly Ser Ala Ser Leu Ala Glu Ala Lys Glu Asp Ala Ile
                165                 170                 175

Lys Glu Leu Asp Lys Tyr Gly Val Ser Asp Tyr Tyr Lys Asn Leu Ile
            180                 185                 190

Asn Lys Ala Lys Thr Val Glu Gly Val Glu Ala Leu Ile Ser Glu Ile
        195                 200                 205

Leu Ala Ala Leu Pro
    210

<210> SEQ ID NO 91
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Met Leu Ala Glu Ala Lys Glu Asp Ala Ile Lys Glu Leu Asp Lys Tyr
1               5                   10                  15

Gly Val Ser Asp Tyr Tyr Lys Asn Leu Ile Asn Lys Ala Lys Thr Val
            20                  25                  30

Glu Gly Val Glu Ala Leu Ile Ser Glu Ile Leu Ala Ala Leu Pro Thr
        35                  40                  45

Gly Gly Gly Gly Ser Gly Gly Gly Ser Gly Gly Gly Ser Gly Gly Gly
    50                  55                  60

Ser Ala Ser Ile Ser Ile Glu Lys Ile Gln Ala Asp Thr Lys Thr Leu
65                  70                  75                  80

Thr Lys Thr Ile Ile Thr Arg Ile Ile Gln Leu Ser Thr Gln Asn Gly
                85                  90                  95

Val Ser Thr Asp Gln Arg Val Ser Gly Leu Asp Phe Ile Pro Gly Asn
            100                 105                 110

```
Gln Gln Phe Gln Asn Leu Ala Asp Met Asp Gln Thr Leu Ala Val Tyr
            115                 120                 125

Gln Gln Ile Leu Ser Ser Leu Pro Met Pro Asp Arg Thr Gln Ile Ser
    130                 135                 140

Asn Asp Leu Glu Asn Leu Arg Ser Leu Phe Ala Leu Leu Ala Thr Leu
145                 150                 155                 160

Lys Asn Cys Pro Phe Thr Arg Ser Asp Gly Leu Asp Thr Met Glu Ile
                165                 170                 175

Trp Gly Gly Ile Val Glu Glu Ser Leu Tyr Ser Thr Glu Val Val Thr
            180                 185                 190

Leu Asp Arg Leu Arg Lys Ser Leu Lys Asn Ile Glu Lys Gln Leu Asp
        195                 200                 205

His Ile Gln Gly Cys
    210

<210> SEQ ID NO 92
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Met Leu Ala Glu Ala Lys Glu Asp Ala Ile Lys Glu Leu Asp Lys Tyr
1               5                   10                  15

Gly Val Ser Asp Tyr Tyr Lys Asn Leu Ile Asn Lys Ala Lys Thr Val
            20                  25                  30

Glu Gly Val Glu Ala Leu Ile Ser Glu Ile Leu Ala Ala Leu Pro Thr
        35                  40                  45

Gly Gly Gly Gly Ser Gly Gly Gly Ser Gly Gly Gly Ser Gly Gly Gly
    50                  55                  60

Ser Ala Ser Val Pro Ile Gln Lys Val Gln Asp Asp Thr Lys Thr Leu
65                  70                  75                  80

Ile Lys Thr Ile Val Thr Arg Ile Asn Asp Ile Ser His Thr Gln Ser
                85                  90                  95

Val Ser Ser Lys Gln Lys Val Thr Gly Leu Asp Phe Ile Pro Gly Leu
            100                 105                 110

His Pro Ile Leu Thr Leu Ser Lys Met Asp Gln Thr Leu Ala Val Tyr
        115                 120                 125

Gln Gln Ile Leu Thr Ser Met Pro Ser Arg Asn Val Ile Gln Ile Ser
    130                 135                 140

Asn Asp Leu Glu Asn Leu Arg Asp Leu Leu His Val Leu Ala Phe Ser
145                 150                 155                 160

Lys Ser Cys His Leu Pro Trp Ala Ser Gly Leu Glu Thr Leu Asp Ser
                165                 170                 175

Leu Gly Gly Val Leu Glu Ala Ser Gly Tyr Ser Thr Glu Val Val Ala
            180                 185                 190

Leu Ser Arg Leu Gln Gly Ser Leu Gln Asp Met Leu Trp Gln Leu Asp
        195                 200                 205

Leu Ser Pro Gly Cys
    210

<210> SEQ ID NO 93
<211> LENGTH: 213
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 93

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Lys Val Thr Gly Leu Asp Phe Ile Pro Gly Leu His Pro
        35                  40                  45

Ile Leu Thr Leu Ser Lys Met Asp Gln Thr Leu Ala Val Tyr Gln Gln
50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys His Leu Pro Trp Ala Ser Gly Leu Glu Thr Leu Asp Ser Leu Gly
            100                 105                 110

Gly Val Leu Glu Ala Ser Gly Tyr Ser Thr Glu Val Val Ala Leu Ser
        115                 120                 125

Arg Leu Gln Gly Ser Leu Gln Asp Met Leu Trp Gln Leu Asp Leu Ser
130                 135                 140

Pro Gly Cys Thr Gly Gly Gly Ser Gly Gly Gly Ser Gly Gly Gly
145                 150                 155                 160

Ser Gly Gly Gly Ser Ala Ser Leu Ala Glu Ala Lys Glu Asp Ala Ile
                165                 170                 175

Lys Glu Leu Asp Lys Tyr Gly Val Ser Asp Tyr Tyr Lys Asn Leu Ile
            180                 185                 190

Asn Lys Ala Lys Thr Val Glu Gly Val Glu Ala Leu Ile Ser Glu Ile
        195                 200                 205

Leu Ala Ala Leu Pro
        210

<210> SEQ ID NO 94
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Met Leu Ala Glu Ala Lys Glu Asp Ala Ile Lys Glu Leu Asp Lys Tyr
1               5                   10                  15

Gly Val Ser Asp Tyr Tyr Lys Asn Leu Ile Asn Lys Ala Lys Thr Val
            20                  25                  30

Glu Gly Val Glu Ala Leu Ile Ser Glu Ile Leu Ala Ala Leu Pro Thr
        35                  40                  45

Gly Gly Gly Gly Ser Gly Gly Gly Ser Gly Gly Gly Ser Gly Gly Gly
    50                  55                  60

Ser Ala Ser Pro Ile Gln Arg Val Gln Asp Asp Thr Lys Thr Leu Ile
65                  70                  75                  80

Lys Thr Ile Ile Thr Arg Ile Asn Asp Ile Ser Pro Pro Gln Gly Val
                85                  90                  95

Cys Ser Arg Pro Arg Val Ala Gly Leu Asp Phe Ile Pro Arg Val Gln
            100                 105                 110

```
Ser Val Arg Thr Leu Ser Gly Met Asp Gln Ile Leu Ala Thr Tyr Gln
            115                 120                 125

Gln Ile Leu Thr Ser Leu Gln Ser Arg Asn Val Ile Gln Ile Ser Asn
        130                 135                 140

Asp Leu Glu Asn Leu Arg Asp Leu Leu His Val Leu Ala Phe Ser Lys
145                 150                 155                 160

Ser Cys Pro Val Pro Arg Ala Arg Gly Ser Asp Thr Ile Lys Gly Leu
                165                 170                 175

Gly Asn Val Leu Arg Ala Ser Val His Ser Thr Glu Val Val Ala Leu
                180                 185                 190

Ser Arg Leu Lys Ala Ala Leu Gln Asp Met Leu Arg Gln Leu Asp Arg
            195                 200                 205

Asn Pro Gly Cys
        210

<210> SEQ ID NO 95
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Met Leu Ala Glu Ala Lys Glu Asp Ala Ile Lys Glu Leu Asp Lys Tyr
1               5                   10                  15

Gly Val Ser Asp Tyr Tyr Lys Asn Leu Ile Asn Lys Ala Lys Thr Val
            20                  25                  30

Glu Gly Val Glu Ala Leu Ile Ser Glu Ile Leu Ala Ala Leu Pro Thr
        35                  40                  45

Gly Gly Gly Gly Ser Gly Gly Gly Ser Gly Gly Gly Ser Gly Gly Gly
    50                  55                  60

Ser Ala Ser Pro Ile Gln Arg Val Gln Asp Asp Thr Lys Thr Leu Ile
65                  70                  75                  80

Lys Thr Ile Ile Thr Arg Ile Asn Asp Ile Ser Pro Pro Gln Gly Val
                85                  90                  95

Ser Ser Arg Pro Arg Val Ala Gly Leu Asp Phe Ile Pro Arg Val Gln
            100                 105                 110

Ser Val Arg Thr Leu Ser Gly Met Asp Gln Ile Leu Ala Thr Tyr Gln
            115                 120                 125

Gln Ile Leu Thr Ser Leu Gln Ser Arg Asn Val Ile Gln Ile Ser Asn
        130                 135                 140

Asp Leu Glu Asn Leu Arg Asp Leu Leu His Val Leu Ala Phe Ser Lys
145                 150                 155                 160

Ser Cys Pro Val Pro Arg Ala Arg Gly Ser Asp Thr Ile Lys Gly Leu
                165                 170                 175

Gly Asn Val Leu Arg Ala Ser Val His Ser Thr Glu Val Val Ala Leu
                180                 185                 190

Ser Arg Leu Lys Ala Ala Leu Gln Asp Met Leu Arg Gln Leu Asp Arg
            195                 200                 205

Asn Pro Gly Cys
        210

<210> SEQ ID NO 96
<211> LENGTH: 193
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 96

Met Leu Ala Glu Ala Lys Glu Asp Ala Ile Lys Glu Leu Asp Lys Tyr
1               5                   10                  15

Gly Val Ser Asp Tyr Tyr Lys Asn Leu Ile Asn Lys Ala Lys Thr Val
                20                  25                  30

Glu Gly Val Glu Ala Leu Ile Ser Glu Ile Leu Ala Ala Leu Pro Thr
            35                  40                  45

Gly Pro Ile Gln Arg Val Gln Asp Asp Thr Lys Thr Leu Ile Lys Thr
        50                  55                  60

Ile Ile Thr Arg Ile Asn Asp Ile Ser Pro Pro Gln Gly Val Cys Ser
65                  70                  75                  80

Pro Arg Val Ala Gly Leu Asp Phe Ile Pro Arg Val Gln Ser Val Arg
                85                  90                  95

Thr Leu Ser Gly Met Asp Gln Ile Leu Ala Thr Tyr Gln Gln Ile Leu
            100                 105                 110

Thr Ser Leu Gln Ser Arg Asn Val Ile Gln Ile Ser Asn Asp Leu Glu
        115                 120                 125

Asn Leu Arg Asp Leu Leu His Val Leu Ala Phe Ser Lys Ser Cys Pro
130                 135                 140

Val Pro Arg Ala Arg Gly Ser Asp Thr Ile Lys Gly Leu Gly Asn Val
145                 150                 155                 160

Leu Arg Ala Ser Val His Ser Thr Glu Val Val Ala Leu Ser Arg Leu
                165                 170                 175

Lys Ala Ala Leu Gln Asp Met Leu Arg Gln Leu Asp Arg Asn Pro Gly
            180                 185                 190

Cys

<210> SEQ ID NO 97
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Met Leu Ala Glu Ala Lys Glu Asp Ala Ile Lys Glu Leu Asp Lys Tyr
1               5                   10                  15

Gly Val Ser Asp Tyr Tyr Lys Asn Leu Ile Asn Lys Ala Lys Thr Val
                20                  25                  30

Glu Gly Val Glu Ala Leu Ile Ser Glu Ile Leu Ala Ala Leu Pro Thr
            35                  40                  45

Gly Gly Gly Gly Ser Gly Gly Ser Gly Gly Ser Gly Gly Gly
        50                  55                  60

Ser Ala Ser Val Pro Ile Gln Lys Val Gln Asp Asp Thr Lys Thr Leu
65                  70                  75                  80

Ile Lys Thr Ile Val Thr Arg Ile Asn Asp Ile Ser His Thr Gln Ser
                85                  90                  95

Val Ser Ser Lys Gln Lys Val Thr Gly Leu Asp Phe Ile Pro Gly Leu
            100                 105                 110

His Pro Ile Leu Thr Leu Ser Lys Met Asp Gln Thr Leu Ala Val Tyr
        115                 120                 125

```
Gln Gln Ile Leu Thr Ser Met Pro Ser Arg Asn Val Ile Gln Ile Ser
        130                 135                 140

Asn Asp Leu Glu Asn Leu Arg Asp Leu Leu His Val Leu Ala Phe Ser
145                 150                 155                 160

Lys Ser Cys His Leu Pro Trp Ala Ser Gly Leu Glu Thr Leu Asp Ser
                165                 170                 175

Leu Gly Gly Val Leu Glu Ala Ser Gly Tyr Ser Thr Glu Val Val Ala
                180                 185                 190

Leu Ser Arg Leu Gln Gly Ser Leu Gln Asp Met Leu Trp Gln Leu Asp
        195                 200                 205

Leu Ser Pro Gly Cys
    210

<210> SEQ ID NO 98
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Met Leu Ala Glu Ala Lys Glu Asp Ala Ile Lys Glu Leu Asp Lys Tyr
1               5                   10                  15

Gly Val Ser Asp Tyr Tyr Lys Asn Leu Ile Asn Lys Ala Lys Thr Val
                20                  25                  30

Glu Gly Val Glu Ala Leu Ile Ser Glu Ile Leu Ala Ala Leu Pro Thr
            35                  40                  45

Gly Gly Gly Gly Ser Gly Gly Gly Ser Gly Gly Gly Ser Gly Gly Gly
        50                  55                  60

Ser Ala Ser Val Pro Ile Gln Lys Val Gln Asp Asp Thr Lys Thr Leu
65                  70                  75                  80

Ile Lys Thr Ile Val Thr Arg Ile Asn Asp Ile Ser His Thr Gln Ser
                85                  90                  95

Val Ser Ser Lys Gln Lys Val Thr Gly Leu Glu Phe Ile Pro Gly Leu
                100                 105                 110

His Pro Ile Leu Thr Leu Ser Lys Met Asp Gln Thr Leu Ala Val Tyr
            115                 120                 125

Gln Gln Ile Leu Thr Ser Met Pro Ser Arg Asn Val Ile Gln Ile Ser
        130                 135                 140

Asn Asp Leu Glu Asn Leu Arg Asp Leu Leu His Val Leu Ala Phe Ser
145                 150                 155                 160

Lys Ser Cys His Leu Pro Gln Ala Ser Gly Leu Glu Thr Leu Glu Ser
                165                 170                 175

Leu Gly Gly Val Leu Glu Ala Ser Gly Tyr Ser Thr Glu Val Val Ala
                180                 185                 190

Leu Ser Arg Leu Gln Gly Ser Leu Gln Asp Met Leu Gln Gln Leu Asp
        195                 200                 205

Leu Ser Pro Gly Cys
    210

<210> SEQ ID NO 99
<211> LENGTH: 213
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 99

Met Leu Ala Glu Ala Lys Glu Asp Ala Ile Lys Glu Leu Asp Lys Tyr
1               5                   10                  15

Gly Val Ser Asp Tyr Tyr Lys Asn Leu Ile Asn Lys Ala Lys Thr Val
            20                  25                  30

Glu Gly Val Glu Ala Leu Ile Ser Glu Ile Leu Ala Ala Leu Pro Thr
        35                  40                  45

Gly Gly Gly Gly Ser Gly Gly Gly Gly Ser Gly Gly Gly
    50                  55                  60

Ser Ala Ser Val Pro Ile Gln Lys Val Gln Asp Thr Lys Thr Leu
65                  70                  75                  80

Ile Lys Thr Ile Val Thr Arg Ile Asn Asp Ile Ser His Thr Gln Ser
                85                  90                  95

Val Ser Ser Lys Gln Lys Val Thr Gly Leu Asp Phe Ile Pro Gly Leu
            100                 105                 110

His Pro Ile Leu Thr Leu Ser Lys Met Asp Gln Thr Leu Ala Val Tyr
        115                 120                 125

Gln Gln Ile Leu Thr Ser Met Pro Ser Arg Asn Val Ile Gln Ile Ser
130                 135                 140

Asn Asp Leu Glu Asn Leu Arg Asp Leu Leu His Val Leu Ala Phe Ser
145                 150                 155                 160

Lys Ser Cys His Leu Pro Gln Ala Ser Gly Leu Glu Thr Leu Asp Ser
                165                 170                 175

Leu Gly Gly Val Leu Glu Ala Ser Gly Tyr Ser Thr Glu Val Val Ala
            180                 185                 190

Leu Ser Arg Leu Gln Gly Ser Leu Gln Asp Met Leu Gln Gln Leu Asp
        195                 200                 205

Leu Ser Pro Gly Cys
    210

<210> SEQ ID NO 100
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Met Leu Ala Glu Ala Lys Glu Asp Ala Ile Lys Glu Leu Asp Lys Tyr
1               5                   10                  15

Gly Val Ser Asp Tyr Tyr Lys Asn Leu Ile Asn Lys Ala Lys Thr Val
            20                  25                  30

Glu Gly Val Glu Ala Leu Ile Ser Glu Ile Leu Ala Ala Leu Pro Thr
        35                  40                  45

Gly Leu Ala Glu Ala Ala Ala Lys Glu Ala Ala Ala Lys Glu Ala Ala
    50                  55                  60

Ala Lys Glu Ala Ala Ala Lys Glu Ala Ala Ala Lys Ala Ala Ala
65                  70                  75                  80

Ser Val Pro Ile Gln Lys Val Gln Asp Thr Lys Thr Leu Ile Lys
                85                  90                  95

Thr Ile Val Thr Arg Ile Asn Asp Ile Ser His Thr Gln Ser Val Ser
            100                 105                 110

Ser Lys Gln Lys Val Thr Gly Leu Glu Phe Ile Pro Gly Leu His Pro

```
                115                 120                 125
Ile Leu Thr Leu Ser Lys Met Asp Gln Thr Leu Ala Val Tyr Gln Gln
        130                 135                 140

Ile Leu Thr Ser Met Pro Ser Arg Asn Val Ile Gln Ile Ser Asn Asp
145                 150                 155                 160

Leu Glu Asn Leu Arg Asp Leu Leu His Val Leu Ala Phe Ser Lys Ser
                165                 170                 175

Cys His Leu Pro Gln Ala Ser Gly Leu Glu Thr Leu Glu Ser Leu Gly
            180                 185                 190

Gly Val Leu Glu Ala Ser Gly Tyr Ser Thr Glu Val Val Ala Leu Ser
        195                 200                 205

Arg Leu Gln Gly Ser Leu Gln Asp Met Leu Gln Gln Leu Asp Leu Ser
    210                 215                 220

Pro Gly Cys
225

<210> SEQ ID NO 101
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Met Leu Ala Glu Ala Lys Glu Asp Ala Ile Lys Glu Leu Asp Lys Tyr
1               5                   10                  15

Gly Val Ser Asp Tyr Tyr Lys Asn Leu Ile Asn Lys Ala Lys Thr Val
            20                  25                  30

Glu Gly Val Glu Ala Leu Ile Ser Glu Ile Leu Ala Ala Leu Pro Thr
        35                  40                  45

Gly Gly Glu Gly Gly Glu Gly Gly Gly Glu Gly Gly Glu Gly
    50                  55                  60

Gly Glu Ala Ser Val Pro Ile Gln Lys Val Gln Asp Asp Thr Lys Thr
65                  70                  75                  80

Leu Ile Lys Thr Ile Val Thr Arg Ile Asn Asp Ile Ser His Thr Gln
                85                  90                  95

Ser Val Ser Ser Lys Gln Lys Val Thr Gly Leu Glu Phe Ile Pro Gly
            100                 105                 110

Leu His Pro Ile Leu Thr Leu Ser Lys Met Asp Gln Thr Leu Ala Val
        115                 120                 125

Tyr Gln Gln Ile Leu Thr Ser Met Pro Ser Arg Asn Val Ile Gln Ile
    130                 135                 140

Ser Asn Asp Leu Glu Asn Leu Arg Asp Leu Leu His Val Leu Ala Phe
145                 150                 155                 160

Ser Lys Ser Cys His Leu Pro Gln Ala Ser Gly Leu Glu Thr Leu Glu
                165                 170                 175

Ser Leu Gly Gly Val Leu Glu Ala Ser Gly Tyr Ser Thr Glu Val Val
            180                 185                 190

Ala Leu Ser Arg Leu Gln Gly Ser Leu Gln Asp Met Leu Gln Gln Leu
        195                 200                 205

Asp Leu Ser Pro Gly Cys
    210

<210> SEQ ID NO 102
<211> LENGTH: 214
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102
```

Met Leu Ala Glu Ala Lys Glu Asp Ala Ile Lys Glu Leu Asp Lys Tyr
1               5                   10                  15

Gly Val Ser Asp Tyr Tyr Lys Asn Leu Ile Asn Lys Ala Lys Thr Val
            20                  25                  30

Glu Gly Val Glu Ala Leu Ile Ser Glu Ile Leu Ala Ala Leu Pro Thr
        35                  40                  45

Gly Gly Lys Gly Gly Lys Gly Gly Lys Gly Gly Lys Gly Gly Lys Gly
    50                  55                  60

Gly Lys Ala Ser Val Pro Ile Gln Lys Val Gln Asp Asp Thr Lys Thr
65                  70                  75                  80

Leu Ile Lys Thr Ile Val Thr Arg Ile Asn Asp Ile Ser His Thr Gln
                85                  90                  95

Ser Val Ser Ser Lys Gln Lys Val Thr Gly Leu Glu Phe Ile Pro Gly
            100                 105                 110

Leu His Pro Ile Leu Thr Leu Ser Lys Met Asp Gln Thr Leu Ala Val
        115                 120                 125

Tyr Gln Gln Ile Leu Thr Ser Met Pro Ser Arg Asn Val Ile Gln Ile
    130                 135                 140

Ser Asn Asp Leu Glu Asn Leu Arg Asp Leu Leu His Val Leu Ala Phe
145                 150                 155                 160

Ser Lys Ser Cys His Leu Pro Gln Ala Ser Gly Leu Glu Thr Leu Glu
                165                 170                 175

Ser Leu Gly Gly Val Leu Glu Ala Ser Gly Tyr Ser Thr Glu Val Val
            180                 185                 190

Ala Leu Ser Arg Leu Gln Gly Ser Leu Gln Asp Met Leu Gln Gln Leu
        195                 200                 205

Asp Leu Ser Pro Gly Cys
    210

```
<210> SEQ ID NO 103
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103
```

Met Leu Ala Glu Ala Lys Glu Asp Ala Ile Lys Glu Leu Asp Lys Tyr
1               5                   10                  15

Gly Val Ser Asp Tyr Tyr Lys Asn Leu Ile Asn Lys Ala Lys Thr Val
            20                  25                  30

Glu Gly Val Glu Ala Leu Ile Ser Glu Ile Leu Ala Ala Leu Pro Thr
        35                  40                  45

Gly Gly Gly Gly Ser Gly Gly Ser Gly Gly Ser Gly Gly Ser Gly Gly
    50                  55                  60

Ser Ala Ser Val Pro Ile Gln Lys Val Gln Asp Asp Thr Lys Thr Leu
65                  70                  75                  80

Ile Lys Thr Ile Val Thr Arg Ile Asn Asp Ile Ser His Thr Gln Ser
                85                  90                  95

```
Val Ser Ser Lys Gln Lys Val Thr Gly Leu Glu Phe Ile Pro Gly Leu
            100                 105                 110

His Pro Ile Leu Thr Leu Ser Lys Met Asp Gln Thr Leu Ala Val Tyr
            115                 120                 125

Gln Gln Ile Leu Thr Ser Met Pro Ser Arg Asn Val Ile Gln Ile Ser
        130                 135                 140

Asn Asp Leu Glu Asn Leu Arg Asp Leu Leu His Val Leu Ala Phe Ser
145                 150                 155                 160

Lys Ser Cys Ser Leu Pro Gln Ala Ser Gly Leu Glu Thr Leu Glu Ser
                165                 170                 175

Leu Gly Glu Val Leu Glu Ala Ser Gly Tyr Ser Thr Glu Val Val Ala
            180                 185                 190

Leu Ser Arg Leu Gln Gly Ser Leu Gln Asp Ile Leu Gln Gln Leu Asp
            195                 200                 205

Leu Ser Pro Glu Cys
        210

<210> SEQ ID NO 104
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Met Leu Ala Glu Ala Lys Val Leu Ala Asn Arg Glu Leu Asp Lys Tyr
1               5                   10                  15

Gly Val Ser Asp Tyr Tyr Lys Asn Leu Ile Asn Lys Ala Lys Thr Val
            20                  25                  30

Glu Gly Val Glu Ala Leu Thr Leu His Ile Leu Ala Ala Leu Pro Thr
        35                  40                  45

Gly Gly Gly Gly Ser Gly Gly Gly Ser Gly Gly Gly Ser Gly Gly Gly
    50                  55                  60

Ser Ala Ser Val Pro Ile Gln Lys Val Gln Asp Asp Thr Lys Thr Leu
65                  70                  75                  80

Ile Lys Thr Ile Val Thr Arg Ile Asn Asp Ile Ser His Thr Gln Ser
                85                  90                  95

Val Ser Ser Lys Gln Lys Val Thr Gly Leu Glu Phe Ile Pro Gly Leu
            100                 105                 110

His Pro Ile Leu Thr Leu Ser Lys Met Asp Gln Thr Leu Ala Val Tyr
            115                 120                 125

Gln Gln Ile Leu Thr Ser Met Pro Ser Arg Asn Val Ile Gln Ile Ser
        130                 135                 140

Asn Asp Leu Glu Asn Leu Arg Asp Leu Leu His Val Leu Ala Phe Ser
145                 150                 155                 160

Lys Ser Cys His Leu Pro Gln Ala Ser Gly Leu Glu Thr Leu Glu Ser
                165                 170                 175

Leu Gly Gly Val Leu Glu Ala Ser Gly Tyr Ser Thr Glu Val Val Ala
            180                 185                 190

Leu Ser Arg Leu Gln Gly Ser Leu Gln Asp Met Leu Gln Gln Leu Asp
            195                 200                 205

Leu Ser Pro Gly Cys
        210

<210> SEQ ID NO 105
```

<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Met Leu Ala Glu Ala Lys Glu Asp Ala Ile Lys Glu Leu Asp Lys Tyr
1               5                   10                  15

Gly Val Ser Asp Tyr Tyr Lys Arg Leu Ile Ser Lys Ala Lys Thr Val
                20                  25                  30

Glu Gly Val Lys Ala Leu Ile Ser Glu Ile Leu Ala Ala Leu Pro Thr
            35                  40                  45

Gly Gly Gly Gly Ser Gly Gly Ser Gly Gly Ser Gly Gly Gly
        50                  55                  60

Ser Ala Ser Val Pro Ile Gln Lys Val Gln Asp Asp Thr Lys Thr Leu
65                  70                  75                  80

Ile Lys Thr Ile Val Thr Arg Ile Asn Asp Ile Ser His Thr Gln Ser
                85                  90                  95

Val Ser Ser Lys Gln Lys Val Thr Gly Leu Glu Phe Ile Pro Gly Leu
            100                 105                 110

His Pro Ile Leu Thr Leu Ser Lys Met Asp Gln Thr Leu Ala Val Tyr
        115                 120                 125

Gln Gln Ile Leu Thr Ser Met Pro Ser Arg Asn Val Ile Gln Ile Ser
    130                 135                 140

Asn Asp Leu Glu Asn Leu Arg Asp Leu Leu His Val Leu Ala Phe Ser
145                 150                 155                 160

Lys Ser Cys His Leu Pro Gln Ala Ser Gly Leu Glu Thr Leu Glu Ser
                165                 170                 175

Leu Gly Gly Val Leu Glu Ala Ser Gly Tyr Ser Thr Glu Val Val Ala
            180                 185                 190

Leu Ser Arg Leu Gln Gly Ser Leu Gln Asp Met Leu Gln Gln Leu Asp
        195                 200                 205

Leu Ser Pro Gly Cys
    210

<210> SEQ ID NO 106
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Met Leu Ala Glu Ala Lys Glu Asp Ala Ile Lys Glu Leu Asp Lys Tyr
1               5                   10                  15

Gly Val Ser Asp Tyr Tyr Lys Asn Leu Ile Asn Lys Ala Lys Thr Val
                20                  25                  30

Glu Gly Val Glu Ala Leu Thr Leu His Ile Leu Ala Ala Leu Pro Thr
            35                  40                  45

Gly Gly Gly Gly Ser Gly Gly Gly Ser Gly Gly Gly Ser Gly Gly Gly
        50                  55                  60

Ser Ala Ser Val Pro Ile Gln Lys Val Gln Asp Asp Thr Lys Thr Leu
65                  70                  75                  80

Ile Lys Thr Ile Val Thr Arg Ile Asn Asp Ile Ser His Thr Gln Ser
                85                  90                  95

```
Val Ser Ser Lys Gln Lys Val Thr Gly Leu Glu Phe Ile Pro Gly Leu
            100                 105                 110

His Pro Ile Leu Thr Leu Ser Lys Met Asp Gln Thr Leu Ala Val Tyr
            115                 120                 125

Gln Gln Ile Leu Thr Ser Met Pro Ser Arg Asn Val Ile Gln Ile Ser
        130                 135                 140

Asn Asp Leu Glu Asn Leu Arg Asp Leu Leu His Val Leu Ala Phe Ser
145                 150                 155                 160

Lys Ser Cys His Leu Pro Gln Ala Ser Gly Leu Glu Thr Leu Glu Ser
            165                 170                 175

Leu Gly Gly Val Leu Glu Ala Ser Gly Tyr Ser Thr Glu Val Val Ala
            180                 185                 190

Leu Ser Arg Leu Gln Gly Ser Leu Gln Asp Met Leu Gln Gln Leu Asp
            195                 200                 205

Leu Ser Pro Gly Cys
    210
```

<210> SEQ ID NO 107
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

```
Met Leu Ala Glu Ala Lys Glu Asp Ala Ile Lys Glu Leu Asp Lys Tyr
1               5                   10                  15

Gly Val Ser Asp Tyr Tyr Lys Asn Leu Ile Asn Lys Ala Lys Thr Val
            20                  25                  30

Glu Gly Val Glu Ala Leu Ile Ser Glu Ile Leu Ala Ala Leu Pro Thr
        35                  40                  45

Gly Gly Gly Gly Ser Gly Gly Gly Ser Gly Gly Gly Ser Gly Gly Gly
    50                  55                  60

Ser Ala Ser Val Pro Ile Gln Lys Val Gln Asp Asp Thr Lys Thr Leu
65                  70                  75                  80

Ile Lys Thr Ile Val Thr Arg Ile Asn Asp Ile Ser His Thr Gln Ser
            85                  90                  95

Val Ser Ser Lys Gln Lys Val Thr Gly Leu Glu Phe Ile Pro Gly Leu
            100                 105                 110

His Pro Ile Leu Thr Leu Ser Lys Met Asp Gln Thr Leu Ala Val Tyr
            115                 120                 125

Gln Gln Ile Leu Thr Ser Met Pro Ser Arg Asn Val Ile Gln Ile Ser
        130                 135                 140

Asn Asp Leu Glu Asn Leu Arg Asp Leu Leu His Val Leu Ala Phe Ser
145                 150                 155                 160

Lys Ser Cys His Leu Pro Gln Ala Ser Gly Leu Glu Thr Leu Glu Ser
            165                 170                 175

Leu Gly Gly Val Leu Glu Ala Ser Gly Tyr Ser Thr Glu Val Val Ala
            180                 185                 190

Leu Ser Arg Leu Gln Gly Ser Leu Gln Asp Met Leu Gln Gln Leu Asp
            195                 200                 205

Leu Ser Pro Gly Cys
    210
```

```
<210> SEQ ID NO 108
<211> LENGTH: 37
<212> TYPE: PRT
<213> ORGANISM: Unknown
<220> FEATURE:
<223> OTHER INFORMATION: Polypeptide from unknown Rattus species

<400> SEQUENCE: 108

Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Pro Thr Asn Val
            20                  25                  30

Gly Ser Asn Thr Tyr
        35

<210> SEQ ID NO 109
<211> LENGTH: 37
<212> TYPE: PRT
<213> ORGANISM: Homo sapiens

<400> SEQUENCE: 109

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 110
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
            20                  25                  30

Gly Ser Asn Thr Tyr
        35

<210> SEQ ID NO 111
<211> LENGTH: 32
<212> TYPE: PRT
<213> ORGANISM: Homo sapiens

<400> SEQUENCE: 111

Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30

<210> SEQ ID NO 112
<211> LENGTH: 32
<212> TYPE: PRT
<213> ORGANISM: Unknown
<220> FEATURE:
<223> OTHER INFORMATION: Polypeptide from unknown Oncorhynchus species

<400> SEQUENCE: 112
```

-continued

```
Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30

<210> SEQ ID NO 113
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 114
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Gly Val Ser Asp Tyr Tyr Lys Asn Leu Ile Asn Lys Ala Lys Thr Val
1               5                   10                  15

Glu Gly Val Glu Ala Leu Thr Leu His Ile
            20                  25

<210> SEQ ID NO 115
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gly Val Ser Asp Tyr Tyr Lys Asn Leu Ile Asn Lys Ala Lys Thr Val
1               5                   10                  15

Glu Gly Val Glu Ala Leu Ile Ser Glu Ile
            20                  25

<210> SEQ ID NO 116
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gly Gly Gly Gly
1

<210> SEQ ID NO 117
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 117

Gly Gly Gly Gly Gly
1               5

<210> SEQ ID NO 118
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gly Gly Gly Lys Gly Gly Gly Gly
1               5

<210> SEQ ID NO 119
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Gly Gly Gly Asn Gly Ser Gly Gly
1               5

<210> SEQ ID NO 120
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gly Gly Gly Cys Gly Gly Gly Gly
1               5

<210> SEQ ID NO 121
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Gly Pro Asn Gly Gly
1               5

<210> SEQ ID NO 122
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(20)
<223> OTHER INFORMATION: This region may encompass 1-10 "Gly Ser"
      repeats

<400> SEQUENCE: 122

Gly Ser Gly Ser Gly Ser Gly Ser Gly Ser Gly Ser Gly Ser Gly Ser
```

Gly Ser Gly Ser
            20

<210> SEQ ID NO 123
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(30)
<223> OTHER INFORMATION: This region may encompass 1-10 "Gly Gly Ser"
      repeats

<400> SEQUENCE: 123

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser
            20                  25                  30

<210> SEQ ID NO 124
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(40)
<223> OTHER INFORMATION: This region may encompass 1-10 "Gly Gly Gly
      Ser" repeats

<400> SEQUENCE: 124

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40

<210> SEQ ID NO 125
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(50)
<223> OTHER INFORMATION: This region may encompass 1-10 "Gly Gly Gly Gly
      Ser" repeats

<400> SEQUENCE: 125

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50

<210> SEQ ID NO 126
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(20)
<223> OTHER INFORMATION: This region may encompass 1-10 "Gly Glu"
      repeats

<400> SEQUENCE: 126

Gly Glu Gly Glu Gly Glu Gly Glu Gly Glu Gly Glu Gly Glu Gly Glu
1               5                   10                  15

Gly Glu Gly Glu
            20

<210> SEQ ID NO 127
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(30)
<223> OTHER INFORMATION: This region may encompass 1-10 "Gly Gly Glu"
      repeats

<400> SEQUENCE: 127

Gly Gly Glu Gly Gly Glu Gly Gly Glu Gly Gly Glu Gly Gly Glu Gly
1               5                   10                  15

Gly Glu Gly Gly Glu Gly Gly Glu Gly Gly Glu Gly Gly Glu
            20                  25                  30

<210> SEQ ID NO 128
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(40)
<223> OTHER INFORMATION: This region may encompass 1-10 "Gly Gly Gly
      Glu" repeats

<400> SEQUENCE: 128

Gly Gly Gly Glu Gly Gly Gly Glu Gly Gly Gly Glu Gly Gly Gly Glu
1               5                   10                  15

Gly Gly Gly Glu Gly Gly Gly Glu Gly Gly Gly Glu Gly Gly Gly Glu
            20                  25                  30

Gly Gly Gly Glu Gly Gly Gly Glu
        35                  40

<210> SEQ ID NO 129
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:

```
<221> NAME/KEY: misc_feature
<222> LOCATION: (1)..(50)
<223> OTHER INFORMATION: This region may encompass 1-10 "Gly Gly Gly Gly
      Glu" repeats

<400> SEQUENCE: 129

Gly Gly Gly Gly Glu Gly Gly Gly Gly Glu Gly Gly Gly Gly Glu Gly
1               5                   10                  15

Gly Gly Gly Glu Gly Gly Gly Gly Glu Gly Gly Gly Gly Glu Gly Gly
            20                  25                  30

Gly Gly Glu Gly Gly Gly Gly Glu Gly Gly Gly Gly Glu Gly Gly Gly
        35                  40                  45

Gly Glu
    50

<210> SEQ ID NO 130
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(20)
<223> OTHER INFORMATION: This region may encompass 1-10 "Gly Asp"
      repeats

<400> SEQUENCE: 130

Gly Asp Gly Asp Gly Asp Gly Asp Gly Asp Gly Asp Gly Asp Gly Asp
1               5                   10                  15

Gly Asp Gly Asp
        20

<210> SEQ ID NO 131
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(30)
<223> OTHER INFORMATION: This region may encompass 1-10 "Gly Gly Asp"
      repeats

<400> SEQUENCE: 131

Gly Gly Asp Gly Gly Asp Gly Gly Asp Gly Gly Asp Gly Gly Asp Gly
1               5                   10                  15

Gly Asp Gly Gly Asp Gly Gly Asp Gly Gly Asp Gly Gly Asp
            20                  25                  30

<210> SEQ ID NO 132
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(40)
<223> OTHER INFORMATION: This region may encompass 1-10 "Gly Gly Gly
      Asp" repeats

<400> SEQUENCE: 132
```

```
Gly Gly Gly Asp Gly Gly Gly Asp Gly Gly Gly Asp Gly Gly Gly Asp
1               5                   10                  15

Gly Gly Gly Asp Gly Gly Gly Asp Gly Gly Gly Asp Gly Gly Gly Asp
                20                  25                  30

Gly Gly Gly Asp Gly Gly Gly Asp
        35                  40
```

<210> SEQ ID NO 133
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(50)
<223> OTHER INFORMATION: This region may encompass 1-10 "Gly Gly Gly Gly
      Asp" repeats

<400> SEQUENCE: 133

```
Gly Gly Gly Gly Asp Gly Gly Gly Gly Asp Gly Gly Gly Gly Asp Gly
1               5                   10                  15

Gly Gly Gly Asp Gly Gly Gly Gly Asp Gly Gly Gly Gly Asp Gly Gly
                20                  25                  30

Gly Gly Asp Gly Gly Gly Gly Asp Gly Gly Gly Gly Asp Gly Gly Gly
        35                  40                  45

Gly Asp
    50
```

<210> SEQ ID NO 134
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(20)
<223> OTHER INFORMATION: This region may encompass 1-10 "Gly Lys"
      repeats

<400> SEQUENCE: 134

```
Gly Lys Gly Lys Gly Lys Gly Lys Gly Lys Gly Lys Gly Lys Gly Lys
1               5                   10                  15

Gly Lys Gly Lys
        20
```

<210> SEQ ID NO 135
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(30)
<223> OTHER INFORMATION: This region may encompass 1-10 "Gly Gly Lys"
      repeats

<400> SEQUENCE: 135

```
Gly Gly Lys Gly Gly Lys Gly Gly Lys Gly Gly Lys Gly Gly Lys Gly
1               5                   10                  15

Gly Lys Gly Gly Lys Gly Gly Lys Gly Gly Lys Gly Gly Lys
```

```
                20                  25                  30

<210> SEQ ID NO 136
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(40)
<223> OTHER INFORMATION: This region may encompass 1-10 "Gly Gly Gly
      Lys" repeats

<400> SEQUENCE: 136

Gly Gly Gly Lys Gly Gly Gly Lys Gly Gly Gly Lys Gly Gly Gly Lys
1               5                   10                  15

Gly Gly Gly Lys Gly Gly Gly Lys Gly Gly Gly Lys Gly Gly Gly Lys
                20                  25                  30

Gly Gly Gly Lys Gly Gly Gly Lys
        35                  40

<210> SEQ ID NO 137
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(50)
<223> OTHER INFORMATION: This region may encompass 1-10 "Gly Gly Gly Gly
      Lys" repeats

<400> SEQUENCE: 137

Gly Gly Gly Gly Lys Gly Gly Gly Gly Lys Gly Gly Gly Gly Lys Gly
1               5                   10                  15

Gly Gly Gly Lys Gly Gly Gly Gly Lys Gly Gly Gly Gly Lys Gly Gly
                20                  25                  30

Gly Gly Lys Gly Gly Gly Gly Lys Gly Gly Gly Gly Lys Gly Gly Gly
        35                  40                  45

Gly Lys
    50

<210> SEQ ID NO 138
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(20)
<223> OTHER INFORMATION: This region may encompass 1-10 "Gly Arg"
      repeats

<400> SEQUENCE: 138

Gly Arg Gly Arg Gly Arg Gly Arg Gly Arg Gly Arg Gly Arg Gly Arg
1               5                   10                  15

Gly Arg Gly Arg
        20

<210> SEQ ID NO 139
```

```
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(30)
<223> OTHER INFORMATION: This region may encompass 1-10 "Gly Gly Arg"
      repeats

<400> SEQUENCE: 139

Gly Gly Arg Gly Gly Arg Gly Gly Arg Gly Gly Arg Gly Gly Arg Gly
1               5                   10                  15

Gly Arg Gly Gly Arg Gly Gly Arg Gly Gly Arg Gly Gly Arg
            20                  25                  30

<210> SEQ ID NO 140
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(40)
<223> OTHER INFORMATION: This region may encompass 1-10 "Gly Gly Gly
      Arg" repeats

<400> SEQUENCE: 140

Gly Gly Gly Arg Gly Gly Gly Arg Gly Gly Gly Arg Gly Gly Gly Arg
1               5                   10                  15

Gly Gly Gly Arg Gly Gly Gly Arg Gly Gly Gly Arg Gly Gly Gly Arg
            20                  25                  30

Gly Gly Gly Arg Gly Gly Gly Arg
            35                  40

<210> SEQ ID NO 141
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(50)
<223> OTHER INFORMATION: This region may encompass 1-10 "Gly Gly Gly Gly
      Arg" repeats

<400> SEQUENCE: 141

Gly Gly Gly Gly Arg Gly Gly Gly Gly Arg Gly Gly Gly Gly Arg Gly
1               5                   10                  15

Gly Gly Gly Arg Gly Gly Gly Gly Arg Gly Gly Gly Gly Arg Gly Gly
            20                  25                  30

Gly Gly Arg Gly Gly Gly Gly Arg Gly Gly Gly Gly Arg Gly Gly Gly
        35                  40                  45

Gly Arg
    50

<210> SEQ ID NO 142
<211> LENGTH: 50
<212> TYPE: PRT
<213> ORGANISM: Artificial Sequence
<220> FEATURE:
```

<223> OTHER INFORMATION: Description of Artificial Sequence: Synthetic
polypeptide
<220> FEATURE:
<221> NAME/KEY: misc_feature
<222> LOCATION: (1)..(50)
<223> OTHER INFORMATION: This region may encompass 1-10 "Glu Ala Ala Ala
Lys" repeats

<400> SEQUENCE: 142

Glu Ala Ala Ala Lys Glu Ala Ala Ala Lys Glu Ala Ala Ala Lys Glu
1               5                   10                  15

Ala Ala Ala Lys Glu Ala Ala Ala Lys Glu Ala Ala Ala Lys Glu Ala
            20                  25                  30

Ala Ala Lys Glu Ala Ala Ala Lys Glu Ala Ala Ala Lys Glu Ala Ala
        35                  40                  45

Ala Lys
    50

<210> SEQ ID NO 143
<211> LENGTH: 146
<212> TYPE: PRT
<213> ORGANISM: Unknown
<220> FEATURE:
<223> OTHER INFORMATION: Polypeptide from unknown Mus species

<400> SEQUENCE: 143

Val Pro Ile Gln Lys Val Gln Asp Asp Thr Lys Thr Leu Ile Lys Thr
1               5                   10                  15

Ile Val Thr Arg Ile Asn Asp Ile Ser His Thr Gln Ser Val Ser Ala
            20                  25                  30

Lys Gln Arg Val Thr Gly Leu Asp Phe Ile Pro Gly Leu His Pro Ile
        35                  40                  45

Leu Ser Leu Ser Lys Met Asp Gln Thr Leu Ala Val Tyr Gln Gln Val
    50                  55                  60

Leu Thr Ser Leu Pro Ser Gln Asn Val Leu Gln Ile Ala Asn Asp Leu
65                  70                  75                  80

Glu Asn Leu Arg Asp Leu Leu His Leu Leu Ala Phe Ser Lys Ser Cys
                85                  90                  95

Ser Leu Pro Gln Thr Ser Gly Leu Gln Lys Pro Glu Ser Leu Asp Gly
            100                 105                 110

Val Leu Glu Ala Ser Leu Tyr Ser Thr Glu Val Val Ala Leu Ser Arg
        115                 120                 125

Leu Gln Gly Ser Leu Gln Asp Ile Leu Gln Gln Leu Asp Val Ser Pro
    130                 135                 140

Glu Cys
145

<210> SEQ ID NO 144
<211> LENGTH: 145
<212> TYPE: PRT
<213> ORGANISM: Unknown
<220> FEATURE:
<223> OTHER INFORMATION: Polypeptide from unknown Mus species

<400> SEQUENCE: 144

Val Pro Ile Gln Lys Val Gln Asp Asp Thr Lys Thr Leu Ile Lys Thr
1               5                   10                  15

Ile Val Thr Arg Ile Asn Asp Ile Ser His Thr Ser Val Ser Ala Lys
            20                  25                  30

Gln Arg Val Thr Gly Leu Asp Phe Ile Pro Gly Leu His Pro Ile Leu

```
                35                  40                  45
Ser Leu Ser Lys Met Asp Gln Thr Leu Ala Val Tyr Gln Gln Val Leu
 50                  55                  60

Thr Ser Leu Pro Ser Gln Asn Val Leu Gln Ile Ala Asn Asp Leu Glu
65                  70                  75                  80

Asn Leu Arg Asp Leu Leu His Leu Leu Ala Phe Ser Lys Ser Cys Ser
                85                  90                  95

Leu Pro Gln Thr Ser Gly Leu Gln Lys Pro Glu Ser Leu Asp Gly Val
            100                 105                 110

Leu Glu Ala Ser Leu Tyr Ser Thr Glu Val Val Ala Leu Ser Arg Leu
            115                 120                 125

Gln Gly Ser Leu Gln Asp Ile Leu Gln Gln Leu Asp Val Ser Pro Glu
        130                 135                 140

Cys
145

<210> SEQ ID NO 145
<211> LENGTH: 147
<212> TYPE: PRT
<213> ORGANISM: Unknown
<220> FEATURE:
<223> OTHER INFORMATION: Polypeptide from unknown Mus species

<400> SEQUENCE: 145

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ala Lys Gln Arg Val Thr Gly Leu Asp Phe Ile Pro Gly Leu His Pro
        35                  40                  45

Ile Leu Ser Leu Ser Lys Met Asp Gln Thr Leu Ala Val Tyr Gln Gln
    50                  55                  60

Val Leu Thr Ser Leu Pro Ser Gln Asn Val Leu Gln Ile Ala Asn Asp
65                  70                  75                  80

Leu Glu Asn Leu Arg Asp Leu Leu His Leu Leu Ala Phe Ser Lys Ser
                85                  90                  95

Cys Ser Leu Pro Gln Thr Ser Gly Leu Gln Lys Pro Glu Ser Leu Asp
            100                 105                 110

Gly Val Leu Glu Ala Ser Leu Tyr Ser Thr Glu Val Val Ala Leu Ser
        115                 120                 125

Arg Leu Gln Gly Ser Leu Gln Asp Ile Leu Gln Gln Leu Asp Val Ser
    130                 135                 140

Pro Glu Cys
145

<210> SEQ ID NO 146
<211> LENGTH: 146
<212> TYPE: PRT
<213> ORGANISM: Unknown
<220> FEATURE:
<223> OTHER INFORMATION: Polypeptide from unknown Mus species

<400> SEQUENCE: 146

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser Ala
            20                  25                  30
```

Lys Gln Arg Val Thr Gly Leu Asp Phe Ile Pro Gly Leu His Pro Ile
            35                  40                  45

Leu Ser Leu Ser Lys Met Asp Gln Thr Leu Ala Val Tyr Gln Gln Val
 50                  55                  60

Leu Thr Ser Leu Pro Ser Gln Asn Val Leu Gln Ile Ala Asn Asp Leu
 65                  70                  75                  80

Glu Asn Leu Arg Asp Leu Leu His Leu Leu Ala Phe Ser Lys Ser Cys
                 85                  90                  95

Ser Leu Pro Gln Thr Ser Gly Leu Gln Lys Pro Glu Ser Leu Asp Gly
            100                 105                 110

Val Leu Glu Ala Ser Leu Tyr Ser Thr Glu Val Val Ala Leu Ser Arg
            115                 120                 125

Leu Gln Gly Ser Leu Gln Asp Ile Leu Gln Gln Leu Asp Val Ser Pro
130                 135                 140

Glu Cys
145

<210> SEQ ID NO 147
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Met Leu Ala Glu Ala Lys Val Leu Ala Asn Arg Glu Leu Asp Lys Tyr
1               5                   10                  15

Gly Val Ser Asp Phe Tyr Lys Arg Leu Ile Asn Lys Ala Lys Thr Val
            20                  25                  30

Glu Gly Val Glu Ala Leu Lys Leu His Ile Leu Ala Ala Leu Pro Thr
            35                  40                  45

Gly Gly Gly Gly Ser Gly Gly Gly Ser Gly Gly Gly Ser Gly Gly Gly
            50                  55                  60

Ser Ala Ser Val Pro Ile Gln Lys Val Gln Asp Asp Thr Lys Thr Leu
 65                  70                  75                  80

Ile Lys Thr Ile Val Thr Arg Ile Asn Asp Ile Ser His Thr Gln Ser
                 85                  90                  95

Val Ser Ser Lys Gln Lys Val Thr Gly Leu Asp Phe Ile Pro Gly Leu
            100                 105                 110

His Pro Ile Leu Thr Leu Ser Lys Met Asp Gln Thr Leu Ala Val Tyr
            115                 120                 125

Gln Gln Ile Leu Thr Ser Met Pro Ser Arg Asn Val Ile Gln Ile Ser
130                 135                 140

Asn Asp Leu Glu Asn Leu Arg Asp Leu Leu His Val Leu Ala Phe Ser
145                 150                 155                 160

Lys Ser Cys His Leu Pro Trp Ala Ser Gly Leu Glu Thr Leu Asp Ser
                 165                 170                 175

Leu Gly Gly Val Leu Glu Ala Ser Gly Tyr Ser Thr Glu Val Val Ala
            180                 185                 190

Leu Ser Arg Leu Gln Gly Ser Leu Gln Asp Met Leu Trp Gln Leu Asp
            195                 200                 205

Leu Ser Pro Gly Cys
    210

<210> SEQ ID NO 148

```
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (25)..(25)
<223> OTHER INFORMATION: Lys(mPEG40K)

<400> SEQUENCE: 148

Cys Asn Thr Ala Thr Cys Ala Thr Gln Arg Leu Ala Asn Phe Leu Val
1               5                   10                  15

Arg Ser Ser Asn Asn Leu Gly Pro Lys Leu Pro Pro Thr Asn Val Gly
            20                  25                  30

Ser Asn Thr Tyr
        35

<210> SEQ ID NO 149
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gly Gly Gly Ser
1

<210> SEQ ID NO 150
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Gly Gly Gly Gly Ser
1               5

<210> SEQ ID NO 151
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gly Gly Gly Ser Gly Gly Gly Ser Gly Gly Gly Ser Gly Gly Gly Ser
1               5                   10                  15

<210> SEQ ID NO 152
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gly Gly Gly Gly Ser Gly Gly Gly Gly Ser Gly Gly Gly Gly Ser
1               5                   10                  15
```

```
<210> SEQ ID NO 153
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Gly Gly Glu Gly Gly Glu Gly Gly Glu Gly Gly Glu Gly Gly Glu Gly
1               5                   10                  15

Gly Glu

<210> SEQ ID NO 154
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Gly Gly Lys Gly Gly Lys Gly Gly Lys Gly Gly Lys Gly Gly Lys Gly
1               5                   10                  15

Gly Lys

<210> SEQ ID NO 155
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Glu Ala Ala Ala Lys Glu Ala Ala Ala Lys Glu Ala Ala Ala Lys
1               5                   10                  15

<210> SEQ ID NO 156
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Glu Ala Ala Ala Lys Glu Ala Ala Ala Lys Glu Ala Ala Ala Lys Glu
1               5                   10                  15

Ala Ala Ala Lys
            20

<210> SEQ ID NO 157
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Glu Ala Ala Ala Lys Glu Ala Ala Ala Lys Glu Ala Ala Ala Lys Glu
1               5                   10                  15

Ala Ala Ala Lys Glu Ala Ala Ala Lys
            20                  25
```

<210> SEQ ID NO 158
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Val Pro Ile Gln Lys Val
1               5

<210> SEQ ID NO 159
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Leu Ala Glu Ala Lys
1               5

<210> SEQ ID NO 160
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: AMIDATION

<400> SEQUENCE: 160

Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Pro Thr Asn Val
            20                  25                  30

Gly Ser Asn Thr Tyr
        35

<210> SEQ ID NO 161
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Cys Asn Thr Ala Thr Cys Ala Thr Gln Arg Leu Ala Asn Phe Leu Val
1               5                   10                  15

His Ser Ser Asn Asn Phe Gly Ala Ile Leu Ser Ser Thr Asn Val Gly
            20                  25                  30

Ser Asn Thr Tyr
        35

<210> SEQ ID NO 162
<211> LENGTH: 37
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 162

Lys Cys Asn Thr Ala Thr Cys Ala Thr Gln Arg Leu Ala Asn Phe Leu
1               5                   10                  15

Val His Ser Ser Asn Asn Phe Gly Pro Val Leu Pro Pro Thr Asn Val
            20                  25                  30

Gly Ser Asn Thr Tyr
        35

<210> SEQ ID NO 163
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Lys Cys Asn Thr Ala Thr Cys Ala Thr Gln Arg Leu Ala Asn Phe Leu
1               5                   10                  15

Val Arg Ser Ser Asn Asn Phe Gly Pro Ile Leu Pro Ser Thr Asn Val
            20                  25                  30

Gly Ser Asn Thr Tyr
        35

<210> SEQ ID NO 164
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Cys Asn Thr Ala Thr Cys Ala Thr Gln Arg Leu Ala Asn Phe Leu Val
1               5                   10                  15

Arg Ser Ser Asn Asn Phe Gly Pro Ile Leu Pro Ser Thr Asn Val Gly
            20                  25                  30

Ser Asn Thr Tyr
        35

<210> SEQ ID NO 165
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Lys Cys Asn Thr Ala Thr Cys Ala Thr Gln Arg Leu Ala Asn Phe Leu
1               5                   10                  15

Val Arg Ser Ser Asn Asn Phe Gly Pro Ile Leu Pro Pro Thr Asn Val
            20                  25                  30

Gly Ser Asn Thr Tyr
        35

<210> SEQ ID NO 166
<211> LENGTH: 36
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 166

Cys Asn Thr Ala Thr Cys Ala Thr Gln Arg Leu Ala Asn Phe Leu Val
1               5                   10                  15

Arg Ser Ser Asn Asn Phe Gly Pro Ile Leu Pro Pro Thr Asn Val Gly
            20                  25                  30

Ser Asn Thr Tyr
        35

<210> SEQ ID NO 167
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Cys Asn Thr Ala Thr Cys Ala Thr Gln Arg Leu Ala Asn Phe Leu Val
1               5                   10                  15

His Ser Ser Asn Asn Phe Gly Pro Ile Leu Pro Pro Thr Asn Val Gly
            20                  25                  30

Ser Asn Thr Tyr
        35

<210> SEQ ID NO 168
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Lys Cys Asn Thr Ala Thr Cys Ala Thr Gln Arg Leu Ala Asn Phe Leu
1               5                   10                  15

Val His Ser Ser Asn Asn Phe Gly Pro Val Leu Pro Pro Thr Asn Val
            20                  25                  30

Gly Ser Asn Thr Tyr
        35

<210> SEQ ID NO 169
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Lys Asp Asn Thr Ala Thr Lys Ala Thr Gln Arg Leu Ala Asn Phe Leu
1               5                   10                  15

Val His Ser Ser Asn Asn Phe Gly Ala Ile Leu Pro Ser Thr Asn Val
            20                  25                  30

Gly Ser Asn Thr Tyr
        35

<210> SEQ ID NO 170
<211> LENGTH: 36
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 170

Cys Asn Thr Ala Thr Cys Ala Thr Gln Arg Leu Ala Asn Phe Leu Val
1               5                   10                  15

His Ser Ser Asn Asn Phe Gly Ala Ile Leu Ser Ser Thr Asn Val Gly
            20                  25                  30

Ser Asn Thr Tyr
        35

<210> SEQ ID NO 171
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Ala Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 172
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Lys Ala Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 173
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Lys Ala Asn Thr Ala Thr Ala Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 174
<211> LENGTH: 37
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 174

Ser Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 175
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Pro Thr Asn Val
            20                  25                  30

Gly Ser Asn Thr Tyr
        35

<210> SEQ ID NO 176
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Ser Thr Asn Val
            20                  25                  30

Gly Ser Asn Thr Tyr
        35

<210> SEQ ID NO 177
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Cys Asn Thr Ala Thr Cys Ala Thr Gln Arg Leu Ala Asn Phe Leu Val
1               5                   10                  15

His Ser Ser Asn Asn Phe Gly Pro Ile Leu Pro Ser Thr Asn Val Gly
            20                  25                  30

Ser Asn Thr Tyr
        35

<210> SEQ ID NO 178
<211> LENGTH: 37
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Lys Cys Asn Thr Ala Thr Cys Ala Thr Gln Arg Leu Ala Asn Phe Leu
1               5                   10                  15

Val His Ser Ser Asn Asn Leu Gly Pro Val Leu Pro Pro Thr Asn Val
            20                  25                  30

Gly Ser Asn Thr Tyr
        35

<210> SEQ ID NO 179
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Lys Cys Asn Thr Ala Thr Cys Ala Thr Gln Arg Leu Ala Asn Phe Leu
1               5                   10                  15

Val His Ser Ser Asn Asn Leu Gly Pro Val Leu Pro Ser Thr Asn Val
            20                  25                  30

Gly Ser Asn Thr Tyr
        35

<210> SEQ ID NO 180
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Cys Asn Thr Ala Thr Cys Ala Thr Gln Arg Leu Ala Asn Phe Leu Val
1               5                   10                  15

His Ser Ser Asn Asn Leu Gly Pro Val Leu Pro Ser Thr Asn Val Gly
            20                  25                  30

Ser Asn Thr Tyr
        35

<210> SEQ ID NO 181
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Ser Thr Asn Val
            20                  25                  30

Gly Ser Asn Thr Tyr
        35

<210> SEQ ID NO 182
```

```
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Lys Cys Asn Thr Ala Thr Cys Ala Thr Gln Arg Leu Ala Asn Phe Leu
1               5                   10                  15

Val Arg Ser Ser Asn Asn Leu Gly Pro Ile Leu Pro Pro Thr Asn Val
            20                  25                  30

Gly Ser Asn Thr Tyr
        35

<210> SEQ ID NO 183
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Lys Cys Asn Thr Ala Thr Cys Ala Thr Gln Arg Leu Ala Asn Phe Leu
1               5                   10                  15

Val Arg Ser Ser Asn Asn Leu Gly Pro Ile Leu Pro Ser Thr Asn Val
            20                  25                  30

Gly Ser Asn Thr Tyr
        35

<210> SEQ ID NO 184
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Lys Cys Asn Thr Ala Thr Cys Ala Thr Gln Arg Leu Ala Asn Phe Leu
1               5                   10                  15

Ile His Ser Ser Asn Asn Leu Gly Pro Ile Leu Pro Pro Thr Asn Val
            20                  25                  30

Gly Ser Asn Thr Tyr
        35

<210> SEQ ID NO 185
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Lys Cys Asn Thr Ala Thr Cys Ala Thr Gln Arg Leu Ala Asn Phe Leu
1               5                   10                  15

Ile His Ser Ser Asn Asn Phe Gly Pro Ile Leu Pro Pro Thr Asn Val
            20                  25                  30

Gly Ser Asn Thr Tyr
        35
```

```
<210> SEQ ID NO 186
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Cys Asn Thr Ala Thr Cys Ala Thr Gln Arg Leu Ala Asn Phe Leu Ile
1               5                   10                  15

His Ser Ser Asn Asn Leu Gly Pro Ile Leu Pro Pro Thr Asn Val Gly
            20                  25                  30

Ser Asn Thr Tyr
        35

<210> SEQ ID NO 187
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Lys Cys Asn Thr Ala Thr Cys Ala Thr Gln Arg Leu Ala Asn Phe Leu
1               5                   10                  15

Ile Arg Ser Ser Asn Asn Leu Gly Ala Ile Leu Ser Ser Thr Asn Val
            20                  25                  30

Gly Ser Asn Thr Tyr
        35

<210> SEQ ID NO 188
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Lys Cys Asn Thr Ala Thr Cys Ala Thr Gln Arg Leu Ala Asn Phe Leu
1               5                   10                  15

Ile Arg Ser Ser Asn Asn Leu Gly Ala Val Leu Ser Pro Thr Asn Val
            20                  25                  30

Gly Ser Asn Thr Tyr
        35

<210> SEQ ID NO 189
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Lys Cys Asn Thr Ala Thr Cys Ala Thr Gln Arg Leu Ala Asn Phe Leu
1               5                   10                  15

Ile Arg Ser Ser Asn Asn Leu Gly Pro Val Leu Pro Pro Thr Asn Val
            20                  25                  30

Gly Ser Asn Thr Tyr
        35
```

```
<210> SEQ ID NO 190
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Lys Cys Asn Thr Ala Thr Cys Ala Thr Gln Arg Leu Thr Asn Phe Leu
1               5                   10                  15

Val His Ser Ser His Asn Leu Gly Ala Ala Leu Leu Pro Thr Asp Val
            20                  25                  30

Gly Ser Asn Thr Tyr
        35

<210> SEQ ID NO 191
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Lys Cys Asn Thr Ala Thr Cys Ala Thr Gln Arg Leu Thr Asn Phe Leu
1               5                   10                  15

Val His Ser Ser His Asn Leu Gly Ala Ala Leu Ser Pro Thr Asp Val
            20                  25                  30

Gly Ser Asn Thr Tyr
        35

<210> SEQ ID NO 192
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Cys Asn Thr Ala Thr Cys Ala Thr Gln Arg Leu Thr Asn Phe Leu Val
1               5                   10                  15

His Ser Ser His Asn Leu Gly Ala Ala Leu Pro Ser Thr Asp Val Gly
            20                  25                  30

Ser Asn Thr Tyr
        35

<210> SEQ ID NO 193
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Lys Cys Asn Thr Ala Thr Cys Ala Thr Gln Arg Leu Thr Asn Phe Leu
1               5                   10                  15

Val Arg Ser Ser His Asn Leu Gly Ala Ala Leu Ser Pro Thr Asp Val
            20                  25                  30

Gly Ser Asn Thr Tyr
        35
```

<210> SEQ ID NO 194
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Lys Cys Asn Thr Ala Thr Cys Ala Thr Gln Arg Leu Thr Asn Phe Leu
1               5                   10                  15

Val Arg Ser Ser His Asn Leu Gly Ala Ile Leu Pro Pro Thr Asp Val
            20                  25                  30

Gly Ser Asn Thr Tyr
        35

<210> SEQ ID NO 195
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Lys Cys Asn Thr Ala Thr Cys Ala Thr Gln Arg Leu Thr Asn Phe Leu
1               5                   10                  15

Val Arg Ser Ser His Asn Leu Gly Pro Ala Leu Pro Pro Thr Asp Val
            20                  25                  30

Gly Ser Asn Thr Tyr
        35

<210> SEQ ID NO 196
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: N-terminal linked to mPEG40KD
<220> FEATURE:
<221> NAME/KEY: MOD_RES
<222> LOCATION: (37)..(37)
<223> OTHER INFORMATION: AMIDATION

<400> SEQUENCE: 196

Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Pro Thr Asn Val
            20                  25                  30

Gly Ser Asn Thr Tyr
        35

<210> SEQ ID NO 197
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES

```
<222> LOCATION: (1)..(1)
<223> OTHER INFORMATION: N-terminal residues linked to mPEG40KD
<220> FEATURE:
<221> NAME/KEY: MOD_RES
<222> LOCATION: (36)..(36)
<223> OTHER INFORMATION: AMIDATION

<400> SEQUENCE: 197

Cys Asn Thr Ala Thr Cys Ala Thr Gln Arg Leu Ala Asn Phe Leu Val
1               5                   10                  15

Arg Ser Ser Asn Asn Leu Gly Pro Val Leu Pro Pro Thr Asn Val Gly
            20                  25                  30

Ser Asn Thr Tyr
        35

<210> SEQ ID NO 198
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(21)
<223> OTHER INFORMATION: Lys(mPEG40KD)
<220> FEATURE:
<221> NAME/KEY: MOD_RES
<222> LOCATION: (37)..(37)
<223> OTHER INFORMATION: AMIDATION

<400> SEQUENCE: 198

Lys Cys Asn Thr Ala Thr Cys Ala Thr Gln Arg Leu Ala Asn Phe Leu
1               5                   10                  15

Val Arg Ser Ser Lys Asn Leu Gly Pro Val Leu Pro Pro Thr Asn Val
            20                  25                  30

Gly Ser Asn Thr Tyr
        35

<210> SEQ ID NO 199
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (20)..(20)
<223> OTHER INFORMATION: Lys(mPEG40KD)
<220> FEATURE:
<221> NAME/KEY: MOD_RES
<222> LOCATION: (36)..(36)
<223> OTHER INFORMATION: AMIDATION

<400> SEQUENCE: 199

Cys Asn Thr Ala Thr Cys Ala Thr Gln Arg Leu Ala Asn Phe Leu Val
1               5                   10                  15

Arg Ser Ser Lys Asn Leu Gly Pro Val Leu Pro Pro Thr Asn Val Gly
            20                  25                  30

Ser Asn Thr Tyr
        35

<210> SEQ ID NO 200
<211> LENGTH: 37
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (26)..(26)
<223> OTHER INFORMATION: Lys(mPEG40KD)
<220> FEATURE:
<221> NAME/KEY: MOD_RES
<222> LOCATION: (37)..(37)
<223> OTHER INFORMATION: AMIDATION

<400> SEQUENCE: 200

Lys Cys Asn Thr Ala Thr Cys Ala Thr Gln Arg Leu Ala Asn Phe Leu
1               5                   10                  15

Val Arg Ser Ser Asn Asn Leu Gly Pro Lys Leu Pro Pro Thr Asn Val
            20                  25                  30

Gly Ser Asn Thr Tyr
            35

<210> SEQ ID NO 201
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (25)..(25)
<223> OTHER INFORMATION: Lys(mPEG40KD)
<220> FEATURE:
<221> NAME/KEY: MOD_RES
<222> LOCATION: (36)..(36)
<223> OTHER INFORMATION: AMIDATION

<400> SEQUENCE: 201

Cys Asn Thr Ala Thr Cys Ala Thr Gln Arg Leu Ala Asn Phe Leu Val
1               5                   10                  15

Arg Ser Ser Asn Asn Leu Gly Pro Lys Leu Pro Pro Thr Asn Val Gly
            20                  25                  30

Ser Asn Thr Tyr
            35

<210> SEQ ID NO 202
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Lys(mPEG40KD)
<220> FEATURE:
<221> NAME/KEY: MOD_RES
<222> LOCATION: (37)..(37)
<223> OTHER INFORMATION: AMIDATION

<400> SEQUENCE: 202

Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Pro Thr Lys Val
            20                  25                  30

Gly Ser Asn Thr Tyr
            35
```

<210> SEQ ID NO 203
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: Lys(mPEG40KD)
<220> FEATURE:
<221> NAME/KEY: MOD_RES
<222> LOCATION: (36)..(36)
<223> OTHER INFORMATION: AMIDATION

<400> SEQUENCE: 203

Cys Asn Thr Ala Thr Cys Ala Thr Gln Arg Leu Ala Asn Phe Leu Val
1               5                   10                  15

Arg Ser Ser Asn Asn Leu Gly Pro Val Leu Pro Pro Thr Lys Val Gly
            20                  25                  30

Ser Asn Thr Tyr
        35

<210> SEQ ID NO 204
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (26)..(26)
<223> OTHER INFORMATION: Lys(Y-shaped-mPEG40KD)
<220> FEATURE:
<221> NAME/KEY: MOD_RES
<222> LOCATION: (37)..(37)
<223> OTHER INFORMATION: AMIDATION

<400> SEQUENCE: 204

Lys Cys Asn Thr Ala Thr Cys Ala Thr Gln Arg Leu Ala Asn Phe Leu
1               5                   10                  15

Val Arg Ser Ser Asn Asn Leu Gly Pro Lys Leu Pro Pro Thr Asn Val
            20                  25                  30

Gly Ser Asn Thr Tyr
        35

<210> SEQ ID NO 205
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (20)..(20)
<223> OTHER INFORMATION: Lys(mPEG40KD)
<220> FEATURE:
<221> NAME/KEY: MOD_RES
<222> LOCATION: (36)..(36)
<223> OTHER INFORMATION: AMIDATION

<400> SEQUENCE: 205

Cys Asn Thr Ala Thr Cys Ala Thr Gln Arg Leu Ala Asn Phe Leu Val
1               5                   10                  15

His Ser Ser Lys Asn Phe Gly Pro Ile Leu Pro Pro Thr Asn Val Gly

Ser Asn Thr Tyr
        35

<210> SEQ ID NO 206
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (25)..(25)
<223> OTHER INFORMATION: Lys(mPEG40KD)
<220> FEATURE:
<221> NAME/KEY: MOD_RES
<222> LOCATION: (36)..(36)
<223> OTHER INFORMATION: AMIDATION

<400> SEQUENCE: 206

Cys Asn Thr Ala Thr Cys Ala Thr Gln Arg Leu Ala Asn Phe Leu Val
1               5                   10                  15

His Ser Ser Asn Asn Phe Gly Pro Lys Leu Pro Pro Thr Asn Val Gly
            20                  25                  30

Ser Asn Thr Tyr
        35

<210> SEQ ID NO 207
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: Lys(mPEG40KD)
<220> FEATURE:
<221> NAME/KEY: MOD_RES
<222> LOCATION: (36)..(36)
<223> OTHER INFORMATION: AMIDATION

<400> SEQUENCE: 207

Cys Asn Thr Ala Thr Cys Ala Thr Gln Arg Leu Ala Asn Phe Leu Val
1               5                   10                  15

His Ser Ser Asn Asn Phe Gly Pro Ile Leu Pro Pro Thr Lys Val Gly
            20                  25                  30

Ser Asn Thr Tyr
        35

<210> SEQ ID NO 208
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (25)..(25)
<223> OTHER INFORMATION: Lys(Y-shaped-mPEG40KD)
<220> FEATURE:
<221> NAME/KEY: MOD_RES
<222> LOCATION: (36)..(36)
<223> OTHER INFORMATION: AMIDATION

<400> SEQUENCE: 208

Cys Asn Thr Ala Thr Cys Ala Thr Gln Arg Leu Ala Asn Phe Leu Val
1               5                   10                  15

His Ser Ser Asn Asn Phe Gly Pro Lys Leu Pro Pro Thr Asn Val Gly
            20                  25                  30

Ser Asn Thr Tyr
        35

<210> SEQ ID NO 209
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (23)..(23)
<223> OTHER INFORMATION: Lys(mPEG40KD)
<220> FEATURE:
<221> NAME/KEY: MOD_RES
<222> LOCATION: (36)..(36)
<223> OTHER INFORMATION: AMIDATION

<400> SEQUENCE: 209

Cys Asn Thr Ala Thr Cys Ala Thr Gln Arg Leu Ala Asn Phe Leu Val
1               5                   10                  15

His Ser Ser Asn Asn Phe Lys Pro Ile Leu Pro Pro Thr Asn Val Gly
            20                  25                  30

Ser Asn Thr Tyr
        35

<210> SEQ ID NO 210
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (24)..(24)
<223> OTHER INFORMATION: Lys(mPEG40KD)
<220> FEATURE:
<221> NAME/KEY: MOD_RES
<222> LOCATION: (36)..(36)
<223> OTHER INFORMATION: AMIDATION

<400> SEQUENCE: 210

Cys Asn Thr Ala Thr Cys Ala Thr Gln Arg Leu Ala Asn Phe Leu Val
1               5                   10                  15

His Ser Ser Asn Asn Phe Gly Lys Ile Leu Pro Pro Thr Asn Val Gly
            20                  25                  30

Ser Asn Thr Tyr
        35

<210> SEQ ID NO 211
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (26)..(26)
<223> OTHER INFORMATION: Lys(mPEG40KD)
<220> FEATURE:

```
<221> NAME/KEY: MOD_RES
<222> LOCATION: (36)..(36)
<223> OTHER INFORMATION: AMIDATION

<400> SEQUENCE: 211

Cys Asn Thr Ala Thr Cys Ala Thr Gln Arg Leu Ala Asn Phe Leu Val
1               5                   10                  15

His Ser Ser Asn Asn Phe Gly Pro Ile Lys Pro Pro Thr Asn Val Gly
            20                  25                  30

Ser Asn Thr Tyr
        35

<210> SEQ ID NO 212
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (27)..(27)
<223> OTHER INFORMATION: Lys(mPEG40KD)
<220> FEATURE:
<221> NAME/KEY: MOD_RES
<222> LOCATION: (36)..(36)
<223> OTHER INFORMATION: AMIDATION

<400> SEQUENCE: 212

Cys Asn Thr Ala Thr Cys Ala Thr Gln Arg Leu Ala Asn Phe Leu Val
1               5                   10                  15

His Ser Ser Asn Asn Phe Gly Pro Ile Leu Lys Pro Thr Asn Val Gly
            20                  25                  30

Ser Asn Thr Tyr
        35

<210> SEQ ID NO 213
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (28)..(28)
<223> OTHER INFORMATION: Lys(mPEG40KD)
<220> FEATURE:
<221> NAME/KEY: MOD_RES
<222> LOCATION: (36)..(36)
<223> OTHER INFORMATION: AMIDATION

<400> SEQUENCE: 213

Cys Asn Thr Ala Thr Cys Ala Thr Gln Arg Leu Ala Asn Phe Leu Val
1               5                   10                  15

His Ser Ser Asn Asn Phe Gly Pro Ile Leu Pro Lys Thr Asn Val Gly
            20                  25                  30

Ser Asn Thr Tyr
        35

<210> SEQ ID NO 214
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (25)..(25)
<223> OTHER INFORMATION: Lys(mPEG40K)

<400> SEQUENCE: 214

Cys Asn Thr Ala Thr Cys Ala Thr Gln Arg Leu Ala Asn Phe Leu Val
1               5                   10                  15

His Ser Ser Asn Asn Phe Gly Pro Lys Leu Pro Pro Thr Asn Val Gly
            20                  25                  30

Ser Asn Thr Tyr
        35

<210> SEQ ID NO 215
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Thr Gly Gly Gly Gly Ser
1               5

<210> SEQ ID NO 216
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Thr Gly Gly Gly Gly Ser Gly Gly Gly Ser
1               5                   10

<210> SEQ ID NO 217
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Thr Gly Gly Gly Gly Ser Gly Gly Gly Ser Gly Gly Gly Ser
1               5                   10

<210> SEQ ID NO 218
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Thr Gly Gly Gly Gly Ser Gly Gly Gly Ser Gly Gly Gly Ser Gly Gly
1               5                   10                  15

Gly Ser

<210> SEQ ID NO 219
<211> LENGTH: 22
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 219

Thr Gly Gly Gly Gly Ser Gly Gly Gly Ser Gly Gly Gly Ser Gly Gly
1               5                   10                  15

Gly Ser Gly Gly Gly Ser
            20

<210> SEQ ID NO 220
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Gly Gly Gly Ser Ala Ser
1               5

<210> SEQ ID NO 221
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Gly Gly Gly Ser Gly Gly Gly Ser Ala Ser
1               5                   10

<210> SEQ ID NO 222
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Gly Gly Gly Ser Gly Gly Gly Ser Gly Gly Gly Ser Ala Ser
1               5                   10

<210> SEQ ID NO 223
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Gly Gly Gly Ser Gly Gly Gly Ser Gly Gly Gly Ser Gly Gly Gly Ser
1               5                   10                  15

Ala Ser

<210> SEQ ID NO 224
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 224

Gly Gly Gly Ser Gly Gly Gly Ser Gly Gly Gly Ser Gly Gly Gly Ser
1               5                   10                  15

Gly Gly Gly Ser Ala Ser
            20

<210> SEQ ID NO 225
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Thr Gly Gly Gly Gly Ser Ala Ser
1               5

<210> SEQ ID NO 226
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Thr Gly Gly Gly Gly Ser Gly Gly Gly Ser Ala Ser
1               5                   10

<210> SEQ ID NO 227
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Thr Gly Gly Gly Gly Ser Gly Gly Gly Ser Gly Gly Gly Ser Ala Ser
1               5                   10                  15

<210> SEQ ID NO 228
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Thr Gly Gly Gly Gly Ser Gly Gly Gly Ser Gly Gly Gly Ser Gly Gly
1               5                   10                  15

Gly Ser Ala Ser
            20

<210> SEQ ID NO 229
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Thr Gly Gly Gly Gly Ser Gly Gly Gly Ser Gly Gly Gly Ser Gly Gly
```

-continued

```
1               5                   10                  15
Gly Ser Gly Gly Gly Ser Ala Ser
            20
```

<210> SEQ ID NO 230

<400> SEQUENCE: 230

000

<210> SEQ ID NO 231

<400> SEQUENCE: 231

000

<210> SEQ ID NO 232

<400> SEQUENCE: 232

000

<210> SEQ ID NO 233

<400> SEQUENCE: 233

000

<210> SEQ ID NO 234

<400> SEQUENCE: 234

000

<210> SEQ ID NO 235

<400> SEQUENCE: 235

000

<210> SEQ ID NO 236

<400> SEQUENCE: 236

000

<210> SEQ ID NO 237

<400> SEQUENCE: 237

000

<210> SEQ ID NO 238

<400> SEQUENCE: 238

000

<210> SEQ ID NO 239

<400> SEQUENCE: 239

000

<210> SEQ ID NO 240

<400> SEQUENCE: 240

000

<210> SEQ ID NO 241

<400> SEQUENCE: 241

000

<210> SEQ ID NO 242

<400> SEQUENCE: 242

000

<210> SEQ ID NO 243

<400> SEQUENCE: 243

000

<210> SEQ ID NO 244

<400> SEQUENCE: 244

000

<210> SEQ ID NO 245

<400> SEQUENCE: 245

000

<210> SEQ ID NO 246

<400> SEQUENCE: 246

000

<210> SEQ ID NO 247

<400> SEQUENCE: 247

000

<210> SEQ ID NO 248

<400> SEQUENCE: 248

000

<210> SEQ ID NO 249

<400> SEQUENCE: 249

000

<210> SEQ ID NO 250

<400> SEQUENCE: 250

000

<210> SEQ ID NO 251

<400> SEQUENCE: 251

000

<210> SEQ ID NO 252

<400> SEQUENCE: 252

000

<210> SEQ ID NO 253

<400> SEQUENCE: 253

000

<210> SEQ ID NO 254

<400> SEQUENCE: 254

000

<210> SEQ ID NO 255

<400> SEQUENCE: 255

000

<210> SEQ ID NO 256

<400> SEQUENCE: 256

000

<210> SEQ ID NO 257

<400> SEQUENCE: 257

000

<210> SEQ ID NO 258

<400> SEQUENCE: 258

000

<210> SEQ ID NO 259

<400> SEQUENCE: 259

000

<210> SEQ ID NO 260

<400> SEQUENCE: 260

000

<210> SEQ ID NO 261

<400> SEQUENCE: 261

000

<210> SEQ ID NO 262

<400> SEQUENCE: 262

000

<210> SEQ ID NO 263
<400> SEQUENCE: 263
000

<210> SEQ ID NO 264
<400> SEQUENCE: 264
000

<210> SEQ ID NO 265
<400> SEQUENCE: 265
000

<210> SEQ ID NO 266
<400> SEQUENCE: 266
000

<210> SEQ ID NO 267
<400> SEQUENCE: 267
000

<210> SEQ ID NO 268
<400> SEQUENCE: 268
000

<210> SEQ ID NO 269
<400> SEQUENCE: 269
000

<210> SEQ ID NO 270
<400> SEQUENCE: 270
000

<210> SEQ ID NO 271
<400> SEQUENCE: 271
000

<210> SEQ ID NO 272
<400> SEQUENCE: 272
000

<210> SEQ ID NO 273
<400> SEQUENCE: 273
000

<210> SEQ ID NO 274

```
<400> SEQUENCE: 274

000

<210> SEQ ID NO 275

<400> SEQUENCE: 275

000

<210> SEQ ID NO 276

<400> SEQUENCE: 276

000

<210> SEQ ID NO 277

<400> SEQUENCE: 277

000

<210> SEQ ID NO 278

<400> SEQUENCE: 278

000

<210> SEQ ID NO 279

<400> SEQUENCE: 279

000

<210> SEQ ID NO 280

<400> SEQUENCE: 280

000

<210> SEQ ID NO 281

<400> SEQUENCE: 281

000

<210> SEQ ID NO 282

<400> SEQUENCE: 282

000

<210> SEQ ID NO 283

<400> SEQUENCE: 283

000

<210> SEQ ID NO 284

<400> SEQUENCE: 284

000

<210> SEQ ID NO 285

<400> SEQUENCE: 285
```

000

<210> SEQ ID NO 286

<400> SEQUENCE: 286

000

<210> SEQ ID NO 287

<400> SEQUENCE: 287

000

<210> SEQ ID NO 288

<400> SEQUENCE: 288

000

<210> SEQ ID NO 289

<400> SEQUENCE: 289

000

<210> SEQ ID NO 290

<400> SEQUENCE: 290

000

<210> SEQ ID NO 291

<400> SEQUENCE: 291

000

<210> SEQ ID NO 292

<400> SEQUENCE: 292

000

<210> SEQ ID NO 293

<400> SEQUENCE: 293

000

<210> SEQ ID NO 294

<400> SEQUENCE: 294

000

<210> SEQ ID NO 295

<400> SEQUENCE: 295

000

<210> SEQ ID NO 296

<400> SEQUENCE: 296

000

<210> SEQ ID NO 297

<400> SEQUENCE: 297

000

<210> SEQ ID NO 298

<400> SEQUENCE: 298

000

<210> SEQ ID NO 299

<400> SEQUENCE: 299

000

<210> SEQ ID NO 300

<400> SEQUENCE: 300

000

<210> SEQ ID NO 301

<400> SEQUENCE: 301

000

<210> SEQ ID NO 302

<400> SEQUENCE: 302

000

<210> SEQ ID NO 303

<400> SEQUENCE: 303

000

<210> SEQ ID NO 304

<400> SEQUENCE: 304

000

<210> SEQ ID NO 305

<400> SEQUENCE: 305

000

<210> SEQ ID NO 306

<400> SEQUENCE: 306

000

<210> SEQ ID NO 307

<400> SEQUENCE: 307

000

<210> SEQ ID NO 308

```
<400> SEQUENCE: 308
000

<210> SEQ ID NO 309
<400> SEQUENCE: 309
000

<210> SEQ ID NO 310
<400> SEQUENCE: 310
000

<210> SEQ ID NO 311
<400> SEQUENCE: 311
000

<210> SEQ ID NO 312
<400> SEQUENCE: 312
000

<210> SEQ ID NO 313
<400> SEQUENCE: 313
000

<210> SEQ ID NO 314
<400> SEQUENCE: 314
000

<210> SEQ ID NO 315
<400> SEQUENCE: 315
000

<210> SEQ ID NO 316
<400> SEQUENCE: 316
000

<210> SEQ ID NO 317
<400> SEQUENCE: 317
000

<210> SEQ ID NO 318
<400> SEQUENCE: 318
000

<210> SEQ ID NO 319
<400> SEQUENCE: 319
```

000

<210> SEQ ID NO 320

<400> SEQUENCE: 320

000

<210> SEQ ID NO 321

<400> SEQUENCE: 321

000

<210> SEQ ID NO 322

<400> SEQUENCE: 322

000

<210> SEQ ID NO 323

<400> SEQUENCE: 323

000

<210> SEQ ID NO 324

<400> SEQUENCE: 324

000

<210> SEQ ID NO 325

<400> SEQUENCE: 325

000

<210> SEQ ID NO 326

<400> SEQUENCE: 326

000

<210> SEQ ID NO 327

<400> SEQUENCE: 327

000

<210> SEQ ID NO 328

<400> SEQUENCE: 328

000

<210> SEQ ID NO 329

<400> SEQUENCE: 329

000

<210> SEQ ID NO 330

<400> SEQUENCE: 330

000

-continued

<210> SEQ ID NO 331

<400> SEQUENCE: 331

000

<210> SEQ ID NO 332

<400> SEQUENCE: 332

000

<210> SEQ ID NO 333

<400> SEQUENCE: 333

000

<210> SEQ ID NO 334

<400> SEQUENCE: 334

000

<210> SEQ ID NO 335

<400> SEQUENCE: 335

000

<210> SEQ ID NO 336

<400> SEQUENCE: 336

000

<210> SEQ ID NO 337

<400> SEQUENCE: 337

000

<210> SEQ ID NO 338

<400> SEQUENCE: 338

000

<210> SEQ ID NO 339

<400> SEQUENCE: 339

000

<210> SEQ ID NO 340

<400> SEQUENCE: 340

000

<210> SEQ ID NO 341

<400> SEQUENCE: 341

000

<210> SEQ ID NO 342

<400> SEQUENCE: 342

000

<210> SEQ ID NO 343

<400> SEQUENCE: 343

000

<210> SEQ ID NO 344

<400> SEQUENCE: 344

000

<210> SEQ ID NO 345

<400> SEQUENCE: 345

000

<210> SEQ ID NO 346

<400> SEQUENCE: 346

000

<210> SEQ ID NO 347

<400> SEQUENCE: 347

000

<210> SEQ ID NO 348

<400> SEQUENCE: 348

000

<210> SEQ ID NO 349

<400> SEQUENCE: 349

000

<210> SEQ ID NO 350

<400> SEQUENCE: 350

000

<210> SEQ ID NO 351

<400> SEQUENCE: 351

000

<210> SEQ ID NO 352

<400> SEQUENCE: 352

000

<210> SEQ ID NO 353

```
<400> SEQUENCE: 353
000

<210> SEQ ID NO 354
<400> SEQUENCE: 354
000

<210> SEQ ID NO 355
<400> SEQUENCE: 355
000

<210> SEQ ID NO 356
<400> SEQUENCE: 356
000

<210> SEQ ID NO 357
<400> SEQUENCE: 357
000

<210> SEQ ID NO 358
<400> SEQUENCE: 358
000

<210> SEQ ID NO 359
<400> SEQUENCE: 359
000

<210> SEQ ID NO 360
<400> SEQUENCE: 360
000

<210> SEQ ID NO 361
<400> SEQUENCE: 361
000

<210> SEQ ID NO 362
<400> SEQUENCE: 362
000

<210> SEQ ID NO 363
<400> SEQUENCE: 363
000

<210> SEQ ID NO 364
<400> SEQUENCE: 364
```

-continued

000

<210> SEQ ID NO 365

<400> SEQUENCE: 365

000

<210> SEQ ID NO 366

<400> SEQUENCE: 366

000

<210> SEQ ID NO 367

<400> SEQUENCE: 367

000

<210> SEQ ID NO 368

<400> SEQUENCE: 368

000

<210> SEQ ID NO 369

<400> SEQUENCE: 369

000

<210> SEQ ID NO 370

<400> SEQUENCE: 370

000

<210> SEQ ID NO 371

<400> SEQUENCE: 371

000

<210> SEQ ID NO 372

<400> SEQUENCE: 372

000

<210> SEQ ID NO 373

<400> SEQUENCE: 373

000

<210> SEQ ID NO 374

<400> SEQUENCE: 374

000

<210> SEQ ID NO 375

<400> SEQUENCE: 375

000

<210> SEQ ID NO 376

<400> SEQUENCE: 376

000

<210> SEQ ID NO 377

<400> SEQUENCE: 377

000

<210> SEQ ID NO 378

<400> SEQUENCE: 378

000

<210> SEQ ID NO 379

<400> SEQUENCE: 379

000

<210> SEQ ID NO 380

<400> SEQUENCE: 380

000

<210> SEQ ID NO 381

<400> SEQUENCE: 381

000

<210> SEQ ID NO 382

<400> SEQUENCE: 382

000

<210> SEQ ID NO 383

<400> SEQUENCE: 383

000

<210> SEQ ID NO 384

<400> SEQUENCE: 384

000

<210> SEQ ID NO 385

<400> SEQUENCE: 385

000

<210> SEQ ID NO 386

<400> SEQUENCE: 386

000

<210> SEQ ID NO 387

```
<400> SEQUENCE: 387
000

<210> SEQ ID NO 388
<400> SEQUENCE: 388
000

<210> SEQ ID NO 389
<400> SEQUENCE: 389
000

<210> SEQ ID NO 390
<400> SEQUENCE: 390
000

<210> SEQ ID NO 391
<400> SEQUENCE: 391
000

<210> SEQ ID NO 392
<400> SEQUENCE: 392
000

<210> SEQ ID NO 393
<400> SEQUENCE: 393
000

<210> SEQ ID NO 394
<400> SEQUENCE: 394
000

<210> SEQ ID NO 395
<400> SEQUENCE: 395
000

<210> SEQ ID NO 396
<400> SEQUENCE: 396
000

<210> SEQ ID NO 397
<400> SEQUENCE: 397
000

<210> SEQ ID NO 398
<400> SEQUENCE: 398
```

000

<210> SEQ ID NO 399
<400> SEQUENCE: 399
000

<210> SEQ ID NO 400
<400> SEQUENCE: 400
000

<210> SEQ ID NO 401
<400> SEQUENCE: 401
000

<210> SEQ ID NO 402
<400> SEQUENCE: 402
000

<210> SEQ ID NO 403
<400> SEQUENCE: 403
000

<210> SEQ ID NO 404
<400> SEQUENCE: 404
000

<210> SEQ ID NO 405
<400> SEQUENCE: 405
000

<210> SEQ ID NO 406
<400> SEQUENCE: 406
000

<210> SEQ ID NO 407
<400> SEQUENCE: 407
000

<210> SEQ ID NO 408
<400> SEQUENCE: 408
000

<210> SEQ ID NO 409
<400> SEQUENCE: 409
000

-continued

<210> SEQ ID NO 410

<400> SEQUENCE: 410

000

<210> SEQ ID NO 411

<400> SEQUENCE: 411

000

<210> SEQ ID NO 412

<400> SEQUENCE: 412

000

<210> SEQ ID NO 413

<400> SEQUENCE: 413

000

<210> SEQ ID NO 414

<400> SEQUENCE: 414

000

<210> SEQ ID NO 415

<400> SEQUENCE: 415

000

<210> SEQ ID NO 416

<400> SEQUENCE: 416

000

<210> SEQ ID NO 417

<400> SEQUENCE: 417

000

<210> SEQ ID NO 418

<400> SEQUENCE: 418

000

<210> SEQ ID NO 419

<400> SEQUENCE: 419

000

<210> SEQ ID NO 420

<400> SEQUENCE: 420

000

```
<210> SEQ ID NO 421
<400> SEQUENCE: 421
000

<210> SEQ ID NO 422
<400> SEQUENCE: 422
000

<210> SEQ ID NO 423
<400> SEQUENCE: 423
000

<210> SEQ ID NO 424
<400> SEQUENCE: 424
000

<210> SEQ ID NO 425
<400> SEQUENCE: 425
000

<210> SEQ ID NO 426
<400> SEQUENCE: 426
000

<210> SEQ ID NO 427
<400> SEQUENCE: 427
000

<210> SEQ ID NO 428
<400> SEQUENCE: 428
000

<210> SEQ ID NO 429
<400> SEQUENCE: 429
000

<210> SEQ ID NO 430
<400> SEQUENCE: 430
000

<210> SEQ ID NO 431
<400> SEQUENCE: 431
000

<210> SEQ ID NO 432
```

<400> SEQUENCE: 432

000

<210> SEQ ID NO 433

<400> SEQUENCE: 433

000

<210> SEQ ID NO 434

<400> SEQUENCE: 434

000

<210> SEQ ID NO 435

<400> SEQUENCE: 435

000

<210> SEQ ID NO 436

<400> SEQUENCE: 436

000

<210> SEQ ID NO 437

<400> SEQUENCE: 437

000

<210> SEQ ID NO 438

<400> SEQUENCE: 438

000

<210> SEQ ID NO 439

<400> SEQUENCE: 439

000

<210> SEQ ID NO 440

<400> SEQUENCE: 440

000

<210> SEQ ID NO 441

<400> SEQUENCE: 441

000

<210> SEQ ID NO 442

<400> SEQUENCE: 442

000

<210> SEQ ID NO 443

<400> SEQUENCE: 443

000

<210> SEQ ID NO 444

<400> SEQUENCE: 444

000

<210> SEQ ID NO 445

<400> SEQUENCE: 445

000

<210> SEQ ID NO 446

<400> SEQUENCE: 446

000

<210> SEQ ID NO 447

<400> SEQUENCE: 447

000

<210> SEQ ID NO 448

<400> SEQUENCE: 448

000

<210> SEQ ID NO 449

<400> SEQUENCE: 449

000

<210> SEQ ID NO 450

<400> SEQUENCE: 450

000

<210> SEQ ID NO 451

<400> SEQUENCE: 451

000

<210> SEQ ID NO 452

<400> SEQUENCE: 452

000

<210> SEQ ID NO 453

<400> SEQUENCE: 453

000

<210> SEQ ID NO 454

<400> SEQUENCE: 454

000

<210> SEQ ID NO 455

<400> SEQUENCE: 455

000

<210> SEQ ID NO 456

<400> SEQUENCE: 456

000

<210> SEQ ID NO 457

<400> SEQUENCE: 457

000

<210> SEQ ID NO 458

<400> SEQUENCE: 458

000

<210> SEQ ID NO 459

<400> SEQUENCE: 459

000

<210> SEQ ID NO 460

<400> SEQUENCE: 460

000

<210> SEQ ID NO 461

<400> SEQUENCE: 461

000

<210> SEQ ID NO 462

<400> SEQUENCE: 462

000

<210> SEQ ID NO 463

<400> SEQUENCE: 463

000

<210> SEQ ID NO 464

<400> SEQUENCE: 464

000

<210> SEQ ID NO 465

<400> SEQUENCE: 465

000

<210> SEQ ID NO 466

```
<400> SEQUENCE: 466
000

<210> SEQ ID NO 467
<400> SEQUENCE: 467
000

<210> SEQ ID NO 468
<400> SEQUENCE: 468
000

<210> SEQ ID NO 469
<400> SEQUENCE: 469
000

<210> SEQ ID NO 470
<400> SEQUENCE: 470
000

<210> SEQ ID NO 471
<400> SEQUENCE: 471
000

<210> SEQ ID NO 472
<400> SEQUENCE: 472
000

<210> SEQ ID NO 473
<400> SEQUENCE: 473
000

<210> SEQ ID NO 474
<400> SEQUENCE: 474
000

<210> SEQ ID NO 475
<400> SEQUENCE: 475
000

<210> SEQ ID NO 476
<400> SEQUENCE: 476
000

<210> SEQ ID NO 477
<400> SEQUENCE: 477
```

000

<210> SEQ ID NO 478

<400> SEQUENCE: 478

000

<210> SEQ ID NO 479

<400> SEQUENCE: 479

000

<210> SEQ ID NO 480

<400> SEQUENCE: 480

000

<210> SEQ ID NO 481

<400> SEQUENCE: 481

000

<210> SEQ ID NO 482

<400> SEQUENCE: 482

000

<210> SEQ ID NO 483

<400> SEQUENCE: 483

000

<210> SEQ ID NO 484

<400> SEQUENCE: 484

000

<210> SEQ ID NO 485

<400> SEQUENCE: 485

000

<210> SEQ ID NO 486

<400> SEQUENCE: 486

000

<210> SEQ ID NO 487

<400> SEQUENCE: 487

000

<210> SEQ ID NO 488

<400> SEQUENCE: 488

000

<210> SEQ ID NO 489

<400> SEQUENCE: 489

000

<210> SEQ ID NO 490

<400> SEQUENCE: 490

000

<210> SEQ ID NO 491

<400> SEQUENCE: 491

000

<210> SEQ ID NO 492

<400> SEQUENCE: 492

000

<210> SEQ ID NO 493

<400> SEQUENCE: 493

000

<210> SEQ ID NO 494

<400> SEQUENCE: 494

000

<210> SEQ ID NO 495

<400> SEQUENCE: 495

000

<210> SEQ ID NO 496

<400> SEQUENCE: 496

000

<210> SEQ ID NO 497

<400> SEQUENCE: 497

000

<210> SEQ ID NO 498

<400> SEQUENCE: 498

000

<210> SEQ ID NO 499

<400> SEQUENCE: 499

000

```
<210> SEQ ID NO 500
<400> SEQUENCE: 500
000

<210> SEQ ID NO 501
<400> SEQUENCE: 501
000

<210> SEQ ID NO 502
<400> SEQUENCE: 502
000

<210> SEQ ID NO 503
<400> SEQUENCE: 503
000

<210> SEQ ID NO 504
<400> SEQUENCE: 504
000

<210> SEQ ID NO 505
<400> SEQUENCE: 505
000

<210> SEQ ID NO 506
<400> SEQUENCE: 506
000

<210> SEQ ID NO 507
<400> SEQUENCE: 507
000

<210> SEQ ID NO 508
<400> SEQUENCE: 508
000

<210> SEQ ID NO 509
<400> SEQUENCE: 509
000

<210> SEQ ID NO 510
<400> SEQUENCE: 510
000

<210> SEQ ID NO 511
```

<400> SEQUENCE: 511

000

<210> SEQ ID NO 512

<400> SEQUENCE: 512

000

<210> SEQ ID NO 513

<400> SEQUENCE: 513

000

<210> SEQ ID NO 514

<400> SEQUENCE: 514

000

<210> SEQ ID NO 515

<400> SEQUENCE: 515

000

<210> SEQ ID NO 516

<400> SEQUENCE: 516

000

<210> SEQ ID NO 517

<400> SEQUENCE: 517

000

<210> SEQ ID NO 518

<400> SEQUENCE: 518

000

<210> SEQ ID NO 519

<400> SEQUENCE: 519

000

<210> SEQ ID NO 520

<400> SEQUENCE: 520

000

<210> SEQ ID NO 521

<400> SEQUENCE: 521

000

<210> SEQ ID NO 522

<400> SEQUENCE: 522

000

<210> SEQ ID NO 523

<400> SEQUENCE: 523

000

<210> SEQ ID NO 524

<400> SEQUENCE: 524

000

<210> SEQ ID NO 525

<400> SEQUENCE: 525

000

<210> SEQ ID NO 526

<400> SEQUENCE: 526

000

<210> SEQ ID NO 527

<400> SEQUENCE: 527

000

<210> SEQ ID NO 528

<400> SEQUENCE: 528

000

<210> SEQ ID NO 529

<400> SEQUENCE: 529

000

<210> SEQ ID NO 530

<400> SEQUENCE: 530

000

<210> SEQ ID NO 531

<400> SEQUENCE: 531

000

<210> SEQ ID NO 532

<400> SEQUENCE: 532

000

<210> SEQ ID NO 533

<400> SEQUENCE: 533

000

<210> SEQ ID NO 534

<400> SEQUENCE: 534

000

<210> SEQ ID NO 535

<400> SEQUENCE: 535

000

<210> SEQ ID NO 536

<400> SEQUENCE: 536

000

<210> SEQ ID NO 537

<400> SEQUENCE: 537

000

<210> SEQ ID NO 538

<400> SEQUENCE: 538

000

<210> SEQ ID NO 539

<400> SEQUENCE: 539

000

<210> SEQ ID NO 540

<400> SEQUENCE: 540

000

<210> SEQ ID NO 541

<400> SEQUENCE: 541

000

<210> SEQ ID NO 542

<400> SEQUENCE: 542

000

<210> SEQ ID NO 543

<400> SEQUENCE: 543

000

<210> SEQ ID NO 544

<400> SEQUENCE: 544

000

<210> SEQ ID NO 545

```
<400> SEQUENCE: 545
000

<210> SEQ ID NO 546
<400> SEQUENCE: 546
000

<210> SEQ ID NO 547
<400> SEQUENCE: 547
000

<210> SEQ ID NO 548
<400> SEQUENCE: 548
000

<210> SEQ ID NO 549
<400> SEQUENCE: 549
000

<210> SEQ ID NO 550
<400> SEQUENCE: 550
000

<210> SEQ ID NO 551
<400> SEQUENCE: 551
000

<210> SEQ ID NO 552
<400> SEQUENCE: 552
000

<210> SEQ ID NO 553
<400> SEQUENCE: 553
000

<210> SEQ ID NO 554
<400> SEQUENCE: 554
000

<210> SEQ ID NO 555
<400> SEQUENCE: 555
000

<210> SEQ ID NO 556
<400> SEQUENCE: 556
```

000

<210> SEQ ID NO 557

<400> SEQUENCE: 557

000

<210> SEQ ID NO 558

<400> SEQUENCE: 558

000

<210> SEQ ID NO 559

<400> SEQUENCE: 559

000

<210> SEQ ID NO 560

<400> SEQUENCE: 560

000

<210> SEQ ID NO 561

<400> SEQUENCE: 561

000

<210> SEQ ID NO 562

<400> SEQUENCE: 562

000

<210> SEQ ID NO 563

<400> SEQUENCE: 563

000

<210> SEQ ID NO 564

<400> SEQUENCE: 564

000

<210> SEQ ID NO 565

<400> SEQUENCE: 565

000

<210> SEQ ID NO 566

<400> SEQUENCE: 566

000

<210> SEQ ID NO 567

<400> SEQUENCE: 567

000

<210> SEQ ID NO 568

<400> SEQUENCE: 568

000

<210> SEQ ID NO 569

<400> SEQUENCE: 569

000

<210> SEQ ID NO 570

<400> SEQUENCE: 570

000

<210> SEQ ID NO 571

<400> SEQUENCE: 571

000

<210> SEQ ID NO 572

<400> SEQUENCE: 572

000

<210> SEQ ID NO 573

<400> SEQUENCE: 573

000

<210> SEQ ID NO 574

<400> SEQUENCE: 574

000

<210> SEQ ID NO 575

<400> SEQUENCE: 575

000

<210> SEQ ID NO 576

<400> SEQUENCE: 576

000

<210> SEQ ID NO 577

<400> SEQUENCE: 577

000

<210> SEQ ID NO 578

<400> SEQUENCE: 578

000

<210> SEQ ID NO 579

<400> SEQUENCE: 579

000

<210> SEQ ID NO 580

<400> SEQUENCE: 580

000

<210> SEQ ID NO 581

<400> SEQUENCE: 581

000

<210> SEQ ID NO 582

<400> SEQUENCE: 582

000

<210> SEQ ID NO 583

<400> SEQUENCE: 583

000

<210> SEQ ID NO 584

<400> SEQUENCE: 584

000

<210> SEQ ID NO 585

<400> SEQUENCE: 585

000

<210> SEQ ID NO 586

<400> SEQUENCE: 586

000

<210> SEQ ID NO 587

<400> SEQUENCE: 587

000

<210> SEQ ID NO 588

<400> SEQUENCE: 588

000

<210> SEQ ID NO 589

<400> SEQUENCE: 589

000

<210> SEQ ID NO 590

-continued

<400> SEQUENCE: 590

000

<210> SEQ ID NO 591

<400> SEQUENCE: 591

000

<210> SEQ ID NO 592

<400> SEQUENCE: 592

000

<210> SEQ ID NO 593

<400> SEQUENCE: 593

000

<210> SEQ ID NO 594

<400> SEQUENCE: 594

000

<210> SEQ ID NO 595

<400> SEQUENCE: 595

000

<210> SEQ ID NO 596

<400> SEQUENCE: 596

000

<210> SEQ ID NO 597

<400> SEQUENCE: 597

000

<210> SEQ ID NO 598

<400> SEQUENCE: 598

000

<210> SEQ ID NO 599

<400> SEQUENCE: 599

000

<210> SEQ ID NO 600

<400> SEQUENCE: 600

000

<210> SEQ ID NO 601

<400> SEQUENCE: 601

000

<210> SEQ ID NO 602

<400> SEQUENCE: 602

000

<210> SEQ ID NO 603

<400> SEQUENCE: 603

000

<210> SEQ ID NO 604

<400> SEQUENCE: 604

000

<210> SEQ ID NO 605

<400> SEQUENCE: 605

000

<210> SEQ ID NO 606

<400> SEQUENCE: 606

000

<210> SEQ ID NO 607

<400> SEQUENCE: 607

000

<210> SEQ ID NO 608

<400> SEQUENCE: 608

000

<210> SEQ ID NO 609

<400> SEQUENCE: 609

000

<210> SEQ ID NO 610

<400> SEQUENCE: 610

000

<210> SEQ ID NO 611

<400> SEQUENCE: 611

000

<210> SEQ ID NO 612

<400> SEQUENCE: 612

000

<210> SEQ ID NO 613

<400> SEQUENCE: 613

000

<210> SEQ ID NO 614

<400> SEQUENCE: 614

000

<210> SEQ ID NO 615

<400> SEQUENCE: 615

000

<210> SEQ ID NO 616

<400> SEQUENCE: 616

000

<210> SEQ ID NO 617

<400> SEQUENCE: 617

000

<210> SEQ ID NO 618

<400> SEQUENCE: 618

000

<210> SEQ ID NO 619

<400> SEQUENCE: 619

000

<210> SEQ ID NO 620

<400> SEQUENCE: 620

000

<210> SEQ ID NO 621

<400> SEQUENCE: 621

000

<210> SEQ ID NO 622

<400> SEQUENCE: 622

000

<210> SEQ ID NO 623

<400> SEQUENCE: 623

000

<210> SEQ ID NO 624

<400> SEQUENCE: 624

000

<210> SEQ ID NO 625

<400> SEQUENCE: 625

000

<210> SEQ ID NO 626

<400> SEQUENCE: 626

000

<210> SEQ ID NO 627

<400> SEQUENCE: 627

000

<210> SEQ ID NO 628

<400> SEQUENCE: 628

000

<210> SEQ ID NO 629

<400> SEQUENCE: 629

000

<210> SEQ ID NO 630

<400> SEQUENCE: 630

000

<210> SEQ ID NO 631

<400> SEQUENCE: 631

000

<210> SEQ ID NO 632

<400> SEQUENCE: 632

000

<210> SEQ ID NO 633

<400> SEQUENCE: 633

000

<210> SEQ ID NO 634

<400> SEQUENCE: 634

000

<210> SEQ ID NO 635

<400> SEQUENCE: 635

000

<210> SEQ ID NO 636

<400> SEQUENCE: 636

000

<210> SEQ ID NO 637

<400> SEQUENCE: 637

000

<210> SEQ ID NO 638

<400> SEQUENCE: 638

000

<210> SEQ ID NO 639

<400> SEQUENCE: 639

000

<210> SEQ ID NO 640

<400> SEQUENCE: 640

000

<210> SEQ ID NO 641

<400> SEQUENCE: 641

000

<210> SEQ ID NO 642

<400> SEQUENCE: 642

000

<210> SEQ ID NO 643

<400> SEQUENCE: 643

000

<210> SEQ ID NO 644

<400> SEQUENCE: 644

000

<210> SEQ ID NO 645

<400> SEQUENCE: 645

000

<210> SEQ ID NO 646

<400> SEQUENCE: 646

000

<210> SEQ ID NO 647

<400> SEQUENCE: 647

000

<210> SEQ ID NO 648

<400> SEQUENCE: 648

000

<210> SEQ ID NO 649

<400> SEQUENCE: 649

000

<210> SEQ ID NO 650

<400> SEQUENCE: 650

000

<210> SEQ ID NO 651

<400> SEQUENCE: 651

000

<210> SEQ ID NO 652

<400> SEQUENCE: 652

000

<210> SEQ ID NO 653

<400> SEQUENCE: 653

000

<210> SEQ ID NO 654

<400> SEQUENCE: 654

000

<210> SEQ ID NO 655

<400> SEQUENCE: 655

000

<210> SEQ ID NO 656

<400> SEQUENCE: 656

000

<210> SEQ ID NO 657

<400> SEQUENCE: 657

000

<210> SEQ ID NO 658

<400> SEQUENCE: 658

000

<210> SEQ ID NO 659

<400> SEQUENCE: 659

000

<210> SEQ ID NO 660

<400> SEQUENCE: 660

000

<210> SEQ ID NO 661

<400> SEQUENCE: 661

000

<210> SEQ ID NO 662

<400> SEQUENCE: 662

000

<210> SEQ ID NO 663

<400> SEQUENCE: 663

000

<210> SEQ ID NO 664
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 664

```
Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Lys Val Thr Gly Leu Glu Phe Ile Pro Gly Leu His Pro
        35                  40                  45

Ile Leu Thr Leu Ser Lys Met Asp Gln Thr Leu Ala Val Tyr Gln Gln
    50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys Ser Leu Pro Gln Ala Ser Gly Leu Glu Thr Leu Glu Ser Leu Gly
            100                 105                 110

Glu Val Leu Glu Ala Ser Gly Tyr Ser Thr Glu Val Val Ala Leu Ser
        115                 120                 125

Arg Leu Gln Gly Ser Leu Gln Asp Ile Leu Gln Gln Leu Asp Leu Ser
    130                 135                 140
```

Pro Glu Cys
145

<210> SEQ ID NO 665
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 665

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
                20                  25                  30

Ser Lys Gln Lys Val Thr Gly Leu Asp Phe Ile Pro Gly Leu His Pro
            35                  40                  45

Ile Leu Thr Leu Ser Lys Met Asp Gln Thr Leu Ala Val Tyr Gln Gln
    50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys Ser Leu Pro Gln Ala Ser Gly Leu Glu Thr Leu Asp Ser Leu Gly
            100                 105                 110

Gly Val Leu Glu Ala Ser Gly Tyr Ser Thr Glu Val Val Ala Leu Ser
        115                 120                 125

Arg Leu Gln Gly Ser Leu Gln Asp Ile Leu Gln Gln Leu Asp Leu Ser
    130                 135                 140

Pro Glu Cys
145

<210> SEQ ID NO 666
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 666

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
                20                  25                  30

Ser Lys Gln Lys Val Thr Gly Leu Asp Phe Ile Pro Gly Leu His Pro
            35                  40                  45

Ile Leu Thr Leu Ser Lys Met Asp Gln Thr Leu Ala Val Tyr Gln Gln
    50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys Ser Leu Pro Gln Ala Ser Gly Leu Glu Thr Leu Asp Ser Leu Gly
            100                 105                 110

Glu Val Leu Glu Ala Ser Gly Tyr Ser Thr Glu Val Val Ala Leu Ser
        115                 120                 125

```
Arg Leu Gln Gly Ser Leu Gln Asp Ile Leu Gln Gln Leu Asp Leu Ser
    130                 135                 140

Pro Glu Cys
145

<210> SEQ ID NO 667
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 667

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Lys Val Thr Gly Leu Asp Phe Ile Pro Gly Leu His Pro
        35                  40                  45

Ile Leu Thr Leu Ser Lys Met Asp Gln Thr Leu Ala Val Tyr Gln Gln
    50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys His Leu Pro Gln Ala Ser Gly Leu Glu Thr Leu Asp Ser Leu Gly
            100                 105                 110

Glu Val Leu Glu Ala Ser Gly Tyr Ser Thr Glu Val Val Ala Leu Ser
        115                 120                 125

Arg Leu Gln Gly Ser Leu Gln Asp Ile Leu Gln Gln Leu Asp Leu Ser
    130                 135                 140

Pro Glu Cys
145

<210> SEQ ID NO 668
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 668

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Lys Val Thr Gly Leu Asp Phe Ile Pro Gly Leu His Pro
        35                  40                  45

Ile Leu Thr Leu Ser Lys Met Asp Gln Thr Leu Ala Val Tyr Gln Gln
    50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys Ser Leu Pro Gln Ala Ser Gly Leu Glu Thr Leu Asp Ser Leu Gly
            100                 105                 110
```

Gly Val Leu Glu Ala Ser Gly Tyr Ser Thr Glu Val Val Ala Leu Ser
            115                 120                 125

Arg Leu Gln Gly Ser Leu Gln Asp Ile Leu Gln Gln Leu Asp Leu Ser
        130                 135                 140

Pro Glu Cys
145

<210> SEQ ID NO 669
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 669

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Lys Val Thr Gly Leu Asp Phe Ile Pro Gly Leu His Pro
        35                  40                  45

Ile Leu Thr Leu Ser Lys Met Asp Gln Thr Leu Ala Val Tyr Gln Gln
    50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys His Leu Pro Gln Ala Ser Gly Leu Glu Thr Leu Asp Ser Leu Gly
            100                 105                 110

Glu Val Leu Glu Ala Ser Gly Tyr Ser Thr Glu Val Val Ala Leu Ser
        115                 120                 125

Arg Leu Gln Gly Ser Leu Gln Asp Ile Leu Gln Gln Leu Asp Val Ser
    130                 135                 140

Pro Glu Cys
145

<210> SEQ ID NO 670
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 670

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Lys Val Thr Gly Leu Asp Phe Ile Pro Gly Leu His Pro
        35                  40                  45

Ile Leu Thr Leu Ser Lys Met Asp Gln Thr Leu Ala Val Tyr Gln Gln
    50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

-continued

Cys Ser Leu Pro Gln Thr Ser Gly Leu Glu Thr Leu Asp Ser Leu Gly
                100                 105                 110

Gly Val Leu Glu Ala Ser Gly Tyr Ser Thr Glu Val Val Ala Leu Ser
            115                 120                 125

Arg Leu Gln Gly Ser Leu Gln Asp Ile Leu Gln Gln Leu Asp Leu Ser
        130                 135                 140

Pro Glu Cys
145

<210> SEQ ID NO 671
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 671

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Lys Val Thr Gly Leu Asp Phe Ile Pro Gly Leu His Pro
        35                  40                  45

Ile Leu Thr Leu Ser Lys Met Asp Gln Thr Leu Ala Val Tyr Gln Gln
    50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys Ser Leu Pro Gln Ala Ser Gly Leu Glu Thr Leu Glu Ser Leu Gly
                100                 105                 110

Glu Val Leu Glu Ala Ser Gly Tyr Ser Thr Glu Val Val Ala Leu Ser
            115                 120                 125

Arg Leu Gln Gly Ser Leu Gln Asp Met Leu Trp Gln Leu Asp Leu Ser
        130                 135                 140

Pro Glu Cys
145

<210> SEQ ID NO 672
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 672

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Lys Val Thr Gly Leu Asp Phe Ile Pro Gly Leu His Pro
        35                  40                  45

Ile Leu Thr Leu Ser Lys Met Asp Gln Thr Leu Ala Val Tyr Gln Gln
    50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
            85                  90                  95

Cys His Leu Pro Gln Ala Ser Gly Leu Glu Thr Leu Asp Ser Leu Gly
            100                 105                 110

Gly Val Leu Glu Ala Ser Gly Tyr Ser Thr Glu Val Val Ala Leu Ser
            115                 120                 125

Arg Leu Gln Gly Ser Leu Gln Asp Ile Leu Gln Gln Leu Asp Leu Ser
            130                 135                 140

Pro Glu Cys
145

<210> SEQ ID NO 673
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 673

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Lys Val Thr Gly Leu Asp Phe Ile Pro Gly Leu His Pro
            35                  40                  45

Ile Leu Thr Leu Ser Lys Met Asp Gln Thr Leu Ala Val Tyr Gln Gln
        50                  55                  60

Ile Leu Thr Ser Met Pro Ser Arg Asn Val Ile Gln Ile Ser Asn Asp
65              70                  75                  80

Leu Glu Asn Leu Arg Asp Leu Leu His Val Leu Ala Phe Ser Lys Ser
            85                  90                  95

Cys His Leu Pro Gln Ala Ser Gly Leu Glu Thr Leu Asp Ser Leu Gly
            100                 105                 110

Gly Val Leu Glu Ala Ser Gly Tyr Ser Thr Glu Val Val Ala Leu Ser
            115                 120                 125

Arg Leu Gln Gly Ser Leu Gln Asp Ile Leu Gln Gln Leu Asp Val Ser
            130                 135                 140

Pro Glu Cys
145

<210> SEQ ID NO 674
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 674

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Lys Val Thr Gly Leu Asp Phe Ile Pro Gly Leu His Pro
            35                  40                  45

Ile Leu Thr Leu Ser Lys Met Asp Gln Thr Leu Ala Val Tyr Gln Gln
        50                  55                  60

```
Ile Leu Thr Ser Met Pro Ser Arg Asn Val Ile Gln Ile Ser Asn Asp
 65                  70                  75                  80

Leu Glu Asn Leu Arg Asp Leu Leu His Val Leu Ala Phe Ser Lys Ser
                 85                  90                  95

Cys Ser Leu Pro Gln Thr Ser Gly Leu Glu Thr Leu Asp Ser Leu Gly
            100                 105                 110

Gly Val Leu Glu Ala Ser Gly Tyr Ser Thr Glu Val Val Ala Leu Ser
        115                 120                 125

Arg Leu Gln Gly Ser Leu Gln Asp Ile Leu Gln Gln Leu Asp Val Ser
        130                 135                 140

Pro Glu Cys
145
```

<210> SEQ ID NO 675
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 675

```
Met Val Pro Ile Gln Lys Val Gln Asp Asp Thr Lys Thr Leu Ile Lys
  1               5                  10                  15

Thr Ile Val Thr Arg Ile Asn Asp Ile Ser His Thr Gln Ser Val Ser
                 20                  25                  30

Ser Lys Gln Lys Val Thr Gly Leu Asp Phe Ile Pro Gly Leu His Pro
            35                  40                  45

Ile Leu Thr Leu Ser Lys Met Asp Gln Thr Leu Ala Val Tyr Gln Gln
 50                  55                  60

Ile Leu Thr Ser Met Pro Ser Arg Asn Val Ile Gln Ile Ser Asn Asp
 65                  70                  75                  80

Leu Glu Asn Leu Arg Asp Leu Leu His Val Leu Ala Phe Ser Lys Ser
                 85                  90                  95

Cys Ser Leu Pro Gln Thr Ser Gly Leu Glu Thr Leu Asp Ser Leu Gly
            100                 105                 110

Glu Val Leu Glu Ala Ser Gly Tyr Ser Thr Glu Val Val Ala Leu Ser
        115                 120                 125

Arg Leu Gln Gly Ser Leu Gln Asp Met Leu Trp Gln Leu Asp Leu Ser
        130                 135                 140

Pro Glu Cys
145
```

<210> SEQ ID NO 676
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 676

```
Met Val Pro Ile Gln Lys Val Gln Asp Asp Thr Lys Thr Leu Ile Lys
  1               5                  10                  15

Thr Ile Val Thr Arg Ile Asn Asp Ile Ser His Thr Gln Ser Val Ser
                 20                  25                  30

Ser Lys Gln Lys Val Thr Gly Leu Asp Phe Ile Pro Gly Leu His Pro
            35                  40                  45
```

```
Ile Leu Thr Leu Ser Lys Met Asp Gln Thr Leu Ala Val Tyr Gln Gln
         50                  55                  60

Ile Leu Thr Ser Met Pro Ser Arg Asn Val Ile Gln Ile Ser Asn Asp
 65                  70                  75                  80

Leu Glu Asn Leu Arg Asp Leu Leu His Val Leu Ala Phe Ser Lys Ser
                 85                  90                  95

Cys His Leu Pro Gln Ala Ser Gly Leu Glu Thr Leu Asp Ser Leu Gly
                100                 105                 110

Glu Val Leu Glu Ala Ser Gly Tyr Ser Thr Glu Val Val Ala Leu Ser
             115                 120                 125

Arg Leu Gln Gly Ser Leu Gln Asp Met Leu Gln Gln Leu Asp Leu Ser
130                 135                 140

Pro Gly Cys
145

<210> SEQ ID NO 677
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 677

Met Val Pro Ile Gln Lys Val Gln Asp Asp Thr Lys Thr Leu Ile Lys
 1               5                  10                  15

Thr Ile Val Thr Arg Ile Asn Asp Ile Ser His Thr Gln Ser Val Ser
                 20                  25                  30

Ser Lys Gln Lys Val Thr Gly Leu Asp Phe Ile Pro Gly Leu His Pro
             35                  40                  45

Ile Leu Thr Leu Ser Lys Met Asp Gln Thr Leu Ala Val Tyr Gln Gln
         50                  55                  60

Ile Leu Thr Ser Met Pro Ser Arg Asn Val Ile Gln Ile Ser Asn Asp
 65                  70                  75                  80

Leu Glu Asn Leu Arg Asp Leu Leu His Val Leu Ala Phe Ser Lys Ser
                 85                  90                  95

Cys His Leu Pro Gln Ala Ser Gly Leu Glu Thr Leu Asp Ser Leu Gly
                100                 105                 110

Glu Val Leu Glu Ala Ser Gly Tyr Ser Thr Glu Val Val Ala Leu Ser
             115                 120                 125

Arg Leu Gln Gly Ser Leu Gln Asp Met Leu Gln Gln Leu Asp Leu Ser
130                 135                 140

Pro Glu Cys
145

<210> SEQ ID NO 678

<400> SEQUENCE: 678

000

<210> SEQ ID NO 679

<400> SEQUENCE: 679

000

<210> SEQ ID NO 680
```

<400> SEQUENCE: 680

000

<210> SEQ ID NO 681

<400> SEQUENCE: 681

000

<210> SEQ ID NO 682

<400> SEQUENCE: 682

000

<210> SEQ ID NO 683

<400> SEQUENCE: 683

000

<210> SEQ ID NO 684

<400> SEQUENCE: 684

000

<210> SEQ ID NO 685

<400> SEQUENCE: 685

000

<210> SEQ ID NO 686

<400> SEQUENCE: 686

000

<210> SEQ ID NO 687

<400> SEQUENCE: 687

000

<210> SEQ ID NO 688

<400> SEQUENCE: 688

000

<210> SEQ ID NO 689

<400> SEQUENCE: 689

000

<210> SEQ ID NO 690

<400> SEQUENCE: 690

000

<210> SEQ ID NO 691

<400> SEQUENCE: 691

000

<210> SEQ ID NO 692
<400> SEQUENCE: 692
000

<210> SEQ ID NO 693
<400> SEQUENCE: 693
000

<210> SEQ ID NO 694
<400> SEQUENCE: 694
000

<210> SEQ ID NO 695
<400> SEQUENCE: 695
000

<210> SEQ ID NO 696
<400> SEQUENCE: 696
000

<210> SEQ ID NO 697
<400> SEQUENCE: 697
000

<210> SEQ ID NO 698
<400> SEQUENCE: 698
000

<210> SEQ ID NO 699
<400> SEQUENCE: 699
000

<210> SEQ ID NO 700
<400> SEQUENCE: 700
000

<210> SEQ ID NO 701
<400> SEQUENCE: 701
000

<210> SEQ ID NO 702
<400> SEQUENCE: 702
000

<210> SEQ ID NO 703

<400> SEQUENCE: 703

000

<210> SEQ ID NO 704

<400> SEQUENCE: 704

000

<210> SEQ ID NO 705

<400> SEQUENCE: 705

000

<210> SEQ ID NO 706

<400> SEQUENCE: 706

000

<210> SEQ ID NO 707

<400> SEQUENCE: 707

000

<210> SEQ ID NO 708

<400> SEQUENCE: 708

000

<210> SEQ ID NO 709

<400> SEQUENCE: 709

000

<210> SEQ ID NO 710

<400> SEQUENCE: 710

000

<210> SEQ ID NO 711

<400> SEQUENCE: 711

000

<210> SEQ ID NO 712

<400> SEQUENCE: 712

000

<210> SEQ ID NO 713

<400> SEQUENCE: 713

000

<210> SEQ ID NO 714

<400> SEQUENCE: 714

000

<210> SEQ ID NO 715

<400> SEQUENCE: 715

000

<210> SEQ ID NO 716

<400> SEQUENCE: 716

000

<210> SEQ ID NO 717

<400> SEQUENCE: 717

000

<210> SEQ ID NO 718

<400> SEQUENCE: 718

000

<210> SEQ ID NO 719

<400> SEQUENCE: 719

000

<210> SEQ ID NO 720

<400> SEQUENCE: 720

000

<210> SEQ ID NO 721

<400> SEQUENCE: 721

000

<210> SEQ ID NO 722

<400> SEQUENCE: 722

000

<210> SEQ ID NO 723

<400> SEQUENCE: 723

000

<210> SEQ ID NO 724

<400> SEQUENCE: 724

000

<210> SEQ ID NO 725

<400> SEQUENCE: 725

000

<210> SEQ ID NO 726

<400> SEQUENCE: 726

000

<210> SEQ ID NO 727

<400> SEQUENCE: 727

000

<210> SEQ ID NO 728

<400> SEQUENCE: 728

000

<210> SEQ ID NO 729

<400> SEQUENCE: 729

000

<210> SEQ ID NO 730

<400> SEQUENCE: 730

000

<210> SEQ ID NO 731

<400> SEQUENCE: 731

000

<210> SEQ ID NO 732

<400> SEQUENCE: 732

000

<210> SEQ ID NO 733

<400> SEQUENCE: 733

000

<210> SEQ ID NO 734

<400> SEQUENCE: 734

000

<210> SEQ ID NO 735

<400> SEQUENCE: 735

000

<210> SEQ ID NO 736

<400> SEQUENCE: 736

000

<210> SEQ ID NO 737

<400> SEQUENCE: 737

000

<210> SEQ ID NO 738

<400> SEQUENCE: 738

000

<210> SEQ ID NO 739

<400> SEQUENCE: 739

000

<210> SEQ ID NO 740

<400> SEQUENCE: 740

000

<210> SEQ ID NO 741

<400> SEQUENCE: 741

000

<210> SEQ ID NO 742

<400> SEQUENCE: 742

000

<210> SEQ ID NO 743

<400> SEQUENCE: 743

000

<210> SEQ ID NO 744

<400> SEQUENCE: 744

000

<210> SEQ ID NO 745

<400> SEQUENCE: 745

000

<210> SEQ ID NO 746

<400> SEQUENCE: 746

000

<210> SEQ ID NO 747

<400> SEQUENCE: 747

000

-continued

<210> SEQ ID NO 748

<400> SEQUENCE: 748

000

<210> SEQ ID NO 749

<400> SEQUENCE: 749

000

<210> SEQ ID NO 750

<400> SEQUENCE: 750

000

<210> SEQ ID NO 751

<400> SEQUENCE: 751

000

<210> SEQ ID NO 752

<400> SEQUENCE: 752

000

<210> SEQ ID NO 753

<400> SEQUENCE: 753

000

<210> SEQ ID NO 754

<400> SEQUENCE: 754

000

<210> SEQ ID NO 755

<400> SEQUENCE: 755

000

<210> SEQ ID NO 756

<400> SEQUENCE: 756

000

<210> SEQ ID NO 757

<400> SEQUENCE: 757

000

<210> SEQ ID NO 758

<400> SEQUENCE: 758

000

<210> SEQ ID NO 759

```
<400> SEQUENCE: 759
000

<210> SEQ ID NO 760
<400> SEQUENCE: 760
000

<210> SEQ ID NO 761
<400> SEQUENCE: 761
000

<210> SEQ ID NO 762
<400> SEQUENCE: 762
000

<210> SEQ ID NO 763
<400> SEQUENCE: 763
000

<210> SEQ ID NO 764
<400> SEQUENCE: 764
000

<210> SEQ ID NO 765
<400> SEQUENCE: 765
000

<210> SEQ ID NO 766
<400> SEQUENCE: 766
000

<210> SEQ ID NO 767
<400> SEQUENCE: 767
000

<210> SEQ ID NO 768
<400> SEQUENCE: 768
000

<210> SEQ ID NO 769
<400> SEQUENCE: 769
000

<210> SEQ ID NO 770
<400> SEQUENCE: 770
```

000

<210> SEQ ID NO 771
<400> SEQUENCE: 771
000

<210> SEQ ID NO 772
<400> SEQUENCE: 772
000

<210> SEQ ID NO 773
<400> SEQUENCE: 773
000

<210> SEQ ID NO 774
<400> SEQUENCE: 774
000

<210> SEQ ID NO 775
<400> SEQUENCE: 775
000

<210> SEQ ID NO 776
<400> SEQUENCE: 776
000

<210> SEQ ID NO 777
<400> SEQUENCE: 777
000

<210> SEQ ID NO 778
<400> SEQUENCE: 778
000

<210> SEQ ID NO 779
<400> SEQUENCE: 779
000

<210> SEQ ID NO 780
<400> SEQUENCE: 780
000

<210> SEQ ID NO 781
<400> SEQUENCE: 781
000

<210> SEQ ID NO 782

<400> SEQUENCE: 782

000

<210> SEQ ID NO 783

<400> SEQUENCE: 783

000

<210> SEQ ID NO 784

<400> SEQUENCE: 784

000

<210> SEQ ID NO 785

<400> SEQUENCE: 785

000

<210> SEQ ID NO 786

<400> SEQUENCE: 786

000

<210> SEQ ID NO 787

<400> SEQUENCE: 787

000

<210> SEQ ID NO 788

<400> SEQUENCE: 788

000

<210> SEQ ID NO 789

<400> SEQUENCE: 789

000

<210> SEQ ID NO 790

<400> SEQUENCE: 790

000

<210> SEQ ID NO 791

<400> SEQUENCE: 791

000

<210> SEQ ID NO 792

<400> SEQUENCE: 792

000

<210> SEQ ID NO 793

```
<400> SEQUENCE: 793

000

<210> SEQ ID NO 794

<400> SEQUENCE: 794

000

<210> SEQ ID NO 795

<400> SEQUENCE: 795

000

<210> SEQ ID NO 796

<400> SEQUENCE: 796

000

<210> SEQ ID NO 797

<400> SEQUENCE: 797

000

<210> SEQ ID NO 798

<400> SEQUENCE: 798

000

<210> SEQ ID NO 799

<400> SEQUENCE: 799

000

<210> SEQ ID NO 800
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (21)..(21)
<223> OTHER INFORMATION: Lys, Cys or Asn
<220> FEATURE:
<221> NAME/KEY: MOD_RES
<222> LOCATION: (24)..(24)
<223> OTHER INFORMATION: Lys, Cys or Gly
<220> FEATURE:
<221> NAME/KEY: MOD_RES
<222> LOCATION: (25)..(25)
<223> OTHER INFORMATION: Lys, Cys or Pro
<220> FEATURE:
<221> NAME/KEY: MOD_RES
<222> LOCATION: (26)..(26)
<223> OTHER INFORMATION: Lys, Cys or Ile
<220> FEATURE:
<221> NAME/KEY: MOD_RES
<222> LOCATION: (27)..(27)
<223> OTHER INFORMATION: Lys, Cys or Leu
```

```
<220> FEATURE:
<221> NAME/KEY: MOD_RES
<222> LOCATION: (28)..(29)
<223> OTHER INFORMATION: Lys, Cys or Pro
<220> FEATURE:
<221> NAME/KEY: MOD_RES
<222> LOCATION: (31)..(31)
<223> OTHER INFORMATION: Lys, Cys or Asn

<400> SEQUENCE: 800

Lys Cys Asn Thr Ala Thr Cys Ala Thr Gln Arg Leu Ala Asn Phe Leu
1               5                   10                  15

Val His Ser Ser Xaa Asn Phe Xaa Xaa Xaa Xaa Xaa Thr Xaa Val
            20                  25                  30

Gly Ser Asn Thr Tyr
        35

<210> SEQ ID NO 801
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: AMIDATION

<400> SEQUENCE: 801

Cys Asn Thr Ala Thr Cys Ala Thr Gln Arg Leu Ala Asn Phe Leu Val
1               5                   10                  15

Arg Ser Ser Asn Asn Leu Gly Pro Val Leu Pro Pro Thr Asn Val Gly
            20                  25                  30

Ser Asn Thr Tyr
        35

<210> SEQ ID NO 802
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: AMIDATION

<400> SEQUENCE: 802

Lys Cys Asn Thr Ala Thr Cys Ala Thr Gln Arg Leu Ala Asn Phe Leu
1               5                   10                  15

Val Arg Ser Ser Lys Asn Leu Gly Pro Val Leu Pro Pro Thr Asn Val
            20                  25                  30

Gly Ser Asn Thr Tyr
        35

<210> SEQ ID NO 803
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
```

<223> OTHER INFORMATION: AMIDATION

<400> SEQUENCE: 803

Cys Asn Thr Ala Thr Cys Ala Thr Gln Arg Leu Ala Asn Phe Leu Val
1               5                   10                  15

Arg Ser Ser Lys Asn Leu Gly Pro Val Leu Pro Pro Thr Asn Val Gly
            20                  25                  30

Ser Asn Thr Tyr
        35

<210> SEQ ID NO 804
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: AMIDATION

<400> SEQUENCE: 804

Lys Cys Asn Thr Ala Thr Cys Ala Thr Gln Arg Leu Ala Asn Phe Leu
1               5                   10                  15

Val Arg Ser Ser Asn Asn Leu Gly Pro Lys Leu Pro Pro Thr Asn Val
            20                  25                  30

Gly Ser Asn Thr Tyr
        35

<210> SEQ ID NO 805
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: AMIDATION

<400> SEQUENCE: 805

Cys Asn Thr Ala Thr Cys Ala Thr Gln Arg Leu Ala Asn Phe Leu Val
1               5                   10                  15

Arg Ser Ser Asn Asn Leu Gly Pro Lys Leu Pro Pro Thr Asn Val Gly
            20                  25                  30

Ser Asn Thr Tyr
        35

<210> SEQ ID NO 806
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: AMIDATION

<400> SEQUENCE: 806

Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Pro Thr Lys Val
            20                  25                  30

Gly Ser Asn Thr Tyr
        35

<210> SEQ ID NO 807
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: AMIDATION

<400> SEQUENCE: 807

Cys Asn Thr Ala Thr Cys Ala Thr Gln Arg Leu Ala Asn Phe Leu Val
1               5                   10                  15

Arg Ser Ser Asn Asn Leu Gly Pro Val Leu Pro Pro Thr Lys Val Gly
            20                  25                  30

Ser Asn Thr Tyr
        35

<210> SEQ ID NO 808
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: AMIDATION

<400> SEQUENCE: 808

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
            20                  25                  30

Gly Ser Asn Thr Tyr
        35

<210> SEQ ID NO 809
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: AMIDATION

<400> SEQUENCE: 809

Cys Asn Thr Ala Thr Cys Ala Thr Gln Arg Leu Ala Asn Phe Leu Val
1               5                   10                  15

His Ser Ser Asn Asn Phe Gly Pro Ile Leu Pro Pro Thr Asn Val Gly
            20                  25                  30

Ser Asn Thr Tyr
        35

```
<210> SEQ ID NO 810
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: AMIDATION

<400> SEQUENCE: 810

Cys Asn Thr Ala Thr Cys Ala Thr Gln Arg Leu Ala Asn Phe Leu Val
1               5                   10                  15

His Ser Ser Lys Asn Phe Gly Pro Ile Leu Pro Pro Thr Asn Val Gly
            20                  25                  30

Ser Asn Thr Tyr
        35

<210> SEQ ID NO 811
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: AMIDATION

<400> SEQUENCE: 811

Cys Asn Thr Ala Thr Cys Ala Thr Gln Arg Leu Ala Asn Phe Leu Val
1               5                   10                  15

His Ser Ser Asn Asn Phe Gly Pro Lys Leu Pro Pro Thr Asn Val Gly
            20                  25                  30

Ser Asn Thr Tyr
        35

<210> SEQ ID NO 812
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: AMIDATION

<400> SEQUENCE: 812

Cys Asn Thr Ala Thr Cys Ala Thr Gln Arg Leu Ala Asn Phe Leu Val
1               5                   10                  15

His Ser Ser Asn Asn Phe Gly Pro Ile Leu Pro Pro Thr Lys Val Gly
            20                  25                  30

Ser Asn Thr Tyr
        35

<210> SEQ ID NO 813
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (36)..(36)
<223> OTHER INFORMATION: AMIDATION

<400> SEQUENCE: 813

Cys Asn Thr Ala Thr Cys Ala Thr Gln Arg Leu Ala Asn Phe Leu Val
1               5                   10                  15

His Ser Ser Asn Asn Phe Lys Pro Ile Leu Pro Pro Thr Asn Val Gly
            20                  25                  30

Ser Asn Thr Tyr
            35

<210> SEQ ID NO 814
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: AMIDATION

<400> SEQUENCE: 814

Cys Asn Thr Ala Thr Cys Ala Thr Gln Arg Leu Ala Asn Phe Leu Val
1               5                   10                  15

His Ser Ser Asn Asn Phe Gly Lys Ile Leu Pro Pro Thr Asn Val Gly
            20                  25                  30

Ser Asn Thr Tyr
            35

<210> SEQ ID NO 815
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: AMIDATION

<400> SEQUENCE: 815

Cys Asn Thr Ala Thr Cys Ala Thr Gln Arg Leu Ala Asn Phe Leu Val
1               5                   10                  15

His Ser Ser Asn Asn Phe Gly Pro Ile Lys Pro Pro Thr Asn Val Gly
            20                  25                  30

Ser Asn Thr Tyr
            35

<210> SEQ ID NO 816
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: AMIDATION

<400> SEQUENCE: 816
```

-continued

```
Cys Asn Thr Ala Thr Cys Ala Thr Gln Arg Leu Ala Asn Phe Leu Val
1               5                   10                  15

His Ser Ser Asn Asn Phe Gly Pro Ile Leu Lys Pro Thr Asn Val Gly
            20                  25                  30

Ser Asn Thr Tyr
        35

<210> SEQ ID NO 817
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: AMIDATION

<400> SEQUENCE: 817

Cys Asn Thr Ala Thr Cys Ala Thr Gln Arg Leu Ala Asn Phe Leu Val
1               5                   10                  15

His Ser Ser Asn Asn Phe Gly Pro Ile Leu Pro Lys Thr Asn Val Gly
            20                  25                  30

Ser Asn Thr Tyr
        35
```